US010441318B2

(12) United States Patent
Donner et al.

(10) Patent No.: US 10,441,318 B2
(45) Date of Patent: *Oct. 15, 2019

(54) ADDITIVELY MANUFACTURED SYSTEMS FOR LOW PROFILE SPINOPELVIC FIXATION AND SACROILIAC JOINT FUSION FOR COMPLEX SPINAL DEFORMITIES

(71) Applicant: JCBD, LLC, Fort Collins, CO (US)

(72) Inventors: Edward Jeffrey Donner, Fort Collins, CO (US); Christopher Thomas Donner, Fort Collins, CO (US)

(73) Assignee: JCBD, LLC, Fort Collins, CO (US)

( * ) Notice: Subject to any disclaimer, the term of this patent is extended or adjusted under 35 U.S.C. 154(b) by 3 days.

This patent is subject to a terminal disclaimer.

(21) Appl. No.: 15/664,862

(22) Filed: Jul. 31, 2017

(65) Prior Publication Data
US 2017/0325846 A1 Nov. 16, 2017

Related U.S. Application Data

(60) Division of application No. 14/216,975, filed on Mar. 17, 2014, now Pat. No. 9,757,154, which is a
(Continued)

(51) Int. Cl.
*A61B 17/68* (2006.01)
*A61F 2/30* (2006.01)
(Continued)

(52) U.S. Cl.
CPC .......... *A61B 17/68* (2013.01); *A61B 17/1757* (2013.01); *A61B 17/7044* (2013.01);
(Continued)

(58) Field of Classification Search
CPC ............ A61B 17/7071; A61B 17/7044; A61B 17/7055; A61B 17/7035; A61B 17/025; A61F 2002/4687; A61F 2002/30995
See application file for complete search history.

(56) References Cited

U.S. PATENT DOCUMENTS 4,805,602 A 2/1989 Puno
5,334,205 A * 8/1994 Cain ............... A61F 2002/4687
606/102
(Continued)

FOREIGN PATENT DOCUMENTS

WO WO 2014/074853 A1 5/2014

OTHER PUBLICATIONS

Globus Medical. Secure-C Cervical Artificial Disc. Copyright 2014.
(Continued)

*Primary Examiner* — Lynnsy M Summit
*Assistant Examiner* — Tara Rose E Carter
(74) *Attorney, Agent, or Firm* — Polsinelli PC; Joshua J. Pranckun; Samuel Wade Johnson

(57) ABSTRACT

An orthopedic anchoring system for attaching a spinal stabilization system and concomitantly fusing a sacroiliac joint is disclosed that includes a delivery tool and an implant assembly for insertion into a joint space of a sacroiliac joint. The implant assembly may be secured using anchors inserted through bores within the implant body and into the underlying sacrum and/or ilium. The implant body may also include an attachment fitting reversibly attached to a guide to provide attachment fittings for elements of the spinal stabilization system. The implant assembly may be releasably coupled to an implant arm of the delivery tool such that the implant arm is substantially aligned with the insertion element of the implant assembly. An anchor arm used to insert the anchor may be coupled to the implant arm in a fixed and nonadjustable arrangement such that the anchor is generally aligned with a bore within the implant assembly.

17 Claims, 144 Drawing Sheets

Related U.S. Application Data continuation-in-part of application No. 13/475,695, filed on May 18, 2012, now Pat. No. 9,381,045, which is a continuation-in-part of application No. 13/236,411, filed on Sep. 19, 2011, now Pat. No. 9,017,407, which is a continuation-in-part of application No. 12/998,712, filed as application No. PCT/US2011/000070 on Jan. 13, 2011, now Pat. No. 8,979,928.

(60) Provisional application No. 61/335,947, filed on Jan. 13, 2010, provisional application No. 61/798,225, filed on Mar. 15, 2013.

(51) Int. Cl.

| | | |
|---|---|---|
| *A61B 17/17* | (2006.01) | |
| *A61F 2/46* | (2006.01) | |
| *A61B 17/70* | (2006.01) | |
| *A61B 17/02* | (2006.01) | |
| *A61F 2/44* | (2006.01) | |
| *A61B 17/86* | (2006.01) | |
| *A61B 17/00* | (2006.01) | |

(52) U.S. Cl.
CPC ...... *A61B 17/7055* (2013.01); *A61F 2/30988* (2013.01); *A61F 2/4611* (2013.01); *A61B 17/025* (2013.01); *A61B 17/7035* (2013.01); *A61B 17/7043* (2013.01); *A61B 17/863* (2013.01); *A61B 17/8645* (2013.01); *A61B 2017/0046* (2013.01); *A61F 2/4455* (2013.01); *A61F 2002/30163* (2013.01); *A61F 2002/30622* (2013.01); *A61F 2002/30995* (2013.01); *A61F 2002/4687* (2013.01); *A61F 2310/00017* (2013.01); *A61F 2310/00023* (2013.01); *A61F 2310/00179* (2013.01); *A61F 2310/00359* (2013.01)

(56) References Cited

U.S. PATENT DOCUMENTS

| | | | |
|---|---|---|---|
| 5,662,652 A | | 9/1997 | Schafer |
| 7,229,448 B2* | | 6/2007 | Goble ............... A61B 17/1714 606/98 |
| 7,935,116 B2 | | 5/2011 | Michelson |
| 7,942,903 B2 | | 5/2011 | Moskowitz et al. |
| 8,882,818 B1 | | 11/2014 | Vestgaarden |
| 9,039,765 B2 | | 5/2015 | Trieu |
| 9,044,321 B2 | | 6/2015 | Mauldin |
| 9,119,732 B2 | | 9/2015 | Schifano |
| 9,149,286 B1 | | 10/2015 | Greenhalgh |
| 9,186,155 B2 | | 11/2015 | Katzman et al. |
| 9,254,130 B2 | | 2/2016 | Hollis et al. |
| 9,452,065 B1 | | 9/2016 | Lawson |
| 9,480,511 B2 | | 11/2016 | Butters |
| 9,486,264 B2 | | 11/2016 | Reiley |
| 9,820,783 B2 | | 11/2017 | Donner et al. |
| 9,833,265 B2 | | 12/2017 | Donner et al. |
| 9,931,212 B1 | | 4/2018 | Donner et al. |
| 9,936,983 B2 | | 4/2018 | Mesiwala |
| 9,949,835 B2 | | 4/2018 | Donner |
| 9,949,843 B2 | | 4/2018 | Reiley |
| 10,130,477 B2 | | 11/2018 | Donner et al. |
| 10,136,995 B2 | | 11/2018 | Donner et al. |
| 2002/0103487 A1 | | 8/2002 | Errico |
| 2004/0193271 A1 | | 9/2004 | Fraser |
| 2005/0261775 A1 | | 11/2005 | Baum |
| 2006/0036251 A1 | | 2/2006 | Reiley |
| 2007/0239278 A1 | | 10/2007 | Heinz |
| 2007/0299445 A1 | | 12/2007 | Shadduck |
| 2008/0021461 A1 | | 1/2008 | Barker et al. |
| 2009/0062914 A1* | | 3/2009 | Marino ............... A61B 17/68 606/301 |
| 2009/0099659 A1 | | 4/2009 | Oh |
| 2009/0204215 A1 | | 8/2009 | McClintock |
| 2009/0281579 A1* | | 11/2009 | Weaver ............... A61B 17/68 606/301 |
| 2010/0145397 A1* | | 6/2010 | Overes ............... A61B 17/68 606/319 |
| 2010/0168798 A1 | | 7/2010 | Clineff |
| 2010/0168861 A1 | | 7/2010 | Yundt |
| 2010/0191088 A1 | | 7/2010 | Anderson |
| 2010/0191100 A1 | | 7/2010 | Anderson |
| 2010/0204796 A1 | | 8/2010 | Bae |
| 2010/0217086 A1 | | 8/2010 | Deshmukh |
| 2011/0160866 A1 | | 6/2011 | Laurence |
| 2011/0213221 A1 | | 9/2011 | Roche |
| 2011/0230968 A1 | | 9/2011 | Perisic |
| 2012/0065548 A1 | | 3/2012 | Morgan |
| 2012/0253406 A1 | | 10/2012 | Bae |
| 2013/0035724 A1 | | 2/2013 | Fitzpatrick |
| 2013/0144393 A1 | | 6/2013 | Mutchler |
| 2013/0173004 A1 | | 7/2013 | Greenhalgh |
| 2013/0238093 A1 | | 9/2013 | Mauldin |
| 2013/0245763 A1 | | 9/2013 | Mauldin |
| 2014/0046380 A1 | | 2/2014 | Asfora |
| 2014/0277463 A1 | | 9/2014 | Yerby |
| 2015/0105828 A1 | | 4/2015 | Reckling |
| 2015/0250612 A1 | | 9/2015 | Schifano |
| 2016/0128838 A1 | | 5/2016 | Assell |
| 2016/0324643 A1 | | 11/2016 | Donner et al. |
| 2017/0007409 A1 | | 1/2017 | Mauldin |
| 2017/0135733 A1 | | 5/2017 | Donner et al. |
| 2017/0164979 A1 | | 6/2017 | Donner et al. |
| 2017/0319240 A1 | | 11/2017 | Donner et al. |
| 2017/0325845 A1 | | 11/2017 | Donner et al. |
| 2018/0035893 A1 | | 2/2018 | Donner et al. |
| 2018/0036017 A1 | | 2/2018 | Donner et al. |
| 2018/0055521 A1 | | 3/2018 | Donner |
| 2018/0085223 A1 | | 3/2018 | Donner |
| 2018/0092669 A1 | | 4/2018 | Donner et al. |
| 2018/0092748 A1 | | 4/2018 | Donner et al. |
| 2018/0104071 A1 | | 4/2018 | Reckling |
| 2018/0185157 A1 | | 7/2018 | Donner et al. |
| 2018/0193154 A1 | | 7/2018 | Donner et al. |
| 2018/0193155 A1 | | 7/2018 | Donner et al. |
| 2018/0318091 A1 | | 11/2018 | Donner et al. |
| 2018/0325675 A1 | | 11/2018 | Donner |
| 2018/0325676 A1 | | 11/2018 | Donner |

OTHER PUBLICATIONS

Synthes Spine. ProDisc-L Total Disc Replacement. For replacement of a diseased and/or degenerated intervertebral disc of the lumbosacral regions. Technique Guide. Copyright 2006.
Amendment Under 1.312, U.S. Appl. No. 14/681,882, dated Aug. 10, 2017.
Australian Examination Report, AU2016204937, dated May 21, 2018.
Canadian Office Action, CA2849095, dated May 28, 2018.
China Office Action, CN201510622898.0, dated Dec. 23, 2016 (English translation).
China Office Action, CN201510622898.0, dated Feb. 1, 2018 (English translation).
China Office Action, CN201510622898.0, dated Sep. 1, 2017 (English translation).
EP Examination Report, EP12799773.2, dated Jun. 4, 2018.
Final Office Action, U.S. Appl. No. 14/344,876, dated Apr. 13, 2018.
Final Office Action, U.S. Appl. No. 14/660,784, dated Jul. 20, 2018.
Non-Final Office Action, U.S. Appl. No. 14/660,784, dated Mar. 5, 2018.
Non-Final Office Action, U.S. Appl. No. 15/385,446, dated Jul. 24, 2018.
Non-Final Office Action, U.S. Appl. No. 15/418,633, dated Aug. 7, 2018.
Non-Final Office Action, U.S. Appl. No. 15/662,045, dated Aug. 10, 2018.
Non-Final Office Action, U.S. Appl. No. 15/729,273, dated May 2, 2018.

(56) References Cited

OTHER PUBLICATIONS

Notice of Allowance, U.S. Appl. No. 14/344,876, dated May 18, 2018.
Notice of Allowance, U.S. Appl. No. 14/447,612, dated Feb. 28, 2017.
Notice of Allowance, U.S. Appl. No. 14/567,956, dated Mar. 13, 2017.
Notice of Allowance, U.S. Appl. No. 15/061,524, dated Jul. 26, 2017.
Notice of Allowance, U.S. Appl. No. 15/178,244, dated Sep. 12, 2017.
Notice of Allowance, U.S. Appl. No. 15/178,291, dated Oct. 11, 2017.
Notice of Allowance, U.S. Appl. No. 15/828,556, dated Feb. 7, 2018.
Notice of Allowance, U.S. Appl. No. 15/828,622, dated Aug. 9, 2018.
Notice of Allowance, U.S. Appl. No. 15/828,677, dated Jan. 19, 2018.
Notice of Allowance, U.S. Appl. No. 15/910,753, dated May 21, 2018.
Notice of Allowance, U.S. Appl. No. 15/912,216, dated Jun. 20, 2018.
Notice of Allowance, U.S. Appl. No. 15/912,260, dated May 10, 2018.
Notice of Allowance, U.S. Appl. No. 15/992,987, dated Aug. 16, 2018.
Notice of Allowance, U.S. Appl. No. 15/993,170, dated Aug. 8, 2018.
Preliminary Amendment, U.S. Appl. No. 15/831,589, dated Jul. 27, 2018.
Response to Final Office Action, U.S. Appl. No. 14/344,876, dated Apr. 27, 2018.
Response to Non-Final Office Action, U.S. Appl. No. 14/127,119, dated Dec. 29, 2016.
Response to Non-Final Office Action, U.S. Appl. No. 14/344,876, dated Mar. 1, 2017.
Response to Non-Final Office Action, U.S. Appl. No. 14/344,876, dated Sep. 5, 2017.
Response to Non-Final Office Action, U.S. Appl. No. 14/660,784, dated Jun. 4, 2018.
Response to Non-Final Office Action, U.S. Appl. No. 15/178,244, dated Aug. 15, 2017.
Response to Non-Final Office Action, U.S. Appl. No. 15/178,291, dated Aug. 16, 2017.
Response to Non-Final Office Action, U.S. Appl. No. 15/729,273, dated Aug. 1, 2018.
Response to Restriction, U.S. Appl. No. 14/660,784, dated Nov. 28, 2017.
Response to Restriction, U.S. Appl. No. 15/216,472, dated Jun. 4, 2018.
Restriction Requirement, U.S. Appl. No. 14/660,784, dated Sep. 28, 2017.
Restriction Requirement, U.S. Appl. No. 15/216,472, dated Apr. 2, 2018.
Amendment Under 1.312, U.S. Appl. No. 15/828,622, dated Oct. 26, 2018.
Amendment Under 1.312, U.S. Appl. No. 15/992,987, dated Sep. 26, 2018.
Amendment Under 1.312, U.S. Appl. No. 15/993,170, dated Sep. 26, 2018.
Corrected Notice of Allowability, U.S. Appl. No. 15/828,622, dated Nov. 19, 2018.
Corrected Notice of Allowability, U.S. Appl. No. 15/992,987, dated Oct. 9, 2018.
Corrected Notice of Allowability, U.S. Appl. No. 15/993,170, dated Oct. 9, 2018.
Final Office Action, U.S. Appl. No. 15/729,273, dated Nov. 20, 2018.
Non-Final Office Action, U.S. Appl. No. 15/216,472, dated Sep. 25, 2018.
Non-Final Office Action, U.S. Appl. No. 15/785,997, dated Nov. 29, 2018.
Non-Final Office Action, U.S. Appl. No. 15/789,515, dated Oct. 29, 2018.
Non-Final Office Action, U.S. Appl. No. 15/789,602, dated Nov. 29, 2018.
Non-Final Office Action, U.S. Appl. No. 15/993,277, dated Nov. 26, 2018.
Notice of Allowance, U.S. Appl. No. 14/660,784, dated Nov. 15, 2018.
Notice of Allowance, U.S. Appl. No. 15/993,277, dated Dec. 4, 2018.
Response to Final Office Action, U.S. Appl. No. 14/660,784, dated Oct. 22, 2018.
Response to Non-Final Office Action, U.S. Appl. No. 15/216,472, dated Dec. 19, 2018.
Response to Non-Final Office Action, U.S. Appl. No. 15/385,446, dated Oct. 24, 2018.
Response to Non-Final Office Action, U.S. Appl. No. 15/418,633, dated Nov. 7, 2018.
Response to Non-Final Office Action, U.S. Appl. No. 15/662,045, dated Nov. 12, 2018.
Response to Non-Final Office Action, U.S. Appl. No. 15/789,515, dated Nov. 21, 2018.
Restriction Requirement, U.S. Appl. No. 15/664,608, dated Oct. 5, 2018.
Response to Restriction, U.S. Appl. No. 15/664,608, dated Dec. 5, 2018.
IN First Examination Report, 6569/DELNP/2012, dated Apr. 30, 2019.
Non-Final Office Action, U.S. Appl. No. 15/664,608, dated Apr. 1, 2019.
Notice of Allowance, U.S. Appl. No. 15/216,472, dated Mar. 20, 2019.
Notice of Allowance, U.S. Appl. No. 15/662,045, dated Mar. 26, 2019.
Notice of Allowance, U.S. Appl. No. 15/789,515, dated Mar. 27, 2019.
Response to Final Office Action, U.S. Appl. No. 15/418,633, dated May 2, 2019.
Response to Non-Final Office Action, U.S. Appl. No. 15/789,602, dated Mar. 25, 2019.

\* cited by examiner

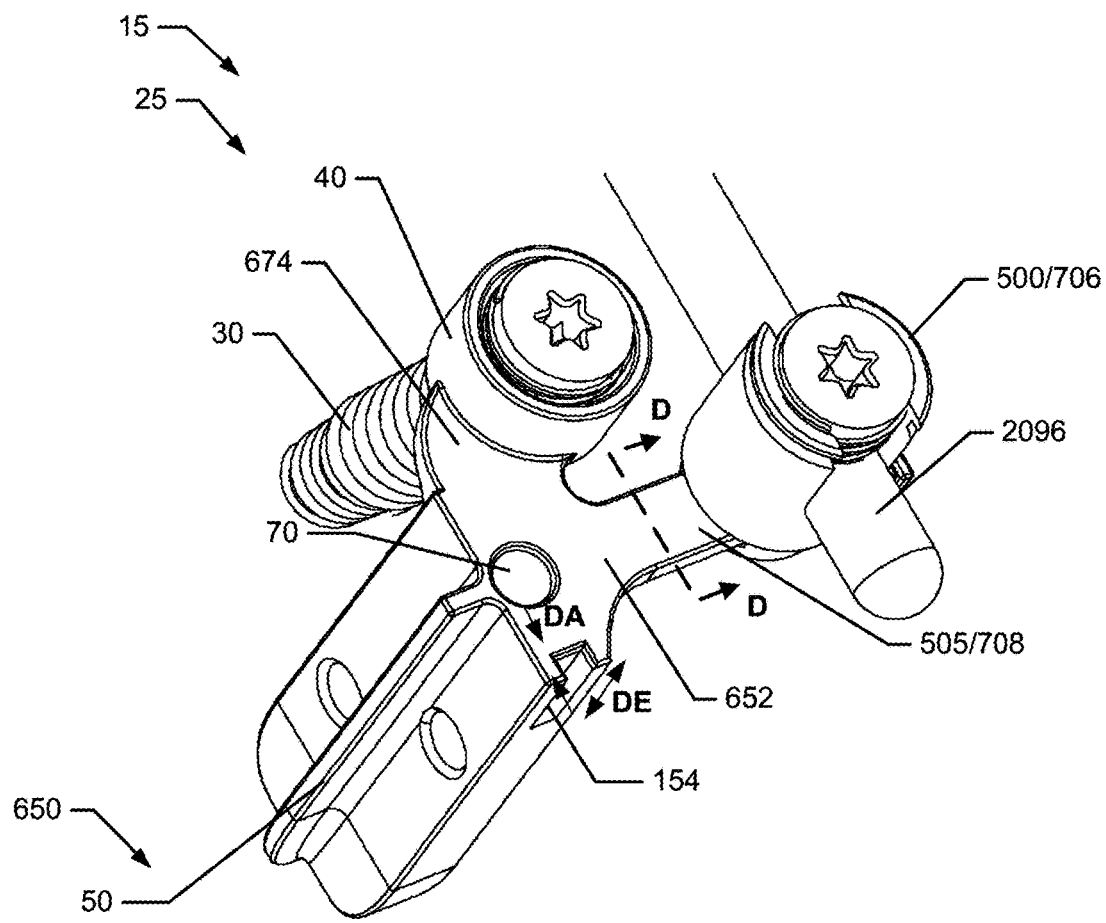
FIG. 12A
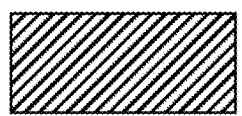
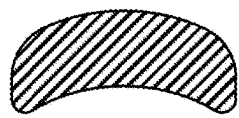
FIG. 12B  FIG. 12C

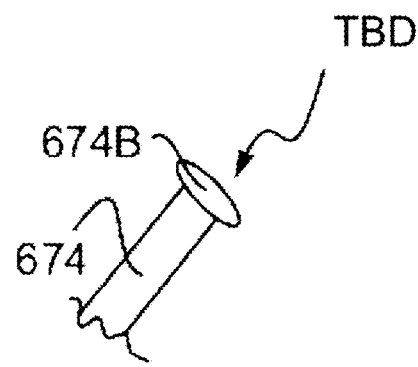
FIG. 12D
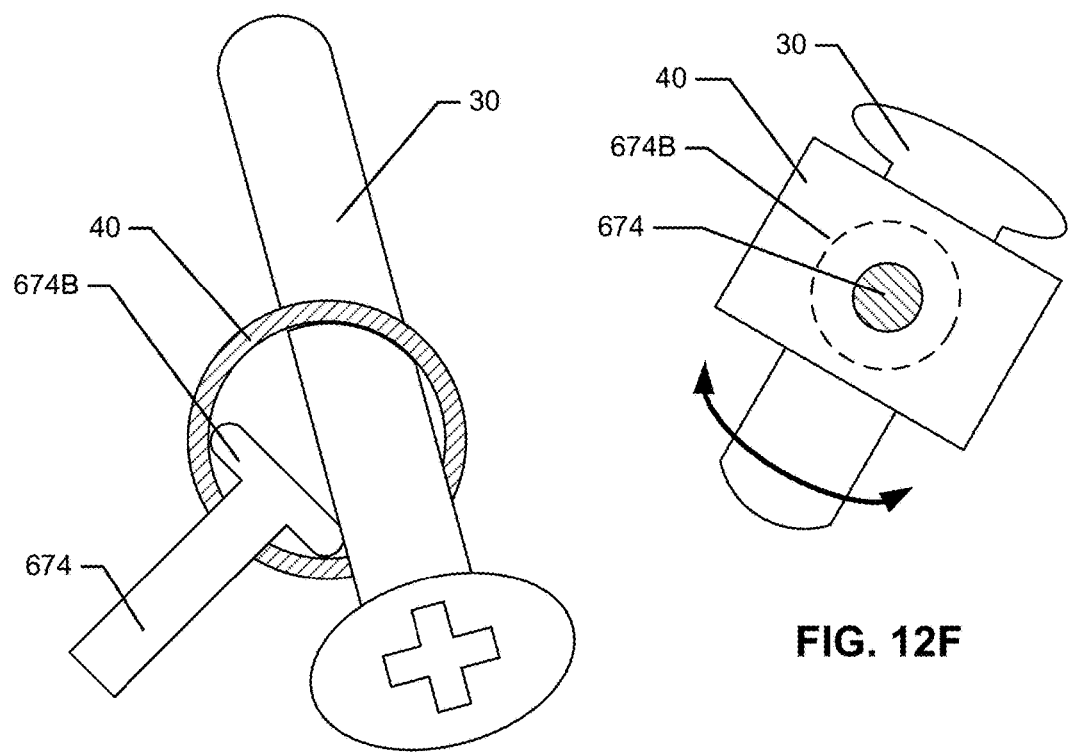
FIG. 12E
FIG. 12F

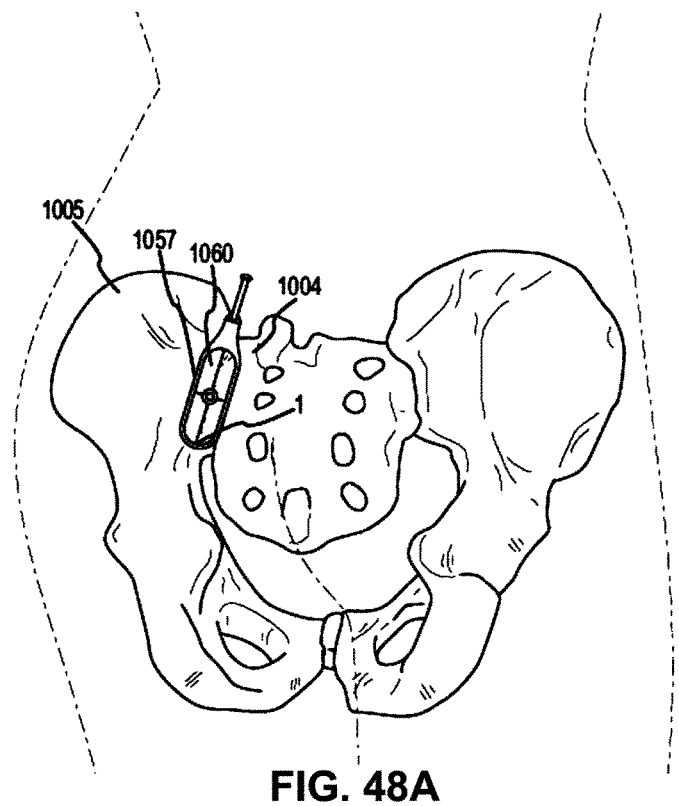
FIG. 48A
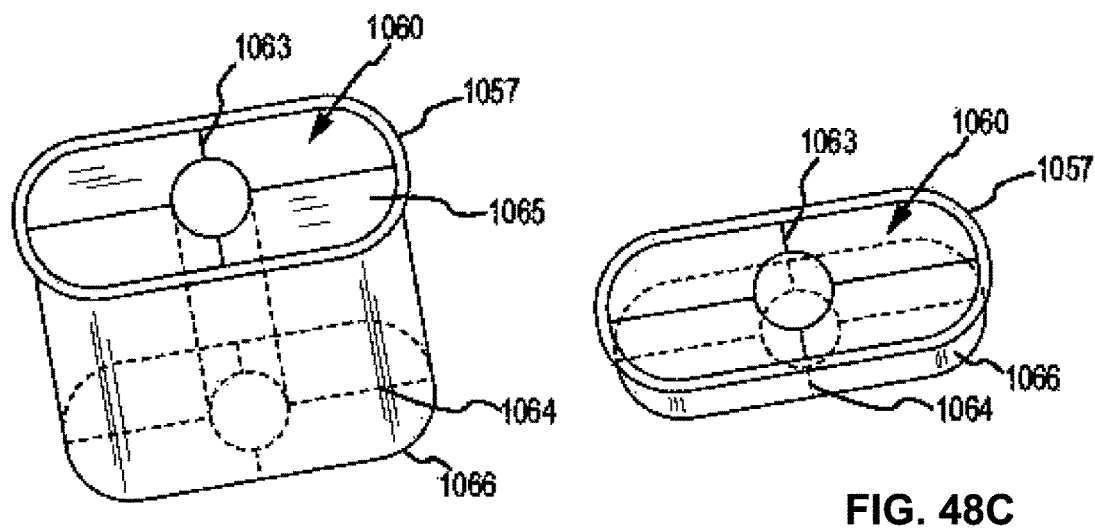
FIG. 48B
FIG. 48C

ADDITIVELY MANUFACTURED SYSTEMS FOR LOW PROFILE SPINOPELVIC FIXATION AND SACROILIAC JOINT FUSION FOR COMPLEX SPINAL DEFORMITIES

CROSS REFERENCE TO RELATED APPLICATIONS

The present application is a divisional application of U.S. application Ser. No. 14/216,975 filed Mar. 17, 2014, which application is a continuation-in-part application of U.S. patent application Ser. No. 13/475,695, entitled "Systems for and Methods of Fusing a Sacroiliac Joint" filed May 18, 2012, now U.S. Pat. No. 9,381,045, which application is a continuation-in-part application of U.S. patent application Ser. No. 13/236,411, entitled "Systems for and Methods of Fusing a Sacroiliac Joint" filed Sep. 19, 2011, now U.S. Pat. No. 9,017,407. U.S. patent application Ser. No. 13/236,411 is also a continuation-in-part application of U.S. patent application Ser. No. 12/998,712 (the '712 application"), filed on May 23, 2011 and entitled "Sacroiliac Joint Fixation Fusion System", now U.S. Pat. No. 8,979,928. The '712 application is the National Stage of International Patent Cooperation Treaty Patent Application PCT/US2011/000070 (the TCT application"), filed on Jan. 13, 2011 and entitled "Sacroiliac Joint Fixation Fusion System". The PCT application claims the benefit under 35 U.S.C. § 119(e) of U.S. Provisional Patent Application No. 61/335,947, which was filed Jan. 13, 2010 and entitled "Sacroiliac Joint Fusion System". U.S. patent application Ser. No. 14/216,975 further claims the benefit of and priority to U.S. Provisional Patent Application 61/798,225, entitled "Systems and Methods for Fusing a Sacroiliac Joint and Anchoring an Orthopedic Appliance" and filed on Mar. 15, 2013.

Each application referenced above is hereby incorporated by reference in its entirety as if fully set forth herein.

FIELD OF THE INVENTION

Aspects of the present invention relate to medical apparatuses and methods. More specifically, the present invention relates to devices and methods for providing an anchoring attachment for a spinal stabilization system and for concomitantly stabilizing, immobilizing, fixating or fusing a sacroiliac joint.

BACKGROUND OF THE INVENTION

Reinforcement, stabilization, replacement, reconstruction, or fusion of a joint or vertebrae may be indicated as a treatment of an afflicted region of a patient. Examples of specific treatments include spinal stabilization, spinal fusion, posterolateral spinal fusion, posterior lumbar interbody fusion, transforaminal lumbar interbody fusion, lateral interbody fusion, anterior lumbar interbody fusion, vertebral immobilization or reinforcement, intervertebral joint immobilization or reinforcement, degenerative disk stabilization, repair of traumatic fracture dislocation of the pelvis, treatment of degenerative arthritis, treatment of sacroiliitis (an inflammation or degenerative condition of the sacroiliac joint), osteitis condensans ilii, and treatments of other degenerative conditions of joints or vertebrae or other musculoskeletal injuries, diseases, conditions or disorders.

This reinforcement of intervertebral joints, sacroiliac joints, or other joint stabilizations may be accomplished by one or more existing methods, including inserting stabilizing implants such as support rods into the afflicted regions. Typically these fusion implants span an afflicted joint and may be anchored to bone tissue on either side of the afflicted joint using existing orthopedic fasteners such as pedicle screws or other orthopedic anchoring devices. These existing fusion implants may completely immobilize the afflicted joint or may allow limited or unconstrained movement to approximate or permit the normal movements of the afflicted joint.

One limitation of many existing fusion procedures involves the challenge of situating a fusion implant in suitably close alignment with the removed tissues of the patient to achieve a stable fixation of the joint or vertebrae. Existing implant structures may have insufficient engagement with the articular surfaces or cortical bone of the joint for adequate fixation or fusion. This failure to sufficiently stabilize and fuse the joint with the conventional implant structures and methods may result in a failure to relieve the condition being treated.

Another limitation of the fusion and fixation implants and associated anchors used in existing fusion procedures is the relatively large profile or prominence of the components. The large footprint of existing fusion implants and associated anchors necessitate the removal of considerable bone and/or soft tissue to prepare the area for the installation of the implant, possibly resulting in considerable post-operative pain. Further, the high profile or prominence of elements of the fusion or fixation implant projecting away from the spine or pelvis may chronically irritate the soft tissues, resulting in chronic pain during long-term use of the fusion implant and may require further surgeries and explanation.

Additional limitations of existing fusion implants are also related to the long-term use of the implants. Over time, the anchoring elements such as pedicle screws may loosen over time due to exposure to repeated loads associated with movements of the patient, thereby reducing the stabilization provided by the implant. Even if more robust anchoring devices or systems are used, the long-term use of these existing fusion implants are associated with an increased chance of injury to one or more joints adjacent to the reinforced joint.

The stabilization of afflicted lumbar intervertebral joints poses a particular challenge with respect to surgical interventions. The lumbar intervertebral joints are particularly vulnerable to injury or degradation because these joints bear the majority of the body's weight but also effectuate about half of the body's overall flexion movements (forward-backward bending). As a result, a sizeable fraction of back pain symptoms are associated with injuries or degradation of the lumbar intervertebral joints, in particular the L3-L4 and L4-L5 joints.

Treatment of spinal pathologies, including scoliosis, using existing lumbosacral fusion or fixation implants may increase the patient's risk of complications including loosening of anchor elements, implant-induced injury of surrounding joints, and/or implant-induced injury or chronic irritation of soft tissues surrounding the implant as described previously. Some existing lumbar fusion implants may provide additional anchoring to the ilium and/or sacrum bones of the pelvic girdle to enhance the robustness of anchoring and/or structural support. However, anchoring a lumbar fusion implant to one or more bones of the pelvic girdle presents additional risks of complications not yet completely addressed by existing implant systems or methods.

Due to the relatively dense concentrations of exposed nerves emerging from the sacrum region, the implantation of a transacrally fixed lumbar fusion implant is associated with an increased risk of nerve injury during implantation and/or chronic use of the implant. In addition, the bone tissue of the sacrum consists largely of lower density cancellous bone tissue, which is less structurally robust and therefore more vulnerable to anchor loosening relative to other bones. Lastly, the increased loading applied to the sacrum via the attached lumbar fusion implant may induce an accelerated degradation or failure of one or both sacroiliac joints.

Other existing lumbosacral fusion or fixation implants may provide additional anchors fixed to the ilium; the ilium contains a much higher proportion of higher-density cortical bone and therefore provides a more robust anchoring surface than the sacrum. However, additional loads induced by an ilium-fixed lumbar fusion implant may induce an accelerated degradation or failure of one or both sacroiliac joints. Although some existing lumbar fusion implants are anchored to both the ilium and the sacrum, alterations to the chronic loading of the articulating surfaces of the sacroiliac joints may induce accelerated degradation or failure of one or both sacroiliac joints.

In the practice of orthopedic and neurologic surgery, while attempting to correct a pathology of the spine by means of fixation or stabilization, strong forces can be concentrated on certain parts of the spine and pelvis. Specifically, the junction above or below a fixated or stabilized segment of the spine can undergo forces which can affect healthy alignment of the spine, or portions of the pelvis such as the sacroiliac joint. Unhealthy alignment of anatomic structures involved in such procedures can result in severe complications for example chronic severe pain, permanent disability and paralysis. The complexity of the spinal reconstruction, the sagittal balance realignment, the number of vertebrae involved, or other factors may increase the risk of complications. In published literature morbidity rates near fifty percent for such procedures. In order to minimize the forces a fixated or stabilized segment of vertebrae can create, a conventional technique employs the use of metal or plastic rods (or bands, cord, etc.) which can be configured to extend to a sacrum or ilium and screws inserted into either or both bones or across both bones which can then connect to the rods to help stabilize the spinal construct. Substantial problems with conventional techniques exist which can significantly affect a patient's recovery from the surgery.

A significant problem with certain conventional methods for pelvic fixation including the procedure mentioned above is the there is a tendency for the screws to pull out, loosen, break or otherwise cause complications due to the strong forces which can be present. Another significant problem with certain conventional methods for pelvic fixation including placement of a (S2 alar iliac (S2AI)) screw into the second sacral body (S2) which then crosses the sacroiliac joint (extra-articularly) and continues into the ilium extending across the cortical bone to better fixate the screw may be that the screw is positioned such that it violates the articular portion of the sacroiliac joint. Literature shows that this can occur up to 60% of the time. Due to the high chances of trauma caused by the screw to the articular portion of the joint severe pain may result.

The inventive anchoring system for one or more elements of a spinal stabilization system described herein addresses the problems associated with conventional methods and apparatuses used to anchor one or more elements of a spinal stabilization system.

BRIEF SUMMARY OF THE INVENTION

One implementation of the present disclosure may take the form of a sacroiliac joint fusion implant assembly including an implant body and an anchor. The implant body may include an insertion element including an elongate body with a proximal insertion element end and a distal insertion element end, as well as an attachment element mechanically attached to the proximal insertion element end. The attachment element includes an anchor fitting formed within the attachment element or mechanically attached to the attachment element. The anchor fitting may be configured to receive the anchor inserted within a predetermined range of anchor insertion trajectories.

In another implementation, the insertion element may be an insertion plate. The insertion plate may include a medial face and a lateral face opposite to the medial face. The insertion plate may also include one or more elongate fins. Each of the one or more fins may project perpendicularly outward from the medial face or the lateral face and may extend longitudinally between the proximal insertion element end and the distal insertion element end. The fins and the insertion plate may taper toward a narrow insertion plate leading edge. The insertion plate leading edge may be configured for insertion into the joint space of a sacroiliac joint.

The insertion plate may further include one or more additional bores. Each additional bore may include a bore cross-sectional profile and a bore axis situated along the bore centerline. The bore centerline may include a line connecting each additional bore's cross-sectional profile centroids. Each additional bore may be situated on the medial face or lateral face and may be directed inward along the bore centerline, and each additional bore may be configured to receive a distal end of an additional orthopedic fastener. Each additional bore may be a blind bore extending partially through the insertion plate to the lateral face or medial face in one implementation. In another implementation, each additional bore may an open bore extending through the insertion plate from the lateral face to the medial face. One of the additional bores may be configured to receive a distal end of the anchor projecting from the anchor fitting after insertion of the anchor into the anchor fitting within the predetermined range of anchor insertion trajectories. One of the additional bores may have a cross-sectional profile chosen from: square, rectangular, circular, oval, triangular and any combination thereof.

In another implementation, the attachment element may be permanently attached at a fixed position and angle to the proximal end of the insertion element. The angle formed between the attachment element and the insertion element may range from about 30° to about 120°. The attachment element and insertion element may be formed as a continuous structure. The attachment element and insertion element may be attached in a hinged attachment; the angle formed between the attachment element and insertion element may range from about 30° to about 120°.

In another implementation, the anchor fitting may include a bore formed within the attachment element. The bore may an open bore passing from a proximal attachment element surface to a distal attachment element surface. The bore may have a cross-sectional profile chosen from: square, rectangular, circular, oval, triangular and any combination thereof. The bore may be configured to allow the insertion of an anchor at any angle of up to about 45° relative to an axis perpendicular to a region of the attachment element in close proximity to the bore.

The anchor fitting may be attached to an anchor support element of the attachment assembly and configured to receive an anchor within a preselected range of anchor insertion trajectories. The anchor support element may include a rectangular cross-sectional profile and the anchor fitting may include a channel with a rectangular cross-sectional contour matched to the cross-sectional profile of the anchor support element; the anchor fitting may resist rotation about the axis of the anchor support. The anchor support element may include a circular cross-sectional profile and the anchor fitting may include an anchor fitting attachment bore with a circular cross-sectional contour matched to the cross-sectional profile of the anchor support element. The anchor fitting may permits rotation about the axis of the anchor support.

The anchor may be chosen from: a cortical screw, a cancellous screw, and a Steffee screw. In one implementation the anchor may be a Steffee screw and the anchor support element may be a Steffee plate formed within the attachment element. In another implementation, the anchor may be a dual-threaded bone screw that includes a head and a shaft. The shaft may include a proximal threaded segment with a first threading pattern and a distal threaded segment with a second threading pattern.

In another implementation, the attachment element may also include an attachment fitting attached to a guide formed within the attachment element. The guide may include a guide bore configured to receive an attachment fitting that includes a head of a polyaxial pedicle screw. The distal end of the polyaxial screw may be inserted through the guide bore within a predetermined range of attachment fitting insertion angles. The head of the polyaxial pedicle screw may include at least two sides forming a lower surface of an upward-facing groove configured to receive a rod and further forming a threaded fitting configured to receive a locking nut.

In another implementation, the attachment fitting may include a sliding attachment fitting configured to translate within a guide slot formed within the attachment element. The guide slot may include an elongate hole passing through the attachment element and directed along a slot pathway. The slot pathway may be selected from any one or more of: a straight line, a curve, an arc, and any combination thereof. The guide slot may also include a raised edge projecting proximally from the proximal surface of the attachment element around a perimeter of the guide slot.

In an implementation, the sliding attachment fitting may include a proximal head including at least two sides forming a lower surface of an upward-facing groove configured to receive a rod and further forming a threaded fitting configured to receive a locking nut. The sliding attachment fitting may also include a shaft configured to slide within the guide slot; a first end of the shaft may be attached to the proximal head opposite to the upward-facing groove. The sliding attachment fitting may further include a distal contact surface attached at a second end of the shaft opposite to the first end. The distal contact surface and proximal head may be situated on opposite sides of the attachment element and connected by the shaft situated within the guide groove.

The distal contact surface of the attachment fitting may include an essentially flat planar surface that restricts the rotation of the attachment fitting to essentially rotations about a shaft axis. The distal contact surface of the attachment fitting may include a curved surface that permits the rotation of the attachment fitting about axes perpendicular to the shaft axis.

In another implementation, the guide may include a guide rail and the attachment fitting may include a sliding attachment fitting configured to translate along the guide rail. The sliding attachment fitting may include a proximal head including at least two sides forming a lower surface of an upward-facing groove configured to receive a rod and further forming a threaded fitting configured to receive a locking nut. The sliding attachment fitting may also include a transverse channel configured to receive the guide rail situated at a distal end of the attachment fitting opposite to the upward-facing groove. The guide rail and the transverse channel may also include a rectangular cross-section; the guide rail may resist rotation of the attachment fitting in any direction.

In another implementation, the sliding attachment fitting may also include: a proximal element forming the lower surface of the upward-facing groove at one end and forming an annular channel at an opposite end; and a distal element forming the transverse rectangular channel at a first end and forming an annular flange at a second end opposite to the first end. The annular channel and the annular flange may engage in a sliding rotational engagement to permit the rotation of the attachment fitting about an axis of rotation coincident with the central axis of the sliding attachment fitting. The guide rail and the transverse channel may have circular cross-sectional profiles, permitting the attachment fitting to rotate about the axis of the guide rail.

Another implementation may take the form of a sacroiliac joint fusion implant assembly including an implant body and one or more anchors. The implant body may include an insertion element having an elongate cylindrical body with a proximal insertion element end, a distal insertion element end, and a threaded outer surface configured for insertion into a joint space of a sacroiliac joint by twisting the insertion element into a cylindrical receiving bore formed within the joint space. Each of the one or more anchors may be configured for insertion through one or more transverse bores formed within the implant body.

In an implementation, the insertion element may further include an attachment fitting attached to the proximal insertion element end. The insertion element may also include an attachment element fastener attached to the proximal insertion element end. The implant assembly may also include an attachment element fastened to the proximal insertion element end at the attachment element fastener.

Another implementation may take the form of a sacroiliac joint fusion and anchoring system that includes an implant assembly and a delivery tool. The implant assembly may include an implant body including an insertion element with an elongate body with a proximal insertion element end and a distal insertion element end, as well as an attachment element mechanically attached to the proximal insertion element end. The attachment element may include an anchor fitting formed within the attachment element or mechanically attached to the attachment element. The implant assembly may also include an anchor.

In this implementation, the delivery tool may include an implant arm with a distal implant arm end configured to releasably couple to the proximal insertion element end as well as an anchor arm including a proximal anchor arm end coupled to the implant arm and a distal anchor arm end opposite to the proximal anchor arm end. The distal anchor arm end distally ends in a sleeve configured to guide the anchor within a predetermined range of anchor insertion trajectories. The sleeve is configured to guide the anchor through the anchor fitting within the predetermined range of anchor insertion trajectories when the distal implant arm end is releasably coupled to the proximal insertion element end.

The insertion element may also include an attachment fitting formed within the proximal insertion element end. The attachment fitting is configured to receive a corresponding attachment fastener situated within the distal end of the delivery tool. The attachment fitting may be a threaded bore and the attachment fastener may be a screw. The attachment fitting may also include one or more alignment features chosen from: one or more additional threaded bores formed within the proximal insertion element end and separated by a lateral distance from the attachment fitting; and one or more alignment peg receptacles configured to receive one or more corresponding alignment pegs projecting distally from an extreme distal face of the delivery tool.

The alignment peg receptacles may be situated within a proximal surface of the attachment element within the lateral edge of the attachment element. The alignment peg receptacles may be inset within the lateral edge of the attachment element. The alignment pegs may be arranged in a pattern corresponding to an edge contour of the lateral edge of the attachment element.

In one implementation, the sleeve of the anchor arm may include a tubular guide with a proximal opening and a distal opening. The proximal opening is configured to receive a distal tip of the anchor or other orthopedic fastener and the distal opening is configured to guide the distal tip of the anchor or other orthopedic fastener within a predetermined range of insertion trajectories. The sleeve of the anchor arm may be narrow relative to the diameter of a head and shaft of an anchor or other orthopedic fastener; the sleeve in this implementation may be configured to guide the distal tip of the anchor or other orthopedic fastener within a narrow predetermined range of insertion trajectories. The sleeve of the anchor arm may be wide relative to the diameter of a head and shaft of an anchor or other orthopedic fastener; the sleeve in this implementation may be configured to guide the distal tip of the anchor or other orthopedic fastener within a wide predetermined range of insertion trajectories. The sleeve of the anchor arm may be relatively wide relative to the diameter of a head and shaft of an anchor or other orthopedic fastener; in this implementation, the sleeve may be configured to guide the distal tip of the anchor or other orthopedic fastener within a wide predetermined range of insertion trajectories. The sleeve may be a conical sleeve with a proximal opening that is large relative to the distal opening; in this implementation, the conical sleeve may be configured to guide the distal tip of the anchor or other orthopedic fastener within a wide predetermined range of insertion trajectories.

Another implementation may be in the form of a method of fusing a sacroiliac joint and providing an anchor for a spinal support system. The method may include providing a sacroiliac joint fusion and anchoring system that may include an implant assembly and delivery tool. The implant assembly may include an implant body and an anchor. The implant body may include: an insertion element that includes an elongate body with a proximal insertion element end and a distal insertion element end; and an attachment element mechanically attached to the proximal insertion element end. The attachment element may include an anchor fitting formed within the attachment element or mechanically attached to the attachment element. The delivery tool may include: an implant arm that includes a distal implant arm end releasably coupled to the proximal insertion element end of the implant body; and an anchor arm that includes a proximal anchor arm end coupled to the implant arm and a distal anchor arm end opposite to the proximal anchor arm end. The distal anchor arm end may distally end in a sleeve configured to guide the anchor within a predetermined range of anchor insertion trajectories.

The method may further include preparing an implant receiving space via an extra-articular recess access region of the sacroiliac joint. The implant receiving space may extend from a posterior portion of the sacroiliac joint toward an anterior portion of the sacroiliac joint by removing an amount of articular cartilage and other tissues from between an ilium articular surface and a sacrum articular surface defining the joint space. The method may also include situating the insertion element of the implant body non-transversely within the implant receiving space such that the attachment fitting projects in a medial direction from a joint line of the sacroiliac joint and the anchor fitting is situated over a region of the sacrum just lateral to the lateral edge of the S1 foramen and just superior to the superior edge of the S1 foramen. The method may also include inserting a driving tool through a lumen of the sleeve of the anchor arm such that a distal end of the driving tool is engaged with a proximal end of the anchor. The method may further include operating the driving tool to insert the anchor on a S2AI trajectory. In the S2AI trajectory the distal end of the anchor may pass through the anchor fitting, enters the sacrum near a first sacral foramen in a medial to lateral direction and further enters the ilium. The method may additionally include detaching the distal end of the delivery tool from the implant body.

The method in this implementation may also include inserting one or more additional fasteners through additional bores formed within the attachment member or insertion member. The one or more additional fasteners may be chosen from one or more of: a) a first additional fastener inserted through the ilium in a lateral to medial direction such that a distal tip of the first additional fastener is situated within a blind bore formed within a lateral face of the insertion element; b) a second additional fastener inserted through the ilium in a lateral to medial direction such that a distal tip of the second additional fastener is driven through an open bore formed transversely through the insertion element and into the sacrum adjacent to a medial face of the insertion element; c) a third additional fastener inserted through the sacrum in a medial to lateral direction such that a distal tip of the third additional fastener is situated within a blind bore formed within a medial face of the insertion element; d) a fourth additional fastener inserted through the sacrum in a medial to lateral direction such that a distal tip of the fourth additional fastener is situated within an open bore formed transversely through the insertion element and into the ilium adjacent to a medial face of the insertion element; and e) a fifth additional fastener inserted through an additional open bore formed through the attachment element in a fifth fastener direction chosen from any one of: a lateral to medial direction into the sacrum, a medial to lateral direction into the sacrum, a medial to lateral direction into the sacrum and ilium, a cranial direction into the sacrum, and a caudal direction into the sacrum.

The implant assembly used in this implementation of the method may further include an attachment fitting attached to the attachment element. In this implementation, the method may further include attaching a support element of a spinal support system to the attachment fitting.

The anchor used in this implementation of the method may be a S2 alar iliac bone screw.

While multiple embodiments are disclosed, still other embodiments of the present disclosure will become apparent to those skilled in the art from the following detailed description, which shows and describes illustrative embodiments of the disclosure. As will be realized, the invention is capable of modifications in various aspects, all without departing from the spirit and scope of the present disclosure.

Accordingly, the drawings and detailed description are to be regarded as illustrative in nature and not restrictive.

BRIEF DESCRIPTION OF THE DRAWINGS

The following figures illustrate various aspects of the invention.

FIG. 12A is a top isometric of a third embodiment of the implant body. FIGS. 12B and 12C are normal cross-sectional view of an anchor support element of the implant body taken at section D-D of FIG. 12A. FIGS. 12D-12F are various views of a portion of a pivoting anchor support element in an additional embodiment.

FIG. 48A is a posterior-lateral view of the hip region of the patient, illustrating the placement of a cannula alignment jig. FIGS. 48B-48C are additional isometric views of the cannula alignment jig.

Corresponding reference characters and labels indicate corresponding elements among the views of the drawings. The headings used in the figures should not be interpreted to limit the scope of the claims.

DETAILED DESCRIPTION

Figure 1:
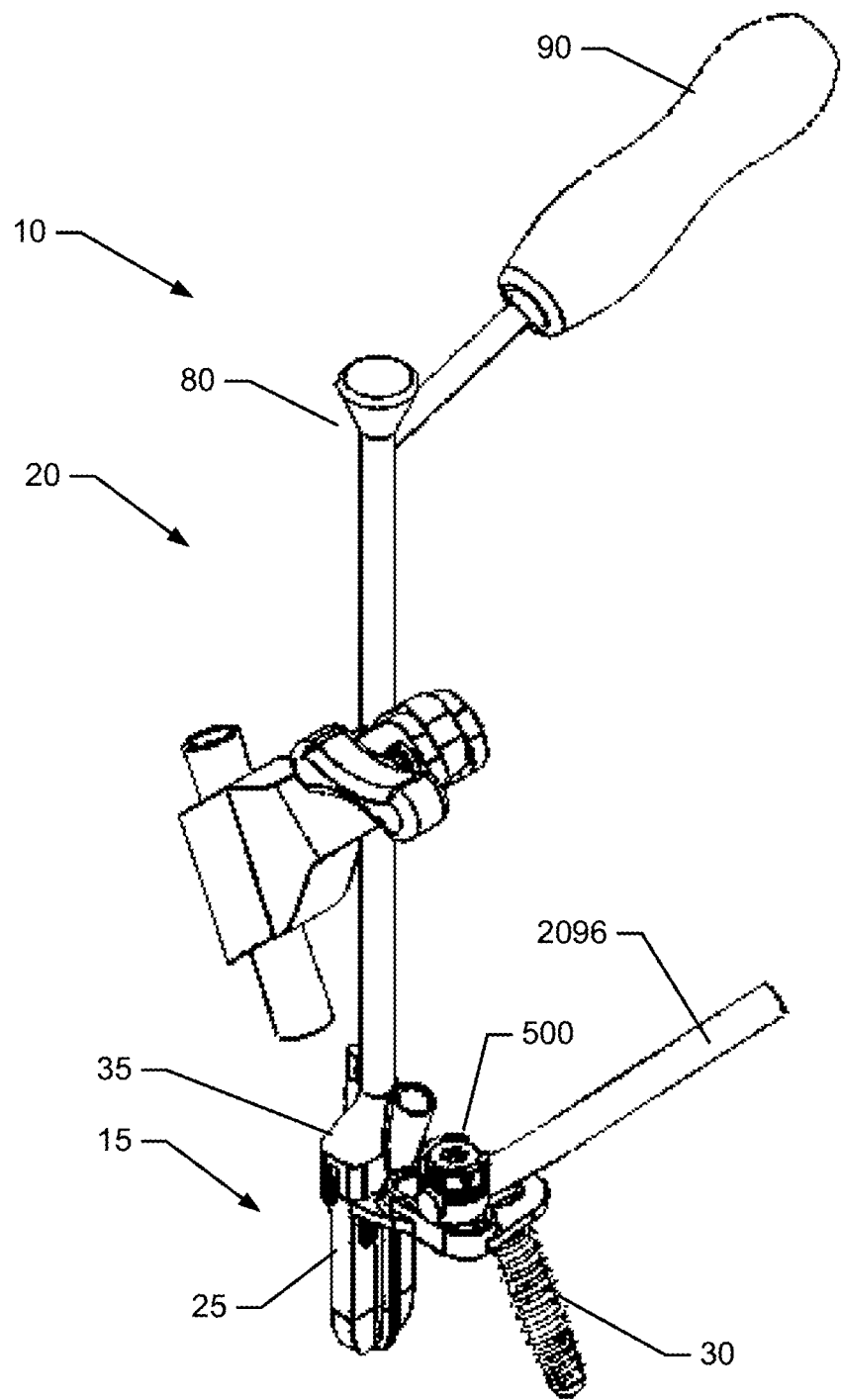
FIG. 1 is an isometric view of a first embodiment of a system for anchoring one or more elements of a spinal stabilization system.

Implementations of the present disclosure involve an anchoring system for attaching one or more elements of a spinal stabilization system and concomitantly fusing, fixating, replacing, reconstructing, stabilizing or otherwise treating a sacroiliac joint. FIG. 1 is an isometric view of an anchoring system 10 in one embodiment. The system 10 includes a delivery tool 20 and an implant assembly 15 for delivery to a sacroiliac joint via the delivery tool 20. The implant assembly 15, which includes an implant body 25 and anchor 30, is configured to fuse or stabilize a sacroiliac joint once implanted at the joint. The implant assembly 15 further includes an attachment fitting 500 configured to attach to an element of a spinal stabilization system such as a rod 2096.

Figure 2:
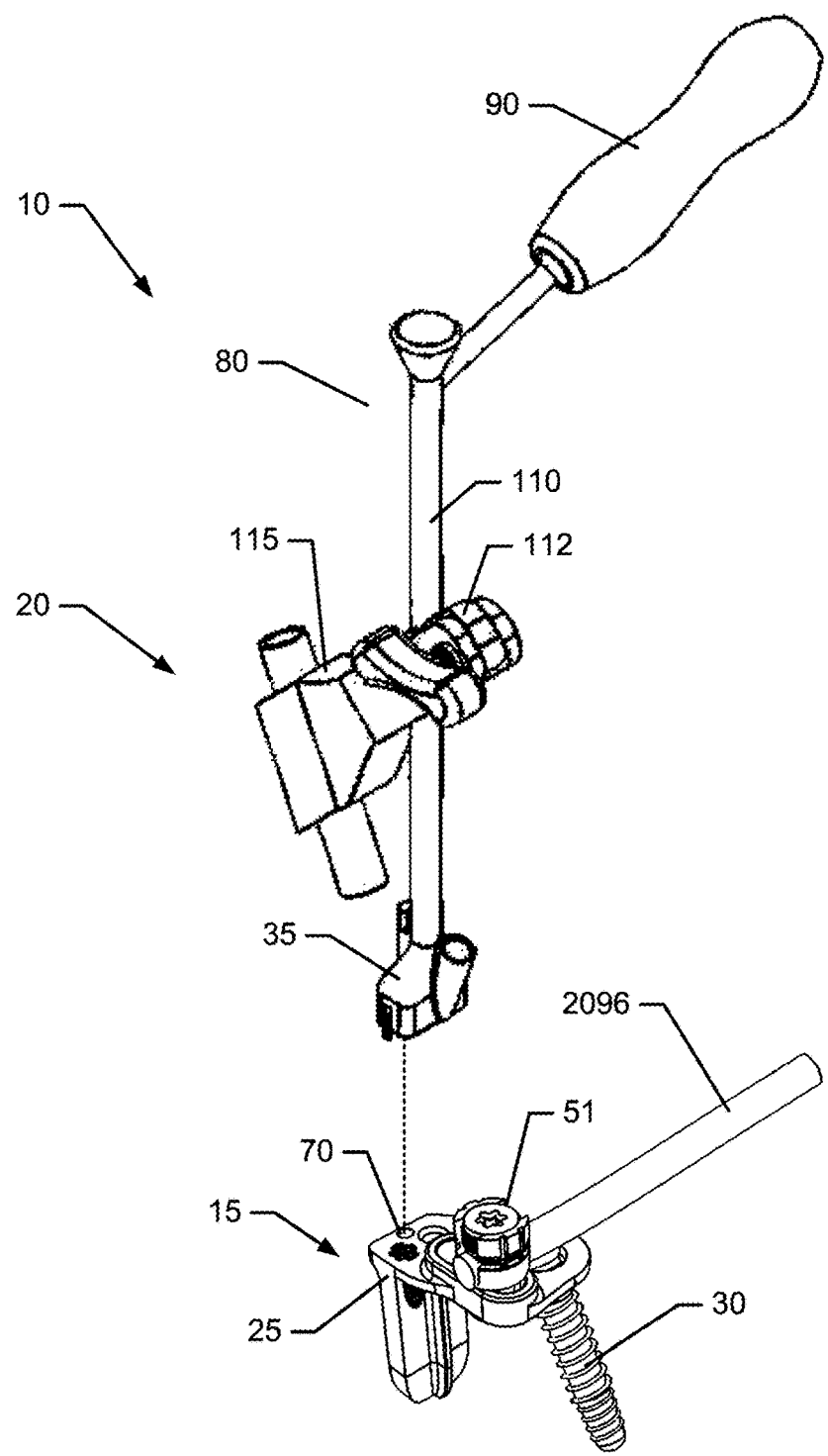
FIG. 2 is an isometric view of the first embodiment of the system with the implant assembly separated from the delivery tool.

The delivery tool 20 is configured such that the anchor 30 can be quickly, accurately and reliably delivered to the implant body 25 supported off of the tool distal end 35 in a sacroiliac joint. Once the implant assembly 15 is delivered to the sacroiliac joint and secured in place using the anchor 30, the implant assembly 15 may be detached from the distal end 35 of the delivery tool 20, as illustrated in FIG. 2.

Figure 3:
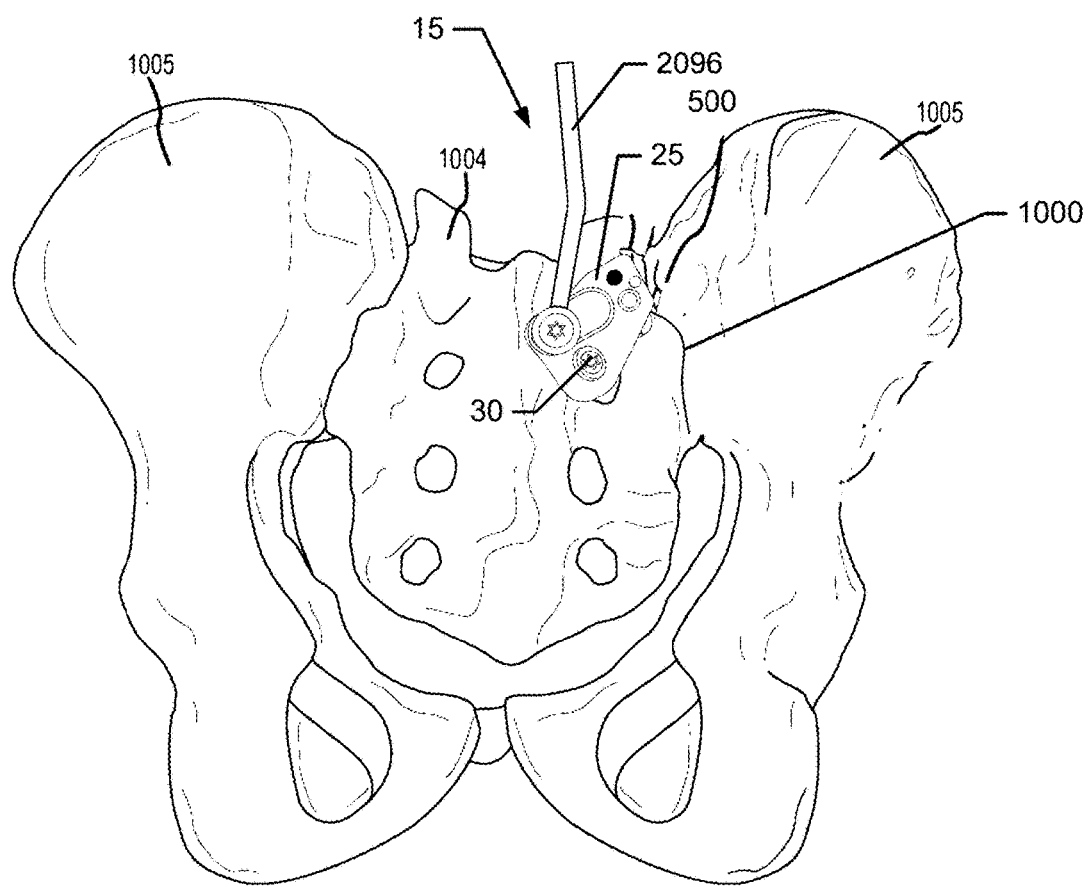
FIG. 3 is a posterior view of a first embodiment of an implant assembly implanted within a sacroiliac joint; a rod element of a spinal stabilization system is attached to an attachment element of the implant assembly.

FIG. 3 is a posterior view of an ilium 1005 and sacrum 1004 forming a sacroiliac joint 1000. The implant assembly 15 is installed in the sacroiliac joint 1000 and secured in place by the anchor 30, which extends from the sacrum 1004 to the ilium 1005 in this embodiment. A rod 2096 from a spinal stabilization system may be attached to an attachment fitting 500 of the implant system 15 and locked into place, thereby providing a robust anchor for the spinal stabilization system. In addition to providing the robust anchor for the rod 2096, the implant assembly 15 also fuses or stabilizes the sacroiliac joint 1000 by virtue of the anchor 30, which may extend distally and laterally from the sacrum into the ilium to form the fused or stabilized joint as illustrated in FIG. 3. In some embodiments, the implant assembly 15 may also fuse or stabilize the sacroiliac joint 1000 by virtue of the insertion element 650 which may be configured to fixate the prepared joint surfaces thereby permitting bony fusion to occur through, around, near, up to or onto the implant body 25.

The embodiments of the anchoring system 15 overcome many of the limitations of previous anchoring methods used in conjunction with previous spinal stabilization systems. The implant body 25 is configured to fuse or stabilize the sacroiliac joint, thereby reducing the risk of degradation or failure of the sacroiliac joint to which the anchoring system 15 is attached. In addition to the anchor 30, which bridges the sacroiliac joint and secures the ilium to the sacrum, the implant body 25 of the implant assembly 15 includes an insertion element (no shown) that is situated within the sacroiliac joint in a distal orientation between the articular surfaces of the ilium and sacrum. The insertion element 650 may incorporate features such as surface textures, fittings, and/or receptacles for additional fasteners that enhance the grip of the insertion element within the sacroiliac joint. In addition, one or more of these features may facilitate the integration of surrounding bone tissue into the peripheral margins of the implant assembly 15 during chronic residence of the implant body 25 to further strengthen the fusion of the sacroiliac joint. This integration of bone tissue may further function as a redundant fusion fixation mechanism to compensate for any loosening of the anchor 30 or other fasteners anchoring the implant assembly 15 in place, thereby maintaining the integrity of the implant assembly 15 as an attachment for the spinal stabilization system.

Further, as discussed in further detail herein below, the implant assembly 15 has a relatively low profile, enabling the implantation procedure to install the implant assembly 15 using a smaller incision surgical procedure that entails removal of less bone and/or soft tissues to prepare the surgical area, resulting in a lower risk of post-operative pain and/or other adverse events. In addition, the low profile of the implant assembly 15 may reduce the risk of chronic soft tissue irritation relative to existing devices and methods during long-term use of the implant assembly 15.

Referring again to FIG. 3, the attachment fitting 500 may be designed to permit the translation and/or rotation of the attached end of the rod 2096 through a wide range of motion and variety of directions, thereby facilitating the alignment of the rod 2096 within its associated spinal stabilization system without need for excessive bending of the rod 2096. This adjustability may reduce reactive forces applied to the underlying implant body 25 and anchor 30 during any required bending of the rod 2096 during the installation of the spinal stabilization system. In addition, the enhanced adjustability afforded by the design of the attachment fitting 500 may result in the reduction of small misalignments of the rod 2096 within the spinal stabilization system, thereby reducing the occurrence of internal forces within the spinal stabilization system; this reduction in internal forces may reduce the risk of developing pain in regions surrounding the spinal stabilization system and/or degradation of joints adjacent to the afflicted joint. Furthermore, the various embodiments described herein may simplify the surgery and reduce operating time, fluoroscopy time (ionizing radiation from imaging technology) and anesthesia time thereby making the surgical procedure safer and more efficacious than conventional methods and systems. Further, the various embodiments described herein may further allow the treatment of patients who might otherwise not be able to undergo conventional surgery to treat a musculoskeletal pathology.

The implant assembly may be further configured to dissipate forces arising from an attached spinal construct over a greater surface area of the pelvis while acting as a shock absorber by a semi constrained communication between the components of a spinal construct and implant assembly 15.

Detailed descriptions of various embodiments of the anchoring system 10 including the implant assembly 15, delivery tool 20, as well as methods of using the system 10 to provide an attachment for a spinal stabilization system are provided herein below.

I. Implant Assembly

Figure 4:
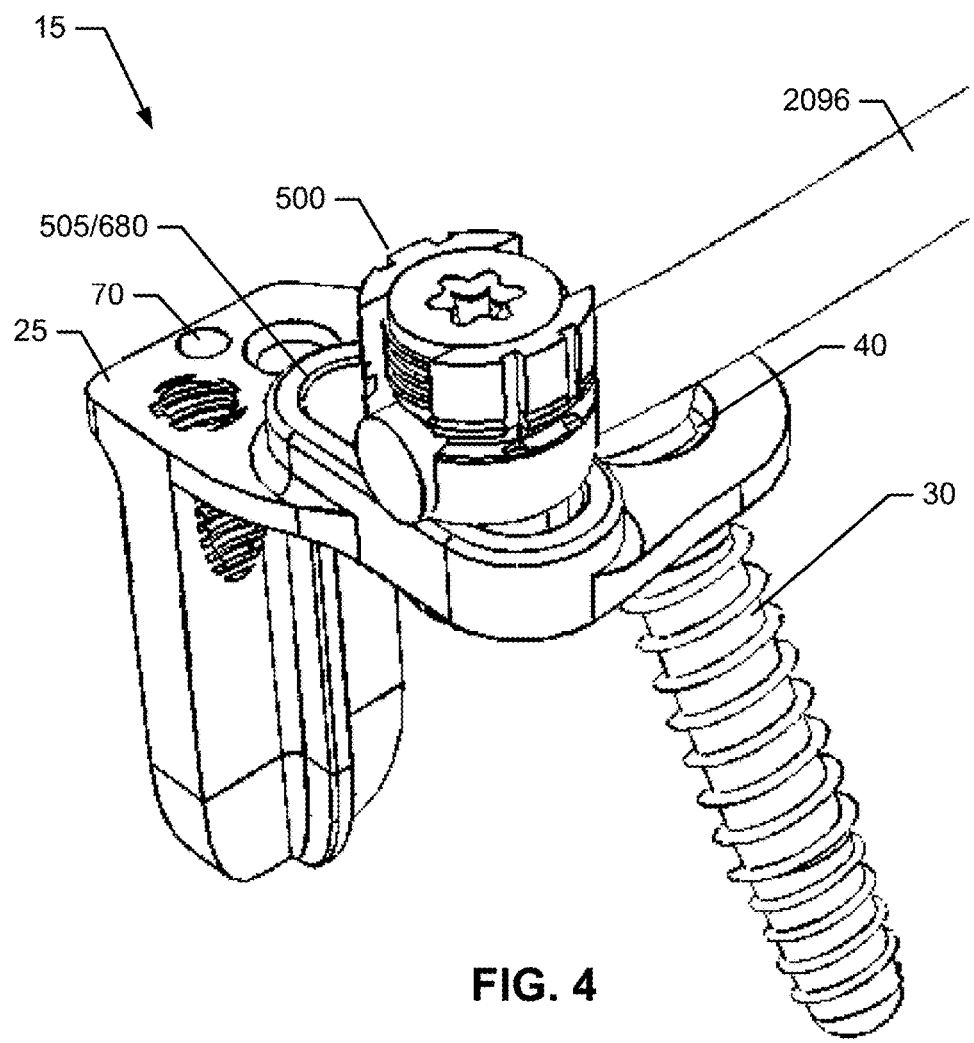
FIG. 4 is a side isometric view of the implant assembly of the first embodiment attached to the rod element from the spinal stabilization system.

To begin a detailed discussion of components of various embodiments of the implant assembly 15, reference is made to FIG. 4, which is a side isometric view of the implant assembly 15 with attached rod 2096 in one aspect. As shown in FIG. 4, the implant assembly 15 includes an implant body 25, an anchor 30, and an attachment fitting 500. The anchor 30 is configured to be received in a bore 40 defined through the implant body 25. The bore 40 extends through the implant body 25 and is sized such that the anchor element 30 can extend through the implant body 25 as illustrated in FIG. 4 and into the underlying bone tissue (not shown).

The attachment fitting 500 in this embodiment is configured to be received within a guide 505 formed within the implant body 25. In general, the guide 505 accommodates limited translations and/or rotations of the attachment fitting 500, and further provides the ability to lock the attachment fitting 500 in a fixed position relative to the implant body 25 when the rod 2096 is locked into place within the attachment fitting 500. The guide 505 may be a slot as illustrated in FIG. 4, or any of a variety of other embodiments discussed in detail herein below.

a. Implant Body

Figure 5:
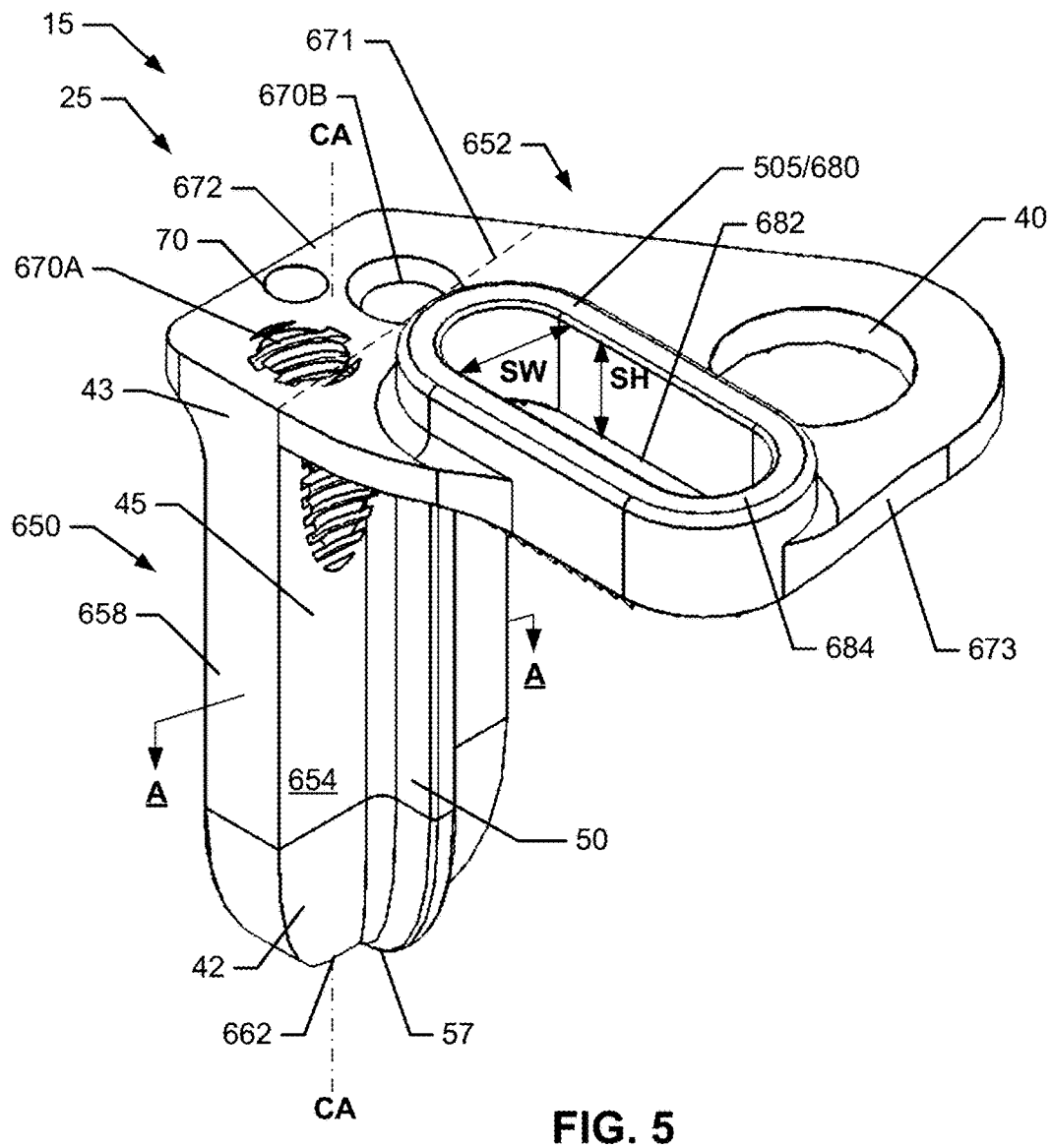
FIG. 5 is a side isometric of an implant body of the implant assembly in the first embodiment.

To begin a detailed discussion of the implant body 25, reference is made to FIG. 5, which is a side isometric view of an implant body 25 in one embodiment. In general, the implant body 25 includes an insertion element 650 and an attachment element 652. The insertion element 650 is configured to be inserted into the joint space of a sacroiliac joint in a direction that is essentially parallel to, or sufficiently engaged with, the articulating surfaces of the sacrum and ilium to implement the robust anchoring of the implant body 25.

Additional features of the insertion element 650 such as open and/or blind bores may interact mechanically with the anchor 30 (not shown) and optional additional fasteners to enhance the anchoring of the implant body 25. Other additional features of the insertion element such as fins 50 or other projections such as surface textures (not shown) may enhance the grip of the insertion element 650 within the joint space of the sacroiliac joint; these other additional features may further enhance the integration of bone tissue within the joint space into the surface of the insertion element 650, thereby strengthening the mechanical fusion and immobilization of the sacroiliac joint.

The implant body 25 also typically includes an attachment element 652 configured to mechanically interact with the anchor 30 to secure the implant body 25 to the sacroiliac joint. In addition, the attachment element 652 typically includes a guide 505, such as the slot 505 illustrated in FIG. 4. In general, the guide 505 is configured to receive the attachment fitting 500 (not shown) and allow limited translation and rotation of the attachment fitting 500 to allow for minor adjustments of the position and/or orientation of the rod 2096 (not shown) within the spinal stabilization system prior to locking the attachment fitting 500 to the guide 505 of the implant body 25.

In various embodiments described herein below, the implant body 25 may have a variety of external shapes and cross-sectional profiles depending upon the desired properties and uses of the implant body 25. For example, different shapes, sizes, and/or cross-sectional profiles of the implant body 25 may be selected to accommodate various patient morphologies, shapes and types of anchors and orthopedic fasteners, and/or any other relevant criteria.

In various embodiments, the implant body 25 may be machined, molded, formed, or otherwise manufactured from stainless steel, titanium, ceramic, polymer, composite, bone or other biocompatible materials.

Other features and aspects of the implant body 25 are discussed in detail herein below.

i. Insertion Element

Referring again to FIG. 5, the implant body 25 includes an insertion element 650 that includes a flattened elongate insertion plate 45. The insertion plate 45 has a medial face 654 and an opposite lateral face 656 (not shown) extending the width of the insertion plate 45 as well as opposed edges 658 extending the thickness of the insertion plate 45. In entering the sacroiliac joint space, the implant body 25 is oriented such that its wide medial face 654 and lateral face 656 are oriented generally parallel to, and aligned with, the sacroiliac joint line and within the joint plane. Within the sacroiliac joint space, the medial face 654 is generally adjacent to the articulating surface of the sacrum and the lateral face 656 is generally adjacent with the articulating surface of the ilium.

Figure 7A:
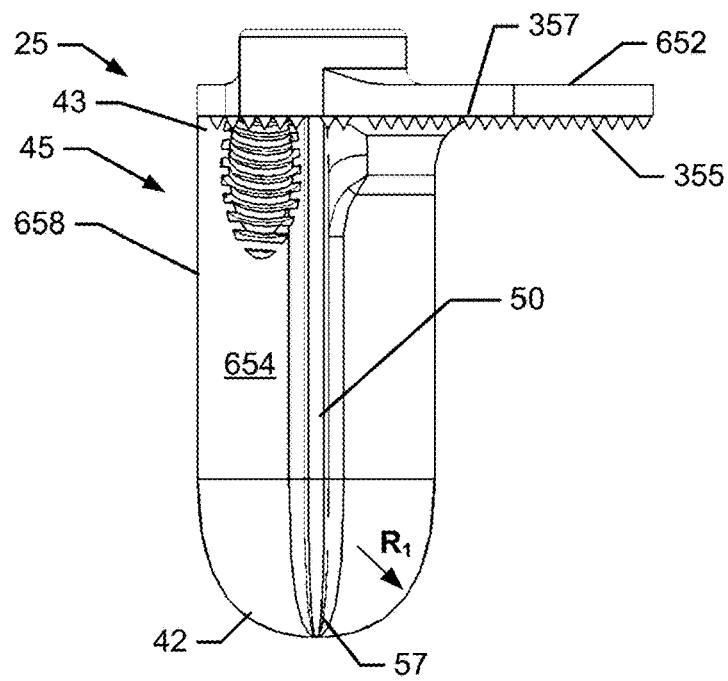
FIG. 7A is a medial side view of the implant body of the first embodiment.

Referring to FIG. 7A, the insertion plate 45 may have a generally rectangular side profile (as viewed from a lateral or medial side). According to other embodiments, e.g., FIG. 9, FIG. 39 and FIG. 43A, the insertion plate 45 may have a generally triangular side profile. The side profile shape of an insertion plate 45 may be configured to match a portion of the articular surfaces of a sacroiliac joint. For example, a generally triangle shaped side profile of an insertion plate 45 may be best suited to match the area footprint of the articular surfaces of the sacroiliac joint, e.g., within an extra-articular space or region, or to substantially fill the area footprint of a substantial majority of the entire articular surfaces of a sacroiliac joint. In another aspect, a generally rectangular side profile may be best suited to match a portion of the articular surfaces within an interarticular region of a sacroiliac joint, e.g., a caudal or cranial arm of the interarticular region. In another aspect, a generally C-shaped or L-shaped side profile may be selected to be configured to substantially cover an area of the articular surfaces of the sacroiliac joint within an interarticular region.

Although the insertion plate 45 illustrated in FIG. 5 has a generally flat planar profile, in general the insertion plate 45 may have any contour including, but not limited to curved, corrugated, and any other suitable contour. In one aspect, the contour of the insertion plate 45 may be selected to match the contour of the joint space in the sacroiliac joint within which the insertion plate 45 is to be inserted. In another aspect, a variety of insertion plates 45 may be formed with varying contours and the contour which best matches the contour of the sacroiliac joint of the patient to be treated is selected for use. In another additional aspect, the insertion plate 45 may be formed to be deformable by the surgeon; in this additional aspect the surgeon may bend or otherwise deform the insertion plate 45 to form an appropriate contour to match the contour of a patient's sacroiliac joint space, sacral surfaces, and/or iliac surfaces.

Figure 92:
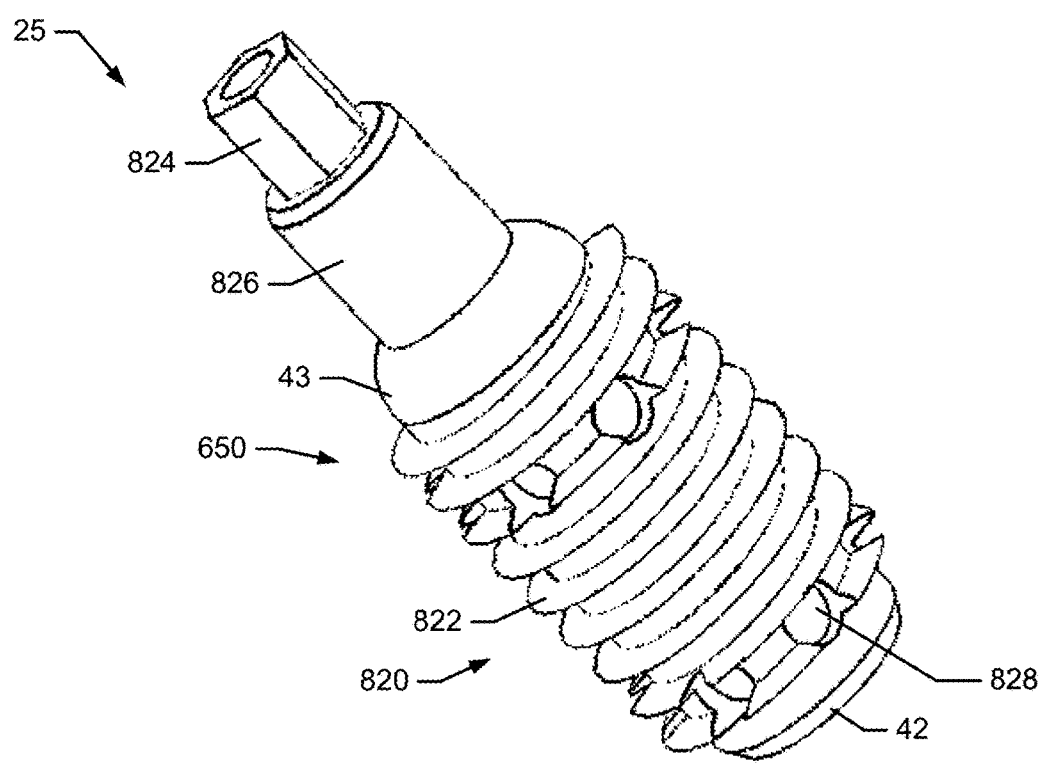
FIG. 92 is a side isometric view of a threaded cylinder insertion element in an embodiment.

FIG. 92 is a side perspective view of an insertion element 650 in another embodiment. As illustrated in FIG. 92, the insertion element 650 may be provided in the form of a threaded cylinder 820. The insertion element 650 may include threads 822 that extend from the proximal end 43 to the distal end 42, thereby allowing the insertion element 650 to be implanted by twisting the insertion element 650 into a preformed bore within a joint space. The proximal end 43 of the threaded cylinder may further include a driver tool fitting 824 including, but not limited to, a hexagonal driver head as illustrated in FIG. 92. In another embodiment, the proximal end 43 may further include a projecting fastener fitting 826 that may function as an anchor for an element of a spinal support system, or alternatively to fasten an attachment element 652 to the insertion element 650. For example, the fastener fitting 826 may be threaded (not shown) and may function in a manner similar to a Steffee bolt.

Figure 93:
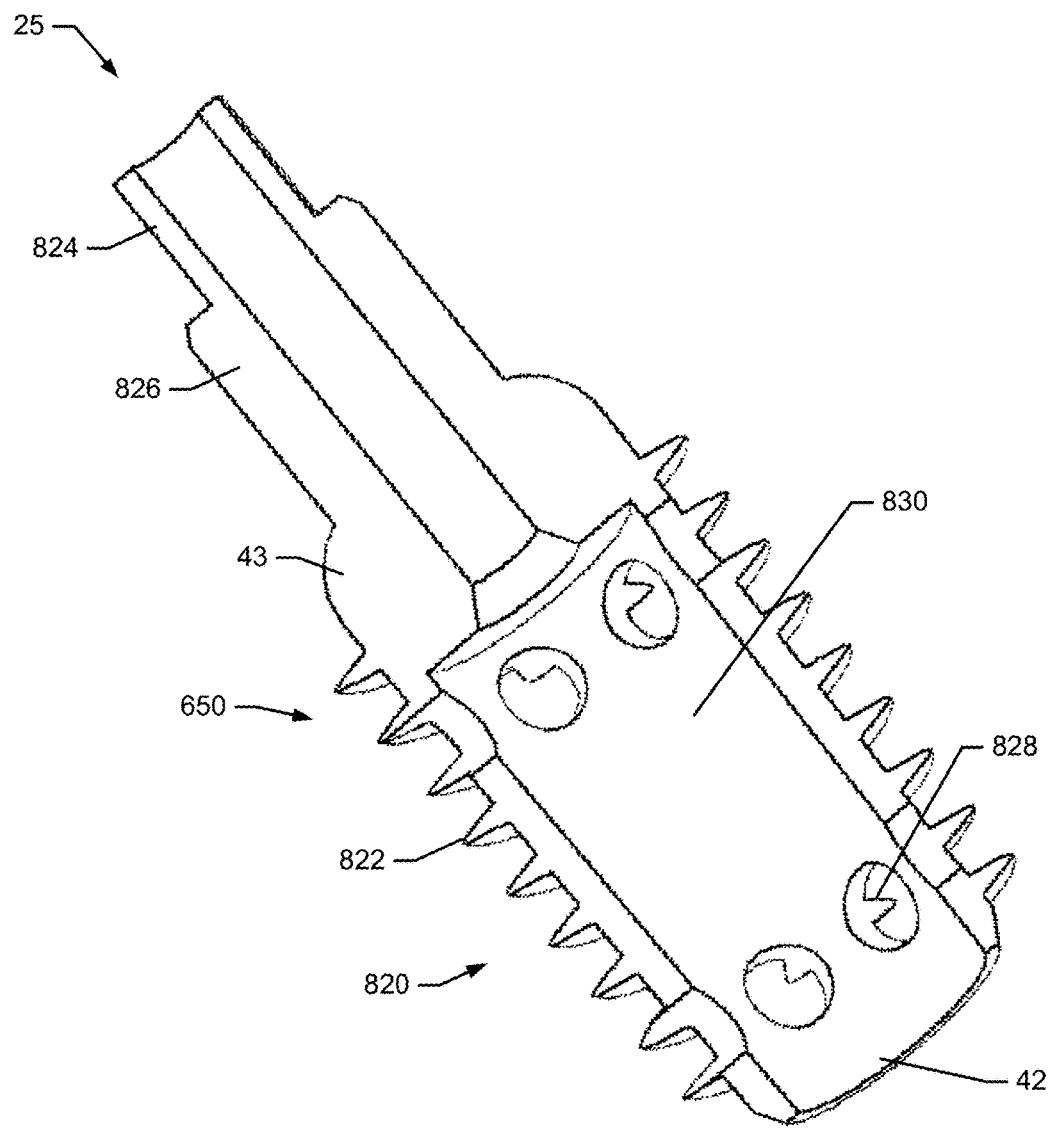
FIG. 93 is a cross-sectional view of the threaded cylinder insertion element in the embodiment.

In this embodiment, the threaded cylinder 820 may further include one or more transverse bores 828 configured to receive one or more additional fasteners inserted transversely through the surrounding ilium bone in a lateral to medial direction, or through the surrounding sacrum bone in a medial to lateral direction in various embodiments. FIG. 93 is a cross-sectional view of the threaded cylinder 820. As illustrated in FIG. 93, in one embodiment the cylinder 820 may be hollow, and the transverse bores 828 may direct a fastener along a diameter of the lumen to corresponding opposite bores aligned along a diagonal path opposite to the first transverse bores 828.

Figure 94:
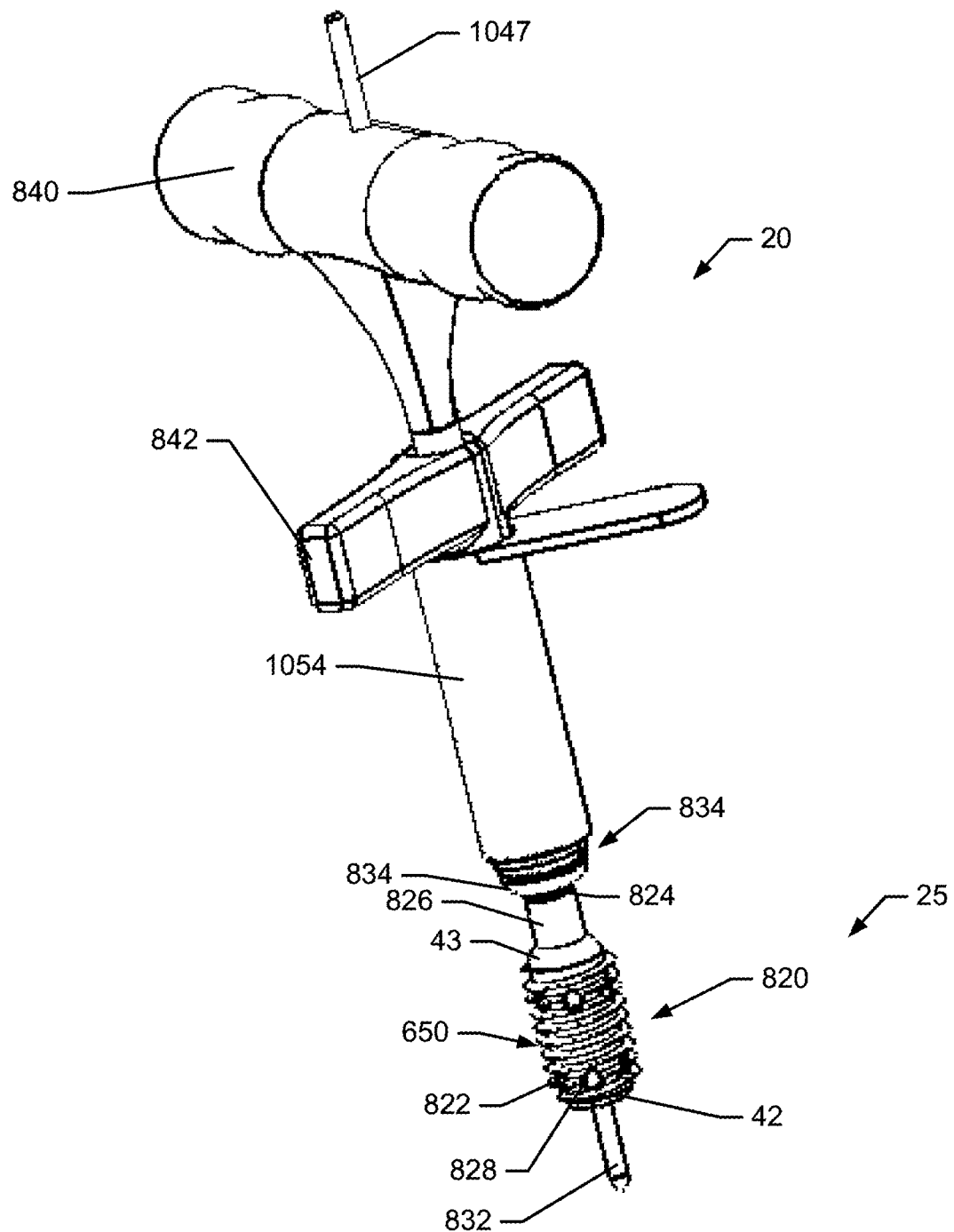
FIG. 94 is a side isometric view of the threaded cylinder insertion element reversibly coupled to a delivery tool in an embodiment.
Figure 95:
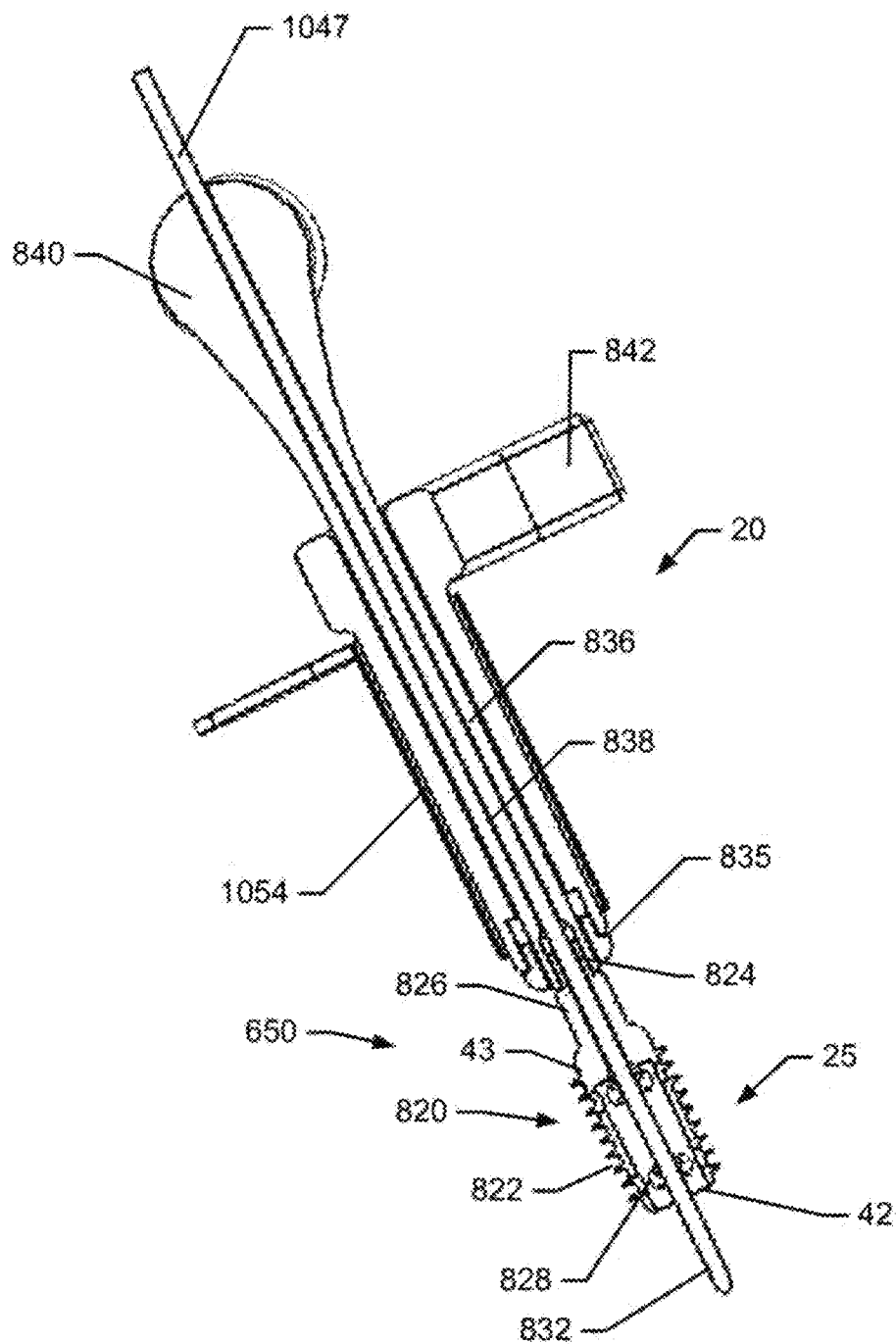
FIG. 95 is a cross-sectional view of the threaded cylinder insertion element reversibly coupled to the delivery tool.
Figure 96:
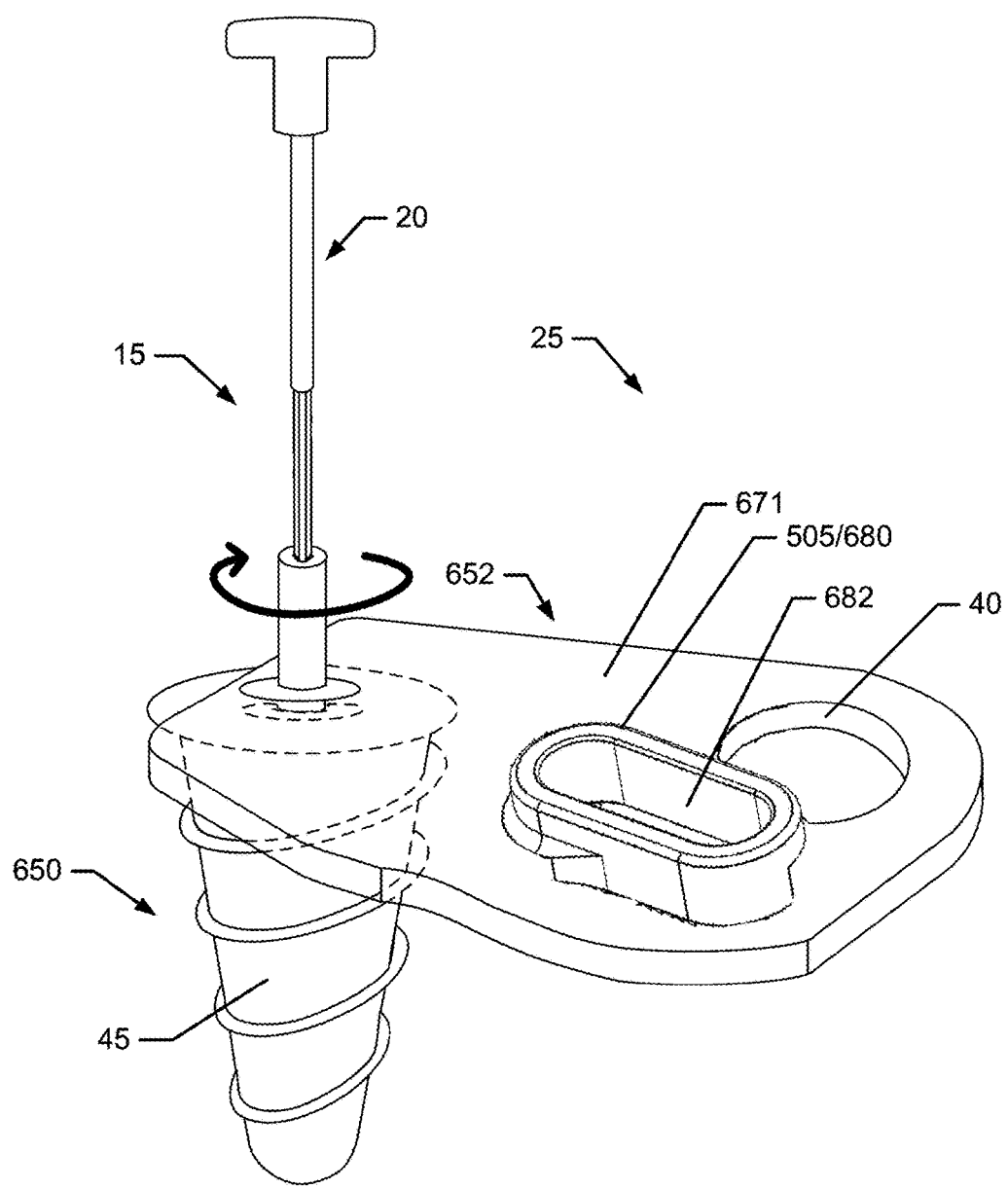
FIG. 96 is an isometric view of an implant assembly that includes a threaded cylinder insertion element reversibly coupled to a driver tool in an embodiment, wherein the insertion element is helically threaded and driven with rotation forces.

FIG. 94 is a side isometric view of the threaded cylinder 820 reversibly coupled to a delivery tool 20. FIG. 95 is a longitudinal cross-section of the threaded cylinder 820 reversibly coupled to the delivery tool 20. Referring to FIG. 94 and FIG. 95, the delivery tool 20 may include a cannula 1054 to guide the insertion of the various other elements of the delivery tool 20. The threaded cylinder 820 may be inserted over the guide pin (not shown) pin or tubular member 1047 in which the distal end 832 may be inserted within a joint space (not shown) within which the threaded cylinder 820 is to be inserted. The driver tool 838 and associated distal hexagonal socket 834 may be inserted such that the distal hexagonal socket 834 is situated over the driver tool fitting 824. A first proximal handle 840 provides torque to drive the threaded cylinder 820 into the joint space (not shown). As illustrated in FIG. 95, a guide ring 835 and associated guide tool 836 may be inserted over the driver tool fitting 824 projecting proximally from the proximal end 43 of the threaded cylinder 820. The guide tool 836 terminates proximally in a second proximal handle 842.

In particular embodiments, the lateral and medial surface contours of the insertion plate 45 may be selected to match the contour of the joint space in the sacroiliac joint within which the insertion plate 45 is to be inserted. For example, the medial or sacral face 654 of insertion plate 45 may be configured to be generally convex to match the contour of a sacral auricular boney surface or to match the contour of an extra-articular region of a sacrum (e.g., a sacral fossa). In one aspect, the sacral or medial bone interface surface 654 of the insertion plate 45 may be generally a surface negative of the articular surfaces 1016 of the extra-articular space 3007 and/or interarticular region 1044 of the sacrum 1004. As another example, the lateral or iliac face 656 of the insertion plate 45 may be configured to be generally concave to match the contour of an iliac auricular boney surface or to match the contour of an extra-articular region of an ilium (e.g., an iliac tuberosity). In one aspect, the iliac or lateral bone interface surface 656 of the insertion plate 45 may be generally a surface negative of the articular surfaces 1016 of the extra-articular space 3007 and/or interarticular region 1044 of the ilium 1005.

1. Fins

In one embodiment, the insertion plate 45 includes a distal or leading end 42, a proximal end 43, and one or more keels, fins or planar members 50 that extend perpendicularly away from the medial face 654 and/or lateral face 656 of the insertion plate 45. The fins 50 typically extend in length from the proximal end 43 to the distal end 42 of the insertion plate 45. In some embodiments, the fins 50 may extend along any one or more portions of the full distance between the proximal end 43 and the distal end 42 of the insertion plate 45.

Figure 6A:
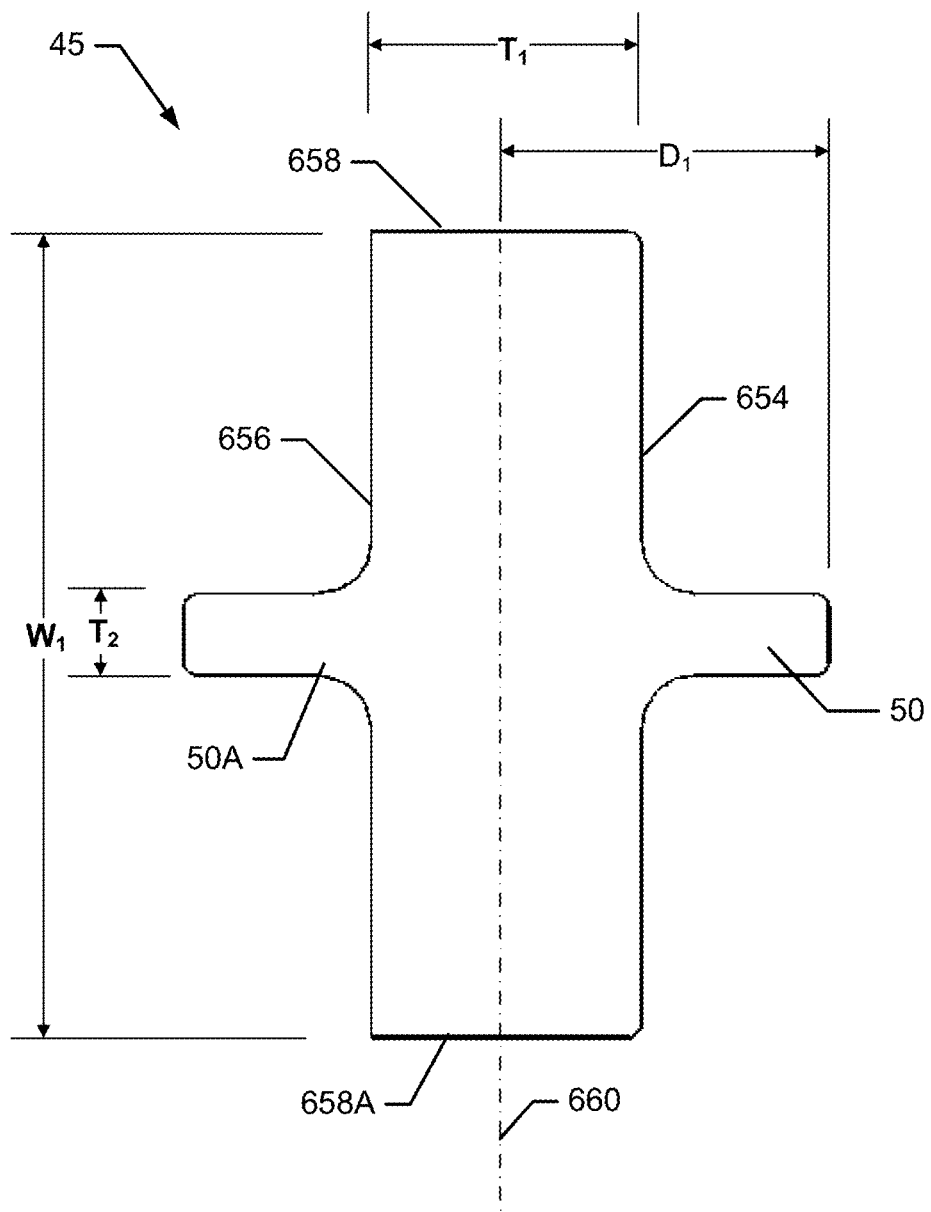
FIG. 6A is a normal cross-sectional view of an insertion body of the first embodiment taken at section A-A of FIG. 5.
Figure 6B:
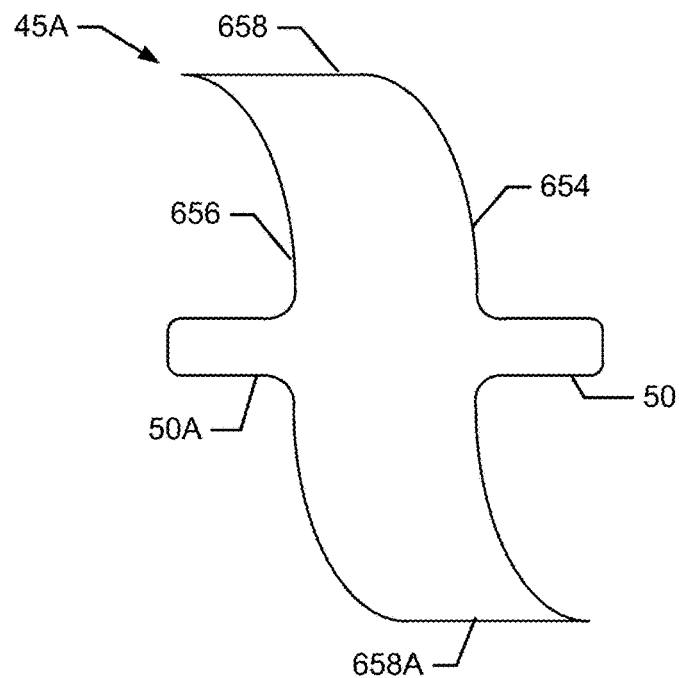
FIGS. 6B and 6C are normal cross-sectional views of alternative embodiments that include insertion elements with curved contours.
Figure 6C:
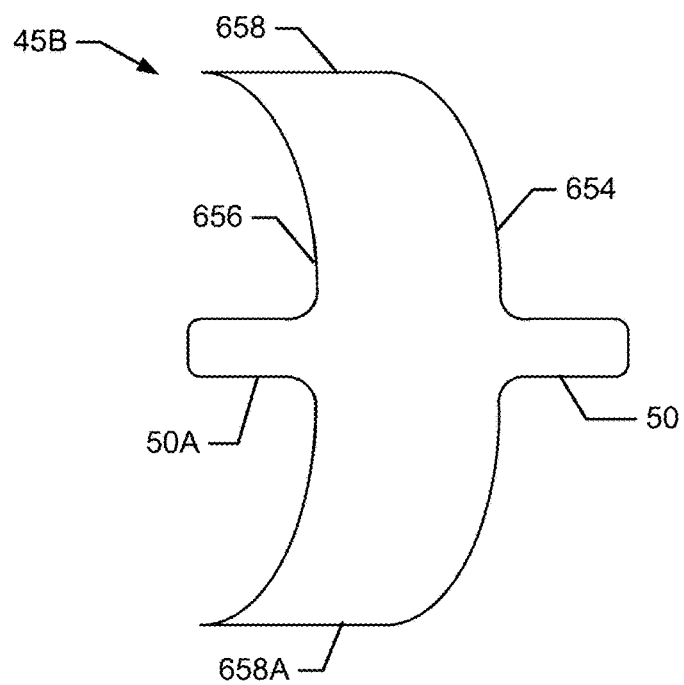

FIG. 6 is a normal cross-sectional view of the insertion plate 45 in FIG. 5 taken at section A-A. Referring to FIG. 6, the fin 50 extends perpendicularly away from the medial face 654 and a second fin 50A extends perpendicularly away from the lateral face 656 of the insertion plate 45 in this embodiment. In one embodiment, the fins 50 and 50A may be grouped into pairs that are generally coplanar with each other, as illustrated in FIG. 6; fins 50 and 50A in this embodiment generally exist in the same plane. In various other embodiments, the fins 50 and 50A may extend in directions that are generally parallel to one another, but not necessarily coplanar as illustrated in FIG. 6. For example, the fin 50 may extend along a plane that is parallel but offset from the extension plane of the second fin 50A.

In various embodiments, the number of fins 50 extending from the medial face 654 and/or lateral face 656 of the insertion plate 45 may vary without limitation. The number of fins 50 extending from the medial face 654 need not be equal to the number of fins 50 extending from the lateral face 656. In one aspect, all fins 50 may be identical in cross-sectional size and shape. In other aspects, one or more fins 50 may differ in cross-sectional size and shape.

Referring again to FIG. 6, the width $W_1$ of the insertion plate 45 extending between the opposed edges 658 may range from approximately 5 mm to approximately 30 mm in one embodiment. In another embodiment, the thickness $T_1$ of the insertion plate 45 between the medial face 654 and the opposite lateral face 656 may range from approximately 2.5 mm to approximately 15 mm. The overall length of the insertion plate 45 extending from the proximal end 43 (not shown) and the distal end 42 (not shown) may range between approximately 5 mm and approximately 70 mm. In other embodiments, $W_1$ may vary at or between ends 42 and 43.

In an additional embodiment, the perpendicular extension distance $D_1$ of the fins 50 measured relative to a plane 660 situated midway between the medial face 654 and lateral face 656 and parallel to both faces 654/656 may range between approximately 2.5 mm and approximately 18 mm. The thickness $T_2$ of the one or more fins 50 width may range from approximately 1 mm to approximately 10 mm.

In these various aspects, the dimensions of the insertion plate 45 and associated one or more fins 50 can and will vary based on various aspects. The thickness $T_1$ of the insertion plate 45 may be selected to exert firm pressure against the articulating surfaces of the sacrum and ilium within the joint space without undue stretching or distortion of the sacroiliac joint and surrounding soft tissues. The width $W_1$ of the insertion plate 45 may be selected to fit within the sacroiliac joint along the joint line, and to provide sufficient structural integrity to the insertion plate 45 while minimizing the extent of bone and soft tissue removal needed to prepare the sacroiliac joint to receive the insertion plate 45.

The perpendicular extension distance $D_1$ of the one or more fins may be selected to result in the incursion of the one or more fins 50 into the articulating bone surfaces within the sacroiliac joint in order to facilitate the integration of bone tissue into the surface of the insertion plate 45. In addition, the perpendicular extension distance $D_1$, fin thickness $T_2$, and/or length of the one or more fins 50 may be configured to provide structural reinforcement to the insertion plate 45 to resist deflection in any direction. In one embodiment, the one or more fins 50 may provide structural reinforcement against bending deflections in the medial and/or lateral directions.

2. Tapered Distal End

Referring back to FIG. 5, the distal end 42 of the insertion plate 45 may taper in a pointed end, a bullet nose, or any other otherwise rounded configuration, wherein the rounded configuration extends outward away from the distal extremity of the insertion plate 45 and along the distal or leading edge 662 of the insertion plate 45 as well as the distal or leading edge 57 of the one or more fins 50. FIG. 7 is a side view of the implant body 25 looking toward the medial face 654 of the insertion plate 45. FIG. 8 is a second side view of the insertion body 25 looking toward one of the edges 658 of the insertion plate 45. Thus, as can be understood from FIGS. 5 and 7, 9-13, the leading or distal edge 42 of the insertion plate 45 and the leading edge 57 of the fins 50 may be rounded in the radially extending length of the lead or distal edges and/or in a direction transverse to the radially extending length of the lead or distal edges. In one embodiment, the leading edges 57 of the fins 50 may each have a radius $R_2$ ranging from approximately 1 mm to approximately 15 mm and the leading edge 42 of the insertion plate 45 may have a radius $R_1$ ranging from approximately 1 mm to approximately 15 mm. In another embodiment, the leading edge 42 of the insertion plate 45 and the leading edges 57 of the fins 50 may have a generally conical pointed configuration, a polygonal configuration, or an elliptical dome configuration.

3. Delivery Tool Fittings

As indicated in FIGS. 5, 7, and 8 the proximal end 43 of the insertion plate 45 may have a generally planar face that is generally perpendicular to a proximal-distal center axis CA of the insertion plate 45 in one embodiment. Referring back to FIG. 5, the generally planar face of the insertion plate 45 may facilitate the secure attachment of the implant assembly 15 to the distal end 35 of the delivery tool 20, which may have a generally planar distal face (not shown). In other embodiments, the proximal end 43 of the insertion plate 45 may be contoured to match a corresponding contour of the distal face of the delivery tool 20. For example, the proximal end 43 of the insertion plate may have a domed contour that matches a corresponding cupped contour of the distal face of the delivery tool 20, or vice-versa.

In various embodiments, the proximal end 43 of the insertion plate 45 may define or contain one or more additional features to effectuate a reversibly locked engagement with the distal end 35 of the delivery tool 20. Referring back to FIG. 5, a center attachment bore 70 may be defined in the proximal end 43 of the insertion plate 45 in one embodiment; this center attachment bore 70 may be centered about the longitudinal center axis CA. In one embodiment, the center attachment bore 70 may be a blind hole in that it only has a single opening. Alternatively, the center attachment bore 70 may be configured as a hole that communicates between the proximal end 43 and distal end 42 of the insertion plate 45. Bore 70 may alternatively or additionally communicate with the lateral or medial surfaces of an insertion element 650 in order to permit the introduction by injection, or by any other known means of introduction, of stem cells or other biocompatible material up to or near the joint surfaces via the bore 70. The center attachment bore 70 may further incorporate additional features to receive an element of the delivery tool 20 in a reversibly locked engagement. For example, the center attachment bore 70 may contain threads matched to the threads of a set screw used to secure the distal end 35 of the delivery tool 20 to the implant assembly 25.

In other embodiments, the proximal end 43 of the insertion plate 45 may include additional features to further enhance the reversibly locked engagement with the delivery tool 20. In one embodiment, the proximal end 43 may contain one or more additional lateral attachment bores 75 (not shown) offset from the center bore 70. These lateral attachment bores 75 may be threaded to receive one or more additional set screws in an embodiment. In another embodiment, these lateral attachment bores may be shaped to match corresponding alignment pegs protruding from the distal end 35 of the delivery tool 20.

Figure 12G:
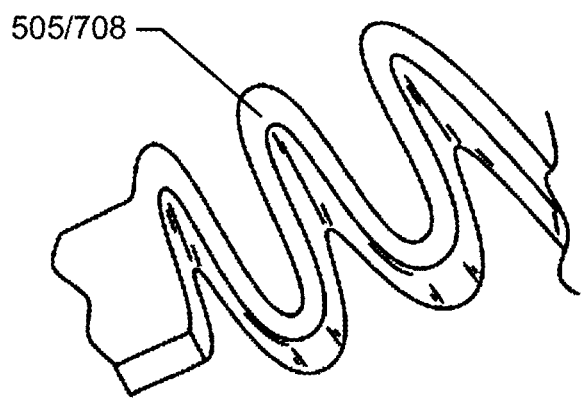
FIGS. 12G-12H are isometric views of a portion of anchor support elements that include energy-absorbing elements in alternative embodiments.
Figure 12H:
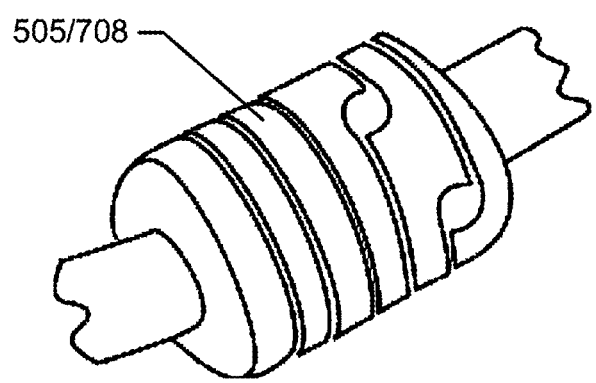
Figure 97A:
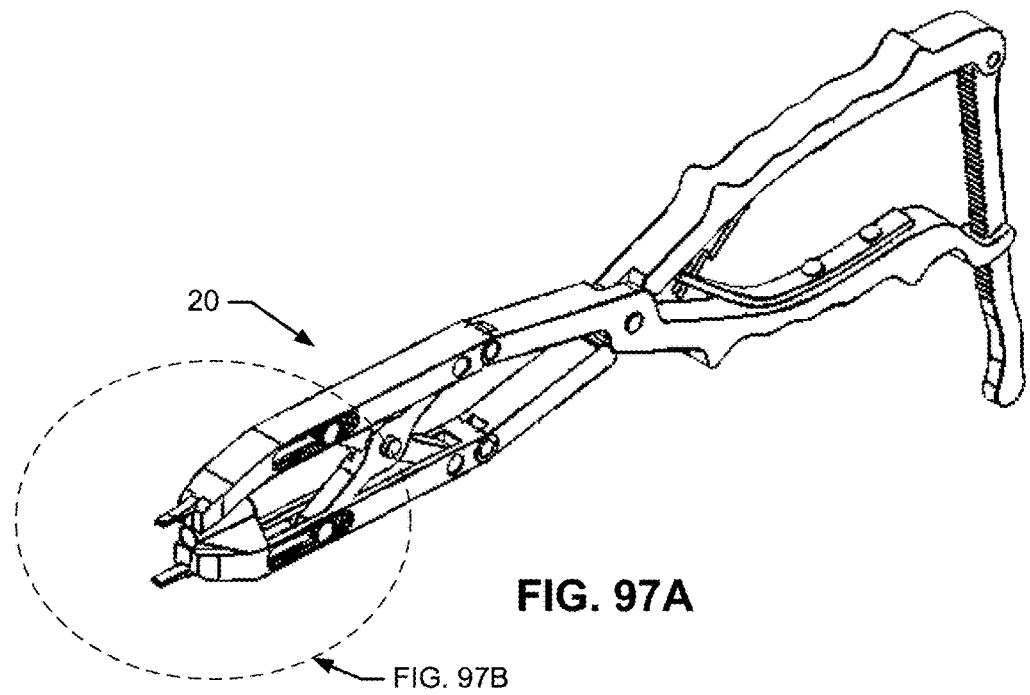
FIG. 97A is an exploded isometric view of an implant assembly mounted to a hemostat-type delivery tool in an embodiment.
Figure 97B:
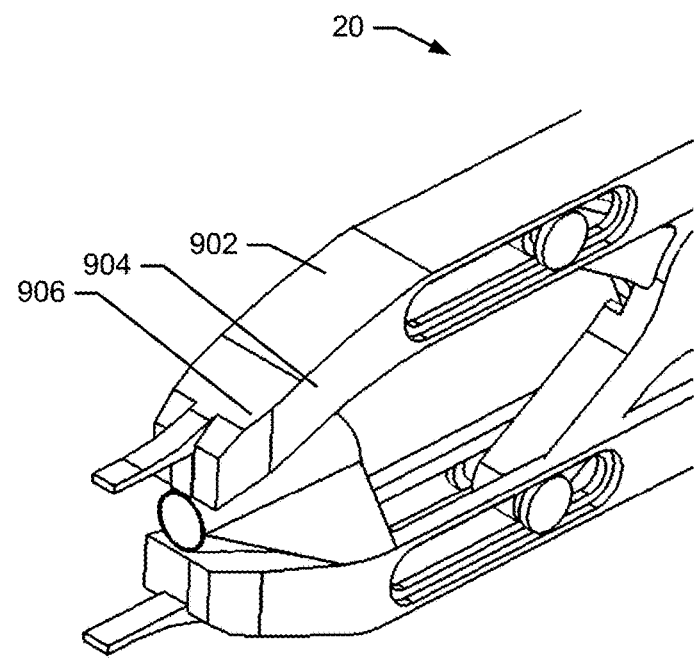
FIG. 97B is a close-up exploded isometric view of the implant assembly mounted to the hemostat-type delivery tool.
Figure 98:
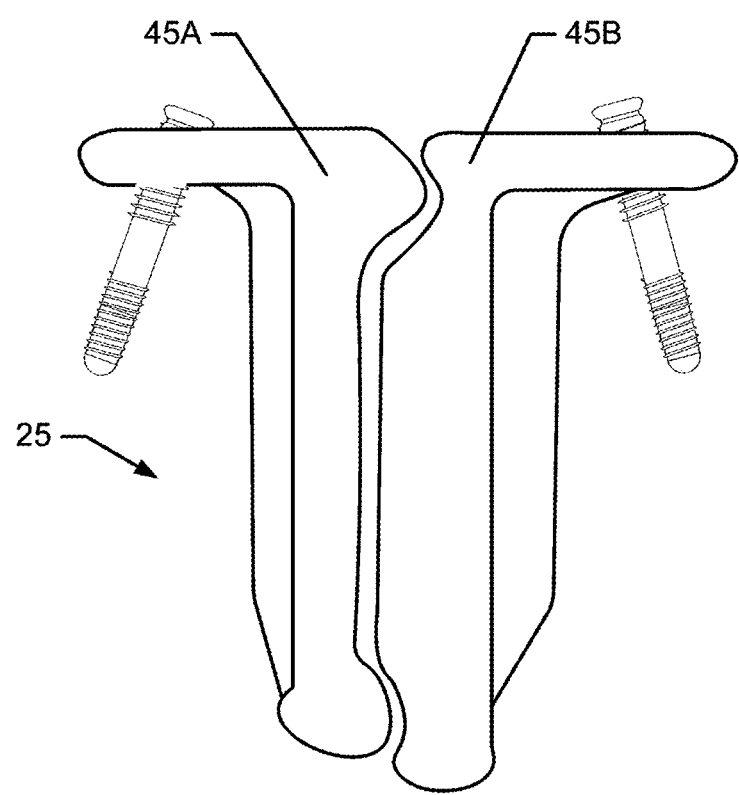
FIG. 98 is a side view of an implant system in which the implant body consists of multiple implant bodies or pieces (e.g., 2 or 3 or more pieces) in one embodiment thereby permitting motion at a sacroiliac joint.

In other additional embodiments, protruding or recessed elements situated on or within the implant assembly 15 may be configured to interface with pliers, hemostats or other delivery tool configurations. FIG. 97A is an isometric view of a hemostat-type of delivery device 20. FIG. 97B is a close isometric view of the jaws 902 of the delivery device 20. As illustrated in FIG. 97B, each of the jaws 902 terminate distally in a projecting alignment peg 904 that fits within a recessed element or other tool attachment fittings formed in or on the implant body 25. The locked engagement of the alignment pegs 904 within the recessed elements or other tool attachment fittings resists any tendency for the implant body 25 to rotate during insertion into a joint space using the delivery tool 20. FIG. 12 illustrates an implant body 25 that includes a recessed element 154 suitable for use with the hemostat-type of delivery device 20 illustrated in FIG. 97A-B.

Figure 9:
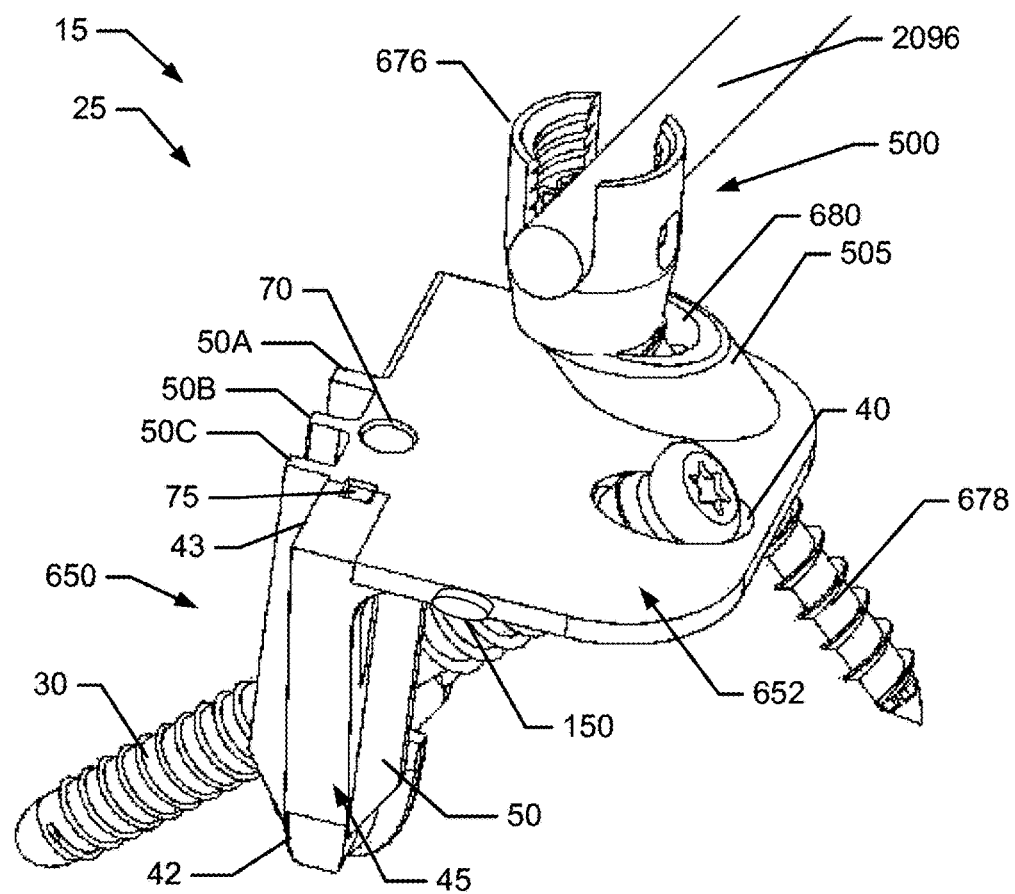
FIG. 9 is an isometric view of a second embodiment of the implant body; and, further includes a tool engagement peg situated on an edge of the attachment element in an embodiment.

FIG. 9 is an isometric view of a second embodiment of an implant body 25. In this embodiment, an additional lateral attachment bore 75 is provided in the form of an alignment peg receptacle. This alignment peg receptacle 75 may be a blind hole configured to receive an alignment peg protruding from the distal end 35 of the delivery tool 20 (not shown).

In one embodiment, the center bore 70 may have a diameter ranging from approximately 2 mm to approximately 10 mm. In another embodiment, the one or more lateral attachment bores may each have a diameter ranging from approximately 0.5 mm to approximately 3 mm.

Figure 10A:
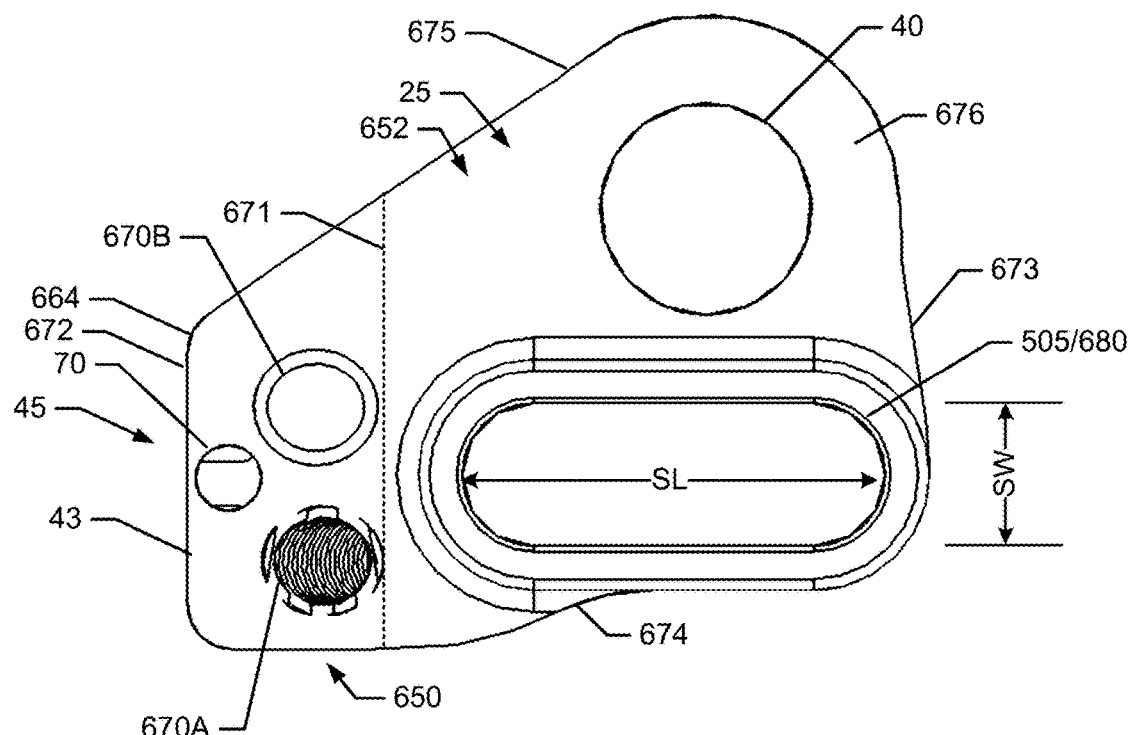
FIG. 10A is a top view of the first embodiment of the implant body.
Figure 10B:
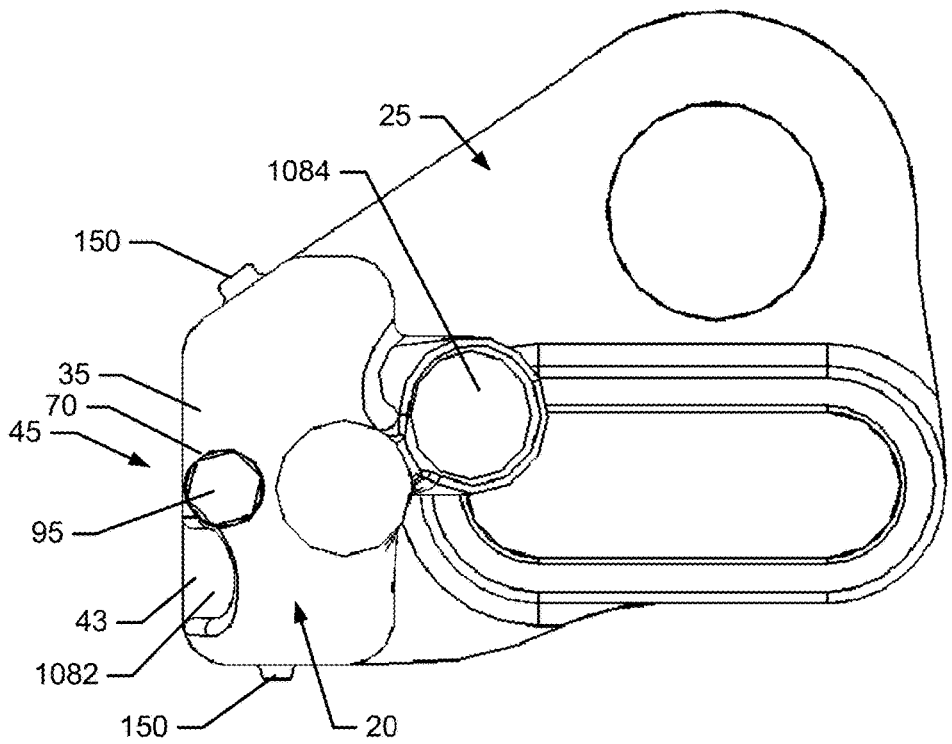
FIG. 10B is a top view of the first embodiment of the implant body attached to a delivery device.
Figure 10C:
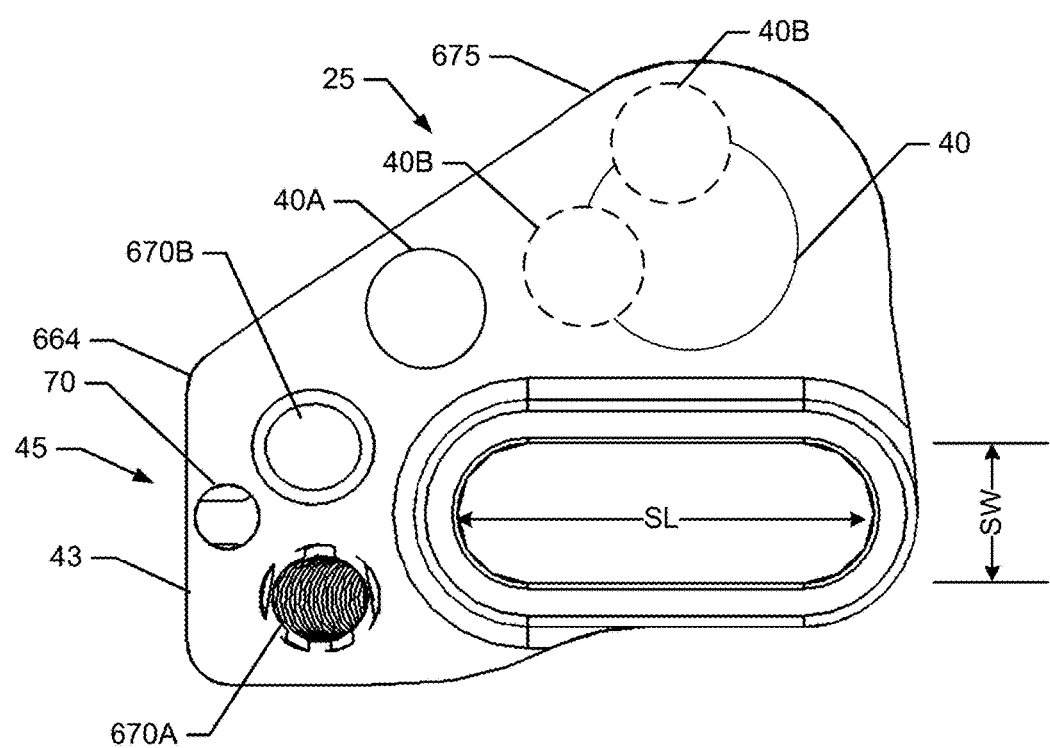
FIG. 10C is a top view of an alternative embodiment that includes additional locations of the bore.

FIG. 10A is a top view of the first embodiment of the implant body 25 illustrated in FIG. 5. In an embodiment, the outer contour 664 of the proximal end 43 of the insertion plate 45 may be contoured to fit within two or more additional alignment pins 150 protruding in a distal direction from the distal end 35 of the delivery tool (not shown). FIG. 10B is the top view of the implant body 25 illustrated in FIG. 10A with the distal end of the delivery tool 20 mounted in place. In this embodiment, the additional alignment pins 150 project in a distal direction to entrap the lateral margin of the proximal end 43. In this configuration, the additional alignment pins 150, in cooperation with a set screw 95 advanced into the central bore 70 of the implant body 25, secure the delivery tool 20 to the implant body 25 and prevent the delivery tool 20 from translating or rotating relative to the implant body 25.

Figure 11A:
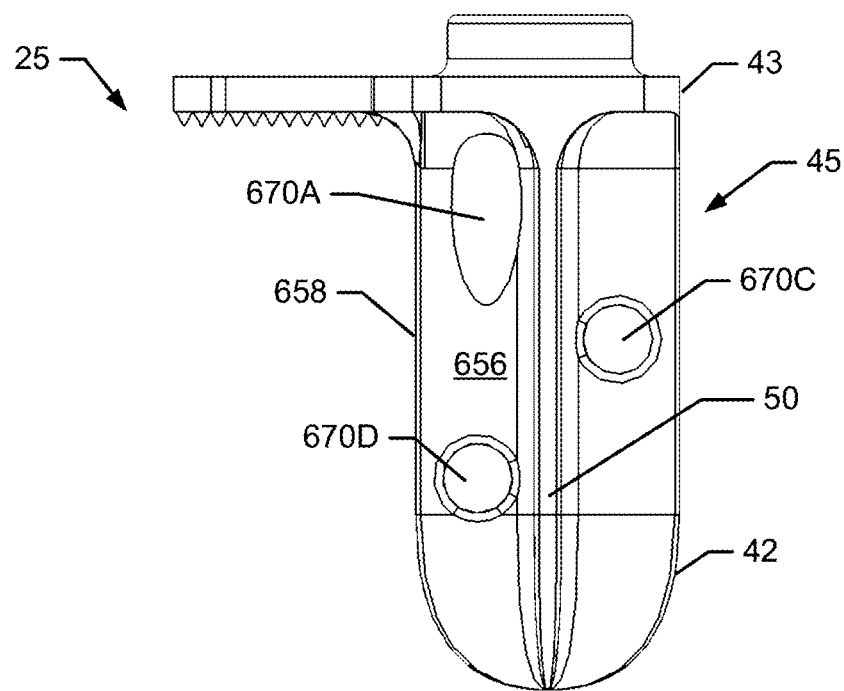
FIG. 11A is a lateral side view of the implant body of the first embodiment.
Figure 11B:
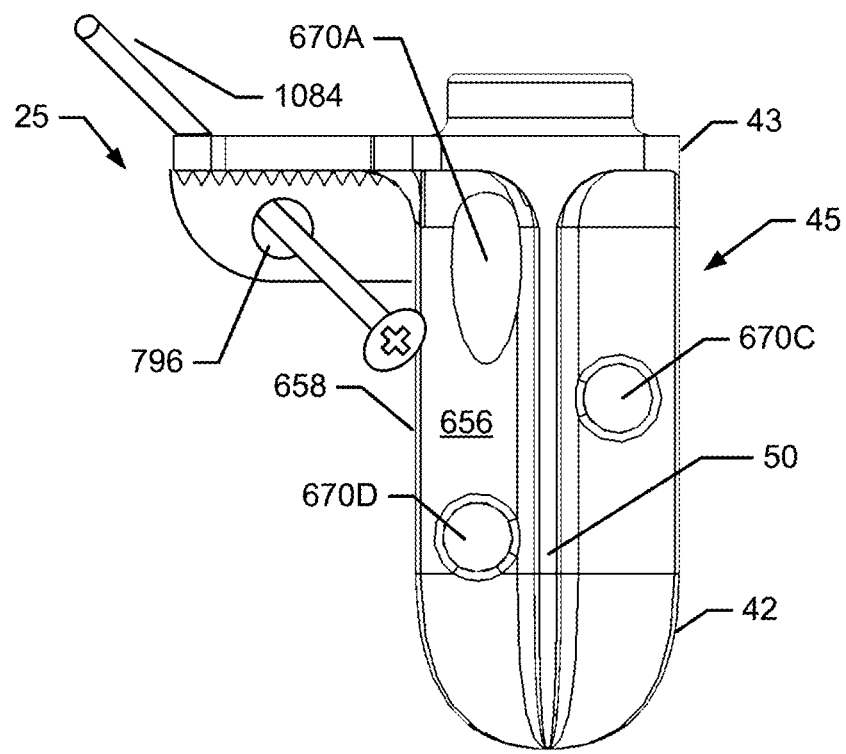
FIG. 11B is a side view of the implant body with a distally projecting extension of the attachment element and an anchor inserted in a lateral-medial trajectory: i) through the ilium (not shown), ii) through a bore in the distally projecting extension and across the sacroiliac joint (not shown), iii) into sacrum (not shown), and iv) toward the sacral promontory (not shown).

In an embodiment, the implant body 25 is fixed in place within the joint space of the sacroiliac joint by means of an anchor 30 directed through a bore 40. In another embodiment, the insertion plate 45 may further include one or more additional bores 670. The additional bores 670 may be directed through the corner formed by the attachment element 652 and the insertion element 650 as illustrated previously in FIG. 5. Referring to FIG. 10A and FIG. 10B, the additional bores 670A and 670B may be accessed via anchor guides 1082 and 1084, respectively. In this embodiment, the anchor guides 1082 and 1084 may direct the anchors 30 along a direction consistent with the central axes of the additional bores 670A and 670B. FIG. 11A is a lateral side view of the implant body 25 viewing the lateral face 656 of the insertion plate 45 in one embodiment. In this embodiment, one or more bores 670 may be formed in the insertion plate. The one or more additional bores 670 may be open bores passing through the insertion plate 45 in one aspect. In another aspect, the one or more additional bores 670 may be blind bores opening to the medial face 654 and/or opening to the lateral face 656. For example, the one or more additional bores 670 may be blind bores opening to the lateral face 656 of the insertion plate 45 as illustrated in FIG. 11A.

The one or more additional bores 670 may be provided with any cross-sectional profile and dimension without limitation. In one embodiment, each of the one or more additional bores 670 may have a cross-sectional profile that is square, rectangular, circular, oval, triangular and any combination thereof. For example an additional bore 670 may have a round cross-sectional profile within a first bore segment and transition to a round cross-sectional profile in a second bore segment. In another embodiment, one or more additional bores 670 may be further configured to permit an anchor 30 directed through a bore 40 to be further advanced through a bore 670, which is substantially greater than the diameter of the anchor 30, within a predetermined range of trajectories. In this other embodiment, the anchor 30 may be inserted as selected by a surgeon within a predetermined range of trajectories at the time of implantation while still passing through a bore 40 and further through an additional bore 670. For example, as illustrated in FIG. 43 and described herein below, a second anchor arm 115B may include a conical sleeve 165B that effectuates the insertion of an anchor 30 within a predetermined range of anchor insertion angles; this predetermined range of insertion angles may be constrained by the contour of the conical sleeve 165B, as well as by the location and cross-sectional profile of the bore 40 and/or the location and cross-sectional profile of any additional bores 670. The conical sleeve 165B may be included in the delivery device 20 to facilitate the placement and insertion of fasteners in which some latitude in placement may be desired. Furthermore, the one or more additional bore 670 may provide an open channel, pathway, other connection to permit bone growth between a sacrum 1004 and ilium 1005 through one of more elements of the implant body 25, including, but not limited to, the insertion element 650. In various embodiments, the conical sleeve 165B may be configured to guide the trajectory of any suitable fastener including, but not limited to, polyaxial bone fasteners and pedicle screws.

4. Additional Fastener Bores

Each of the one or more additional bores 670 may be configured to receive an orthopedic fastener including, but not limited to a screw, a pin, or any other known orthopedic fastener. In one aspect, if the one or more additional bores 670 may be blind bores, each additional bore 670 may be configured to receive the distal end or tip of the orthopedic fastener; in this aspect, each additional bore may be provided with a locking mechanism to mechanically retain the shaft, distal end, and/or tip of the orthopedic fastener. In another aspect, if the one or more additional bores 670 may be open bores, each of the additional bores 670 may be configured to receive a center portion of the shaft of the orthopedic fastener. In this other aspect, the diameter of each additional bore 670 may be sized to allow the passage of the shaft of the orthopedic fastener with little mechanical play to restrict the orientation the orthopedic fastener relative to the insertion plate 45. Alternatively, the diameter of each additional bore 670 may permit some degree of mechanical play in order to permit a limited variation in the orientation of the orthopedic fastener relative to the insertion plate 45.

In one embodiment, the orientation of the bore axis of each additional bore 670 may be aligned perpendicular to the medial face 654 and/or lateral face 656 of the insertion plate 45, as illustrated in FIG. 11A. In other embodiments, the bore axis of each additional bore may have any orientation without limitation. In general, the orientation of the one or more additional bores 670 may be selected in order to facilitate the incorporation of additional orthopedic fasteners directed medially toward the implant body 25 from the ilium and/or directed laterally toward the implant body 25 from the sacrum. For example, an orthopedic fastener may be directed from the ilium, through an additional open bore 670, and into the sacrum; the fastener may enhance the anchoring of the implant body 25 within the joint space of the sacroiliac joint as well as strengthening the fusion and fixation of the sacroiliac joint and subsequent spinal construct from the lumbar spine.

Figure 13A:
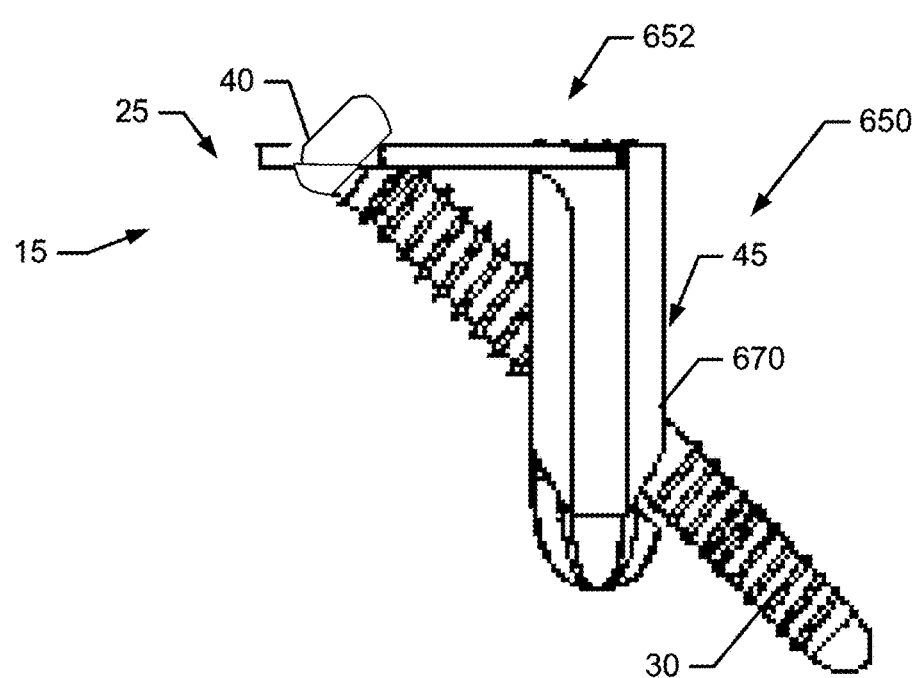
FIG. 13A is a cranial side view of a fourth embodiment of the implant body.

In an additional embodiment, an additional bore 670 may be an open bore configured to guide the anchor 30 in cooperation with the bore 40 within the attachment element 652 of the implant body 25. FIG. 13A is a side view of an implant body 25 with an anchor 30 inserted though the bore 40 in the attachment element 652 and additionally through the additional bore 670 in the insertion plate 45. As illustrated in FIG. 13A, the aligned bore axes of the bore 40 and the additional bore 670 are configured to guide the anchor 30 into the underlying bone tissue at a laterally-directed downward angle. In general, the bore axes of the bore 40 and the additional bore 670 may be aligned at any angle without limitation, constrained only by dimensions of the insertion element 650 and the attachment element 652 of the implant body 45.

In another embodiment, illustrated in FIG. 5, additional bores 670A and 670B may be at least partially directed through the corner formed by the attachment element 652 and the insertion element 650. The additional bores 670A and 670B are configured to guide the anchor 30 into the underlying bone tissue at a laterally-directed downward angle. The additional bores 670 in this embodiment may be threaded as illustrated as additional bore 670A or unthreaded as illustrated as additional bore 670B in FIG. 5.

In other additional alignments, the additional bores 670 may be open bores formed within additional attachment plates of various sizes projecting in various orientations relative to the attachment element 652 of the implant body 45. In one aspect, illustrated in FIG. 7B, the attachment element 652 may include an additional attachment plate 794 containing one or more additional bores 796; an anchor 30 may be inserted through each additional bore 796 to secure the implant assembly 25 in place. The additional attachment plate 796 may vary in length and may be relatively short as illustrated in the additional attachment plate 796 shown in solid lines in FIG. 7B or may extend up to the full extent of the edge of the implant assembly 25 from which the additional attachment plate 794 projects.

Figure 7B:
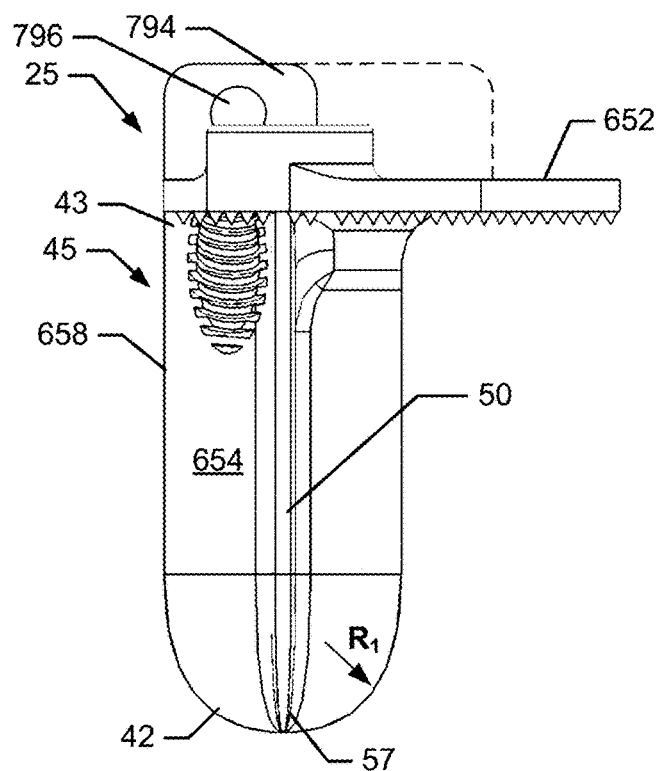
FIGS. 7B and 7C are medial side views of implant bodies in alternative embodiments with proximally projecting extensions of the attachment elements.
Figure 7C:
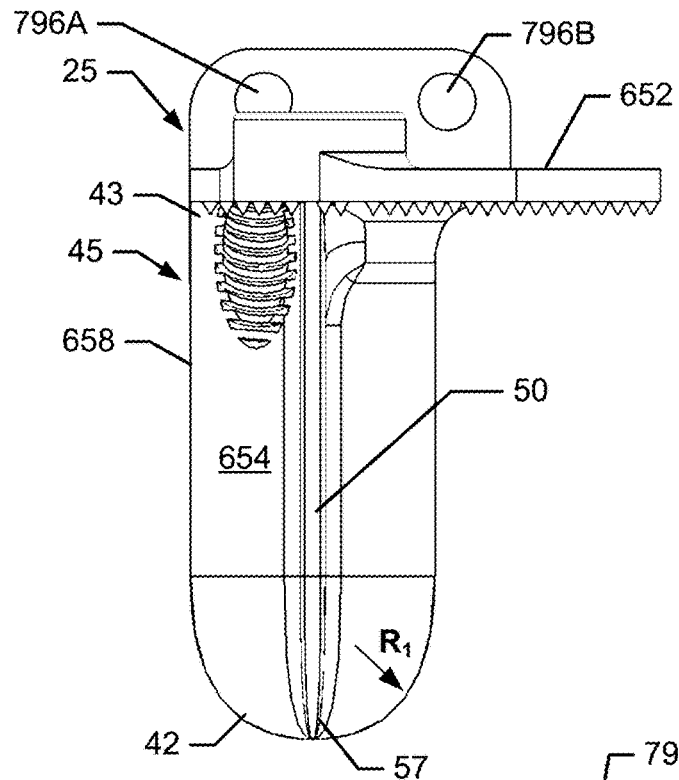

In these other additional aspects, the additional attachment plate 794 may contain one or more additional bores 796. By way of non-limiting example, the additional attachment plate 794 may include a single additional bore 796 as illustrated in FIG. 7B. By way of another non-limiting example, the additional attachment plate 794 may include multiple additional bore 796A-796B as illustrated in FIG. 7C.

Figure 7D:
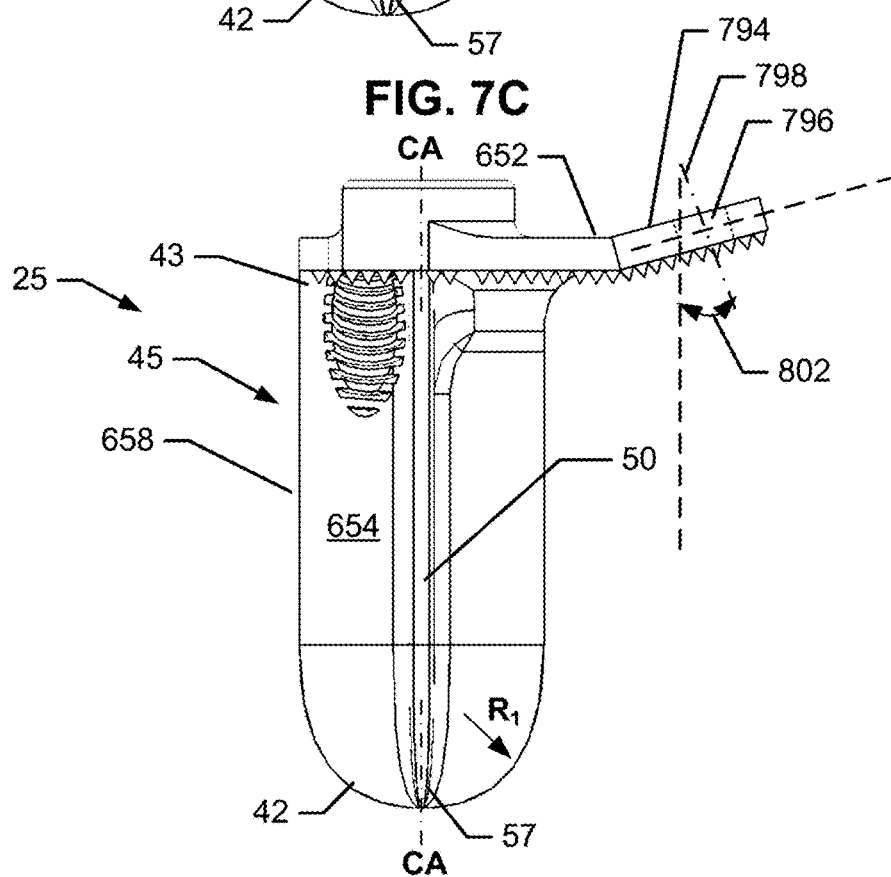
FIG. 7D and FIG. 7E are medial side views of additional alternative embodiments that include proximally bent sections of the attachment elements.

Also in these additional other aspects, the additional attachment plate 794 may project at a variety of orientations relative to the attachment element 652 of the implant body 45. In one aspect, the additional attachment plate 794 may project in a proximal direction as illustrated in FIG. 7B and FIG. 7C, as well as in side view in FIG. 8B. In this one aspect, the additional bore axis 798 is essentially perpendicular to the proximal-distal center axis CA. In a second aspect, illustrated in FIG. 8C the additional attachment plate 794 may project at an angle such that the additional bore axis 798 is shifted an angle 800 away from perpendicular to the proximal-distal center axis CA. In a third aspect, the additional attachment plate 794 may project in a cranial or caudal direction as illustrated in FIG. 7D and the additional bore axis 798 may be deflected at an angle 802 relative to the proximal-distal center axis CA.

The angle at which the additional attachment plate 794 projects may be preformed in the implant assembly 25, or the angle may be set and or adjusted by deforming the additional attachment plate 794 along the edge at which the additional attachment plate 794 joins the attachment element 652. By way of non-limiting example, a surgeon may select an implant assembly 25 with a preformed additional attachment plate 794 in order to achieve a closer fit of the regions of the implant assembly 25 with the local topology of the underlying bone tissue. In another non-limiting example, a surgeon may iteratively deform an additional attachment plate 794 during a surgical procedure in order to fine-tune the closeness of fit of the implant assembly 25 within the surgical region.

Figure 7E:
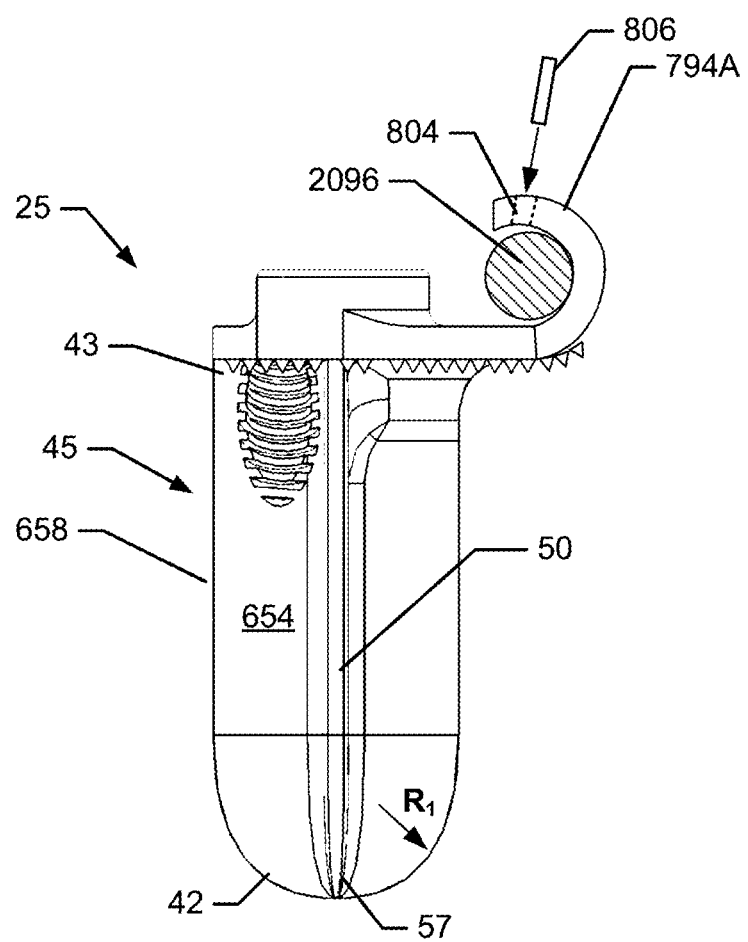

In various other aspects, the additional attachment plate 794 may be non-planar and may contain accessory bores configured to contain accessory fasteners used for purposes other than securing the implant assembly 25 in place. In one aspect, the additional attachment plate 794 may project in a curved profile as illustrated in FIG. 7E. In this example, the curved additional attachment plate 794A may contain an accessory bore 804 configured to receive a set screw or pin 806. As illustrated in FIG. 7E, the curved additional attachment plate 794A may form a fitting within which a rod 2096 or other element of a spinal stabilization system may be secured using the set screw or pin 806.

Figure 13B:
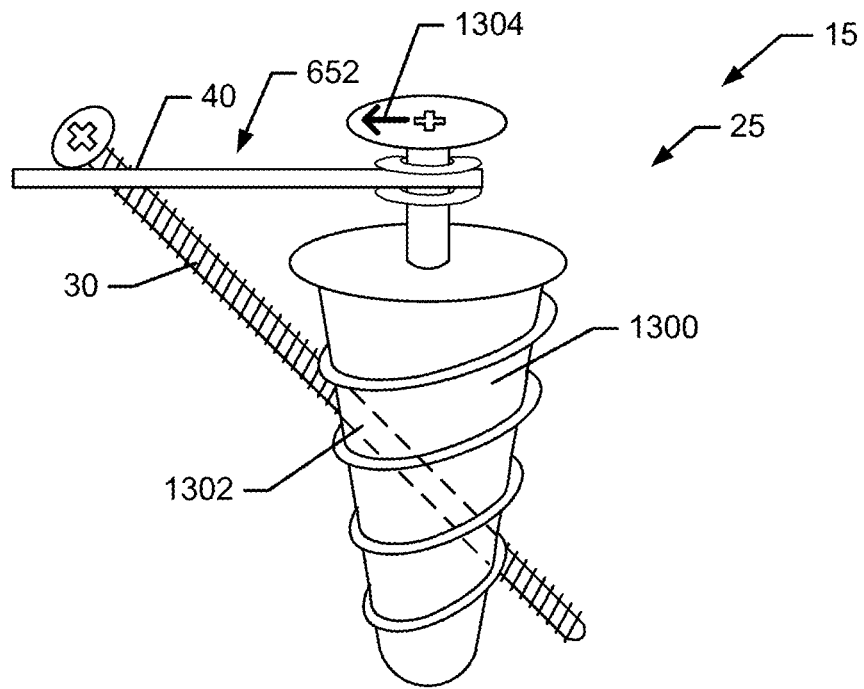
FIG. 13B and FIG. 13C are cranial side and top views, respectively, of an implant system that includes an anchor, a rotatable insertion element, and an indicator indicating an alignment of a bore of the rotatable insertion element with a bore of the attachment element.
Figure 13C:
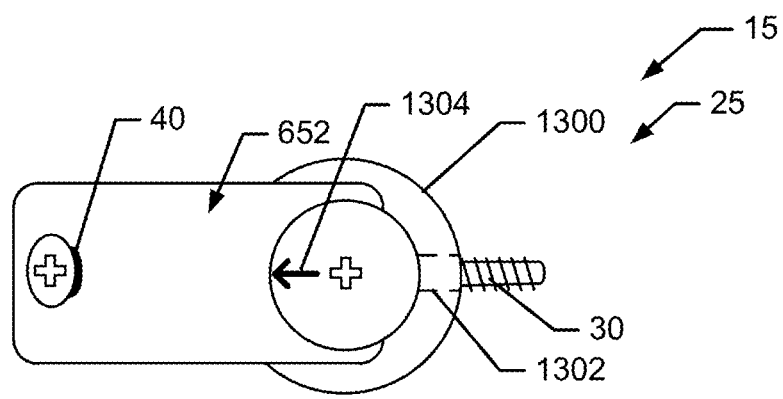

In yet other additional embodiments, the additional bore 670 may be provided within certain elements of the implant assembly 15 that may require alignment in addition to the alignment inherently provided by the delivery tool. In one embodiment, illustrated as cranial and side views in FIG. 13B and FIG. 13C, the implant assembly 15 may include an anchor 30 inserted through a bore 1302 formed through a rotatable insertion element 1300. The rotatable insertion element 1300 may be helically threaded as illustrated in FIG. 13B and may be driven into the joint space of the sacroilial joint using torques delivered by an insertion tool (not shown). In this embodiment, an indicator 1304 may be provided to indicate an alignment of the bore 1302 of the rotatable insertion element 1300 with a bore 40 of the attachment element 652.

ii. Attachment Element

Referring back to FIG. 5, the implant body 25 may further include an attachment element 652 configured to provide a guide 505 for the attachment fitting 500 that provides robust mechanical anchoring throughout a predetermined range of positions and orientations. In addition, the attachment element 652 is configured to receive the anchor 30 through a bore 40 formed in the attachment element 652. The bore 40 permits the insertion of the anchor 30 through the implant body 25 and into the underlying bone tissue at a predetermined range of positions and orientations.

In one embodiment, the attachment element 652 may include a lateral edge 672 that is mechanically attached to the proximal end 43 of the insertion element 650. In another embodiment, the attachment element 652 may include a medial edge 671 that is mechanically attached to the proximal end 43 of the insertion element 650. In an additional embodiment, the lateral edge 672 of the attachment element 652 may be welded, glued, joined using fasteners such as screws, or otherwise permanently attached at a fixed position and angle to the proximal end 43 of the insertion element 650 as illustrated in FIG. 5. In another embodiment, the attachment element 652 and the insertion element 650 may be formed as a single integrated structural element. In yet other embodiments, the lateral and/or medial edges of the attachment element 652 may be attached to the proximal end 43 of the insertion element 650 in a hinged attachment such that the angle formed between the insertion element 650 and the attachment element 652 may be varied within a predetermined range prior to fixing within the sacroiliac joint space to accommodate variations in patient morphologies.

FIG. 8 illustrates the angle θ formed between the insertion element 650 and the attachment element 652. In various embodiments, this angle θ may range between approximately 30° and approximately 120° to accommodate a range of patient morphologies. In one embodiment, the angle θ may be approximately a right angle, or may be approximately 90°, as illustrated in FIG. 8. Any intersection between attached edges of various elements of the implant body including, but not limited to, the insertion element 650 and the attachment element 652 may include filleting, chamfering and/or ribbing along the interior and/or exterior corners.

In one embodiment, a variety of implant bodies 25 with a range of angles θ may be provided, and an implant body 25 with a particular angle θ that most closely matches the morphology of the patient to be treated may be selected for use. In another embodiment, a single implant body 25 in which the lateral or medial edge of the attachment element 652 and the proximal end 43 of the insertion element 650 are attached in a hinged attachment may provide a variable angle θ that may be customized to best accommodate the patient's morphology during the insertion of the implant body 25 into the sacroiliac joint space of the patient. In yet another embodiment, an implant body 25 with an initial angle θ in which the implant body 25 may be elastically and/or plastically deformed to alter the angle θ within a predetermined range (e.g., by a medical person) may be provided to the surgeon. In this other embodiment, a practitioner including, but not limited to a surgeon or other medical person, an apparatus, a surgical robot or a computer controlled device may deform the implant body 25 to accommodate the patient's morphological variation prior to inserting the implant body 25 into the sacroiliac joint space of the patient.

1. Anchor Fitting

In various embodiments, the attachment element 652 may include an anchor fitting 40 configured to receive an anchor 30. The anchor fitting 40 mechanically interacts with the anchor 30 to mechanically fix the insertion plate 45 within the sacroiliac joint space of the patient. Referring back to FIG. 5, the anchor fitting 40 may be provided in the form of an open bore 40. In one embodiment, the open bore 40 may be provided with a bore diameter sufficiently large to permit limited mechanical play such that the anchor 30 may be inserted through the bore 40 throughout a range of insertion angles. In another embodiment, one or more portions of the attachment element 652 situated near an anchor fitting 40 may be further configured like a Steffee plate. In various other embodiments, the bore 40 may have any cross-sectional profile without limitation. Non-limiting examples of cross-sectional profiles suitable for the bore 40 include: circular, oval, slotted, square, rectangular and/or any combination and permutation of any cross-sectional profile.

Figure 14:
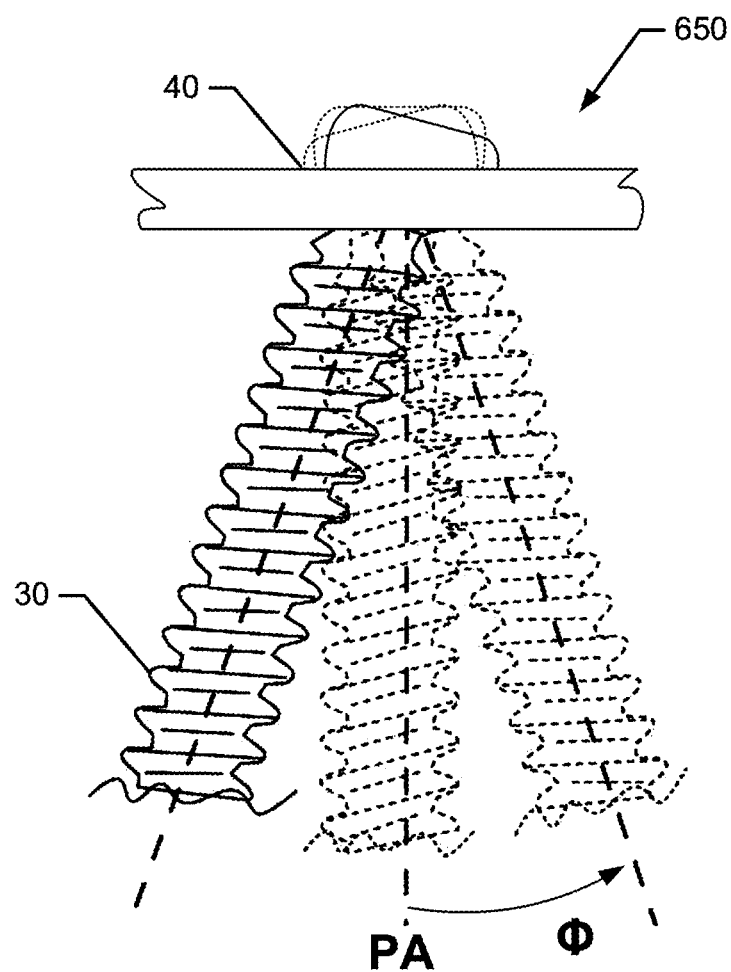
FIG. 14 is a general side view of a section of the attachment element according to certain embodiments showing the anchor inserted through the anchor fitting at various anchor insertion angles.

FIG. 14 is a side view of a section of the attachment element 652 showing the anchor 30 inserted through the anchor fitting 40 in one embodiment. As illustrated in FIG. 14, the anchor may be inserted at any of a variety of insertion angles Φ. The insertion angle Φ, as defined herein refers to an angle relative to a perpendicular axis PA aligned perpendicular to the attachment element 652. In one embodiment, the attachment element 652 may be provided with a non-planar or contoured profile; in this embodiment, the perpendicular axis PA may be aligned perpendicular to a region of the attachment element 652 in close proximity to the bore 40. In another embodiment, the insertion angle Φ may range between approximately 0° (i.e. perpendicular to the attachment element 652) and approximately 45°. In another embodiment, the insertion angle Φ may be directed in any direction without limitation including, but not limited to anterior, lateral, medial, cranial, caudal, anterior, posterior, ventral, dorsal, and any intermediate direction without limitation. Other desired trajectories and starting locations are discussed throughout herein.

Figure 16A:
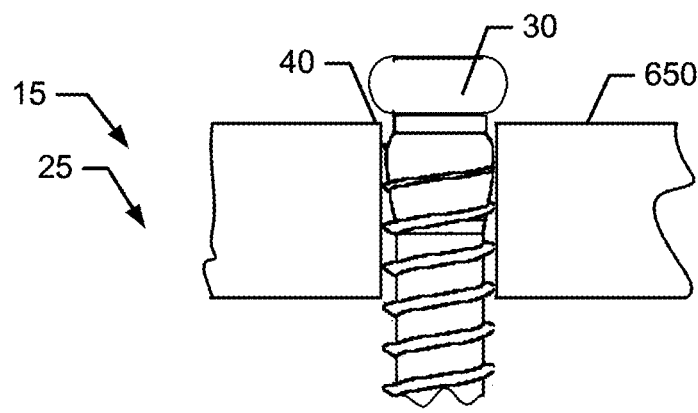
FIG. 16A is a cross-sectional view of a vertical bore with a constant cross-sectional diameter.
Figure 16B:
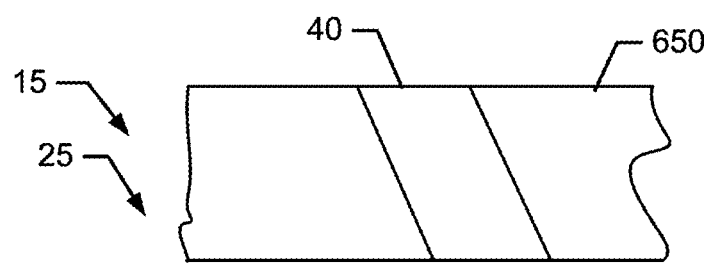
FIG. 16B is a cross-sectional view of an angled bore with a constant cross-sectional diameter.
Figure 16C:
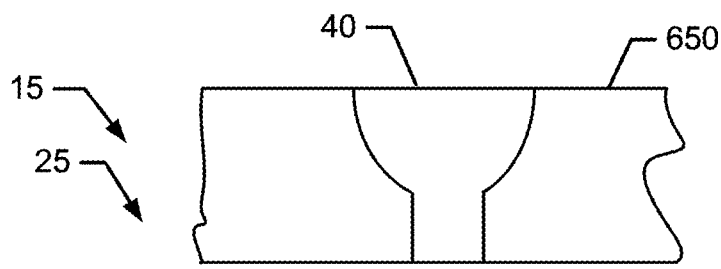
FIG. 16C is a cross-sectional view of a vertical bore with a hemispherical cross-sectional segment.
Figure 16D:
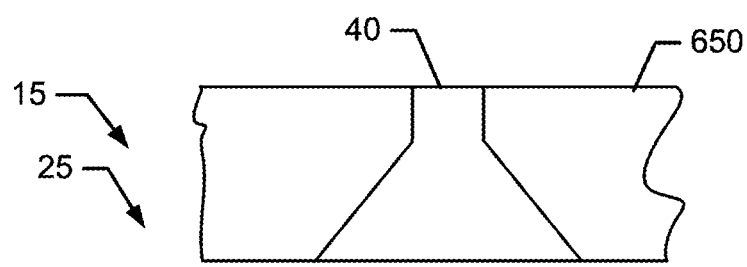
FIG. 16D is a cross-sectional view of a vertical bore with a conical cross-sectional segment.
Figure 16E:
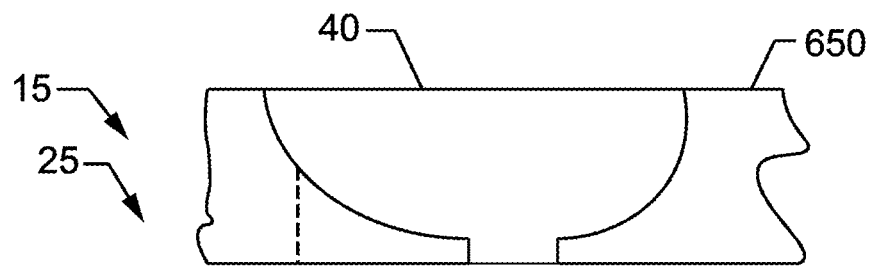
FIG. 16E is a cross-sectional view of a vertical bore with a "compression plate" cross-sectional contour.
Figure 16F:
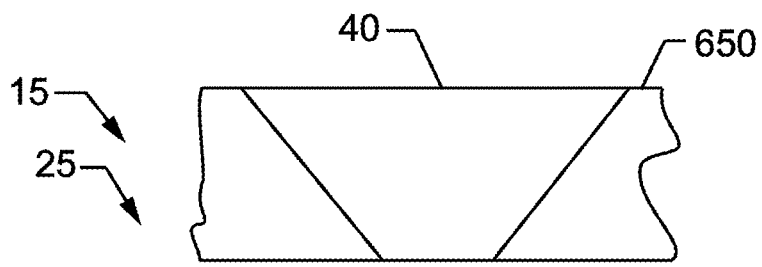
FIGS. 16F-16G are cross-sectional views of additional bore cross-sectional contours.
Figure 16G:
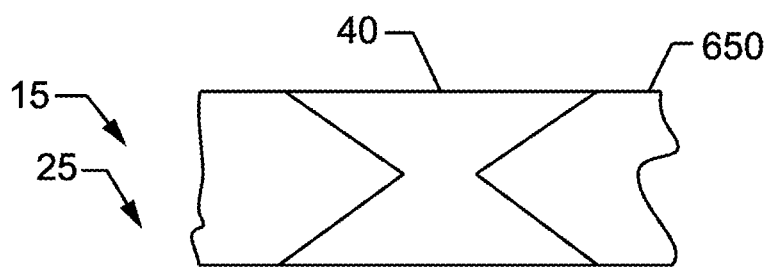

In various embodiments, the anchor insertion angle may be constrained to varying degrees by variations in the cross-sectional profile of the bore 40. FIGS. 16A-16D are a series of cross-sectional views of the cross-sectional anchor bores 40 in various embodiments. In one embodiment, the bore 40 may be a vertical bore with a constant diameter cross-sectional profile as illustrated in FIG. 16A; an anchor 30 is shown inserted in the bore 40 to provide the orientation of the view. FIG. 16B illustrates an angled bore 40 with a constant diameter cross-sectional profile. The embodiment illustrated in FIG. 16C is a bore 40 that includes a hemispherical cross-sectional profile configured to permit a wider range of anchor insertion angles. FIG. 16D is illustrates a bore 40 that includes a conical cross-sectional profile configured to permit a wider range of anchor insertion angles.

Referring to FIGS. 9 and 13, the anchor fitting 40 may act in cooperation with an additional bore 670 formed in the insertion element 652 as described previously herein. In this embodiment, the insertion path of the anchor 30 through the bore 40 and additional bore 670 may permit relatively limited mechanical play, thereby constraining the anchor insertion angle to a relatively narrow range. In another embodiment, the additional bore 670 may be provided in the form of a slot to provide for a wider range of mechanical play and permitted anchor insertion angles.

Figure 15A:
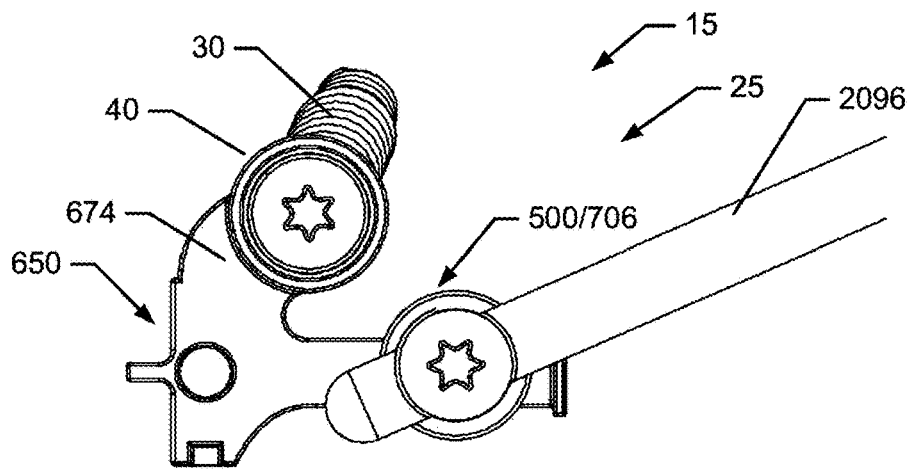
FIG. 15A is a top view of the implant body in the third embodiment with the anchor inserted in a distal direction.
Figure 15B:
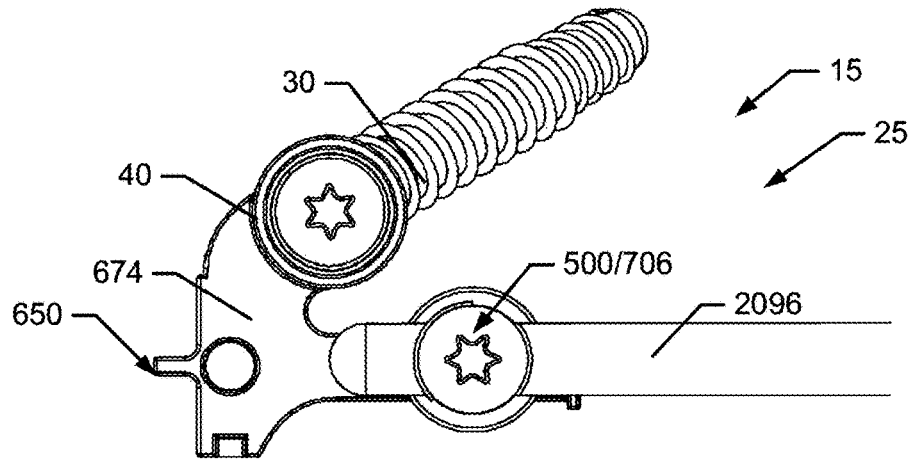
FIG. 15B is a top view of the implant body in the third embodiment with the anchor inserted in a medial direction.
Figure 15C:
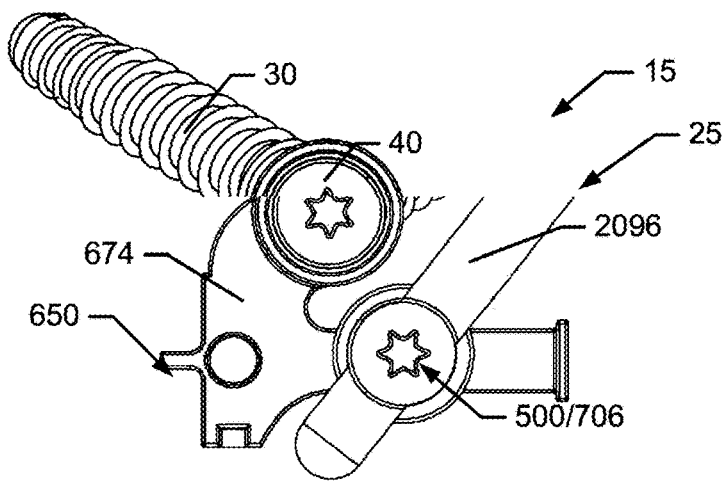
FIG. 15C is a top view of the implant body in the third embodiment with the anchor inserted in a lateral direction.

In various embodiments including, but not limited to the implant bodies 25 illustrated in FIG. 5 and FIG. 9, the anchor fitting 40 may be provided as a bore, a slot, or any other suitable fastener guide formed in an essentially planar material. In various other embodiments, the anchor fitting 40 may be a discrete structure mechanically attached to an anchor support element of the attachment element 652. Referring back to FIG. 12, the anchor fitting 40 may be provided in the form of an anchor socket 40 mechanically attached to an anchor support element 674. In this embodiment, the anchor socket 40 may be configured to permit anchor insertion angles through a relatively wide range of angles and directions. FIGS. 15A-15C are top views of the implant assembly illustrated in FIG. 12, illustrating anchors 30 inserted into anchor sockets 40 at a variety of anchor insertion angles and directions. The anchor 30 may be inserted at a relatively vertical insertion angle as illustrated in FIG. 15A, in a more medial direction as illustrated in FIG. 15B, or in a more lateral direction as illustrated in FIG. 15C.

The anchor support element 674 is configured to mechanically hold the anchor fitting 40 in a fixed position and orientation in various embodiments. In one embodiment, the anchor fitting 40 may be attached in a fixed position to the anchor support element 674. Referring back to FIG. 12, the anchor support element 674 may have a rectangular cross-sectional profile to provide a fixed support for the anchor fitting 40 that is resistant to rotation. In general, the anchor support element 674 may have any cross-sectional shape without limitation. In another embodiment, the anchor support element 674 may have a circular cross section to permit the rotation of the anchor fitting 40 about the anchor support element 674 to permit a wider range of anchor insertion angles and directions.

Figure 17:
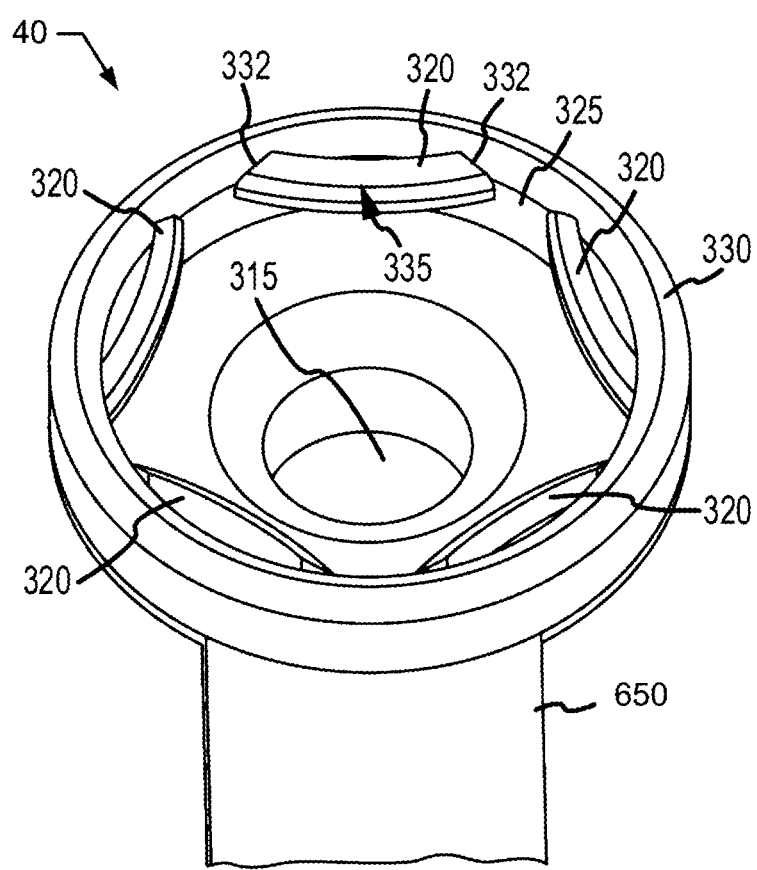
FIG. 17 is front view of an anchor fitting with an anchor retention feature in one embodiment.

In one embodiment, the anchor fitting 40 may be provided with additional anchor retention features to retain the anchor 30 in place during long-term use of the implant assembly 15. As illustrated in FIG. 17, which is an enlarged view of the anchor fitting 40, the anchor fitting 40 has a plurality of arcuate members 320 distributed along an inner circumferential boundary 325 of a rim 330 of the anchor fitting 40. There may be five or more or less arcuate members 320 distributed generally evenly about the inner circumferential surface 325 of the rim 330.

In one embodiment, each arcuate member 320 has ends 332 that intersect the inner circumferential surface 325 of the rim 330, with a center point 335 of the arcuate member 320 that is offset or spaced apart from inner circumferential surface 325 of the rim 330. Thus, in one embodiment, the arcuate members 320 may be deflectable so as to allow the head of the anchor member 30 (not shown) to pass between the center points 335 of the members 330 as the head of the anchor member 30 is seated in the anchor fitting 40. As a result, the arcuate members 320 can act against the head of the anchor member 30 to prevent the anchor member 30 from working its way out of the anchor fitting 40 and opening 315 of the implant body 25, thereby serving as an anchor member locking mechanism.

In another embodiment, the anchor fitting 40 may be provided with additional anchor retention features, such as a set screw, to retain the anchor 30 in place during long-term use of the implant assembly 15.

2. Anchor

Referring again to FIG. 4 and FIG. 5, an anchor 30 may be used to mechanically fix the insertion blade 45 of the insertion element 650 within the joint space of the sacroiliac joint in various embodiments. The anchor 30 may be in the form of an elongated body such as, for example, a nail, rod, pin, threaded screw, expanding body, a cable (e.g., configured with a ball end), etc. The anchor element 30 is configured to be received in a bore 40 defined through the implant body 25. According to particular embodiments, the anchor 30 includes a flange located proximal to a threaded portion and protruding beyond the main anchor shaft diameter and sized larger than the attachment element bore in order to resist pullout and may further include a proximal end configured to allow the attachment of an attachment fitting including, but not limited to a poly-head attachment fitting.

Figure 30:
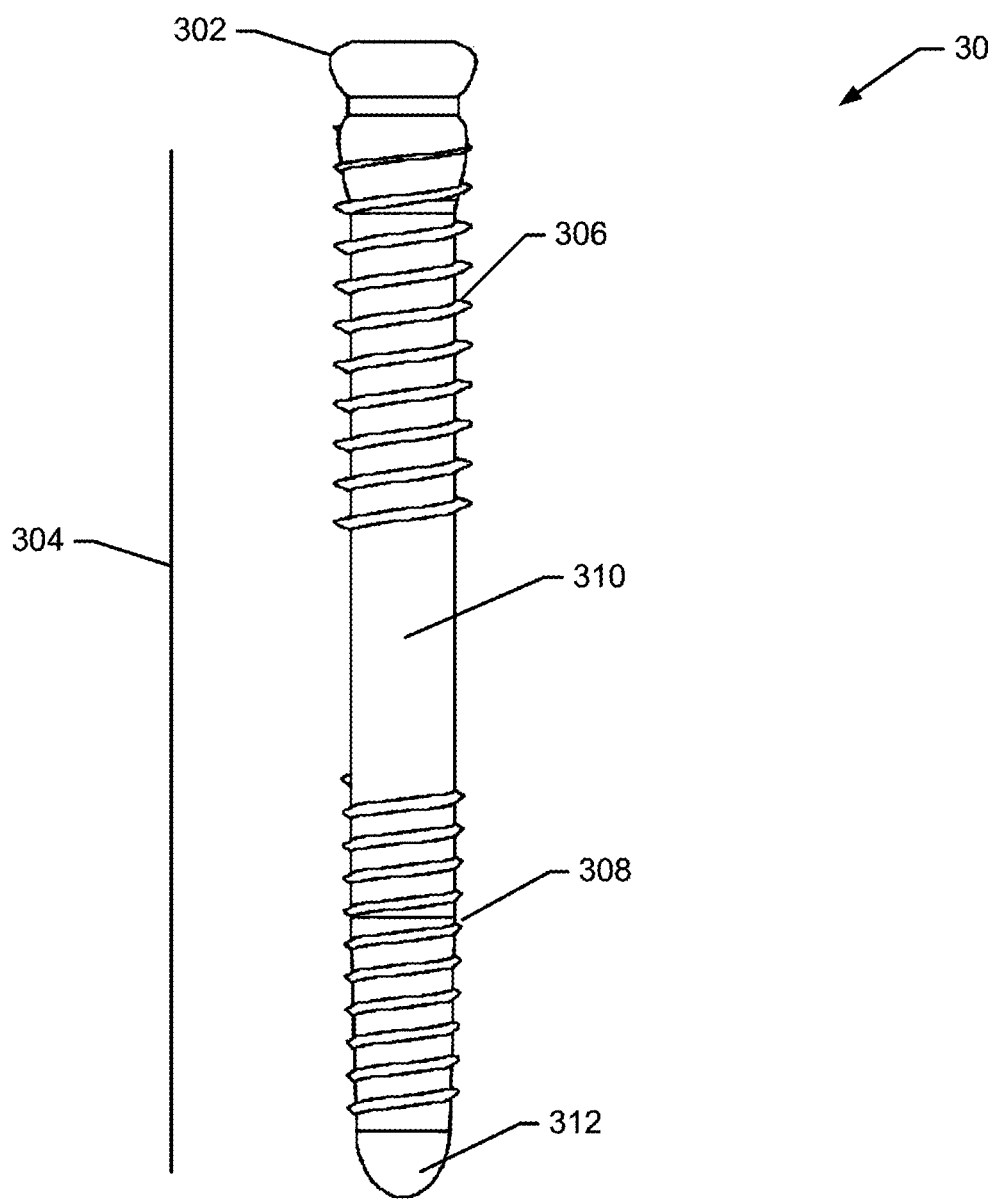
FIG. 30 is a side view of an anchor in a first embodiment.

In one embodiment, the anchor 30 may be a bone screw. Any suitable orthopedic-grade bone screw may be used as the anchor 30 including, but not limited a cortical screw, a cancellous screw, a Steffee screw, and any other suitable orthopedic bone screw. FIG. 30 is a side view of an anchor 30 in one embodiment. The anchor 30 may include a head 302 and a shaft 304. In various embodiments, the shaft 304 may be threaded along the full length of the shaft. The threads may be configured for insertion into cortical bone and/or cancellous bone in various other embodiments. The threads and/or shaft may be tapered. In various other embodiments the anchor 30 may be cannulated along the longitudinal axis of the anchor 30. Additionally, the anchor 30 may be provided with bone windows communicating with the lumen of the cannulated anchor 30.

Figure 31:
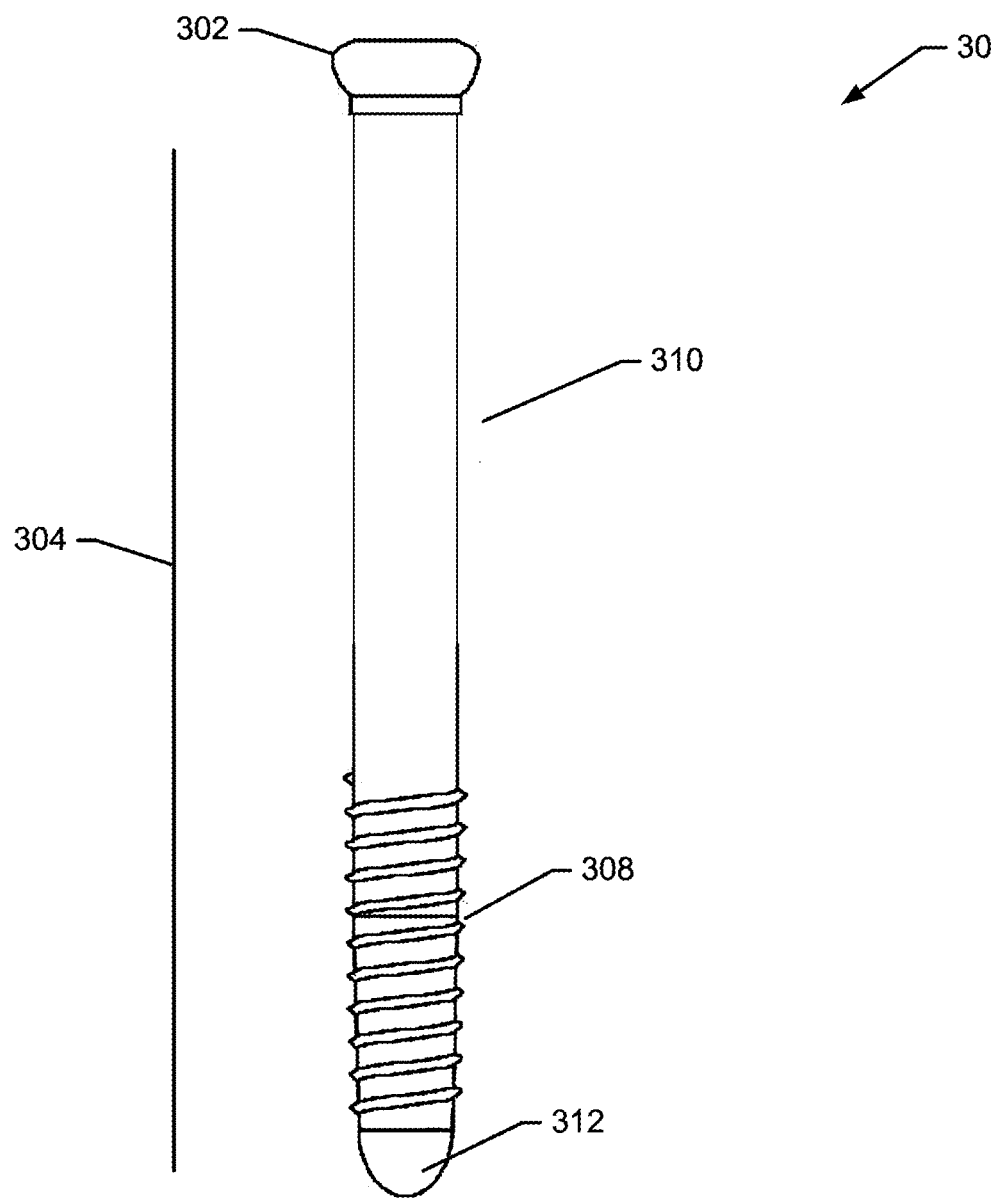
FIG. 31 is a side view of an anchor in a second embodiment.

In one embodiment, the shaft 304 may contain one or more threaded segments including, but not limited to a proximal threaded segment 306 and a distal threaded segment 308 as illustrated in FIG. 30. The shaft 304 may further include one or more non-threaded segment 310. In one embodiment, the non-threaded segment may be situated between the proximal threaded segment 306 and the distal threaded segment 308, as illustrated in FIG. 30. FIG. 31 is a side view of an another embodiment of the anchor 30, in which the non-threaded segment 310 is situated between the head 302 and the distal threaded segment 308; this embodiment may function as a lag screw.

Referring back to FIG. 30, the proximal threaded segment 306 and the distal threaded segment 308 may include similar thread patterns or dissimilar thread patterns according to the intended use of the anchor 30. The anchor 30 may be inserted within the sacrum 1004, which contains largely cancellous bone and may be additionally be inserted within the ilium, which contains cortical bone. In addition, the anchor 30 may receive additional threaded fasteners including but not limited to threaded nuts, threaded sleeves, and other threaded fittings associated with elements of the spinal stabilization system. In various embodiments, one or more washers including, but not limited to curved washers and/or locking washers may be used in conjunction with the anchor 30 and/or any additional threaded fasteners. In various embodiments, the one or more threaded segments may be provided with any one or more thread patterns including, but not limited to a cortical thread pattern, a cancellous thread pattern, a metal screw thread pattern, and any other appropriate thread pattern known in the art.

In one embodiment, the proximal threaded segment 306, which may be situated within the sacrum, may be provided with a cancellous thread pattern, as illustrated in FIG. 30. In this same embodiment, the distal threaded segment 308, which may be situated within the ilium, may be provided with a cortical thread pattern.

The anchor 30 may further include a tip 312 situated on a distal end of the shaft 304 opposite to the head 302. In one embodiment, the tip 312 may be a rounded tip as illustrated in FIG. 30. In other embodiments, the tip 312 may be self-tapping tip or any other suitable tip for an orthopedic bone screw known in the art.

Figure 32:
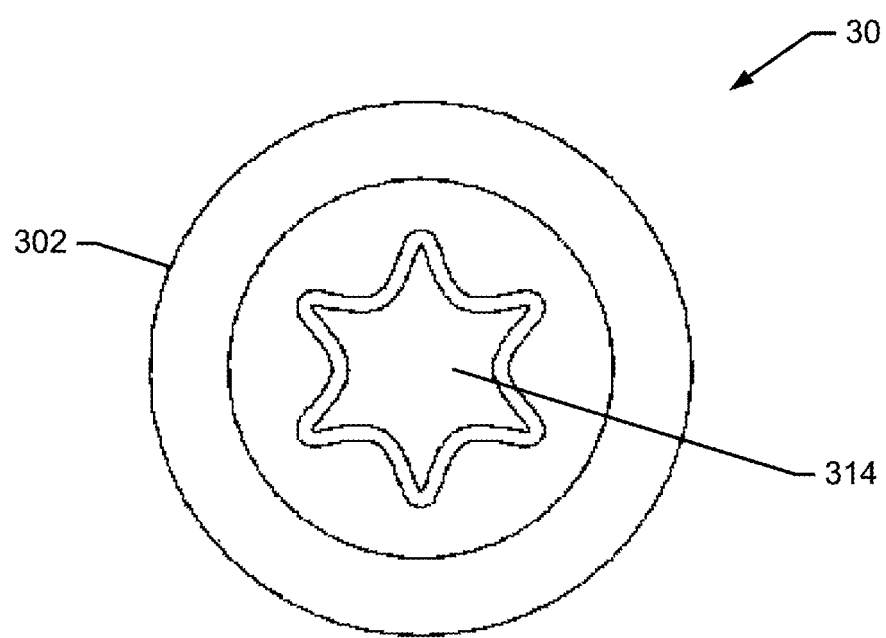
FIG. 32 is a top view of the anchor in the first embodiment.

The head 302 of the anchor 30 may be provided with any known screw head shape including, but not limited to: round, flat, hexagonal, square, and any other known screw head shape. Referring back to FIG. 30, the head 302 may be a round head in one embodiment. A top view of the head 302 is illustrated in FIG. 32. The head 302 may include a screwdriver fitting 314 configured to receive a screwdriver blade or fitting. The screwdriver fitting shape may be any known fitting shape including, but not limited to: a single slot, a cross insert (Phillips head fitting), a hexagonal inset, a star-shaped inset (TORX fitting), and any other known fitting shape.

Figures 33A, 33B:
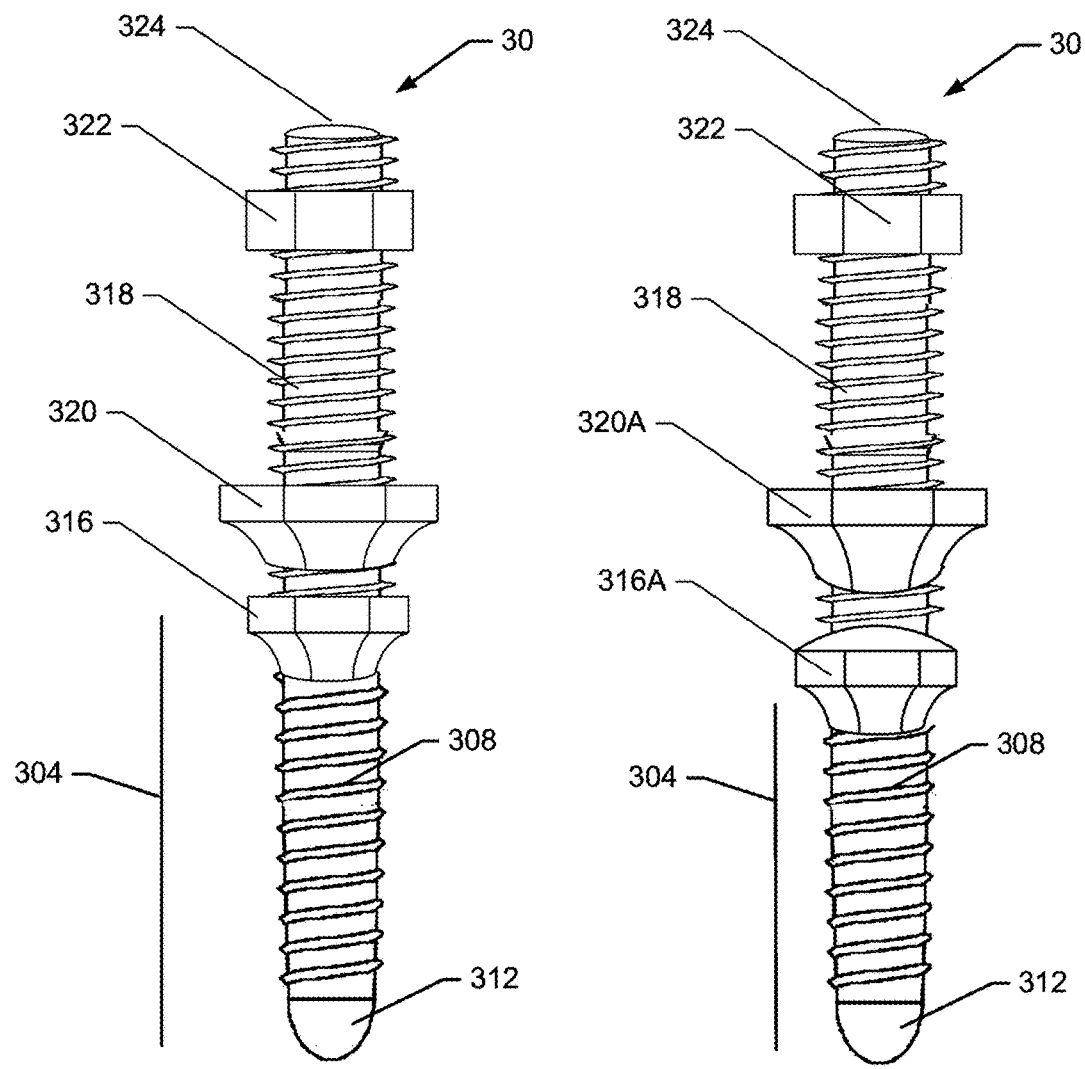
FIG. 33A is a side view of a Steffee-type anchor in one embodiment.
FIG. 33B is a side view of a Steffee-type anchor in a second embodiment including a nut and a driver segment configured with rounded/curved opposing faces to allow different angles between an anchor and plate.

In an additional embodiment, the anchor 30 may be a Steffee-type screw, as illustrated in side view in FIG. 33. The Steffee-type anchor 30 may include the shaft 304, the distal threaded portion 308, and the distal tip 312, as in previous anchor 30 embodiments. In addition, the Steffee-type anchor may include a driver segment 316 configured to be compatible with a known screwdriving or bolt insertion tool including, but not limited to, a wrench. For example, the driver segment 316 may have a hexagonal cross-section, thereby rendering the driver segment 316 compatible with a hexagonal wrench. In addition, the Steffee-type anchor 30 may include a threaded attachment segment 318 ending in a headless proximal end 324. The headless proximal end provides the ability for additional fastener elements to be attached to the threaded attachment segment 318 including, but not limited to a first nut 320 and/or and a second nut 322.

Figure 34A:
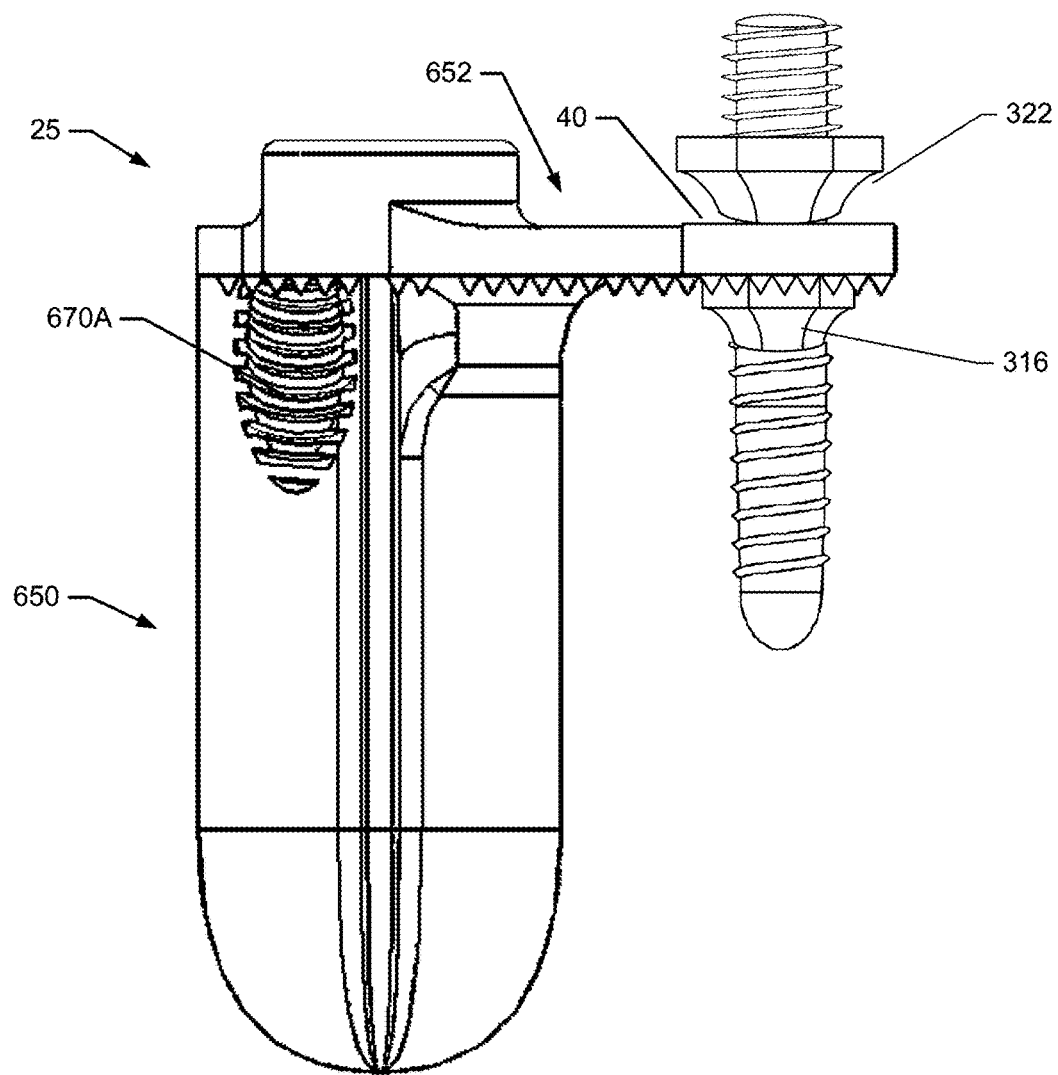
FIG. 34A is a medial side view of the implant body of the first embodiment secured using the Steffee-type anchor illustrated in FIG. 33A.
Figure 34B:
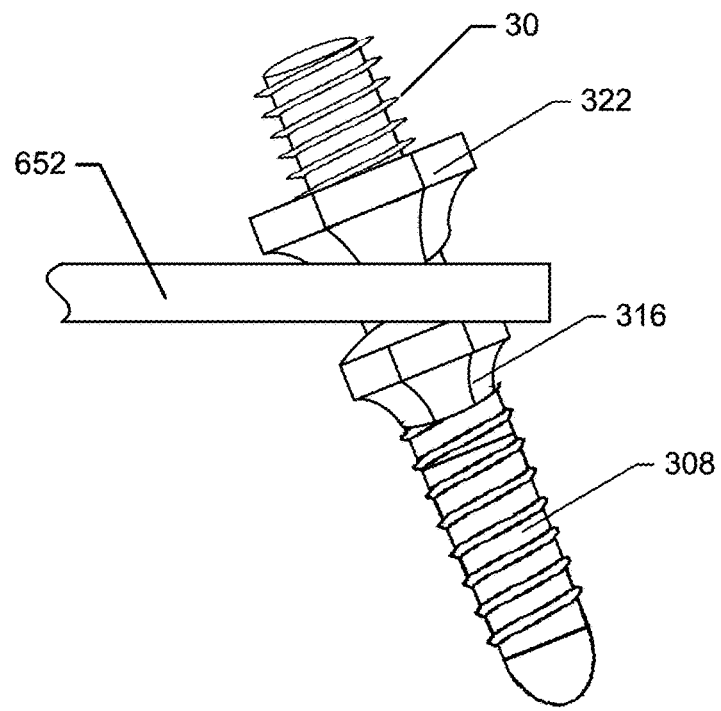
FIG. 34B is a medial side view of the implant body of the first embodiment secured using the Steffee-type anchor illustrated in FIG. 33B in which the longitudinal axis of the anchor is secured in a non-perpendicular alignment relative to the surface of the attachment element.
Figure 34C:
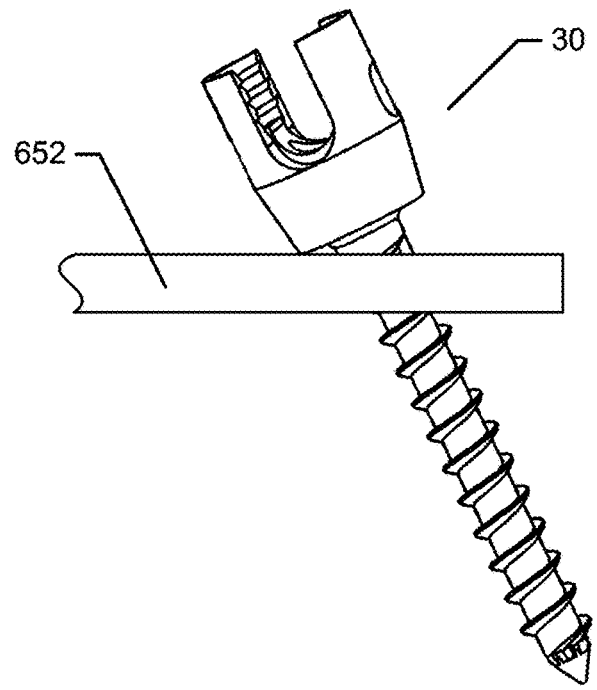
FIG. 34C is a medial side view of the implant body of the first embodiment secured using a polyaxial screw similar to the one illustrated in FIG. 18.

FIG. 34 is a side view of the Steffee-type anchor 30 installed through the bore 40 of an implant body 25 to fix the implant body to the underlying bone tissue. In use, the distal threaded portion 308 may be inserted into the underlying bone tissue using a tool such as wrench attached to the driver segment 316. Once the anchor 30 is situated in place, the implant body 25 may be situated over the protruding distal threaded portion 308 of the anchor such that the bore 40 is centered over the distal threaded portion 308. The implant body 25 may then be situated such that the insertion element 650 is situated within the joint space of the sacroiliac joint. One or more fasteners, such as the second nut 322 may be installed on the distal threaded portion 308 such that the attachment element 652 is sandwiched between the driver segment 316 and the second nut 322, as illustrated in FIG. 34.

In one aspect, the anchor 30 and associated fasteners such the first and second nuts 320 and 322 may be machined, molded, formed, or otherwise manufactured from stainless steel, titanium, ceramic, polymer, composite, bone or other biocompatible materials. The material of the anchor 30 may be compatible for continuous contact with the implant body 25 and associated fasteners.

3. Attachment Fitting

In addition to the anchor fitting 40, the attachment element 652 further includes an attachment fitting 500 in various embodiments. Referring back to FIG. 3, the attachment fitting 500 is configured to attach to an element of a spinal stabilization system including, but not limited to, a rod 2096 in a locked mechanical position, thereby providing robust anchoring to the spinal stabilization system. In various embodiments, the attachment fitting 500 may be provided with one of more features to facilitate the positioning and orientation of the rod 2096 or other element of the spinal stabilization system; typically these one or more features may provide the ability to translate and rotate the attachment fitting in a variety of different directions. In various other embodiments, the attachment fitting 500 is configured to be located on and/or supported off attachment element 652. For example, the attachment fitting 500 may be provided as a monoaxial or polyaxial attachment fitting 500 and the associated attachment element 652 may be configured substantially as a monolithic structural element.

In various embodiments, the attachment fitting 500 is configured to be received by a guide 505 formed within attachment element 652. The guide 505 is configured to effectuate limited translational and rotational movements of the attachment fitting 500 prior to engagement of the attachment fitting 500 with the element of the spinal stabilization system. In addition, the guide 505 is configured to lock the attachment fitting 500 in a fixed position and orientation when the element of the spinal stabilization system is locked into place within the attachment fitting 500.

Referring to FIG. 9, the attachment fitting 500 may be a head 676 of a polyaxial orthopedic fastener 678 including, but not limited to a pedicle screw. In this embodiment, the polyaxial screw 678 may be inserted through a guide 505 in the form of a bore 680. In this embodiment, the bore 680 is similar to the anchor bore 40 illustrated previously in FIG. 5 and discussed herein above. The cross-section profile of the bore 680 may be a slanted profile, as illustrated in FIG. 9, or any other cross-sectional profile discussed herein above for the anchoring bore 40 and illustrated in FIGS. 16A-16D. The cross-sectional profile of the bore 680 may be configured to permit the insertion of the polyaxial orthopedic fastener 678 within a predefined range of fastener angles and directions. In addition to providing an attachment point for an element of the spinal stabilization system, the polyaxial screw may further supplement the implant holding force provided by the anchor 30.

Figure 18:
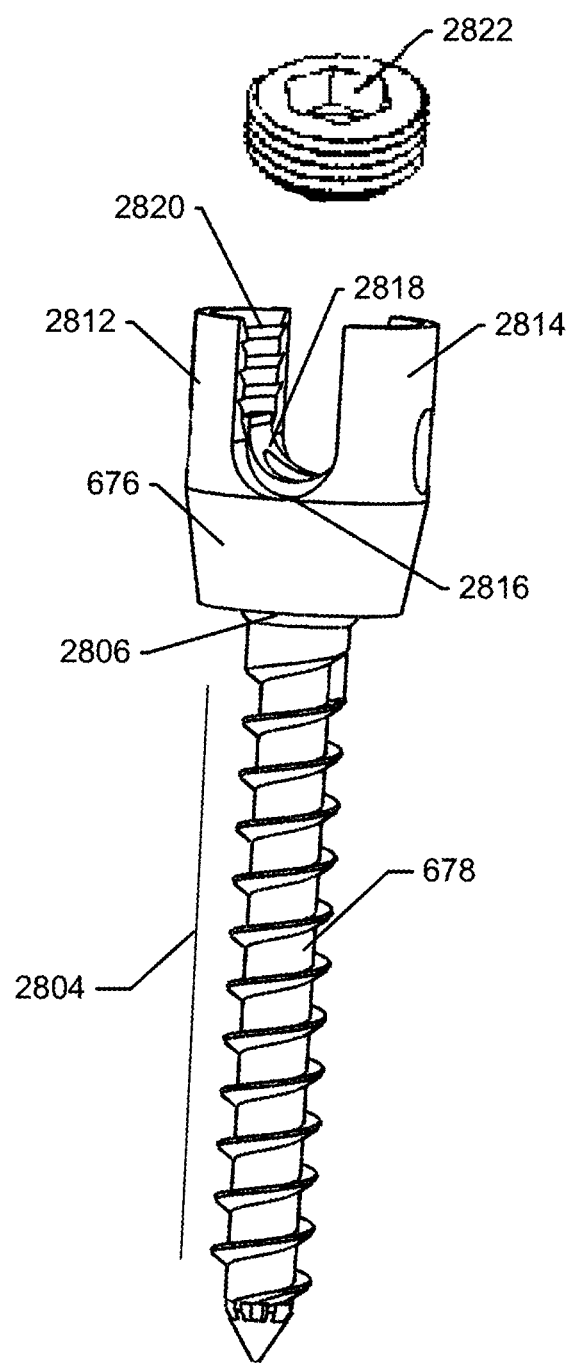
FIG. 18 is a side view of a polyaxial screw in one embodiment.

FIG. 18 is a side view of a polyaxial screw 678 in one embodiment. The head 676 may be provided in the form of a tulip-like head 676 in one embodiment. In this embodiment, the head 676 may include at least two support elements 2812 and 2814 forming the sides of at least one upward-opening groove 2816. The head 676 may further include a compression element 2818 forming the bottom surface of the groove 2816. The inner surfaces of the at least two support elements 2812 and 2814 may further form a threaded fitting 2820 into which a threaded compression nut 2822 may be inserted during use.

In this embodiment, the head 676 may be attached to the top end 2806 of the shaft 2804 such that the head 676 may rotate freely about a longitudinal axis of the shaft 2804 and/or in additional directions offset from the longitudinal axis of the shaft 2804. In use, a rod 2096 (not shown) may be situated within the groove 2816. The compression nut 2822 may be situated within the threaded fitting 2820 and advanced until the reinforcing element is held fixed between the compression nut 2822 and the compression element 2818. In another aspect, the introduction of a compressive force onto the compression element 2818 by the compression nut 2822 via the reinforcement element may further introduce a holding force within the attachment of the head 676 to the top end 2806 of the shaft 2804 such that the head 676 may no longer rotate freely.

In one aspect, the polyaxial screw 678 may be machined, molded, formed, or otherwise manufactured from stainless steel, titanium, ceramic, polymer, composite, bone or other biocompatible materials. The material of the polyaxial screw 678 may be compatible for continuous contact material with the implant body 25.

Referring back to FIG. 4, the attachment fitting 500 may be provided in the form of a dedicated attachment fitting 500 in another embodiment. The attachment fitting 500 includes a tulip-head fitting similar to the head 676 of the polyaxial screw 678 described herein previously. In this other embodiment, the attachment fitting 500 is configured to translate within a guide 505 in the form of a slot 680. Referring back to FIG. 5, the slot 680 includes an opening 682 passing through the attachment element 652. The slot 680 further includes a raised rim 684 protruding in a proximal direction from the attachment element 652 and forming the perimeter of the slot 680.

The slot 680 may define any shape of pathway without limitation including, but not limited to: a straight line; a curve or arc; and any combination thereof. Referring again to FIG. 5 the slot dimensions may include a slot width SW, a slot height SH, and any other relevant slot dimension (not shown) including, but not limited to: slot length, slot curvature, slot orientation, and any other relevant slot dimension. In one aspect, the slot dimensions may be selected to be compatible with elements of the attachment fitting 500.

Figure 19:
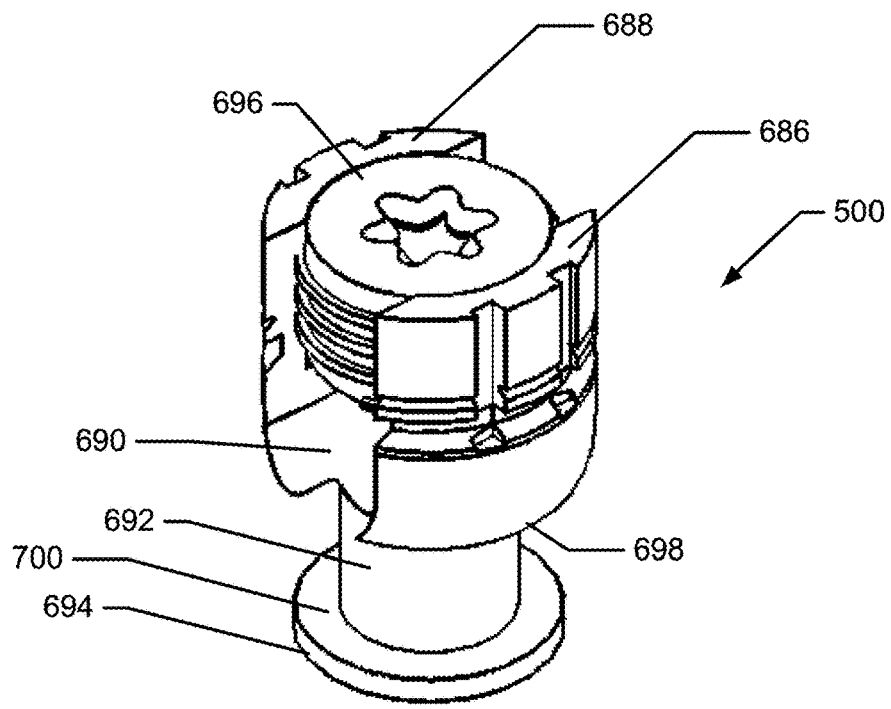
FIG. 19 is a side view of an attachment fitting in one embodiment.
Figure 20:
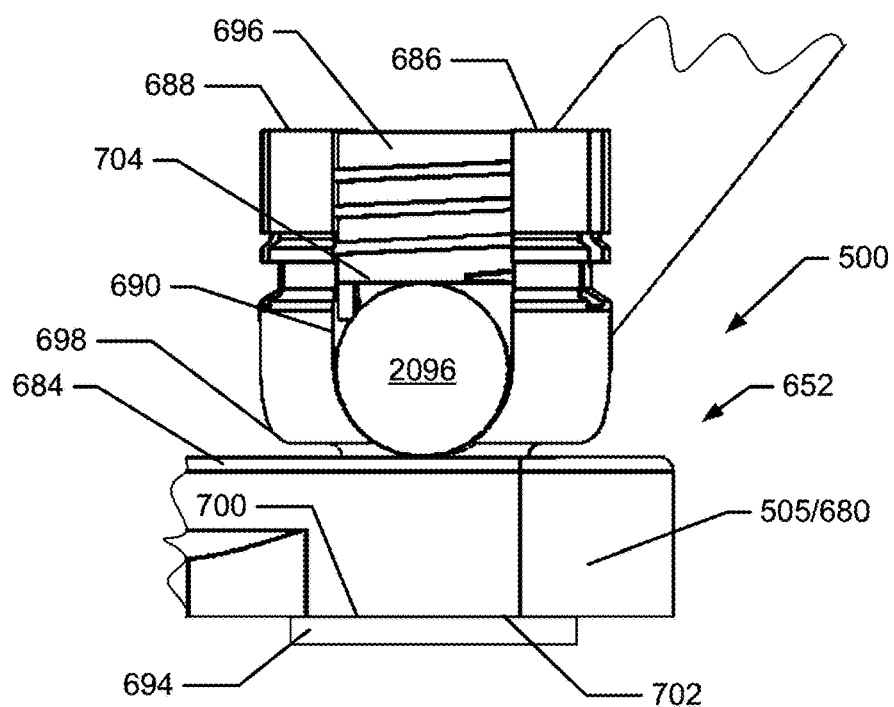
FIG. 20 is a side view of the attachment fitting attached to the rod of a spinal stabilization system and fixed in place on the implant body.

FIG. 19 is an isometric view of the attachment fitting 500 in one embodiment. FIG. 20 is a close-up side view of the attachment fitting 500 in this embodiment. Referring to FIGS. 19 and 20, the attachment fitting 500 may include at least two support elements 686 and 688 forming the sides of at least one upward-opening groove 690. In addition at least two support elements 686 and 688 may be configured to receive a locking nut 696 in a threaded engagement.

In this embodiment, the attachment fitting 500 further includes a shaft 692 configured to pass through the opening 682 of the slot 680 and an expanded distal portion 694. In one non-limiting example, the shaft 692 may be a cylindrical element with a cylinder diameter that is slightly less than the slot width SW. The attachment fitting 500 is retained within the slot 680 due to the mechanical interference of the distal contact surface 700 of the expanded distal portion 694, which protrudes distally from the slot 680. In addition, the diameter of the proximal contact surface 698 of the attachment fitting 500 is larger than the slot width SW to prevent the attachment fitting 500 from passing through the slot in a proximal direction.

In use, a rod 2096 or other element of a spinal stabilization system may be inserted within the groove 690 and held in a fixed attachment within the groove 690 by tightening down the locking nut 696, thereby pressing the rod 2096 against the lower surface 704 of the locking nut 696, the walls of the groove 690, and the raised rim 684 of the slot 680. In addition, the tightening of the locking nut 696 presses the contact surface 700 of the attachment fitting 500 against the distal surface 702 of the slot 680, effectuating a locked mechanic engagement between the attachment fitting 500 and the attachment element 652.

In one embodiment, a spinal rod reducer tool may be used to place a rod 2096 extending from a lumbar spine into or near the attachment fitting 500. In another embodiment, a spinal rod (parallel) distractor may be used to distract a lumbar vertebra situated a distance from one or more elements of the implant assembly 15. In this other embodiment, the lumbar vertebra may be distracted to restore a lost disc height between the lumbar vertebra and an adjacent vertebra including, but not limited to the L5-S1 disc height during a procedure to treat a medical condition. In an additional embodiment, a spinal rod (parallel) compressor may be used to compress and/or draw together certain components of the implant assembly 15 and/or associated tissues. For example, the spinal rod compressor may be used to draw adjacent surfaces of an ilium and a sacrum toward one another during a procedure to treat a medical condition.

In one embodiment, the contact surface 700 of the attachment fitting 500, the distal surface 702 of the slot 680, and the proximal contact surface 698 of the attachment fitting 500 may be essentially planar surfaces. In other embodiments (not shown), these contact surfaces may be curved in order to permit limited rotation about one or more axes to facilitate the placement and alignment of the rod 2096 or other element within the spinal support system.

Figure 21:
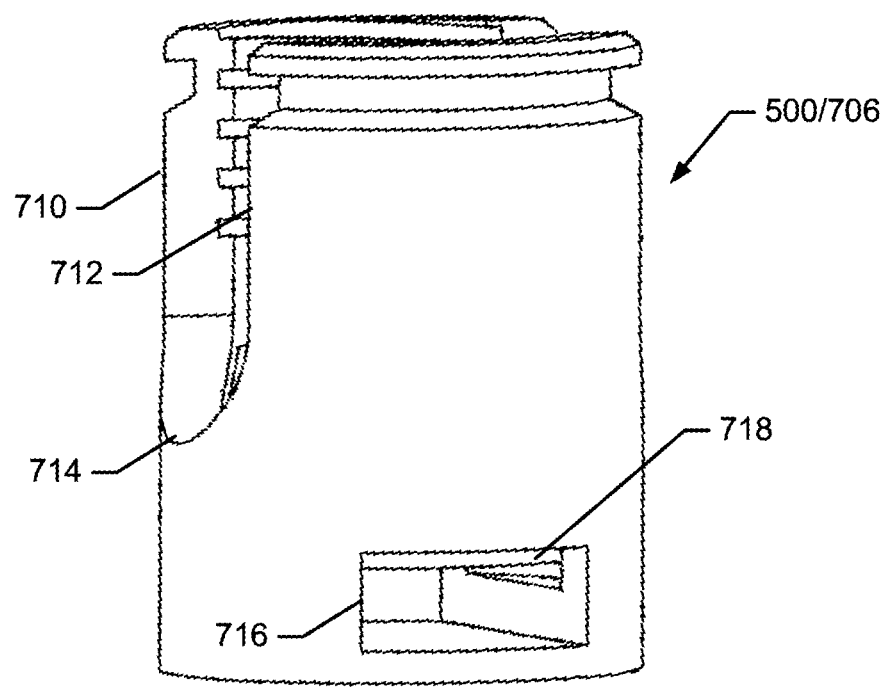
FIG. 21 is an isometric view of a slideable socket in one embodiment.

Referring again to FIG. 12, the attachment fitting 500 may be provided in the form of a slideable socket 706 configured to attach in a reversibly locked mechanical engagement with a guide 505 in the form of a guide rail 708. FIG. 21 is an isometric view of the slideable socket 706 in one embodiment. Referring to FIG. 21, the slideable socket 706 may include at least two support elements 710 and 712 forming the sides of at least one upward-opening groove 714. In this embodiment, the slideable socket 706 may further include a channel 716 configured to receive the guide rail 708 in a sliding engagement. The proximal surface of the channel 716 may be formed by a slideable insert 718 configured to press on the proximal surface of the guide rail 708 to lock the slideable socket 706 onto the guide rail 708 in use.

Figure 22:
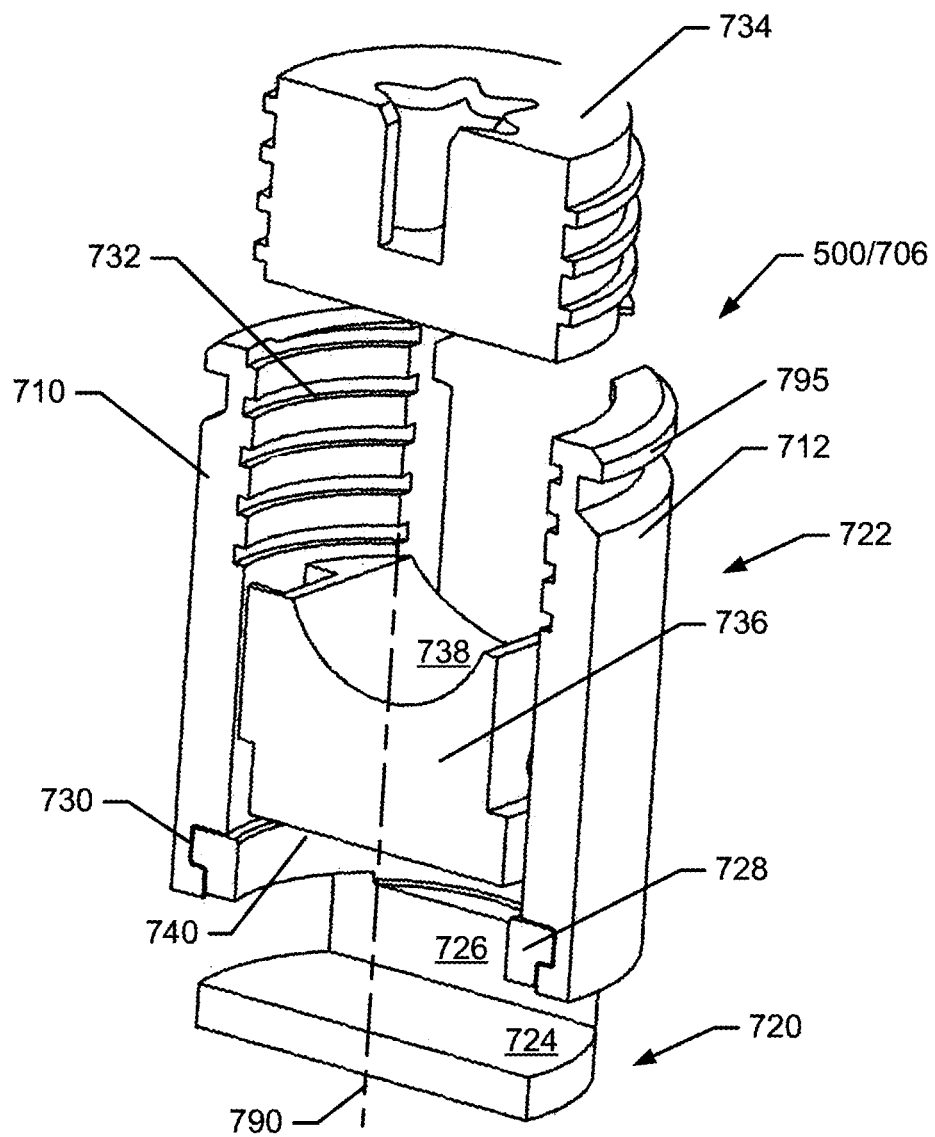
FIG. 22 is a cross-sectional isometric view of the slideable socket in the one embodiment.

FIG. 22 is a cross-sectional isometric view of the slideable socket 706 in another embodiment. In this other embodiment, the slideable socket 706 includes a distal element 720 and a proximal element 722. The distal element 720 forms the lower channel surface 724 and side channel surfaces 726. In addition, the distal element 720 includes a circular flange 728 that slideably engages a corresponding annular channel 730; this slideable engagement allows the proximal segment to rotate about a central axis 790 of the proximal segment 722. This rotation permits the rod 2096 or other element of a spinal stabilization system to be aligned along a wide range of angles, as illustrated in FIGS. 15A-15C.

Referring again to FIG. 22, the proximal portion 722 of the slideable socket 706 includes the at least two support elements 710 and 712 that include a threaded inner surface 732 configured to receive a locking nut 734 in a threaded engagement. Alternatively, the outer surface 795 may be threaded and configured to receive a locking nut (not shown). The proximal portion 722 further includes a slideable insert 736 configured to slide proximally and distally within the essentially cylindrical lumen formed by the at least two support elements 710 and 712. The proximal surface 738 of the slideable insert 736 forms the bottom surface of the groove 714 and the distal surface 740 of the slideable insert 736 forms the proximal surface 718 of the channel 716 illustrated in FIG. 21.

Figure 23:
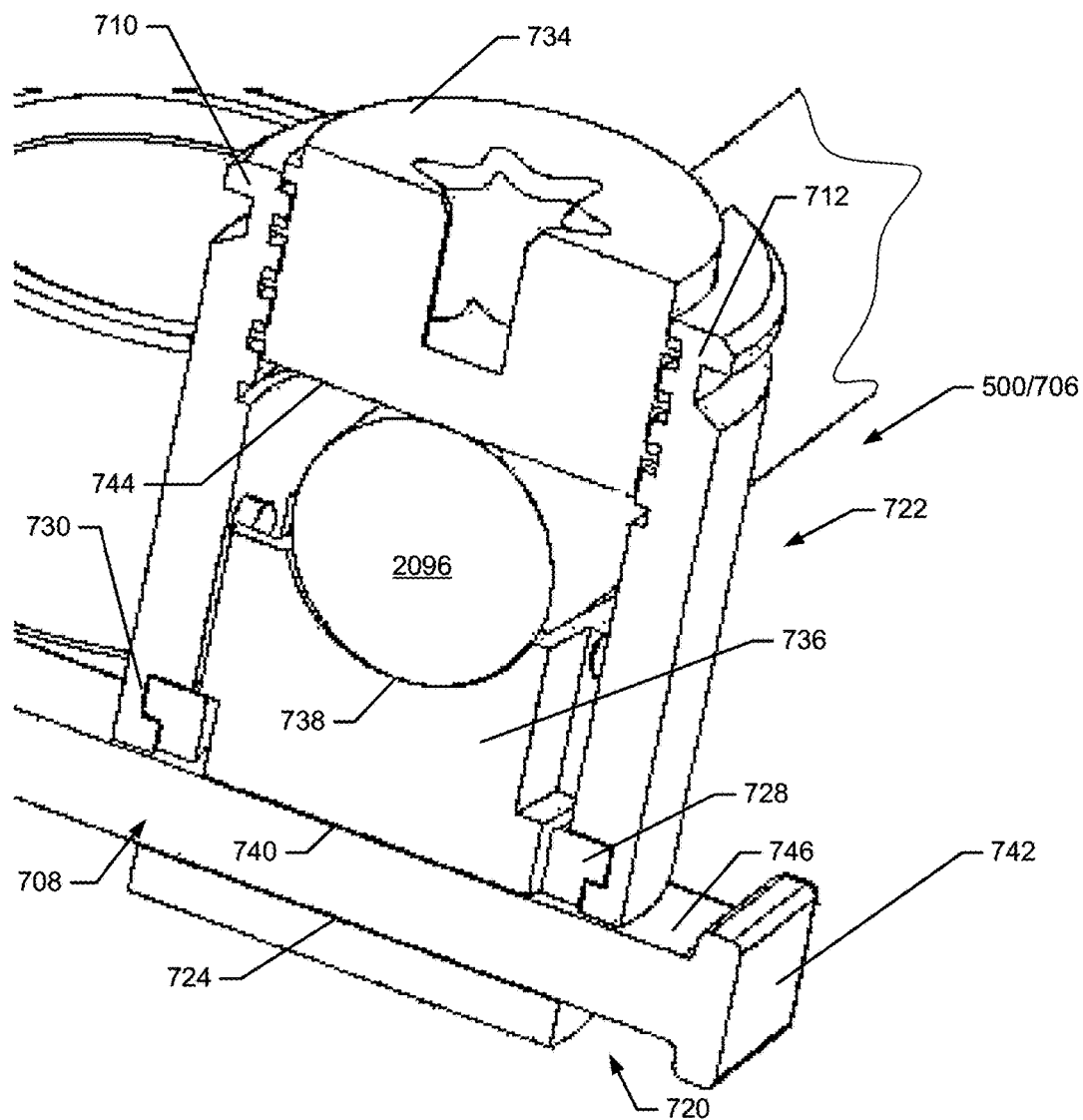
FIG. 23 is a side cross-sectional isometric view of the slideable socket in the one embodiment attached to the rod of a spinal stabilization system and fixed in place on the implant body.

FIG. 23 is a cross-sectional view of the slideable socket 706 mounted on the guide rail 708 and engaging a rod 2096 of a spinal stabilization system in a mechanically locked engagement. In use, the rod 2096 or other element of a spinal stabilization system may be inserted within the groove 714 formed by the proximal surface 738 of the slideable insert 736 and held in a fixed attachment within the groove 714 by tightening down the locking nut 734, thereby pressing the rod 2096 between the lower surface 744 of the locking nut 734 and the proximal surface 738 of the slideable insert 736. As the locking nut 734 is advanced into the slideable socket 706, the slideable insert 736 is shifted in a distal direction until the distal surface 740 of the slideable insert 736 contacts that proximal surface 746 of the guide rail 708. As the locking nut is further tightened, the guide rail 708 is pressed between the distal surface 740 of the slideable insert 736 and the lower surface 724 of the channel 716, thereby mechanically locking the slideable socket 706 in a fixed engagement on the guide rail 708.

In one embodiment, the guide rail 708 may include an end stop 742 with a cross-sectional area that is larger than the cross-sectional area of the channel 716 to prevent the slideable socket 706 from slipping off of the end of the guide rail 708 as illustrated in FIG. 23. In this embodiment, the guide rail 708 has a rectangular cross-sectional shape to prevent the slideable socket 706 from rotating about the longitudinal axis of the guide rail 708 as illustrated in FIG. 21. In general the guide rail may have any cross-sectional shape without limitation so long as the cross-sectional shape and dimensions of the channel 716 permit the insertion of the guide rail 708 in a sliding engagement.

In another embodiment (not shown) the guide rail 708 may have a circular cross-sectional shape to permit the slideable socket 706 to rotate about the longitudinal axis of the guide rail 708, thereby enhancing the ability of the slideable socket 706 to position the rod 2096 of the spinal stabilization system into a desired position and orientation. In this other embodiment, as before, the slideable socket may be locked into place by tightening the locking nut 734 into the slideable socket 706 as described herein previously.

Figure 10D:
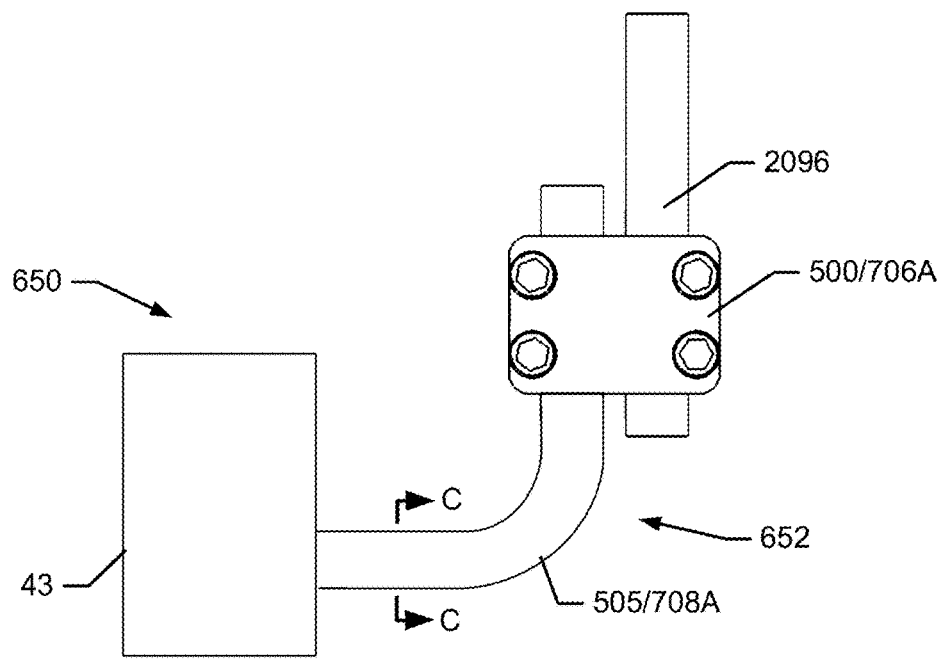
FIG. 10D is a top view of an additional alternative embodiment that includes a projection projecting from a proximal end of the insertion element coupled to a rod element of a spinal stabilization system.
Figure 10E:
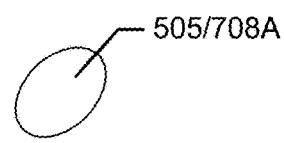
FIGS. 10E-10H are cross-sectional views of the projection taken at section C-C of FIG. 10D.
Figure 10F:
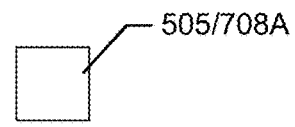
Figure 10G:
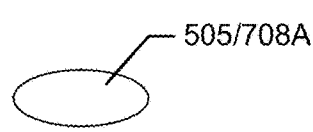
Figure 10H:
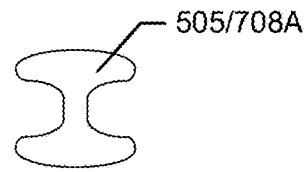
Figure 10I:
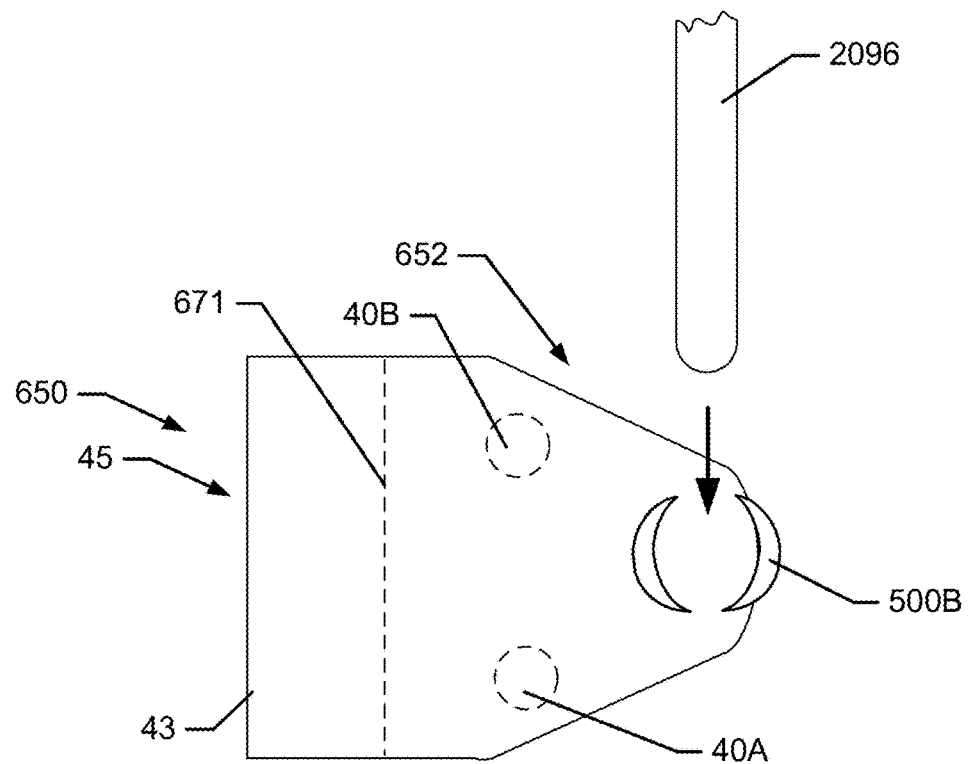
FIGS. 10I-10J are top views of attachment elements of implant bodies in other embodiments that include alternative planform profiles of the attachment elements.
Figure 10J:
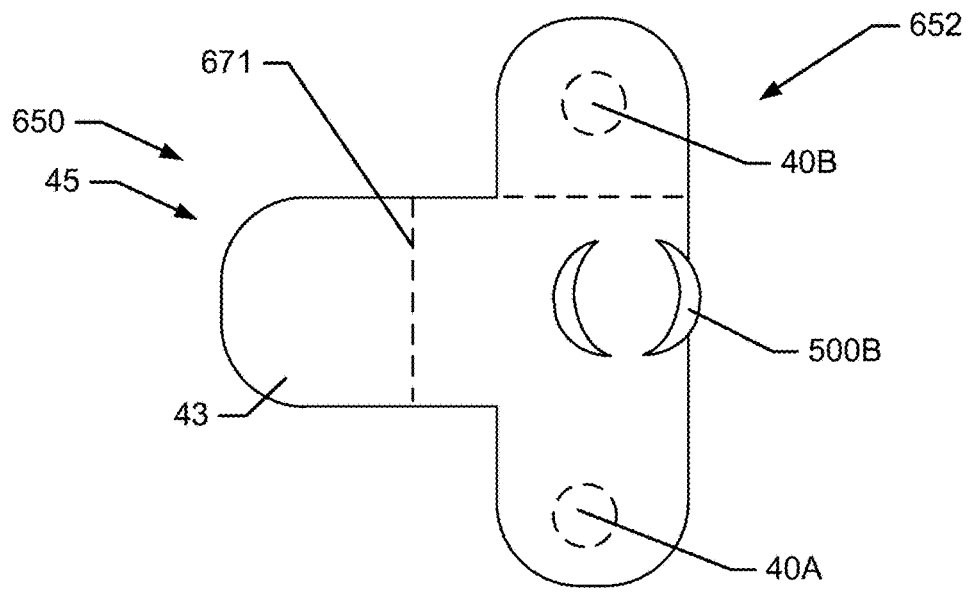

In an additional embodiment, illustrated in FIG. 10D, the attachment element 652 may be provided in the form of a projection 708A projecting from the proximal end 45 of the insertion element 650. In this embodiment, a rod 2096 of a spinal support system may be attached to the projection 708A using a connector 706A. The projection 708A may have any cross-sectional profile without limitation. FIGS. 10E-10H illustrate non-limiting examples of suitable cross-sectional profiles of the projection 708A taken at section C-C of FIG. 10D in various embodiments.

Figure 24:
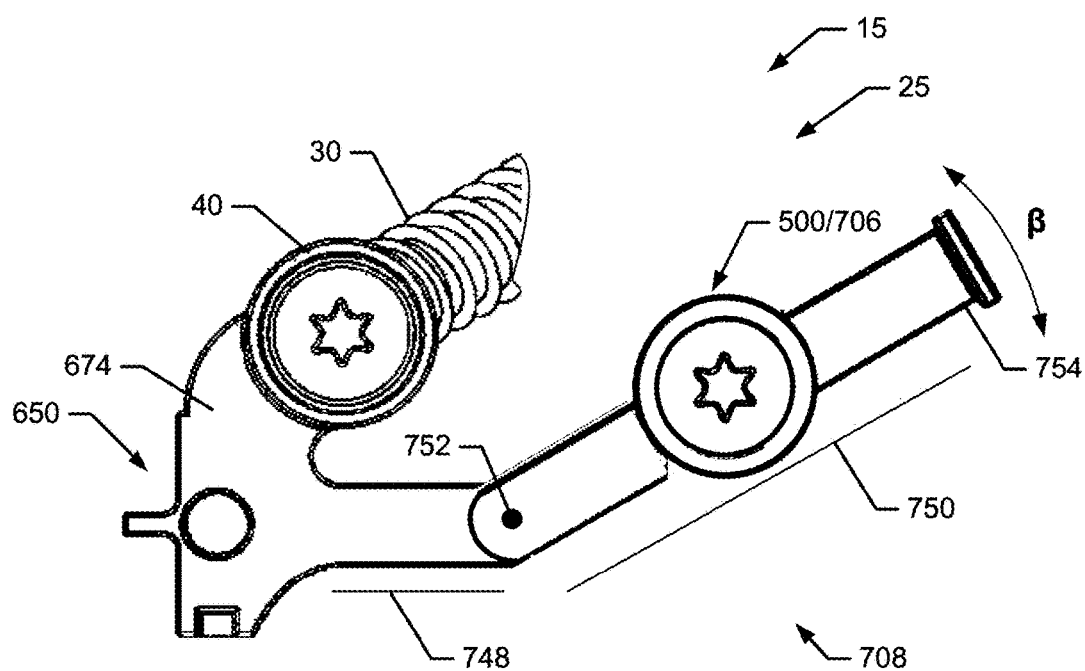
FIG. 24 is a top view of the implant body in a fourth embodiment with a slideable attachment socket situated on a pivoting guide rail.

FIG. 24 is a top view of an implant body 25 in an additional embodiment. In this additional embodiment, the guide rail 708 is divided into a fixed segment 748 and a pivotable segment 750 mechanically attached in a pivoting engagement including, but not limited to, a pin joint 752. The pin joint 752 permits the free end 754 of the pivotable segment 750 to rotate a pivot angle β within a predetermined range, thereby enhancing the ability of the slideable socket 706 to position the rod 2096 (not shown) of the spinal stabilization system into a desired position and orientation. In this additional embodiment, the pin joint 752 may be locked to fix the pivot angle β at a desired position; non-limiting examples of suitable locking mechanisms include a locking pin, a set screw, and any other suitable hinge joint locking mechanism. In another additional embodiment, the guide rail 708 of the implant body 25 may include two or more pivotable segments 750.

Figure 25:
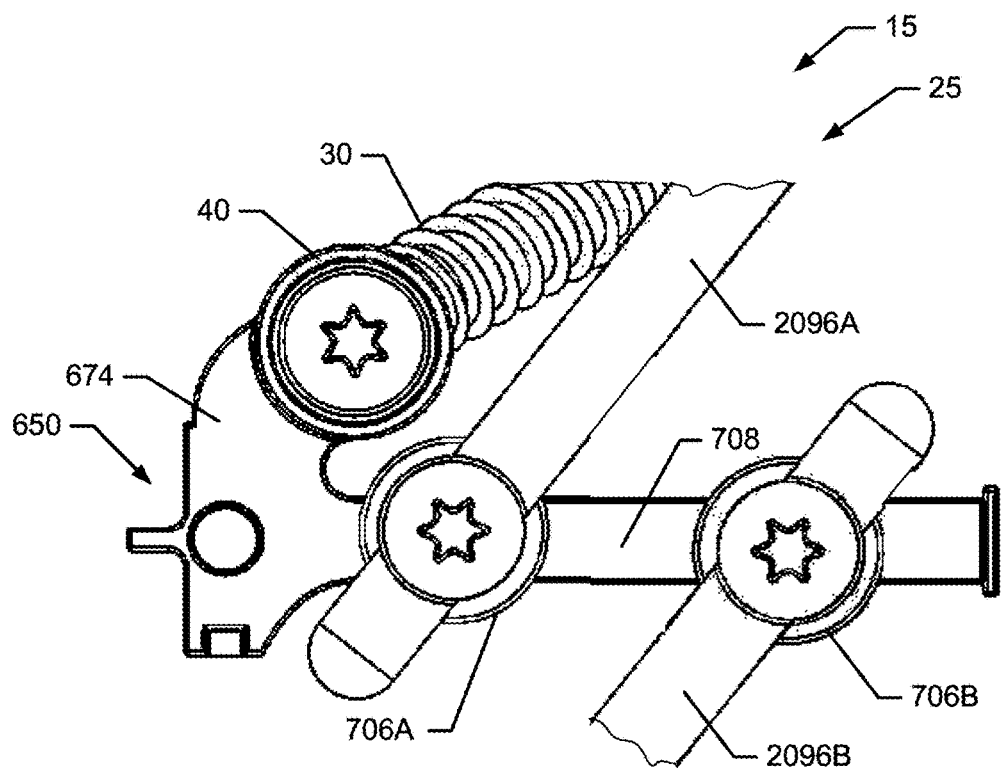
FIG. 25 is a top view of the implant body in a fifth embodiment with a first and second slideable attachment sockets situated on an elongated pivoting guide rail.

In yet other embodiments, the implant body 25 may include two or more slideable sockets 706 situated on the guide rail 708 of the attachment element 652. FIG. 25 is a top view of an implant body 25 in one other embodiment. As illustrated in FIG. 25, the guide rail 708 may be relatively elongated to accommodate a first slideable socket 706A and a second slideable socket 706B. In this other embodiment, the second slideable socket 706B may be used to anchor a second element 2096B of a spinal stabilization system. In additional embodiments, these elements may be configured to connect at least two implants in a fixed or stabilized relation.

Figure 43A:
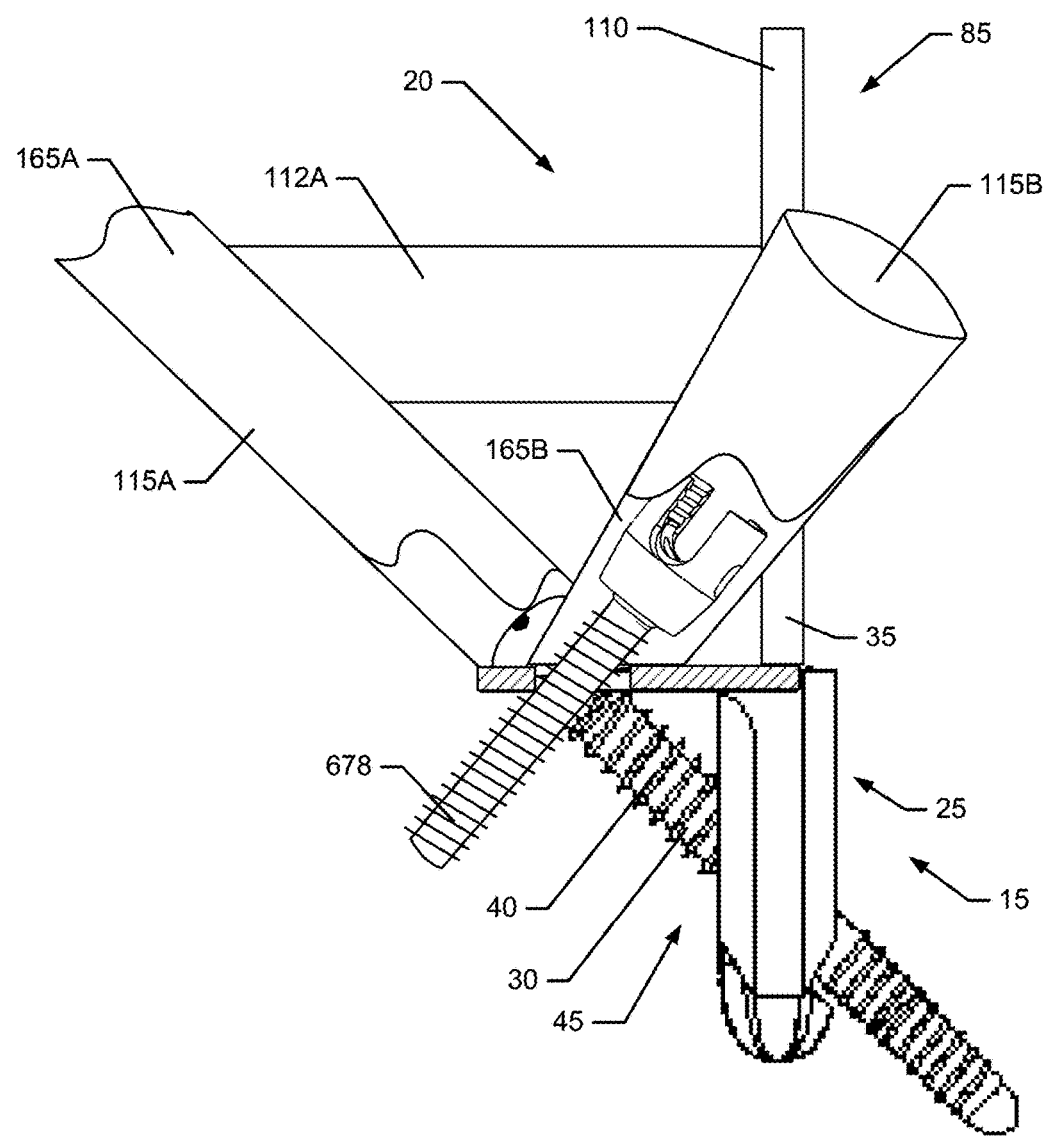
FIG. 43A is a side cross-sectional/cutaway view of the delivery tool in a second embodiment attached to an implant body with an anchor and polyaxial screw installed.
Figure 43B:
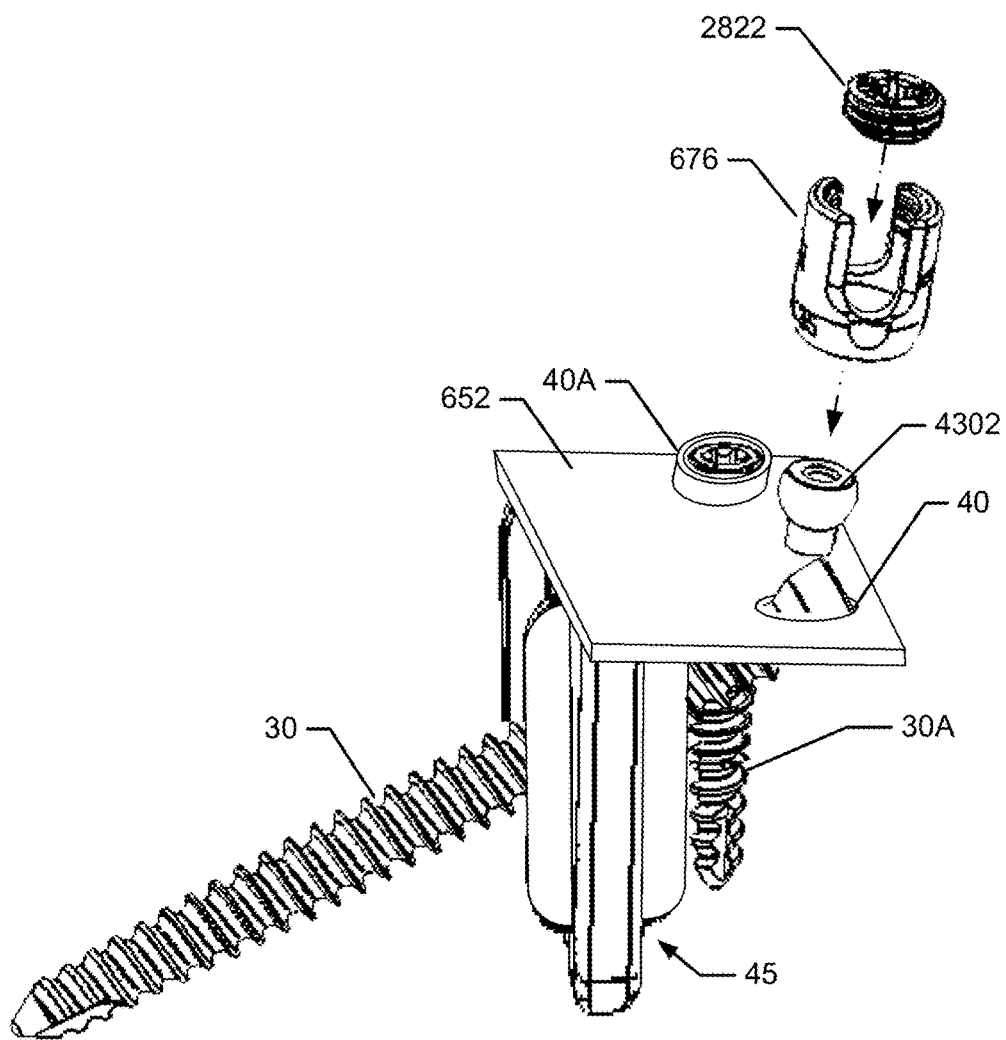
FIG. 43B is an isometric view of another embodiment of an implant assembly including an implant body with a polyaxial or monoaxial attachment fitting situated on the attachment element wherein the attachment fitting is located between a first and second attachment element bore.

In various other embodiments, the attachment fitting 500 may be attached in a fixed position to the attachment element 652 of the implant body 25. In one aspect, illustrated in FIG. 43B, the attachment fitting may be provided in the form of a tulip-like head 676 similar to the head of the polyaxial screw 678 described previously herein and illustrated in FIG. 18. In this embodiment, the head 676 is attached to a post 4302 protruding proximally from the attachment element 652. In various embodiments, the post 4302 may be fixed in position on the attachment element 652. In one aspect, the post 4302 may be situated between one or more bores 40 and 40A through which one or more anchors 30 and 30A may be inserted into the underlying bone tissue as described previously herein. The shape of the post 4302 may be spherical to accommodate a polyaxial head 676 as illustrated in FIG. 43B. In other embodiments, the post 4302 may be configured to attach to other forms of attachment fittings, such as monoaxial heads (not shown).

iii. Anti-Migration Features on Bone Contact Surfaces

In various embodiments, the implant body 25 may further include surface features and/or textures on any exposed surface making contact with underlying bone tissue. These surface features may interact with the bone tissue within the sacroiliac joint space mechanically and/or biologically and may include anti-migration surface features. These anti-migration surface features may assist in preventing the insertion plate 45 from loosening, moving, and/or or migrating within the afflicted area during prolonged use by the patient. Non-limiting examples of exposed surfaces of the implant body 25 making contact with underlying bone tissue include: the insertion plate 45 including the medial face 654, the lateral face 656, the edges 658, and/or the one or more fins 50; the attachment element 652 including the distal surface. Non-limiting examples of anti-migration surface features include a plurality of projections, a plurality of serrated teeth or ridges, a plurality of perforations, or any other surface feature which may reduce the migration of insertion plate 45 and/or implant body 25.

Figure 26:
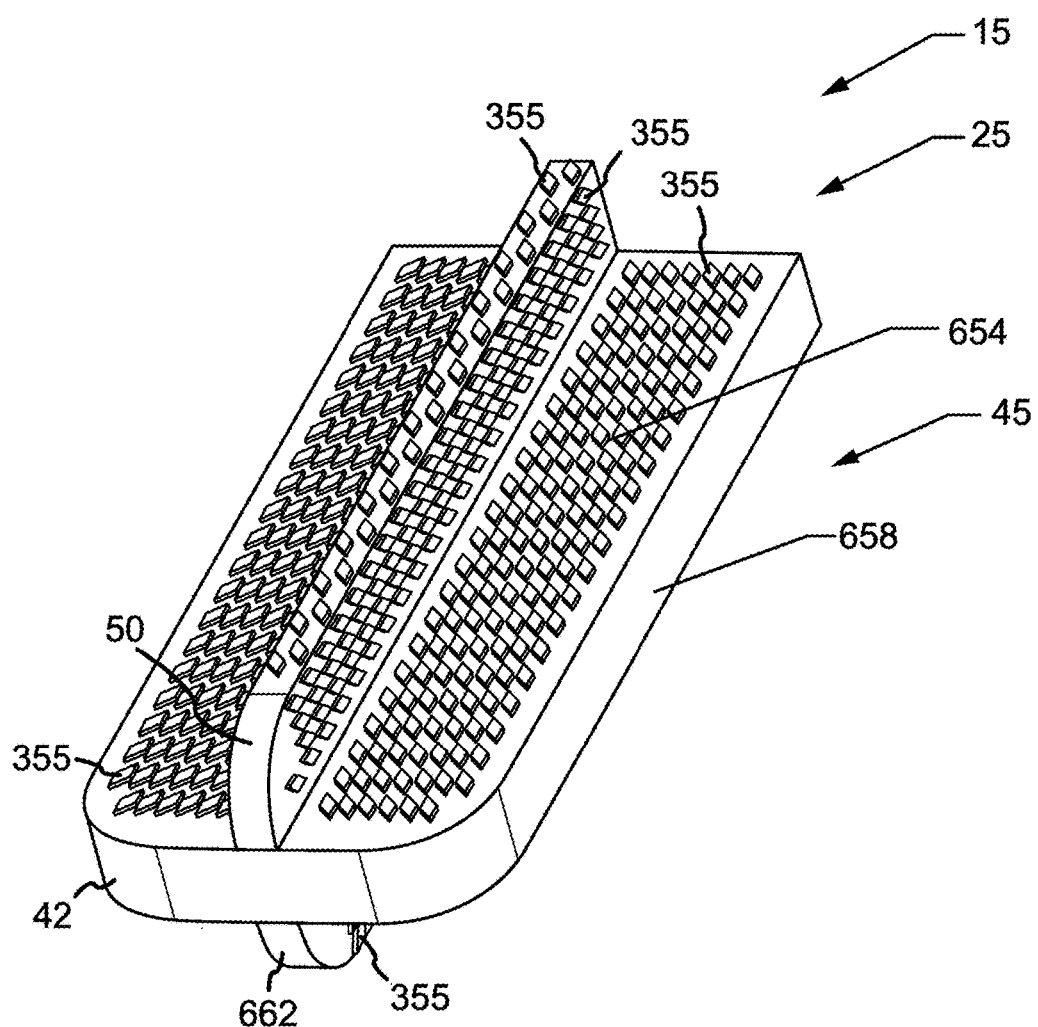
FIG. 26 is a bottom isometric view of an insertion plate of an implant body with a first embodiment of anti-migration surface features included on the exposed surfaces.

The surface features may be unidirectional in one embodiment. FIG. 26 is a bottom isometric view of an insertion plate 45 of an implant body 25 with anti-migration surface features 355 included on the exposed surfaces of the insertion plate 45 of the implant body 25. As shown in FIG. 26, the anti-migration features 355 are generally evenly distributed along the medial face 654, the lateral face 656 (not shown), and each of the fins 50 in a rows and columns arrangement. The anti-migration features 355 are generally similarly distributed along the planar surfaces of the edges of the fins 50. The anti-migration features 355 may be in the form of trapezoids, squares, rectangles, etc. The anti-migration features 355 may have a rectangular cross sectional elevation with a thickness ranging from approximately 0.2 mm to approximately 5 mm. In another aspect, illustrated in FIG. 7A, the anti-migration surface features 355 may be generally evenly distributed along a distal face 357 of the attachment element 652. In this other aspect, the distal face 357 contacts the underlying bone tissue once the implant assembly 25 is inserted within the joint space of the sacroilial joint.

Figure 27:
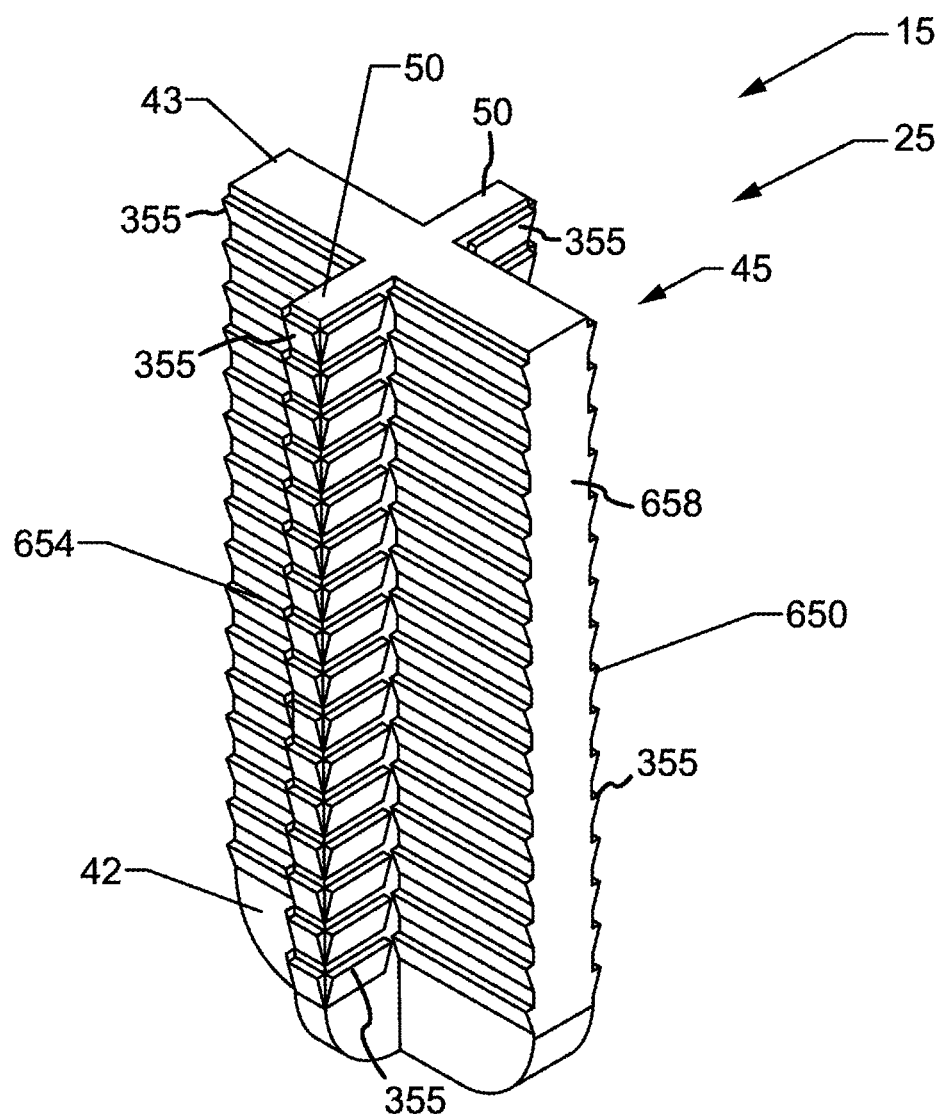
FIG. 27 is a front isometric view of an insertion plate of an implant body with a second embodiment of anti-migration surface features included on the exposed surfaces of the insertion plate.

As another example, as shown in FIG. 27 which is a front isometric view of an insertion plate 45 of an implant body 25 with another type of anti-migration surface features 355 included on the exposed surfaces of the insertion plate 45. As shown in FIG. 27, the anti-migration features 355 are in the form of unidirectional serrated teeth or ridges 355, wherein the ridges 355 have a triangular cross sectional elevation wherein the rearward or trailing end of the features 355 are the truncated or vertical end of the triangle cross sectional elevation, and the front or leading end of the features 355 are the point end of the triangle cross sectional elevation. The anti-migration features 355 with the triangular cross sectional elevations have a thickness ranging from approximately 0.2 mm and approximately 5 mm, with one embodiment having a thickness FT of approximately 1 mm to approximately 15 mm. The triangular ridges 355 may be generally evenly distributed along the fins 50 in ridges that run transverse to the length of the insertion plate 45. The anti-migration features 355 are generally similarly distributed along the planar surfaces of the edges of the fins 50.

Although the anti-migration features 355 are depicted in the form of unidirectional serrated teeth or ridges 355 on each of the textured surfaces of the insertion plate 45 in this embodiment, the invention is not so limited and, as to particular embodiments, can be configured to have said features 355 arranged in multiple directions, unidirectional, or a combination of multiple direction on some surfaces of the insertion plate 45 and unidirectional on other surfaces of the insertion plate 45. Accordingly, the features 355 can be so arranged on the various surfaces of the insertion plate 45 so as to prevent undesired migration in particular directions due to the forces present at the sacroiliac joint 1000.

Figure 8A:
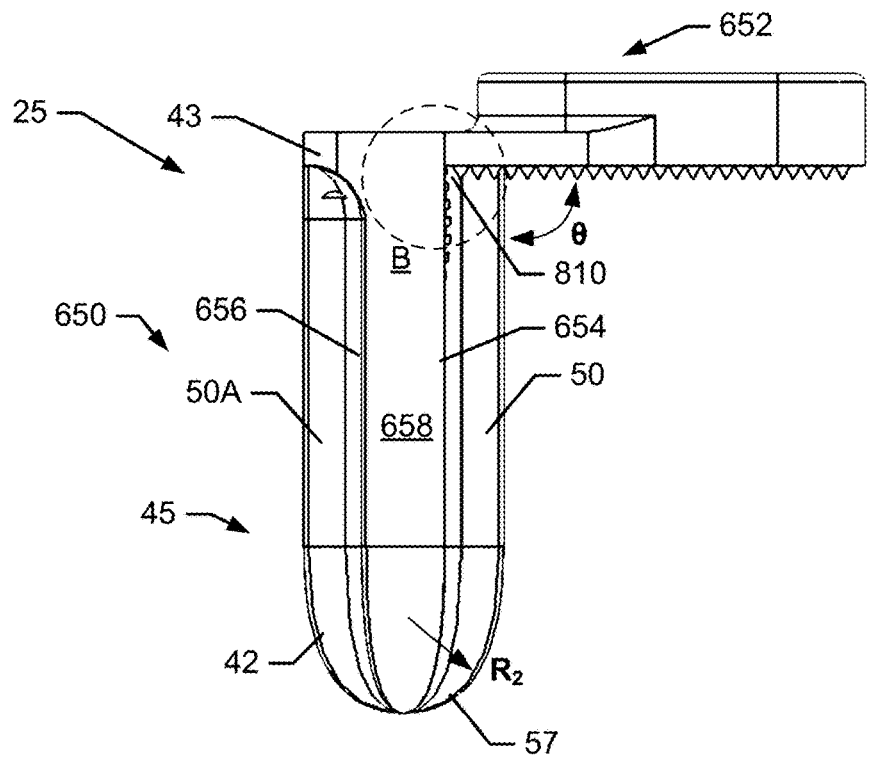
FIG. 8A is a caudal side view of the implant body of the first embodiment.
Figure 8B:
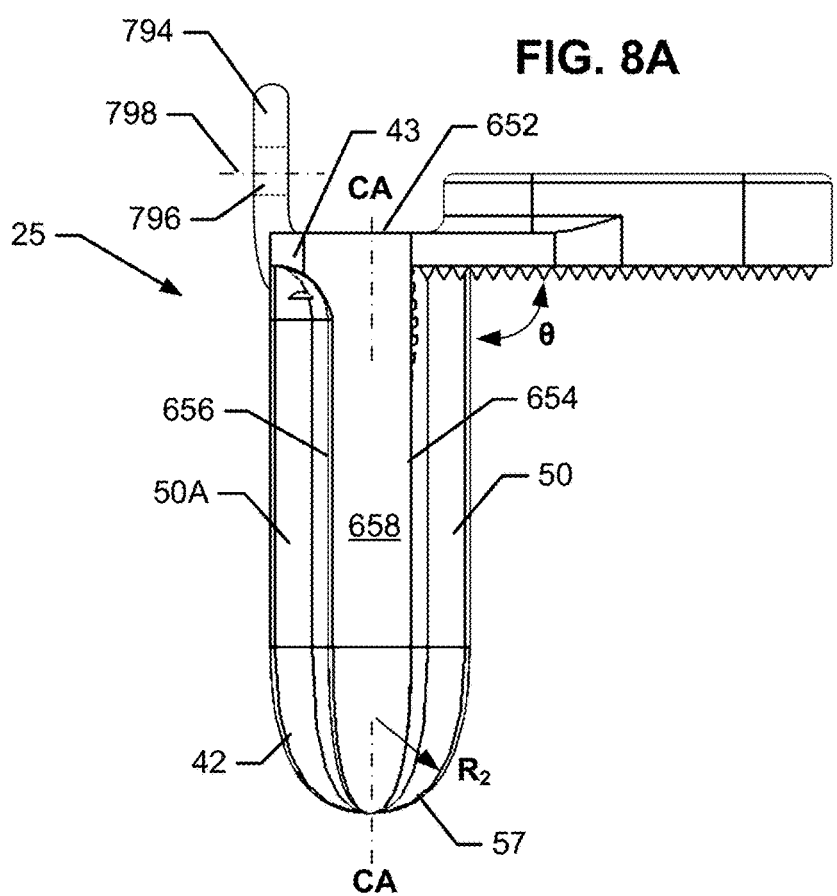
FIG. 8B is a caudal side view of an implant body with a proximally projecting extension of the insertion element similar to the alternative embodiments illustrated in FIGS. 7B-7C.
Figure 8C:
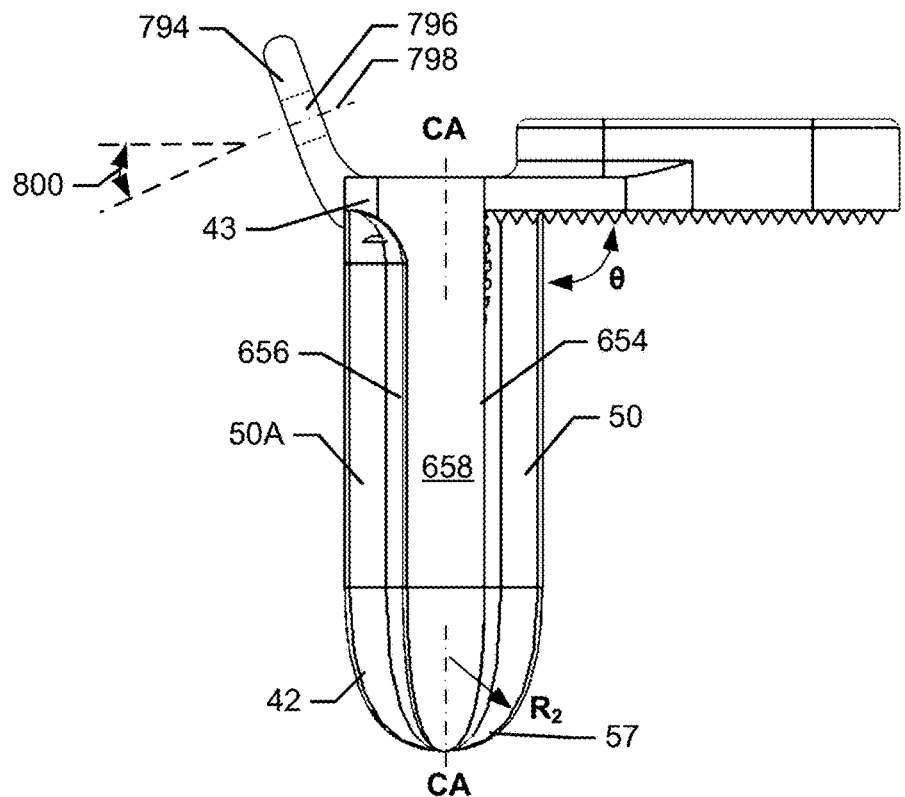
FIG. 8C is a caudal side view of an implant body with a proximal/lateral projecting extension of the insertion element.
Figure 8D:
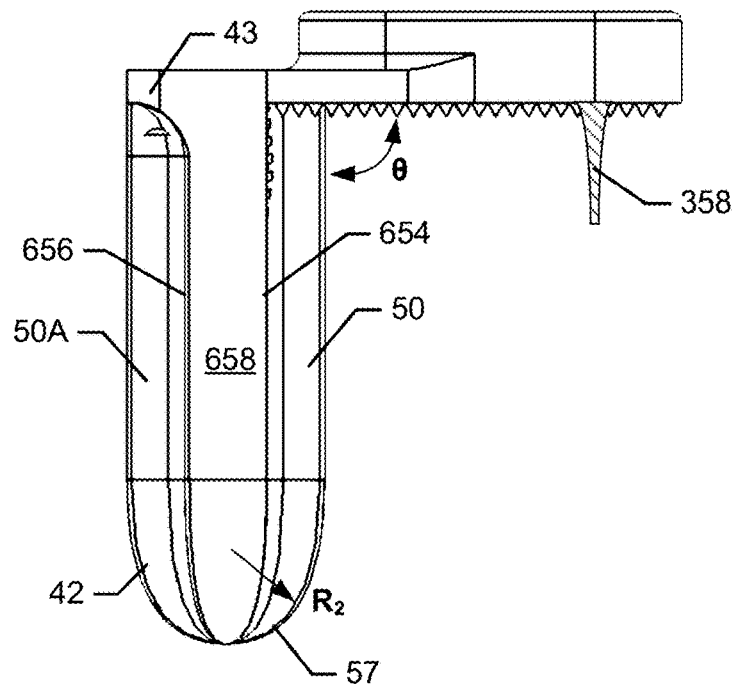
FIG. 8D is a caudal side view of an implant body with a surface feature projecting distally from an attachment element.
Figure 8E:
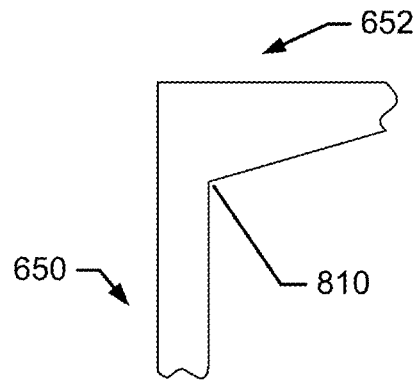
FIGS. 8E-8H are alternative embodiments that include chamfering, filleting, and ribbing along the interior corner of the implant body; the interior corner is an enlargement of region B within FIG. 8A.
Figure 8F:
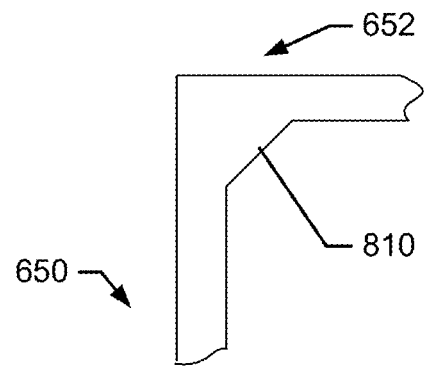
Figure 8G:
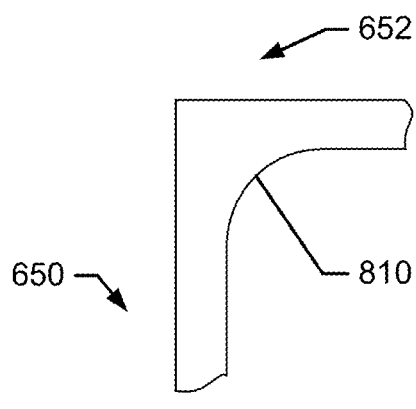
Figure 8H:
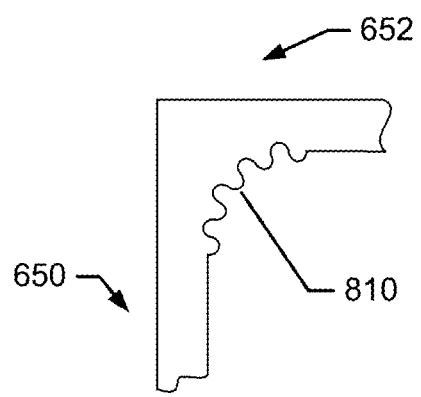

In another embodiment, illustrated in FIG. 8D, the anti-migration features 355 may include one or more discrete projections 358. As illustrated in FIG. 8D, the discrete projections 358 may project in a direction toward the underlying bone and may further enhance the anti-migration features 355 of the implant assembly 25. In one aspect, the discrete projections 358 may be in the form of a tapered perpendicular projection from a contact surface including, but not limited to, the tapered discrete projection 358 projecting distally from the distal face 357 of the attachment element 652 as illustrated in FIG. 8D.

Figure 28A:
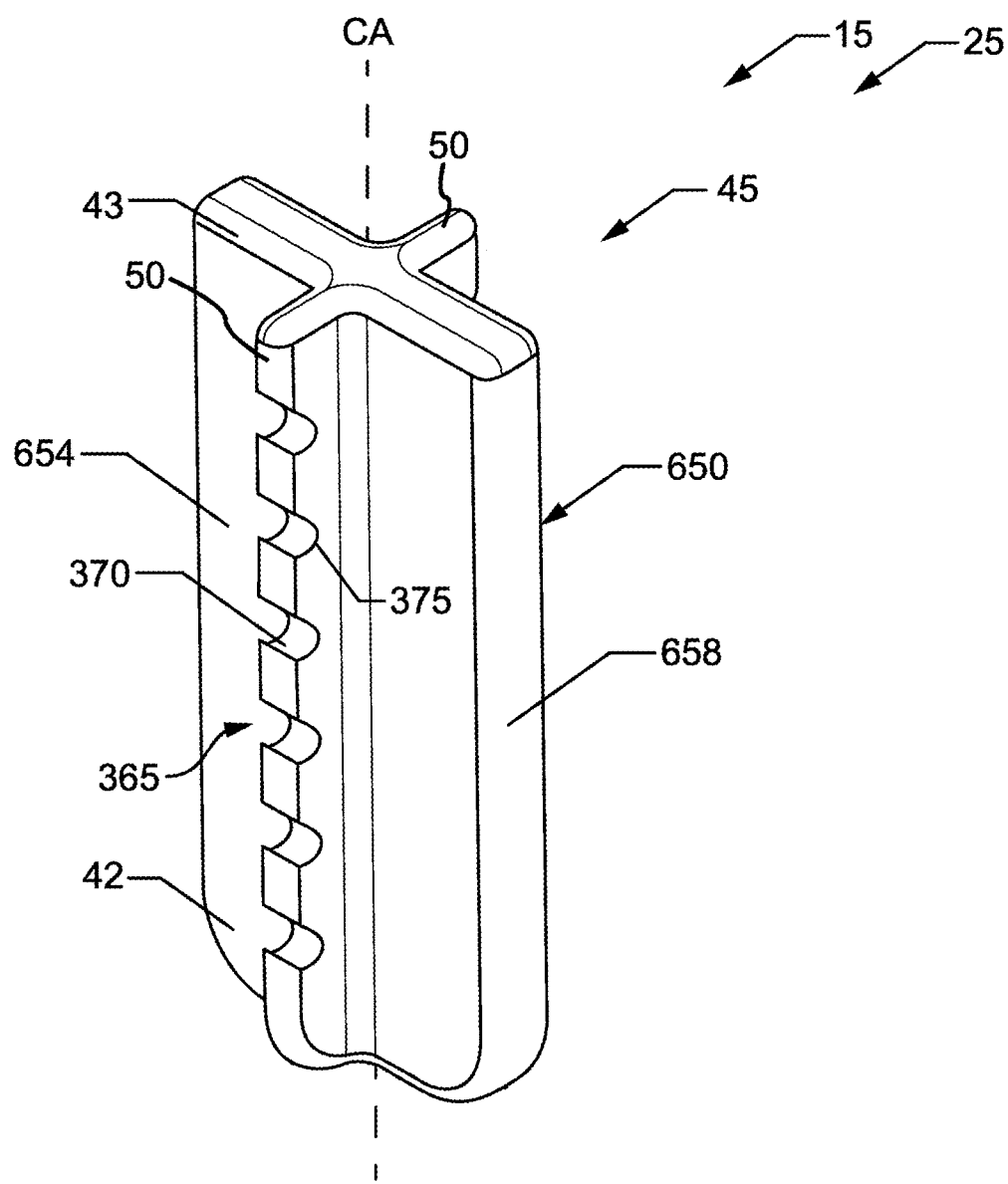
FIG. 28A is a front isometric view of an insertion plate of an implant body with a third embodiment of anti-migration surface features included in the form of notches distributed along longitudinally extending free edges or ends of the fins.
Figure 28B:
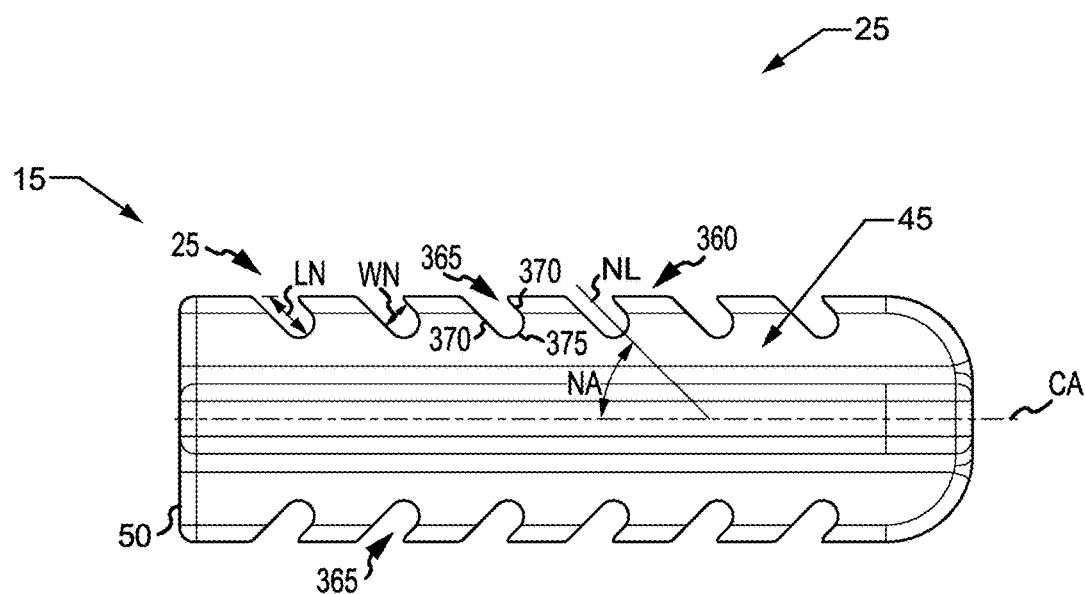
FIG. 28B is a rotated side view of the insertion plate illustrated in FIG. 28A.

Depending on the embodiment, the insertion plate 45 may have an edge configuration of the fins 50 designed to prevent migration of the implant body 25 once implanted in the sacroiliac joint space. For example, as shown in FIG. 28A which is a front isometric view of an insertion plate 45 of an implant body 25, the anti-migration edges 360 of the fins 50 are in the form of notches 365 generally evenly distributed along longitudinally extending free edges or ends of the fins 50. As indicated in FIG. 28B, a rotated side view of the insertion plate 45 illustrated in FIG. 28A, the notches 365 may have parallel sides 370 inwardly terminating as an arcuate end 375. The orientation of each notch 365 may be such that the center line NL of the notch 365 forms an angle NA with the center axis CA of the insertion plate 45 that ranges between approximately 90 degrees and approximately 15 degrees. As indicated in FIG. 28, each notch 365 may have a length LN between the extreme point on the arcuate end 375 and the outer edge boundary of the notch of between approximately 0.2 mm and approximately 10 mm. Each notch 365 may have a width WN of between approximately 0.5 mm and approximately 20 mm.

Figure 29A:
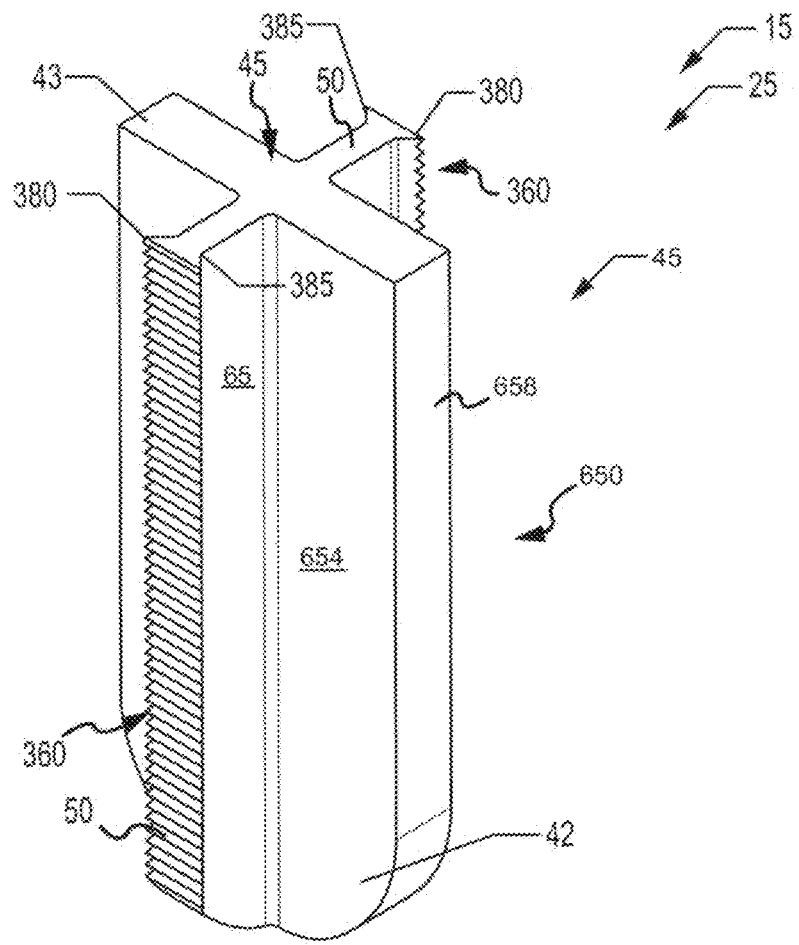
FIG. 29A is a front isometric view of an insertion plate of an implant body with a fourth embodiment of anti-migration surface features included in the form of are flared longitudinally extending free edges or ends of the fins.
Figure 29B:
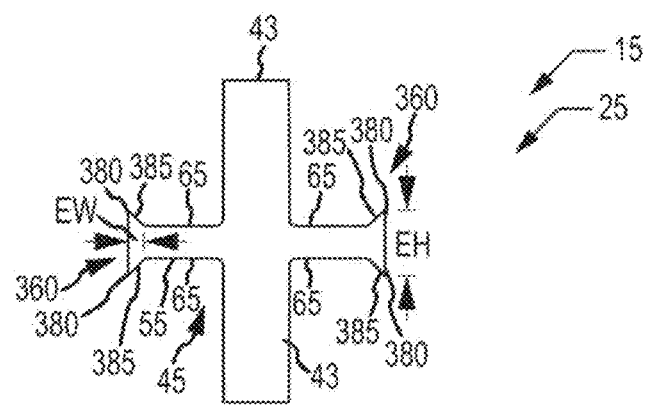
FIG. 29B is a transverse cross-sectional view of the insertion plate illustrated in FIG. 29A.

As another example, as shown in FIG. 29 which is a front isometric of an insertion plate 45 of an implant body 25, the anti-migration edges 360 are flared longitudinally extending free edges or ends of the fins 50. The edges 360 include a series of ridges 370 that are generally evenly distributed along the length of the edges 360 and oriented transverse to the length of the edges 360.

As indicated in FIG. 29, the ridges 370 have triangular cross sectional elevations with an overall height of between approximately 0.2 mm and approximately 8 mm. As illustrated in FIG. 29, the flared longitudinally extending free edges or ends of the fins 50 have rim edges 380 defining the edges of the anti-migration edges 360 of the fins 50, wherein the rim edges 380 have slopes 385 transitioning between the planar surfaces 65 of the fins 50 and the rim edges 380.

The edges 360 have a height EH between the edges 380 of between approximately 0.5 mm and approximately 15 mm, with one embodiment having a height EH of approximately 4 mm. The width EW of the flared edge 360 from the beginning of the sloped transition 385 to the face of the edge 360 is between approximately 0.2 mm and approximately 9 mm, with one embodiment having a width EW of approximately 1 mm.

In particular embodiments, the insertion plates 45 of the implant bodies 25 with features as described above with respect to FIGS. 26-29 can alternatively be configured to function as a broach or other surgical site preparation tool that can assist in the removal of certain tissues, for example, cartilage or bone, during certain steps of a procedure. In certain aspects, the implant body 25 may be configured as a trial to allow a surgeon presented with a number of different embodiments of implant bodies 25 to evaluate the different embodiments to assess the suitability of any particular embodiment for the treatment of a particular patient, an idiopathic anatomy, a particular implant receiving space and/or other application.

In one additional aspect, the exposed surfaces of the implant body 25 making contact with underlying bone tissue may be treated with a bone growth factor or other compounds to encourage bone tissue growth around the implant assembly 200. Non-limiting examples of exposed surfaces of the implant body 25 making contact with underlying bone tissue include: the insertion element 650 including the medial face 654, the lateral face 656, the edges 658, and/or the one or more fins 50; the attachment element 652 including the distal surface.

II. Delivery Tool

To begin a detailed discussion of components of an embodiment of the delivery tool 20, reference is again made to FIGS. 1 and 2. As shown in FIG. 2, the delivery tool 20 includes a distal end 35 and a proximal end 80. The distal end 35 supports the implant assembly 15 components including, but not limited to, the implant body 25. The proximal end 80 is configured to be grasped and manipulated to facilitate the implantation of the implant assembly 15 in the sacroiliac joint.

The delivery tool 20 further includes an arm assembly 85 made up of an implant arm 110 configured to retain the implant body 25 and an anchor arm 115 supported off of the implant arm 110 at a predetermined angle by an anchor arm fitting 112. In this embodiment, the delivery tool 20 may further include a handle 90.

a. Implant Arm and Locking Screw

Figure 35:
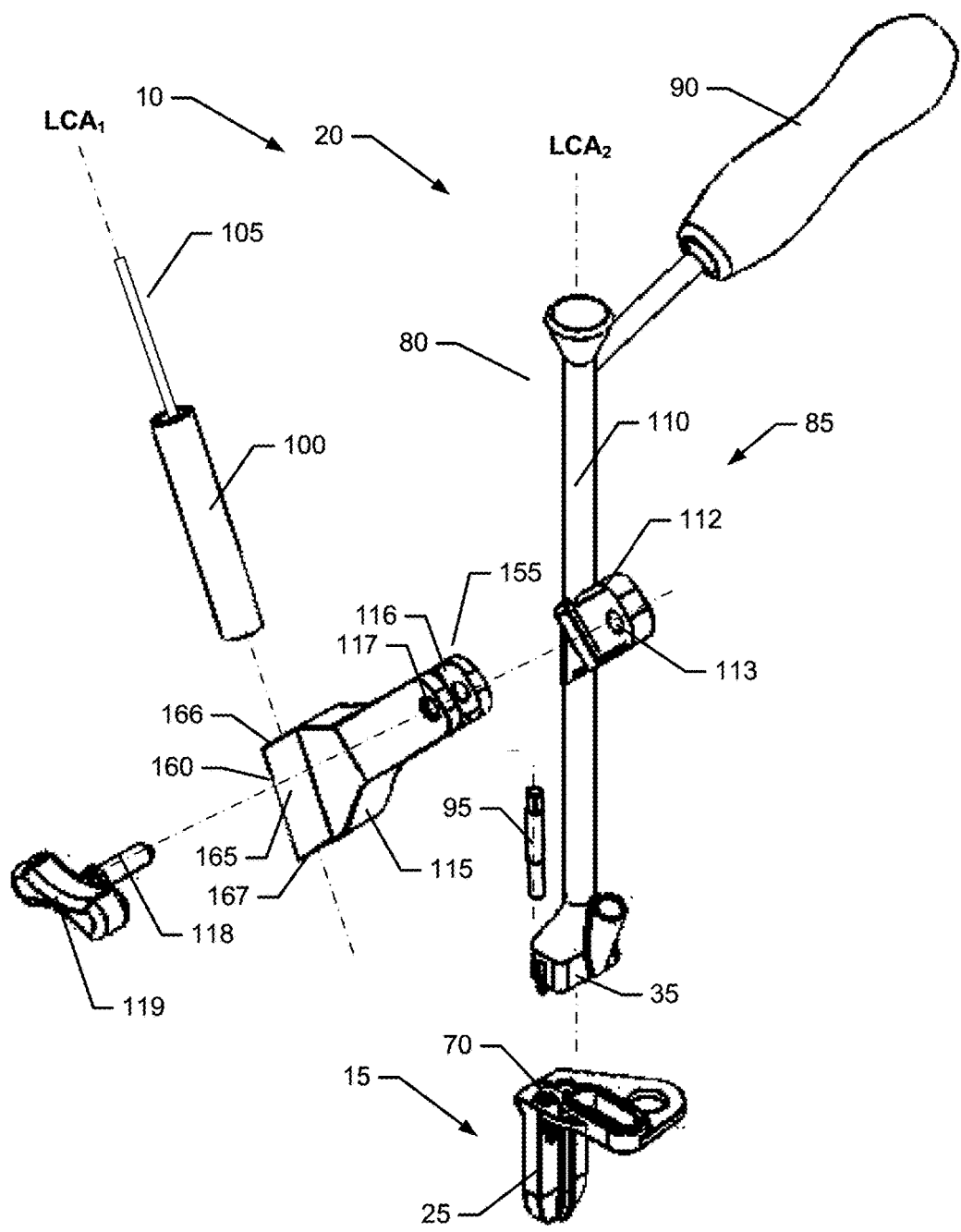
FIG. 35 is an exploded view of the delivery tool in the first embodiment.
Figure 36:
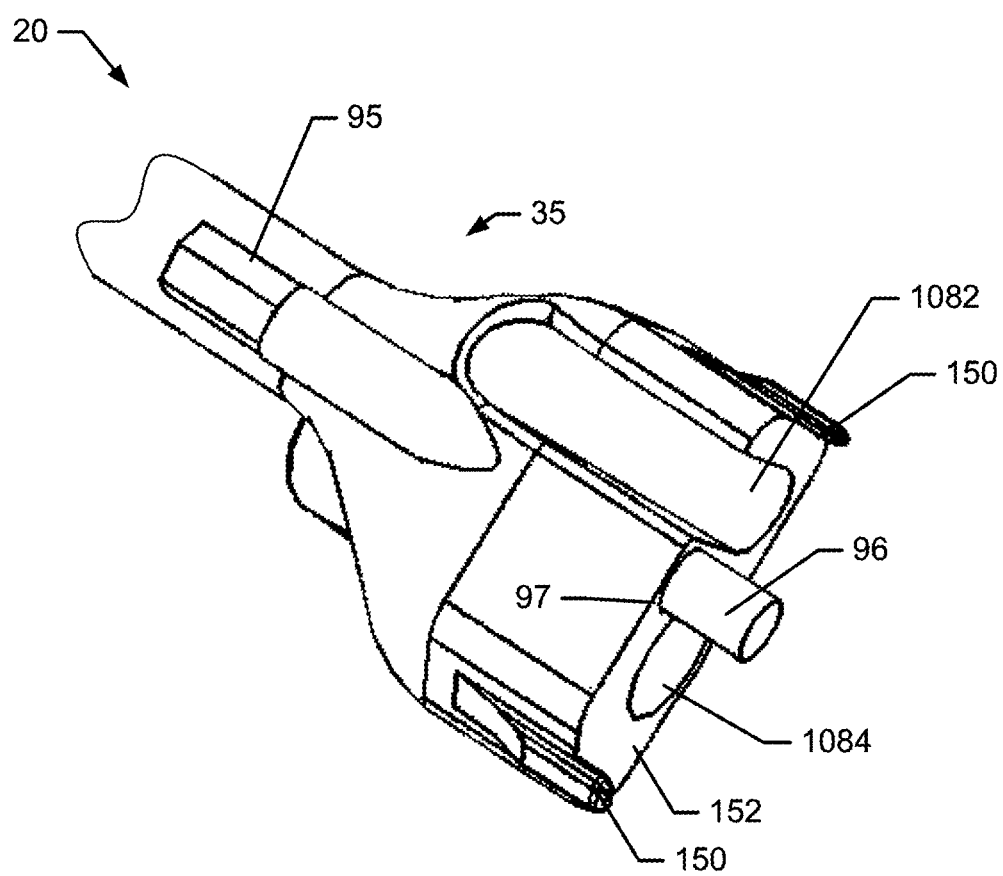
FIG. 36 is a close-up perspective view of the distal end of the delivery tool in the first embodiment.

FIG. 35 is an exploded isometric view of the delivery tool 20 illustrated previously in FIGS. 1 and 2. As illustrated in FIG. 35, the delivery tool 20 further includes an arm assembly 85, a handle 90, a locking screw 95, a sleeve 100 and a trocar or guidewire 105. The implant body 25 may be reversibly attached to the distal end 35 of the delivery tool 20 by inserting the locking screw 95 into the attachment bore 70 within the implant body 25 in one embodiment. FIG. 36 is a bottom isometric view of the distal end 35 of the delivery tool 20 in one embodiment. The locking screw 95 may be inserted through a bore 97 formed through the distal end 35 such that a distal tip 96 of the locking screw 95 may protrude from a planar extreme distal face 152 of the delivery tool 20. The locking screw 95 and attachment bore 70 may be provided with meshing threads to enable a reversibly locked engagement when the distal tip 96 of the locking screw 95 is advanced into the attachment bore 70.

Figure 37:
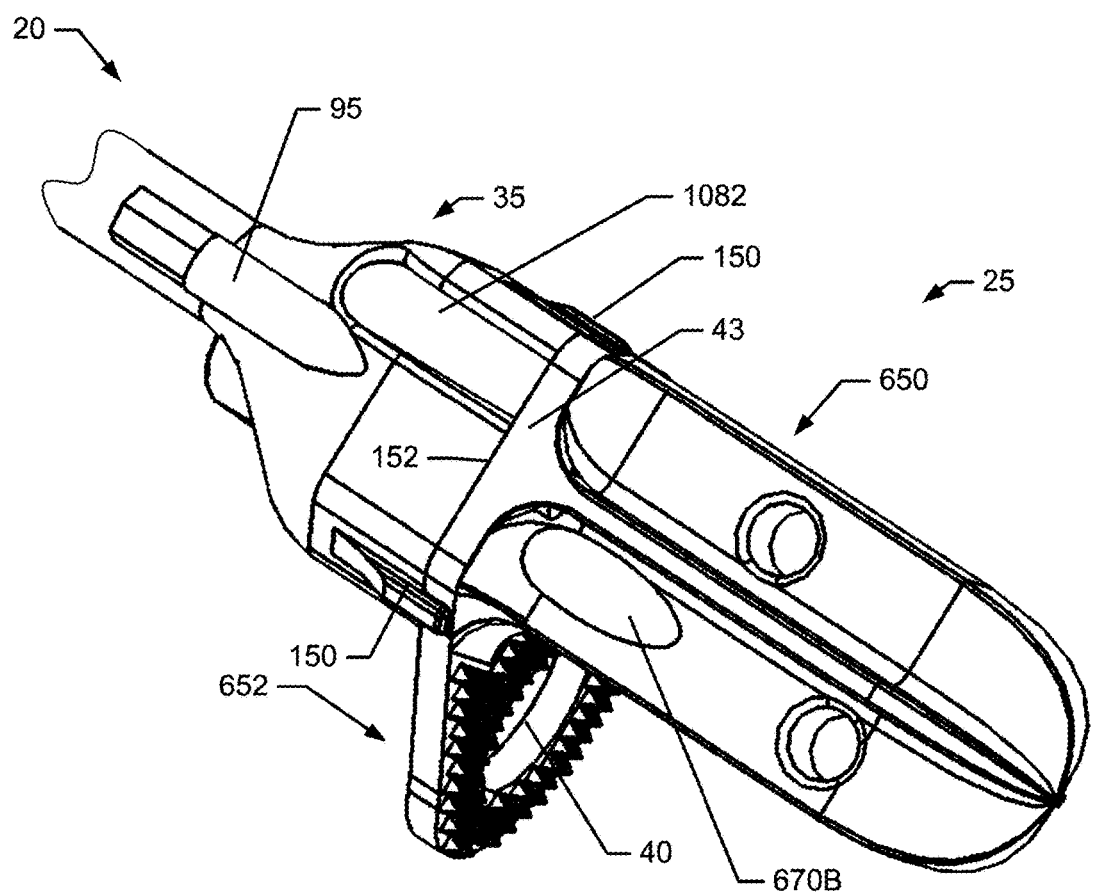
FIG. 37 is a close-up perspective view of the distal end of the delivery tool in the first embodiment with an attached implant body.

In various embodiments, the attachment bore 70 and locking screw 95 are essentially aligned with the implant arm 110 as well as the direction of insertion of the insertion element 650 of the implant body 25, as illustrated in FIG. 36 and FIG. 37. In addition, the attachment bore 70 and locking screw 95 may be situated well away from the bore 40 within the attachment element 652. Without being limited to any particular theory, the arrangement reduces the potential for mechanical interference of the locking screw 95 with the other fasteners such as an anchor 30, associated implant assembly tools, and/or any other surgical instruments involved in implanting the implant body 25 within the joint space of a sacroiliac joint.

Figure 39:
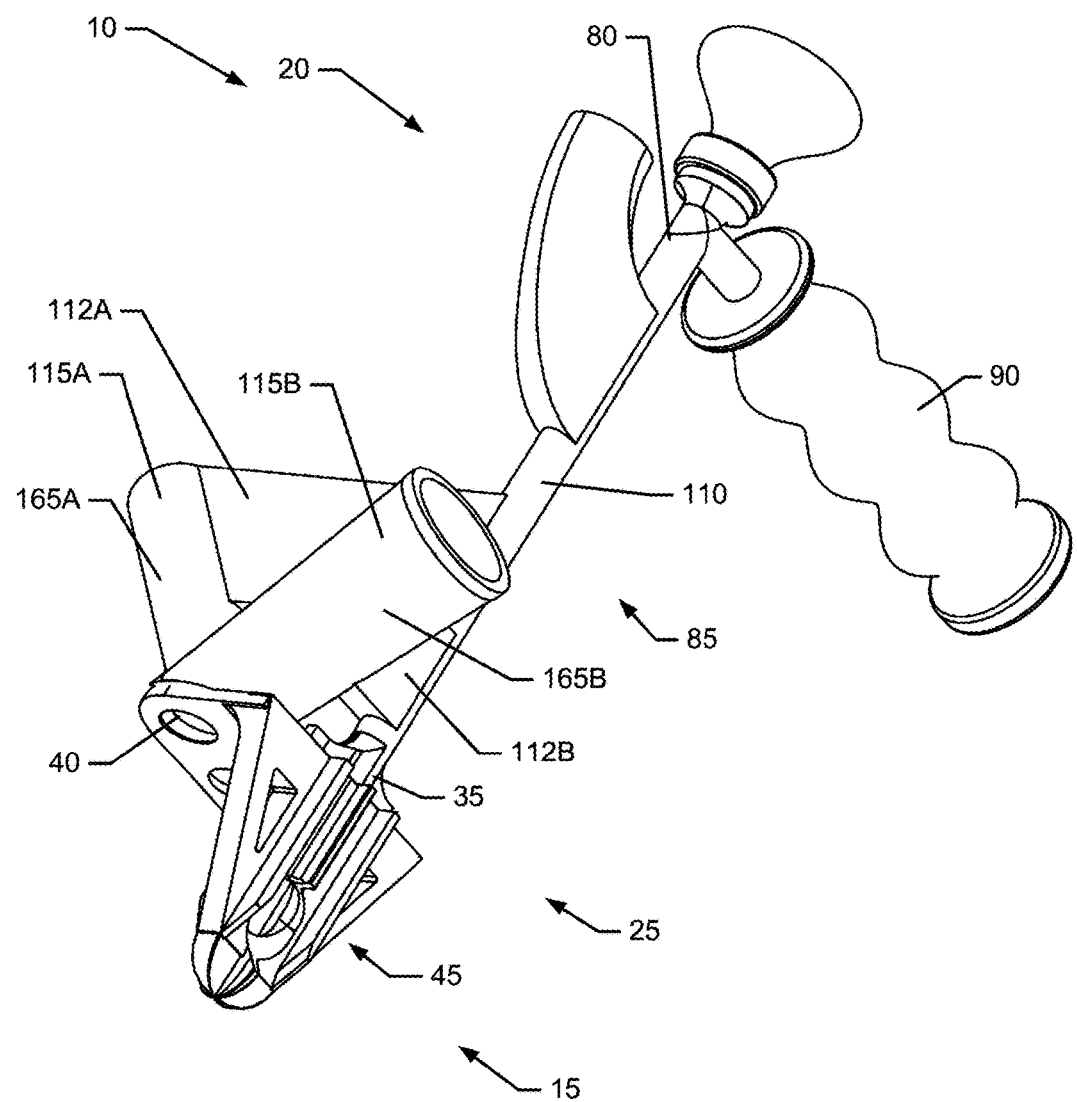
FIG. 39 is a perspective view of a delivery tool in a second embodiment attached to an implant body.

FIG. 39 is a bottom isometric view of a delivery tool 20 in a second embodiment. In this second embodiment, the arm assembly 85 includes a cannulated implant arm 110. In this embodiment, a first anchor arm 115A may supported off of the implant arm 110 at first and second predetermined angles by a first anchor arm fitting 112A and second anchor arm fitting 112B, respectively.

Figure 40:
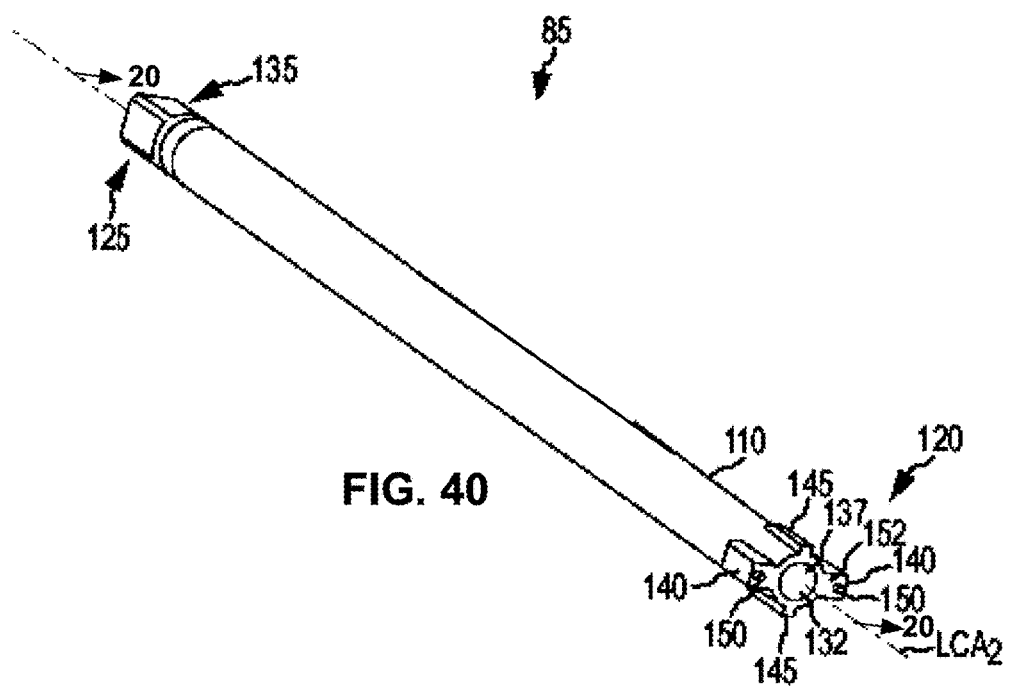
FIG. 40 is a perspective view of the implant arm of the delivery tool in the second embodiment.
Figure 41:
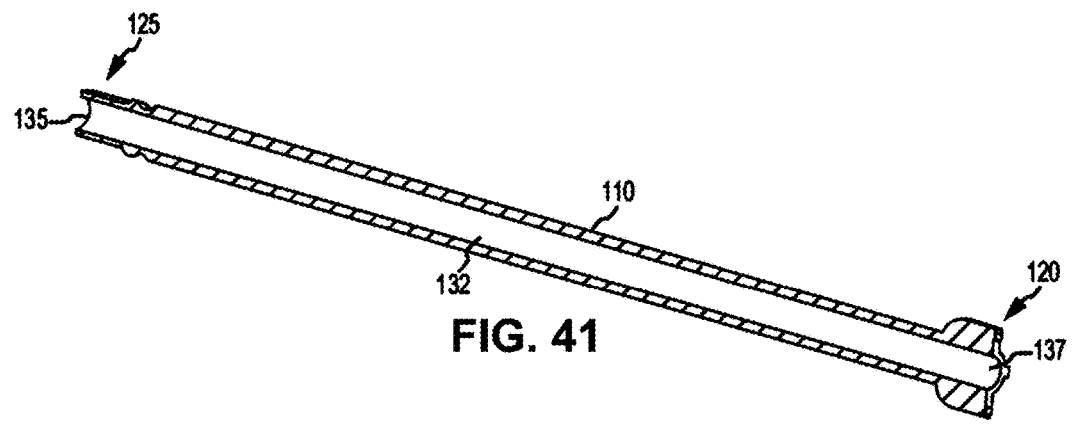
FIG. 41 is a longitudinal cross-sectional view of the implant arm of the delivery tool in the second embodiment.

FIG. 40 is a distal isometric view of the arm assembly 85 in one embodiment in which the anchor arms 115A/115B and anchor arm fittings 112A/112B have been removed for better visualization. In tone or his embodiment, the distal end 120 includes a cylindrical opening 137 of a cylindrical bore 132, one or more fins 140/145, pins 150, and a planar extreme distal face 152. As depicted in FIG. 41, which is a longitudinal cross section of the implant arm 110 as taken along section line 20-20 in FIG. 40, the cylindrical bore 132 extends the full length of the implant arm 110 between the proximal opening 135 and the distal opening 137.

Figure 42:
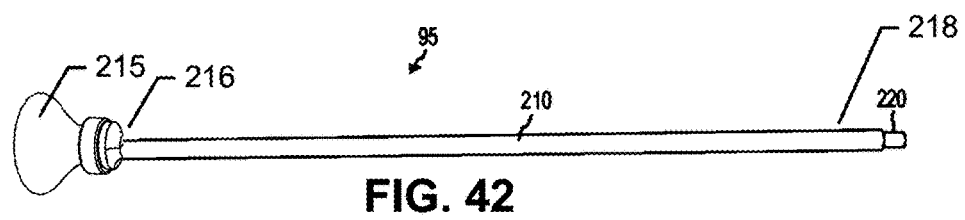
FIG. 42 is a side view of an implant retaining arm.

As illustrated in FIG. 42, which is a full isometric view of an implant retainer 95, the implant retainer 95 includes a longitudinal cylindrical member 210, a handle 215 on a proximal end 216 of the longitudinal cylindrical member 210, and a threaded implant retaining screw 220 on a distal end 218 of the longitudinal cylindrical member 210. As can be understood from FIGS. 9 and 39-42, when the system 10 is assembled for the delivery of the implant assembly 15 to the sacroiliac joint, the longitudinal cylindrical member 210 extending from the handle 215 (see FIG. 42) and implant arm bore 132 (see FIG. 41) such that a distal side of the handle 215 abuts or nearly abuts with the implant arm proximal end 125 (see FIG. 41) and the threaded implant retaining screw 220 is received in the implant attachment bore 70 (see FIG. 9). In one embodiment, the implant retaining screw 220 is in the form of a threaded shaft for engaging complementary threads in the attachment bore 70 of the implant body 25, thereby securing the implant proximal face against the implant arm distal face. In other embodiments, the implant retaining screw 220 and the attachment bore 70 are configured so as to form an interference fit between the two such that an intentional separating force is required to remove the implant engagement feature from within the attachment bore 70 and allow the release of the implant body 25 from the distal end 120 of the implant arm 110.

b. Alignment Pegs

Referring again to FIG. 36, the extreme distal face 152 has an essentially planar surface contour in order to match the essentially planar surface contour of the implant body 25, particularly in the region surrounding the attachment bore 70 in various aspects. In addition, the distal face 152 may include additional alignment features including, but not limited to, one or more alignment pegs 150. These alignment pegs 150 may mechanically interlock with corresponding features on the implant body including, but not limited to, peg receptacles, and notches.

In one embodiment, the alignment pegs 150 may be arranged in a pattern matched to an edge contour of the proximal end 43 of the insertion element 650 of the implant body 25. FIG. 37 is a bottom isometric view illustrating the implant body 25 mounted to the distal end 35 of the delivery tool 20 illustrated in FIG. 36. In one embodiment, the locking screw 95 has been advanced and tightened into the attachment bore 70, thereby securing the proximal end 43 of the insertion element 650 against the distal face 152 of the delivery tool 20. The one or more alignment pegs 150 closely fit the edge contour of the proximal end 43, thereby providing alignment mechanisms and resistance against twisting of the implant body 25 relative to the delivery tool 20.

In another embodiment, the proximal end 43 of the implant body 25 may include one or more recesses 154 formed in the exterior surface of the implant body 25 to receive one or more alignment pegs 150 protruding distally from the distal face 152 of the delivery tool 20. Referring back to FIG. 12, one or more recesses 154 may be provided to receive the one or more alignment pegs 150 (not shown). In one aspect, the one or more recesses 154 may extend distally from the surface of the attachment element 652 for a distance DE ranging between about 0.2 mm and about 20 mm. According to particular embodiments, the recess 154 can extend from said exterior surfaces in the general direction of the attachment bore 70 a distance DA ranging between about 0.25 mm to about 5 mm. In a non-limiting example of a particular embodiment, the distal face 152 of the implant arm distal end 35 can be further configured to wrap completely or only a portion of the periphery of the proximal end 43 of the implant body 25.

In an additional embodiment, the surface of the implant body 25 contacting the distal face 152 of the delivery tool 20 may further contain one or more lateral bores 75 configured to receive one or more alignment pegs 150 protruding distally from the distal face 152 of the delivery tool 20. Referring back to FIG. 9, the pegs 150 (not shown) being received in the lateral bores 75 prevent the implant body 25 from pivoting relative to the distal face 152 of the delivery tool 20. The pegs 150 can be configured to have a rectangular, circular or any other cross section and the corresponding lateral bores 75 can also be configured to have corresponding shapes in cross section.

c. Anchor Arms

Figure 38:
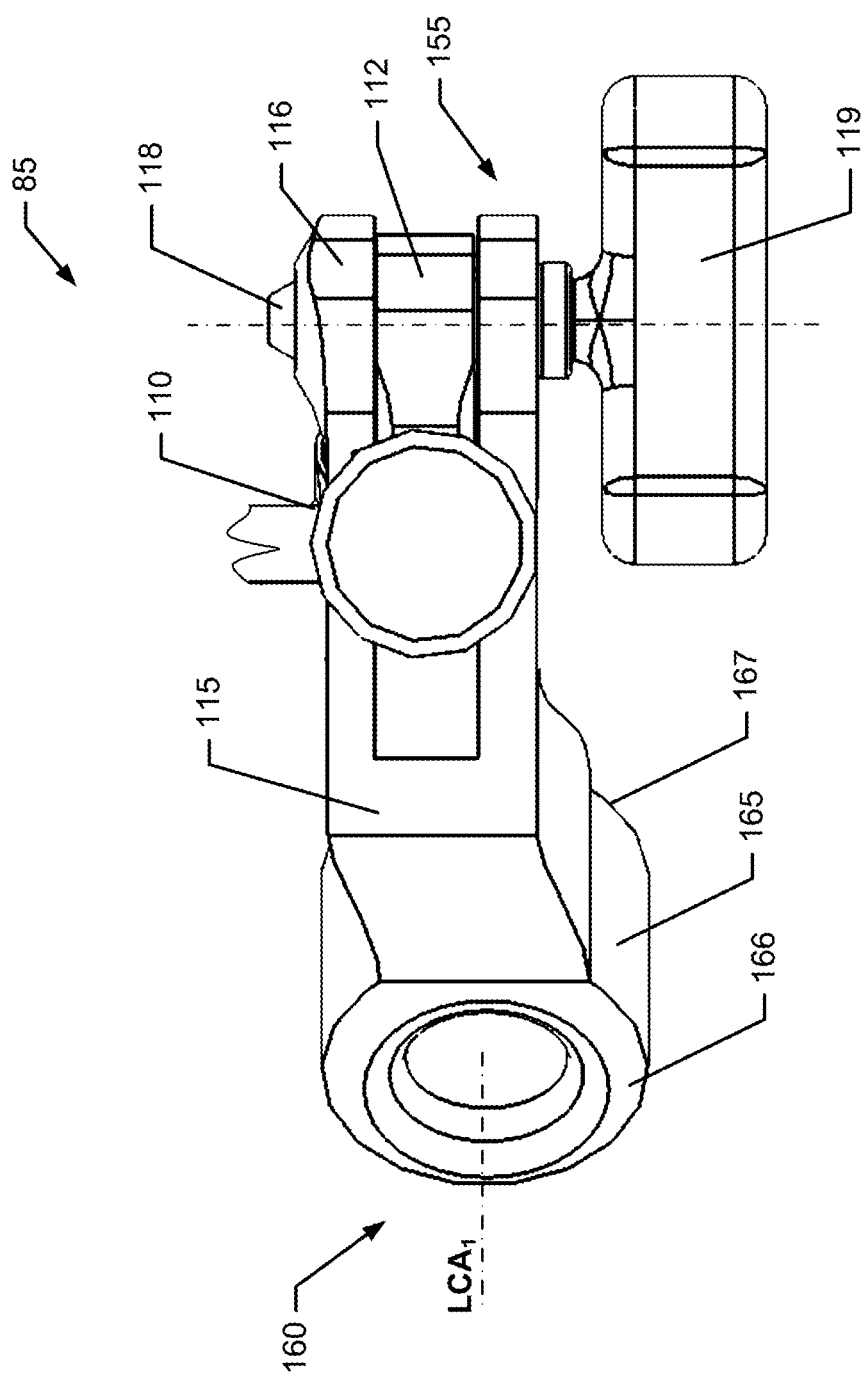
FIG. 38 is a top view of an anchor arm attached to an implant arm of the delivery tool in the first embodiment.

Referring again to FIGS. 1, 2, and 35, the arm assembly 85 includes an implant arm 110 and an anchor arm 115 supported off of the implant arm 110 at a predetermined angle by an anchor arm fitting 112. The anchor arm fitting 112 may be mechanically attached to the implant arm 110 and may include a bore 113. The anchor arm 115 may be mounted by situating the tines 116 projecting from the anchor arm on either side of the anchor arm fitting such that the fastener holes 117 formed within the tines 116 are aligned with the bore 113. The shaft 118 of the handscrew 119 may by inserted through the aligned fastener holes 117 and bore 113 to lock the anchor arm 115 in place. FIG. 38 is a top view of the anchor arm 115 mounted to the anchor arm fitting 112 on the implant arm 110 and secured in place by the handscrew 119. In one embodiment, the shaft 118 of the handscrew 119 may be threaded, and one or more of the fastener holes 117 and/or bore 113 may be provided with corresponding matching threads. In other embodiments, the shaft 118 of the handscrew 119 may be provided in the form of a retaining pin or any other reversibly locking alignment device.

As shown in FIGS. 1, 2, and 35, the anchor arm 115 is supported off of the implant arm 110 at an angle and includes a proximal end 155 and a distal end 160 distally terminating in a sleeve or collar 165 having a longitudinal center axis $LCA_1$ that is generally transverse to the longitudinal axis of the anchor arm 115. The collar 165 has a length of between approximately 10 mm and approximately 60 mm (e.g., 20 mm) disposed between collar ends 166 and 167 configured to permit and maintain accurate alignment of the first sleeve 100 along $LCA_1$ during the course of the procedure. The targeting proximal end 155 intersects the implant arm 110 at a location between the proximal and distal ends of the implant arm 110. In one embodiment, the proximal end 155 of the anchor arm 115 intersects proximal end 80 of implant arm 110. In another embodiment, the proximal end 155 of the anchor arm 115 is coupled to and/or supported off of the handle 90. Referring back to FIG. 39, the arm assembly 85 of the delivery tool 20 may include a first anchor arm 115A and second anchor arm 115B in another embodiment.

In various embodiments, each of the one or more anchor arms 115 are configured to guide one or more fasteners including, but not limited to the anchor 30 (see FIGS. 2 and 15) and the polyaxial screw 678 (see FIG. 9). In an embodiment, the anchor arm 115 may align the fastener along the direction $LCA_1$ (see FIG. 35) during insertion of the fastener. FIG. 43A is a side cross-sectional view of the implant body 25 attached to the delivery tool 20 in the embodiment illustrated previously in FIG. 39. As shown in FIG. 39, the anchor 30 may be guided through the first anchor arm 115A and the polyaxial screw 678 may be guided through the second anchor arm 115B.

In this embodiment, the first anchor arm 115A may have a sleeve 165A that is relatively narrow and of constant cross-sectional profile. As a result, the direction of insertion of the anchor 30 from the first anchor arm falls within a relatively narrow range. The second anchor arm 115B may have a conical sleeve 165B that permits the insertion of the polyaxial screw 678 along a range of insertion angles constrained by the contour of the conical sleeve 165B. The conical sleeve may be included in the delivery device 20 to facilitate the placement and insertion of fasteners in which some latitude in placement may be desired.

For example, the incorporation of a second anchor arm 115B with a conical sleeve 165B may permit a surgeon to select a desired insertion trajectory for the anchor 30 while still passing the anchor 30 through, for example, a bore 40 and/or additional bore 670. Non-limiting characteristics of a desired trajectory of the anchor may include one or more of: 1) entering at or near a S1 pedicle and further advanced in an anteromedial direction, and further toward or into sacral promontory and/or parallel to an S1 endplate; 2) entering the bone structure near or immediately adjacent a S1 or S2 foramen, and in a generally mediolateral direction further advanced to cross a sacroiliac joint, and further advanced to terminate in or through an ilium (e.g., along a midline between an inner and outer iliac wing table); or 3) be advanced down the plane of a sacroiliac joint.

Referring back to FIG. 35, the longitudinal center axis $LCA_1$ of the targeting collar 165 forms an angle $A_{LCA1\text{-}LCA2}$ with the longitudinal center axis LCA2 of the implant arm 110. For example, the angle $A_{LCA1\text{-}LCA2}$ may be range between approximately 15 degrees and approximately 135 degrees. As can be understood from FIG. 39, in one embodiment, the above-described coaxial and angular relationships between the anchor arm 115 and the implant arm 110 are rigidly maintained due to the anchor arm 115 and its anchor arm fitting 112 being in a fixed, non-adjustable configuration, and the interconnection between the proximal end of the targeting 115 and the implant arm 110 being a fixed, non-adjustable configuration at least with respect to the angle $A_{LCA1\text{-}LCA2}$ between the longitudinal center axis $LCA_1$ of the targeting collar 165 and the longitudinal center axis LCA2 of the implant arm 110. Thus, in one embodiment, the delivery tool 20 comes from the manufacture to the physician in a fixed, non-adjustable configuration having the coaxial and angular relationships articulated above with respect to FIG. 21A.

Referring to FIG. 35, the anchor arm 115 coaxial and angular relationships between the anchor arm 115 and the implant arm 110 may be adjustable in another embodiment. In this other embodiment, the anchor arm fitting 112 may be translated in a proximal or distal direction along the implant arm 110. In addition, the angle of the axis LCA1 may be adjusted by rotating the anchor arm 115 about the shaft 118 of the handscrew 119. The angle of the axis LCA1 may be maintained by locking the anchor arm 115 in place by tightening the handscrew 119.

III. Method of Use

In various embodiments, a method of implanting the implant system 15 non-transversely into the joint space of the sacroiliac joint is provided. The method includes preparing an implant insertion space within the joint space, inserting the insertion plate 45 of the implant body 25 into the implant insertion space using the delivery tool 20, and inserting an anchor 30 through a bore 40 within the implant body 25 to fix the implant body 25 in place using the delivery tool 20. A detailed description of the anatomical landmarks associated with the method, as well as a description of the various stages of the method, including insertion space preparation, insertion of the insertion plate into the joint space, and anchoring of the implant is provided in detail herein below. The implant body 25 may be inserted via the extra-articular recess of the sacroiliac joint in an extra-articular approach in one embodiment. In another embodiment, the implant body 25 may be inserted via interarticular region 1044 in an interarticular approach.

a. Anatomical Landmarks

Figure 44A:
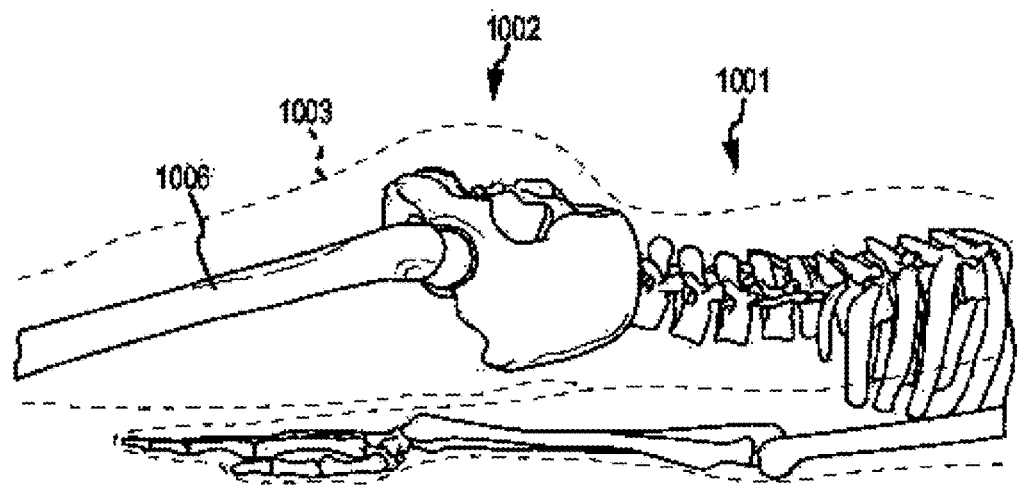
FIG. 44A is a right lateral side view of a hip region of a patient lying prone, wherein the soft tissue surrounding the skeletal structure of the patient is shown in dashed lines.
Figure 44B:
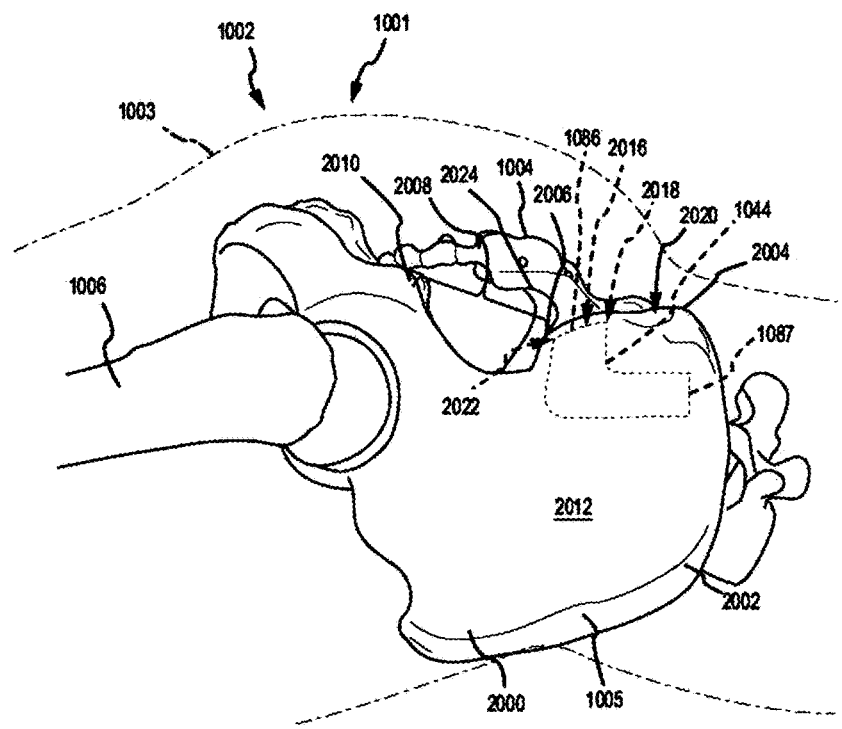
FIG. 44B is an enlarged view of the hip region of FIG. 44A.

To begin a discussion regarding the methodology associated with employing any of the above-described delivery tools 20 in implanting any of the above-described implant bodies 25 in the sacroiliac joint 1000 of a patient 1001, reference is first made to FIGS. 44A-46B to identify the bone landmarks adjacent, and defining, the sacroiliac joint 1000. FIG. 44A is a right lateral side view of a hip region 1002 of a patient 1001 lying prone, wherein the soft tissue 1003 surrounding the skeletal structure 1006 of the patient 1001 is shown in dashed lines. FIG. 44B is an enlarged view of the hip region 1002 of FIG. 44A. As illustrated in FIGS. 44A and 44B, a lateral view of the patient's hip region 1002 reveals certain features of the ilium 1005, including the anterior superior iliac spine 2000, the iliac crest 2002, the posterior superior iliac spine (PSIS) 2004, the posterior inferior iliac spine (PIIS) 2006, the greater sciatic notch 2008 extending from the posterior inferior iliac spine 2006 to the ischial spine 2010, and the tubercle of iliac crest 2012. The sacroiliac joint articular region 1044 is shown in dashed lines. A posterior inferior access region 2016 of the sacroiliac joint articular region 1044 has a superior end 2018 on the sacroiliac joint line 2019 that is between approximately 0 mm and approximately 40 mm inferior the posterior inferior overhang 2020 of the posterior superior iliac spine 2004. The posterior inferior access region 2016 of the sacroiliac joint articular region 1044 has an inferior end 2022 on the sacroiliac joint line that is at approximately the intersection of the posterior inferior iliac spine 2006 with the lateral anterior curved boundary 2024 of the sacrum 1004. In other words, the posterior inferior access region 2016 of the sacroiliac joint articular region 1044 has an inferior end 2022 on the sacroiliac joint line that is at approximately the superior beginning of the greater sciatic notch 2008.

Figure 45A:
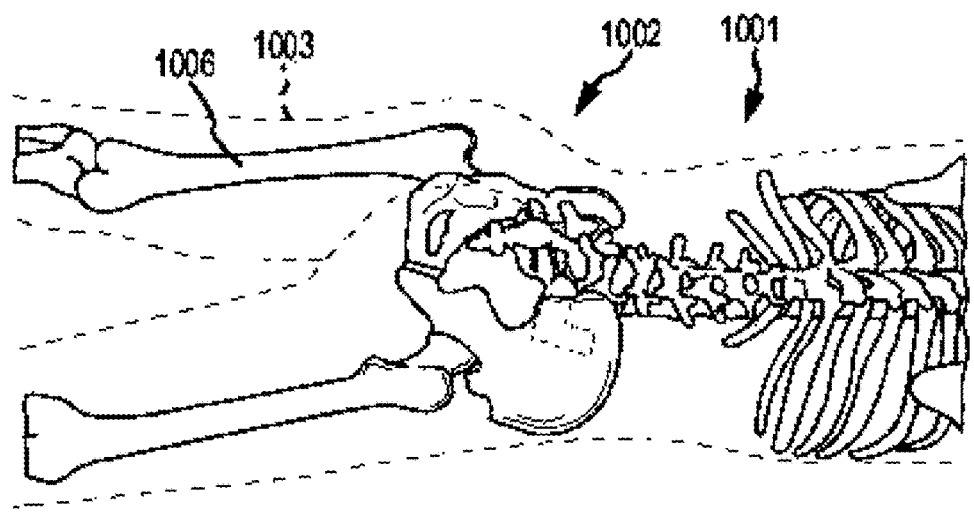
FIG. 45A is a lateral-posterior view of the hip region of the patient of FIG. 44A, wherein the patient is lying prone and the soft tissue surrounding the skeletal structure of the patient is shown in dashed lines.
Figure 45B:
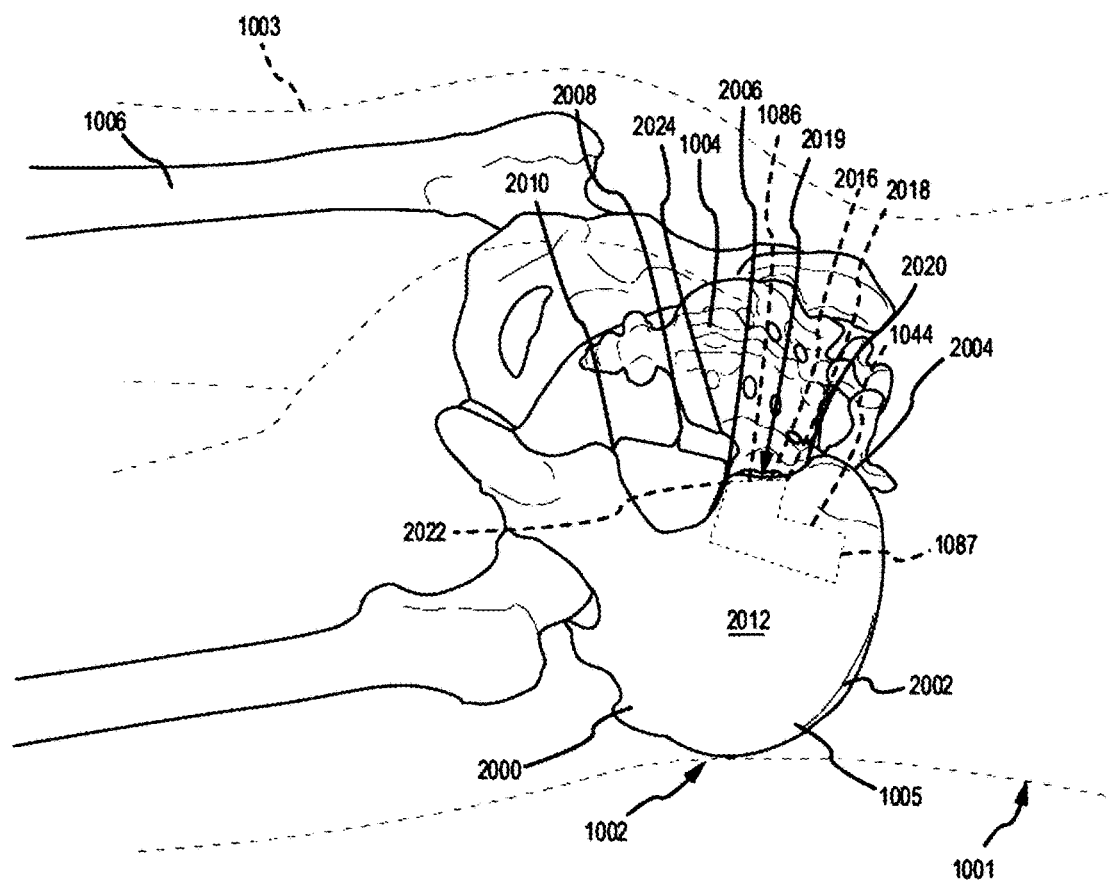
FIG. 45B is an enlarged view of the hip region of FIG. 45A.

FIG. 45A is a lateral-posterior view of the hip region 1002 of the patient 1001 of FIG. 44A, wherein the patient 1001 is lying prone and the soft tissue 1003 surrounding the skeletal structure 1006 of the patient 1001 is shown in dashed lines. FIG. 45B is an enlarged view of the hip region 1002 of FIG. 45A. As shown in FIGS. 45A and 45B, a lateral-posterior view of the patient's hip region 1002 reveals the same features of the sacrum 1004 and ilium 1005 as discussed above with respect to FIGS. 44A and 44B, except from another vantage point. The vantage point provided via FIGS. 45A and 45B provides further understanding regarding the posterior inferior access region 2016 of the sacroiliac joint articular region 1044 and superior end 2018 and inferior end 2022 of the posterior inferior access region 2016 relative to nearby anatomical features, such as, for example, the posterior inferior overhang 2020 of the posterior superior iliac spine 2004, the intersection of the posterior inferior iliac spine 2006 with the lateral anterior curved boundary 2024 of the sacrum 1004, and the superior beginning of the greater sciatic notch 2008.

Figure 46A:
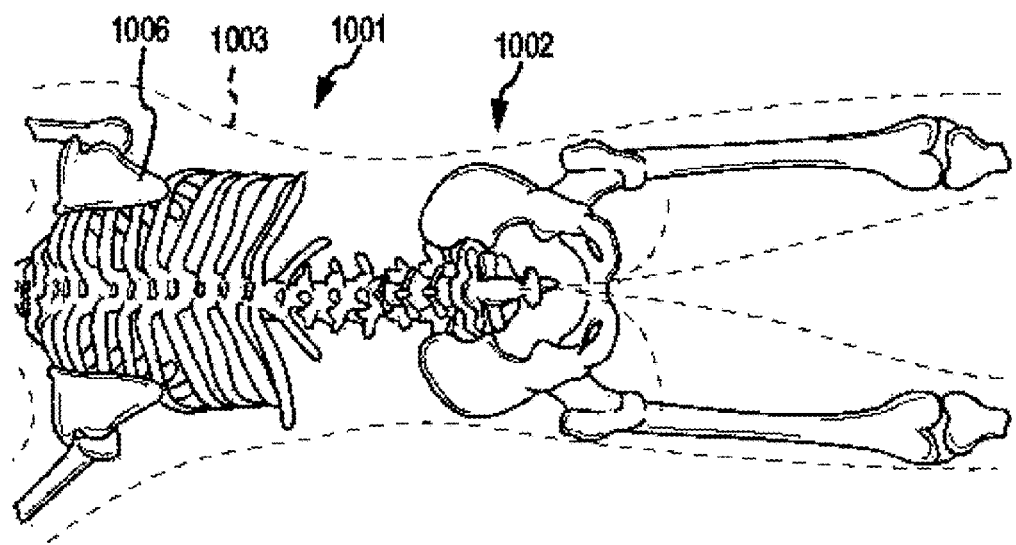
FIG. 46A is a posterior view of the hip region of the patient of FIG. 45A, wherein the patient is lying prone and the soft tissue surrounding the skeletal structure of the patient is shown in dashed lines.
Figure 46B:
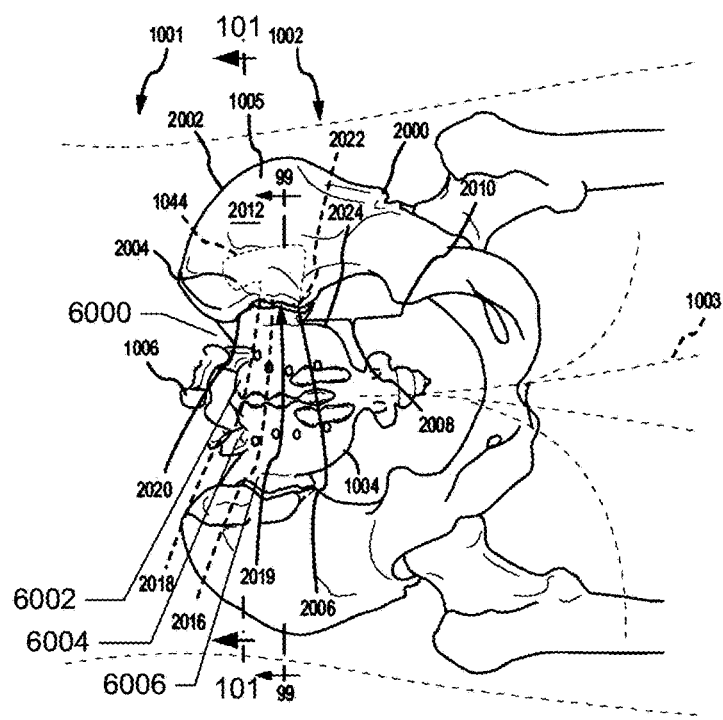
FIG. 46B is an enlarged view of the hip region of FIG. 46A.
Figure 60A:
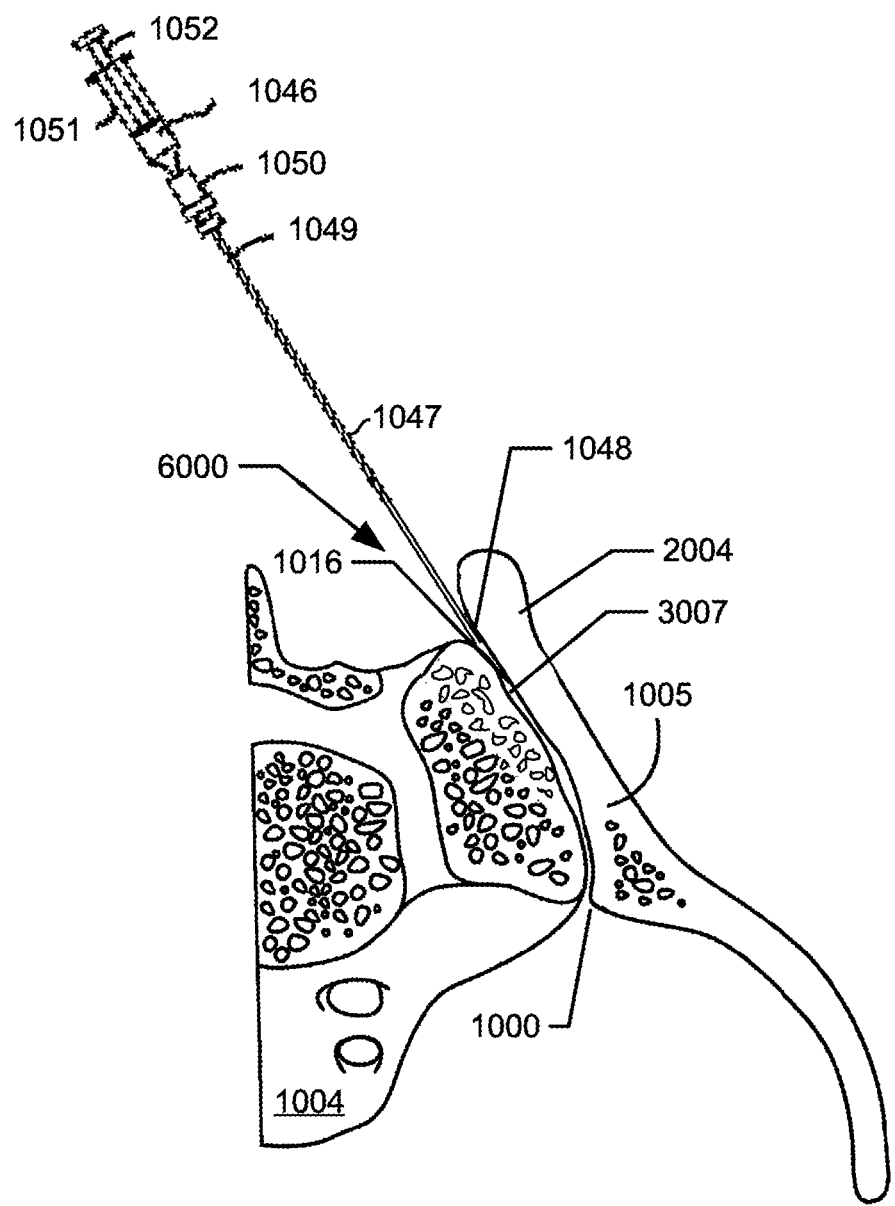
FIGS. 60A-60P illustrate successive steps in a second methodology embodiment; each step is illustrated within the transverse cross section taken along a plane extending medial-lateral and anterior posterior along section line 101-101 in FIG. 46B.
Figure 60B:
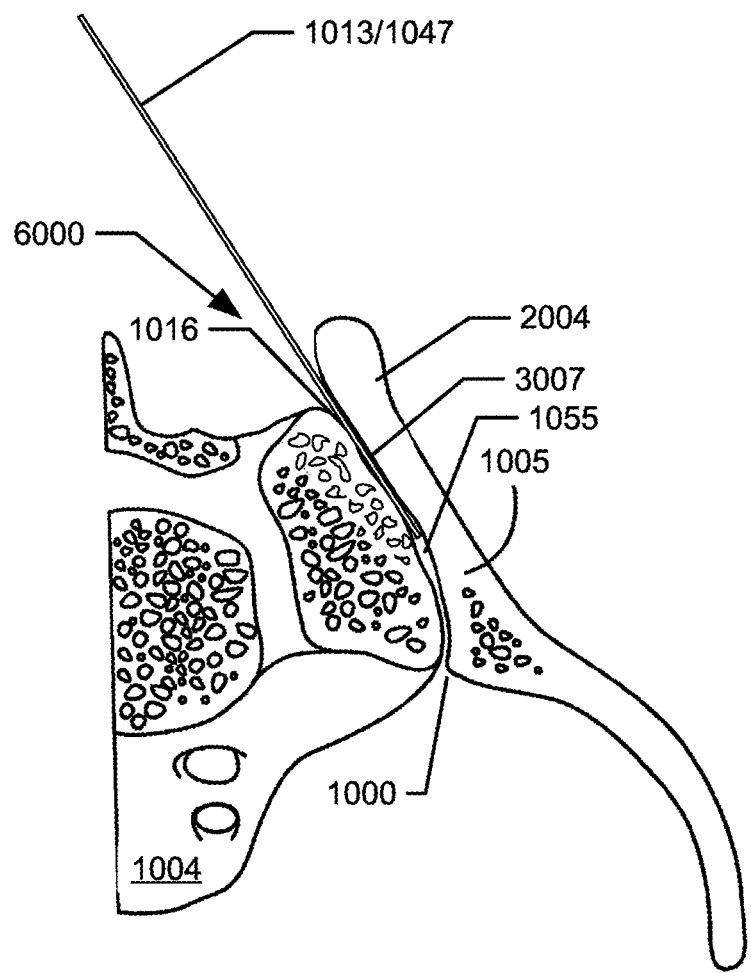

FIG. 46A is a posterior view of the hip region 1002 of the patient 1001 of FIG. 44A, wherein the patient 1001 is lying prone and the soft tissue 1003 surrounding the skeletal structure 1006 of the patient 1001 is shown in dashed lines. FIG. 46B is an enlarged view of the hip region 1002 of FIG. 46A. As shown in FIGS. 46A and 46B, a posterior view of the patient's hip region 1002 reveals the same features of the sacrum 1004 and ilium 1005 as discussed above with respect to FIGS. 44A and 44B, except from yet another vantage point. The vantage point provided via FIGS. 46A and 46B provides yet further understanding regarding the posterior inferior access region 2016 of the sacroiliac joint articular region 1044 and superior end 2018 and inferior end 2022 of the posterior inferior access region 2016 relative to nearby anatomical features, such as, for example, the posterior inferior overhang 2020 of the posterior superior iliac spine 2004, the intersection of the posterior inferior iliac spine 2006 with the lateral anterior curved boundary 2024 of the sacrum 1004, and the superior beginning of the greater sciatic notch 2008. In addition, FIGS. 46A and 46B provide a view of the sacral promontory 6002, the S1 superior articular process or S1 facet joint 6004, and sacral ala 6006.

a. Implantation Via Extra-Articular Approach i. Preparation of Implant Receiving Space Now that the relevant anatomical landmarks have been identified with respect to FIGS. 44A-46B, the methodology associated with employing any of the above-described delivery tools 20 in implanting any of the above-described implant bodies 25 in the sacroiliac joint 1000 of a patient 1001 can be discussed. In doing so, reference will be made to FIGS. 60A-60P, which are each a step in the methodology and illustrated as the same transverse cross section taken in along a plane extending medial-lateral and ventral dorsal along section line 101-101 in FIG. 46B. In this cross section, the anterior portion of the articular surfaces 1016 are covered by a thick layer of articular cartilage with a joint space existing between them while the dorsal or posterior portion of the articular surfaces in this cross section are covered by ligaments. FIGS. 60A-60P are simplified for illustrative purposes and do not show these features to scale. Now referring primarily to FIG. 60A, an embodiment of the method can include the step of placing a patient under sedation prone on a translucent operating table (or other suitable surface). The sacroiliac joint 1000 can be locally anesthetized to allow for injecting a radiographic contrast 1046 (as a non-limiting example, ISOVIEW 300 radiographic contrast) under fluoroscopic guidance into the extra-articular space 3007 of the sacroiliac joint 1000 via the extra-articular recess access region 6000 to outline the articular surfaces 1016 of the sacroiliac joint 1000) defined between the sacrum 1004 and ilium 1005. Injection of the radiographic contrast 1046 within the sacroiliac joint 1000 can be accomplished utilizing a tubular member 1047 (such as a syringe needle) having first tubular member end 1048 which can be advanced between the articulating surfaces 1016 of the sacroiliac joint 1000 and having a second tubular member end 1049 which removably couples to a hub 1050. The hub 1050 can be configured to removably couple to a syringe barrel 1051 (or other device to contain and deliver an amount of radiographic contrast 1046). In the example of a syringe barrel 1051, the syringe barrel 1051 can have an internal volume capable of receiving an amount of the radiographic contrast 1046 sufficient for outlining the articular surfaces 1016 of the sacroiliac joint 1000, for example, under lateral fluoroscopy. A plunger 1052 can be slidingly received within the barrel 1051 to deliver the radiographic contrast 1046 through the tubular member 1047 into the sacroiliac joint 1000. The tubular member 1047 can have a gauge ranging between about 16 gauge and about 20 gauge and can further be incrementally marked on the external surface to allow determination of the depth at which the first needle end 1048 has advanced within the sacroiliac joint 1000. As the first needle end 1048 advances into the sacroiliac joint 1000 the radiographic dye 1046 can be delivered from within the syringe barrel 1051 into the sacroiliac joint 1000 to allow visualization of the sacroiliac joint 1000 and location of the tubular needle 1047 within the sacroiliac joint 1000.

Now referring primarily to FIG. 60B, once the first tubular member end 1048 has been sufficiently advanced into the sacroiliac joint 1000 and the articular surfaces 1016 of the sacroiliac joint 1000 have been sufficiently visualized, the hub 1050 can be removed from the tubular member 1047 leaving the tubular member 1047 fixed within the sacroiliac joint 1000 as an initial guide for tools subsequently used to locate or place the implant body 25 non-transversely between the articulating surfaces 1016 of the sacroiliac joint 1000 (e.g., locate the implant body 25 non-transversely to the joint plane 1030 generally defined by the articulating surfaces 1016 of the interarticular region 1044 of the sacroiliac joint 1000) or in removal of a portion of the sacroiliac joint 1000 within the region defined by the articular surfaces 1016 to generate an implant receiving space 1029 (see FIG. 60H). Alternately, one or more guide pins 1013 can be inserted along substantially the same path of the tubular member 1047 for fixed engagement within the sacroiliac joint 1000 and used in subsequent steps as a guide(s).

Figure 59:
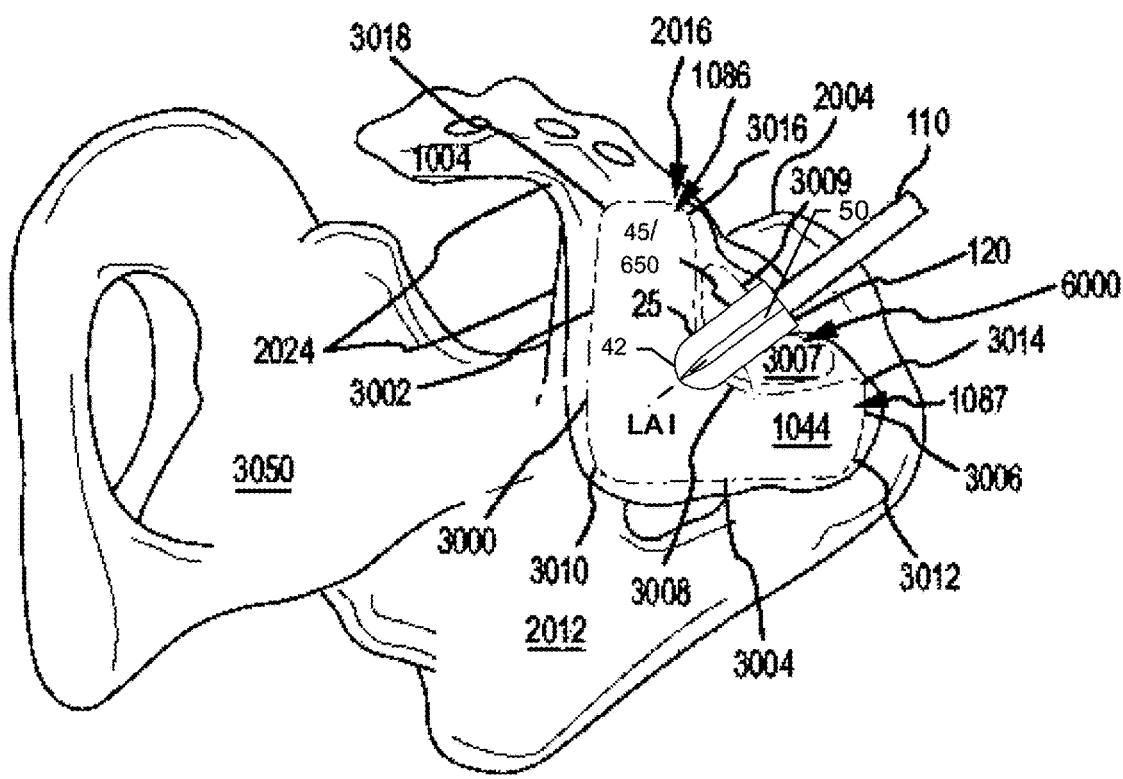
FIG. 59 is a lateral side view of a hip region of a patient lying prone with the ilium removed showing the implant body positioned for implantation within the extra-articular space.
Figure 60C:
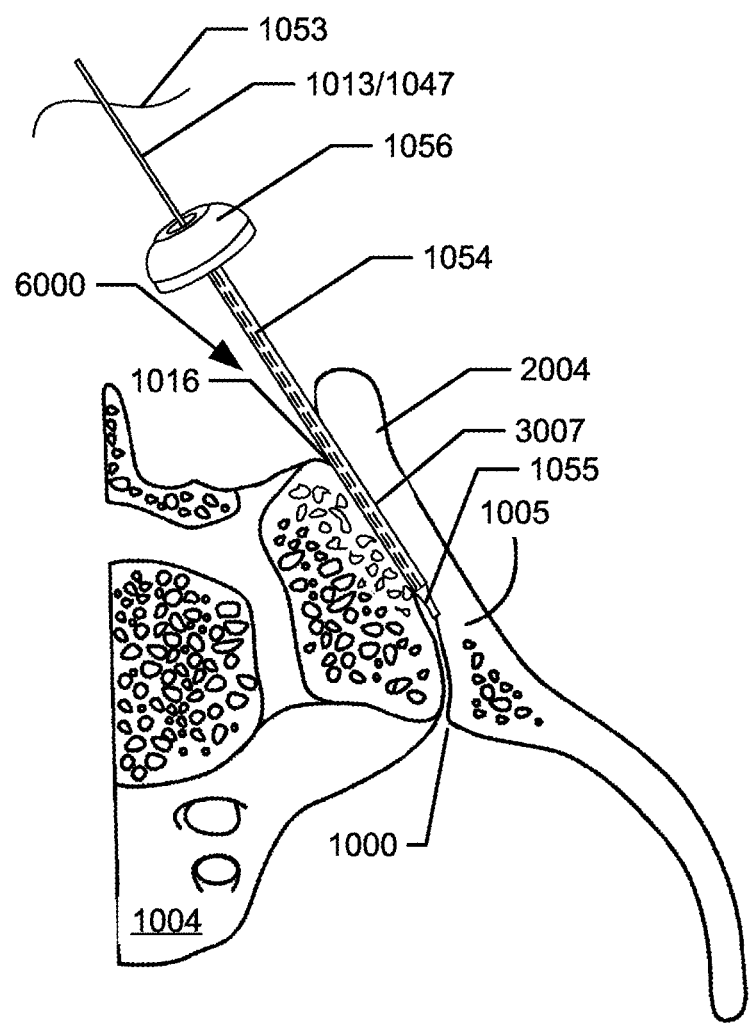

Now referring primarily to FIG. 60C, a small incision 1053 can be made in the skin at the extra-articular recess access region 6000 aspect of the sacroiliac joint 1000, extending proximal and distal to the tubular member 1047 along the line of the sacroiliac joint 1000 to provide a passage to access the interarticular space between the articulating surfaces 1016 (see FIG. 47B) of the sacroiliac joint 1000. More specifically, as can be understood from FIGS. 57-61, in one embodiment, the small incision 1053 can be made along the joint line 2019 of the sacroiliac joint 1000 in the tissue covering the extra-articular recess access region 6000 of the sacroiliac joint 1000. A cannulated probe 1054 can be slidingly engaged with the tubular member 1047 (or guide pin 1013) extending outwardly from the sacroiliac joint 1000 (while the sacroiliac joint 1000 may be shown in the figures as being substantially linear for illustrative purposes, it is to be understood that the normal irregular features of the sacroiliac joint have not been necessarily removed). The cannulated probe 1054 can have a probe body 1054 of generally cylindrical shape terminating in a spatulate tip 1055 at the end advanced into the sacroiliac joint 1000. A removable cannulated probe handle 1056 couples to the opposed end of the probe body 1054. The spatulate tip 1055 can be guided along the tubular needle 1047 or guide wire 1013 into the posterior portion of the sacroiliac joint 1000 and advanced to the anterior portion of the sacroiliac joint 1000 under lateral fluoroscopic visualization. The cannulated probe handle 1056 can then be removed providing the generally cylindrical probe body 1054 extending outwardly from the sacroiliac joint 1000 through the incision 1053 made in the skin. Alternatively, probe 1054 can be used to guide, advance or place a needle, guide wire or other instrument up to, near, or into the sacroiliac joint 1000.

Additionally, in particular embodiments, probe handle 1056 or the opposed end of the probe body 1054, or both, can be configured to have an interference fit or a Luer lock hub to communicate with a syringe barrel 1051 in order to advance contrast, in situ curable biocompatible materials, stem cells, or any other suitable materials through the cannulated probe 1054 or cannulated probe handle 1056.

Figure 60D:
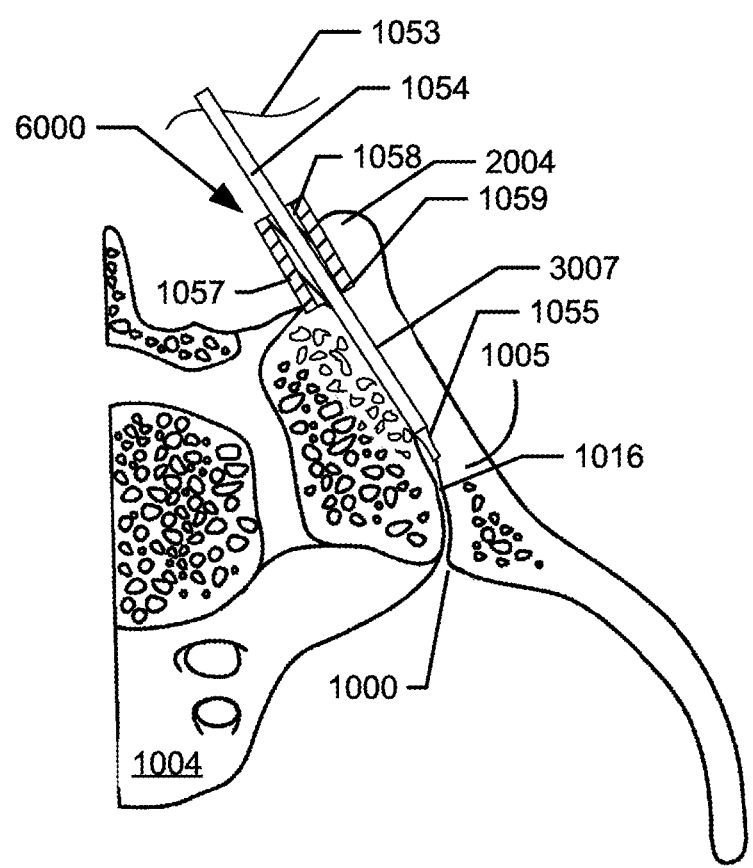

Now referring primarily to FIG. 60D, a passage from the incision 1053 (see FIG. 47C) to the sacroiliac joint 1000 can be generated by inserting a cannula 1057 into the incision. A soft tissue dilator 1058 having a blunt end 1059 can be advanced over the probe body 1054, or a plurality of soft tissue dilators of increasing size, until the blunt end 1059 of the soft tissue dilator 1058 and the corresponding cannula end contact the extra-articular recess access region 6000 of the sacroiliac joint 1000. The soft tissue dilator 1058 can be removed from within the cannula 1057. The external surface of the cannula 1057 can be sufficiently engaged with the surrounding tissue to avoid having the tissue resituate within the hollow inside of the cannula 1057. A non-limiting embodiment of the cannula 1057 provides a tubular body having substantially parallel opposed side walls which terminate in a radius at both ends (lozenge shape) into which a plurality of different jigs can be inserted. Alternatively, as a non-limiting example, according to particular embodiments, cannula 1057 and corresponding dilators 1058 and alignment jigs 1060 can be configured to have tubular bodies with an elliptical or circular cross section.

In some embodiments, the cannula 1057 may be additionally configured to have within or near its walls a light source such as, for example, a fiber optic or a LED light source to assist in visualization of the working area. Also, in some embodiments, irrigation and suction tubing may communicate with the inside passage of cannula 1057.

Figure 60E:
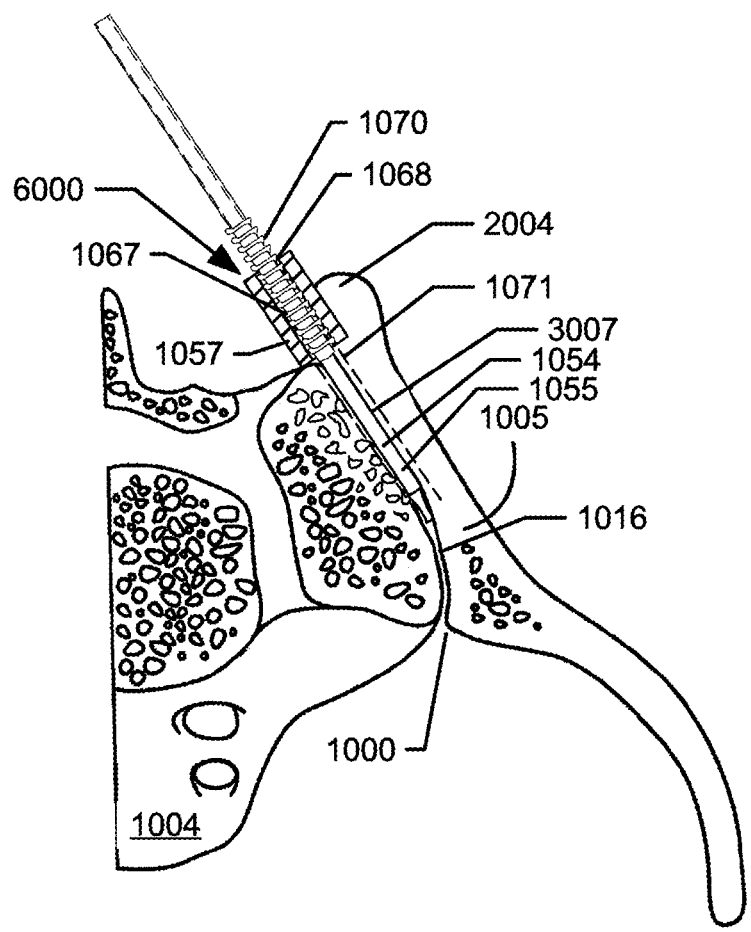

Now referring to FIG. 60E, a cannulated drill bit 1070 can be advanced over the probe body 1054 and within a drill guide hole 1068 (see FIGS. 49A and 49B) of the first drill jig 1067. The cannulated drill bit 1070 under fluoroscopic guidance can be advanced into the interarticular region 1044 between the articulating surfaces 1016 of the sacroiliac joint 1000 to produce a first bore 1071 (shown in broken line) to a predetermined depth. As to certain embodiments of the method, an amount of articular cartilage or other tissues from between the articular surfaces 1016 of the sacroiliac joint 1000 can be removed sufficient to allow embodiments of the implant body 25 to be implanted in replacement of the removed articular cartilage or tissue. Because the method may remove the degenerative articular cartilage or tissue between the articular surfaces 1016 of the sacroiliac joint 1000, the articular surfaces 1016 of the sacroiliac joint 1000 can remain intact or substantially intact allowing implant body 25 to be non-transversely located between the articular surfaces 1016 of the sacroiliac joint 1000. Other instruments can be utilized separately or in combination with a cannulated drill bit 1062 for the removal of articular cartilage or tissue between articular surfaces 1016 such as: endoscopy tools, box chisels, side cutting router bits, burs, flexible burs and bits, hole saws, curettes, lasers (such as $CO_2$, Nd:YAG (neodymium-doped yttrium-aluminum-garnet), argon, and ruby), and electrosurgical equipment employing electromagnetic energy.

In an embodiment, the cutting electrode of the electrosurgical equipment may be a fine micro-needle, a lancet, a knife, a wire or band loop, a snare, an energized scalpel, or the like. The electrosurgical waveforms delivered by the cutting electrode may be set to promote two types of tissue effects, namely coagulation (temperature rises within cells, which then dehydrate and shrink) or cut (heating of cellular water occurs so rapidly that cells burst). The proportion of cells coagulated to those cut can be varied, resulting in a "blended" or "mixed" effect. Additionally, a fully rectified current, or a partially rectified current, or a fulguration current where a greater amount or lateral heat is produced can be employed to find the articular surfaces of the joint and aid in advancing a probe or guide wire into a position in between the articulating surfaces. These currents can effectively degrade the cartilage and allow advance into the joint without grossly penetrating much beyond the cartilage.

In one embodiment, the electrical energy delivered via the cutting electrode can be either monopolar or bipolar and operate with high frequency currents, for example, in the range of about 300 kHz and about 1000 kHz. The waveform of the delivered electrical energy may be a pure sinusoidal current waveform where the "crest factor" can be constant at about 1.4 for every sinus waveform, and a voltage peak of approximately 300 V to enable a "pure" cutting effect with the smallest possible coagulation effect. Alternatively, the electrical energy may be delivered as amplitude modulated current waveforms where the crest factor varies between 1.5 and 8, with decreasing crest factors providing less of a coagulation effect.

Figure 60F:
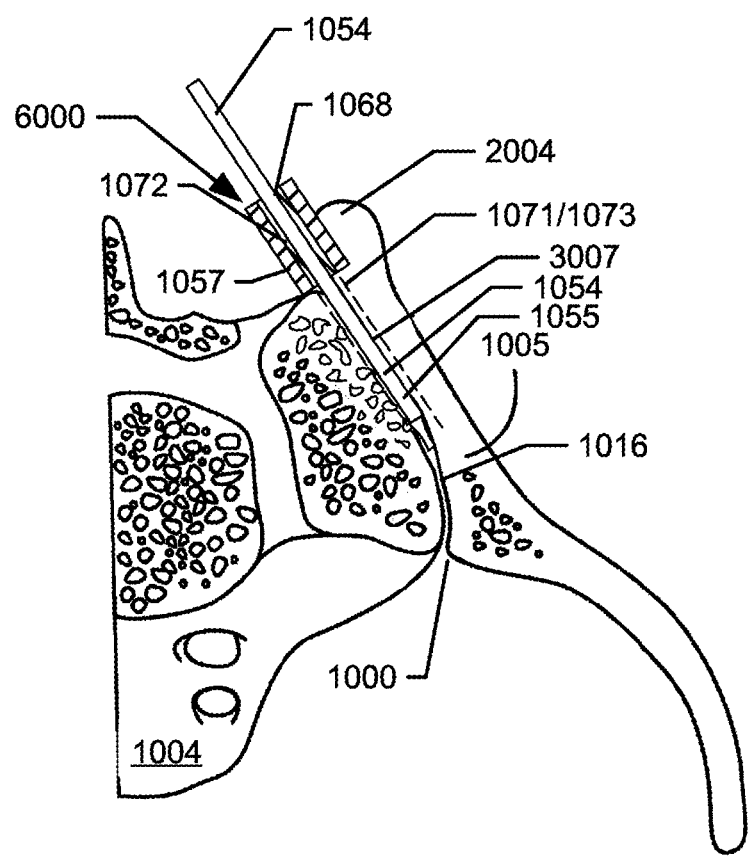

Now referring to FIG. 60F, as to certain embodiments of the invention, the first drill jig 1067 can be removed from within the cannula 1057 and a second drill jig 1072 can be advanced over the probe body 1054 and received within the cannula 1057; however, the invention is not limited to any particular number of drill jigs and as to certain embodiments of the method the first drill jig 1067 can include all the required drill guide hole(s) 1068 (or slots or other configurations of the drill guide) and as to other embodiments of the method a plurality of drill jigs can be utilized in serial order to provide all the drill guide holes 1068. As to the particular embodiment of the invention shown by the figures, the first drill jig 1067 can provide one or more additional drill guide holes 1068 which guide in relation to the first bore 1071 a second or more cannulated drills 1062 of the same or different configuration to be inserted within and advanced into the sacroiliac joint 1000 to produce a second bore 1073 (generally shown in broken line as 1071/1073) or a plurality of bores within the sacroiliac joint 1000 spaced apart in predetermined pattern to allow removal of sufficient articular cartilage 1016 or other tissue from the interarticular space of sacroiliac joint 1000 for placement of embodiments of the sacroiliac joint implant 25 within the region defined by and between the paired articular surfaces 1016 of the sacroiliac joint 1000. As to certain methods of the invention, the first drill jig 1067 or the second drill jig 1072 or a plurality of drill jigs can be utilized in serial order to remove a portion of the sacroiliac joint 1000 for generation of an implant receiving space 1029 (see, for example, FIG. 60H). As these embodiments of the method, articular cartilage or other tissues and sufficient subchondral bone can be removed from between the articular surfaces 1016 of the sacroiliac joint 1000 sufficient to allow placement of certain embodiments of the sacroiliac joint implant body 25. In other embodiments, one or more transverse receiving channels 1074 aligned with the direction of the receiving space and extending in a direction perpendicular to the joint plane 1030 can be cut into at least one of the articular surfaces 1016 of said sacroiliac joint 1000 sufficient to receive certain elements of the implant body 25 including, but not limited to one or more fins 50, as illustrated in FIG. 5 in one embodiment of the implant body 25. The one or more transverse receiving channels 1074 can be cut a depth into the subchondral, cortical bone or cancellous bone of the sacrum 1004 and/or ilium 1005. A transverse receiving channel 1074 in one embodiment is illustrated in FIG. 60H as dashed lines.

Figure 60G:
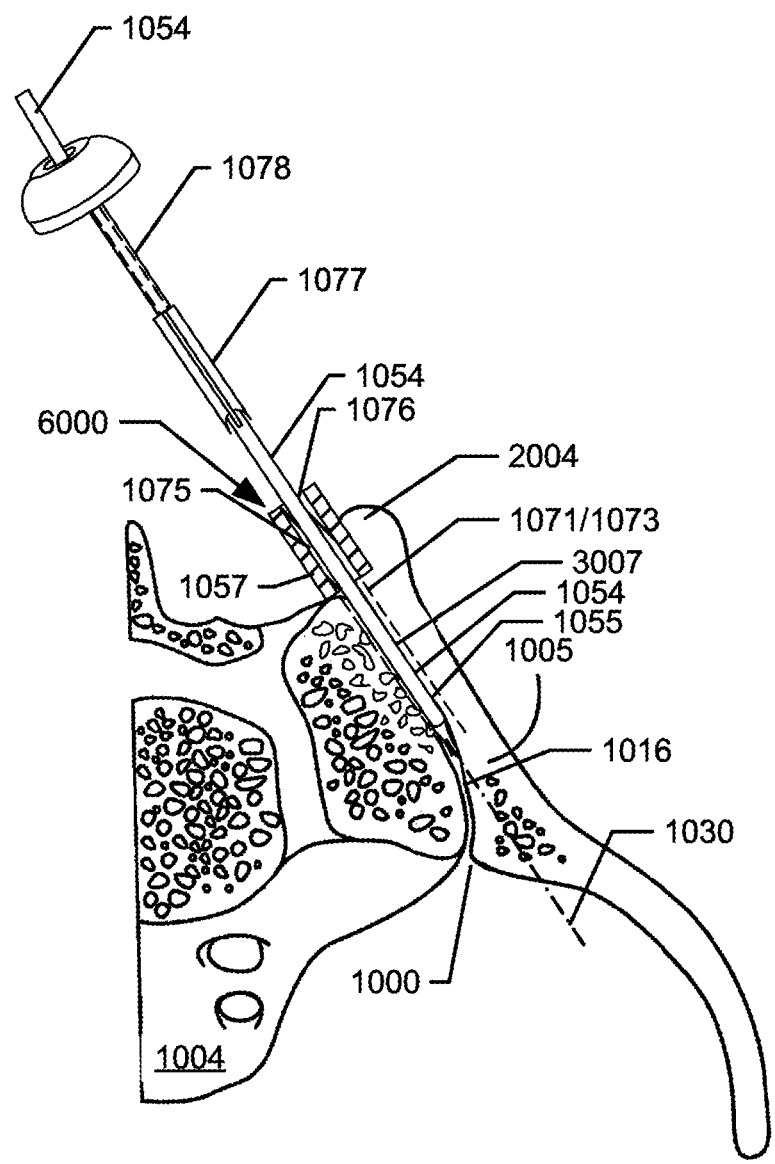
Figure 60H:
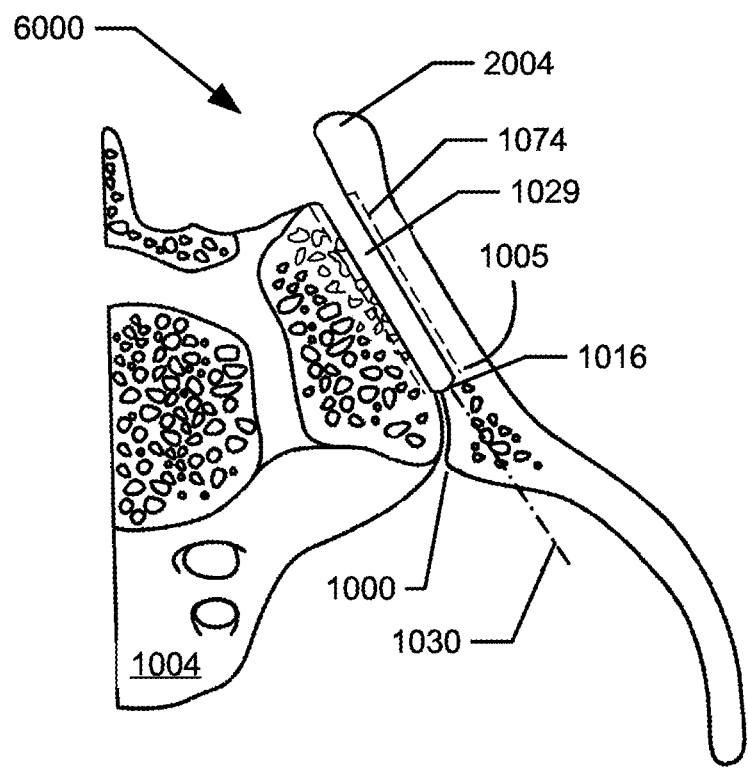

Now referring primarily to FIG. 60G, in a subsequent step, the last drill jig 1072 in the series can be removed from within the cannula 1057 and a broach jig 1075 can be advanced over the probe body 1054 and situated within the cannula 1057. The broach jig 1075 can include a broach guide hole 1076 which receives a first broach end 1077 of a cannulated broach 1078 advanced over the probe body 1054. The first broach end 1077 can have a configuration which can be advanced into the sacroiliac joint 1000. As to certain embodiments of the method, the first broach end 1077 can be adapted to remove an amount of articular cartilage and other tissue from between the articular surfaces 1016 within the articular region 1044 of the sacroiliac joint 1000 for non-transverse placement of the sacroiliac joint implant body 25. Referring to FIG. 60H, in various other embodiments of the method, the cannulated broach 1078 can further remove a sufficient portion of the sacroiliac joint 1000 to generate an implant receiving space 1029 to receive various embodiments of the sacroiliac joint implant 25, as illustrated in FIGS. 5, 9, and 12 by way of non-limiting examples. In yet other embodiments, the cannulated broach 1078 can further remove a sufficient portion of the sacroiliac joint 1000 to generate one or more transverse receiving channels 1074 to receive one or more fins 50 adapted to extend into the bone of the sacrum 1004 or the ilium 1005 in various embodiments of the sacroiliac joint implant 25 (see FIGS. 5, 9, and 12).

Figure 61:
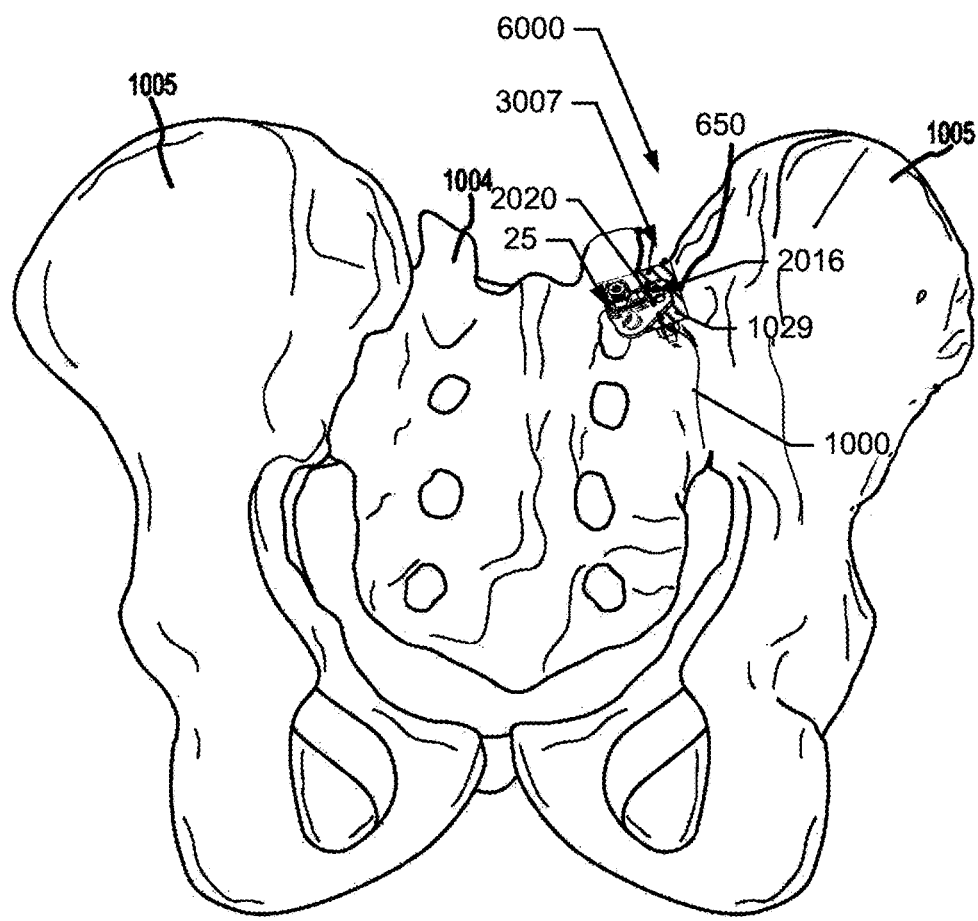
FIG. 61 is a posterior view of the implant assembly fully inserted within the implantation area.
Figure 62:
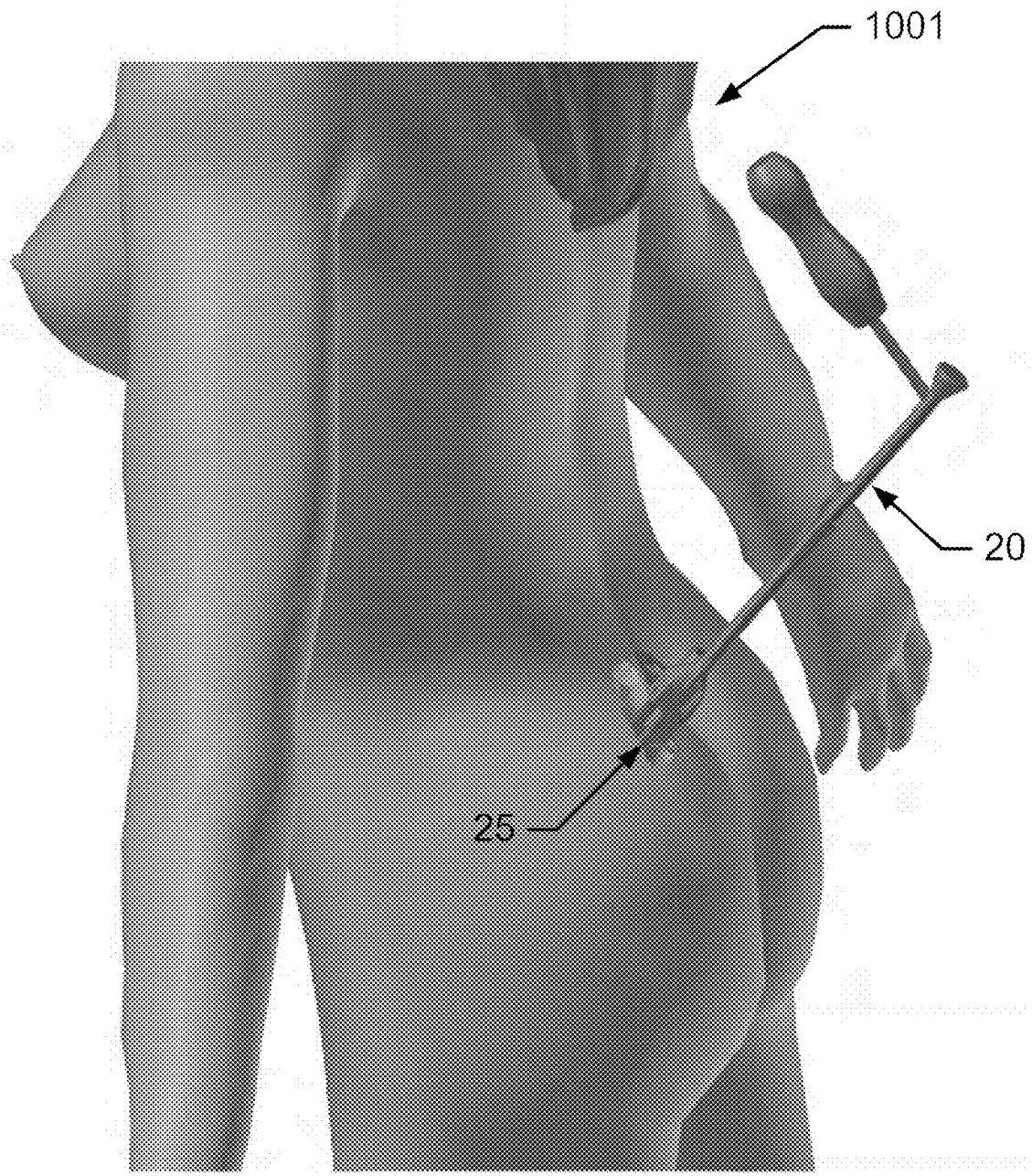
FIGS. 62-91 are various views of the sacroiliac joint and associated skeletal structures of a patient illustrating the position and orientation of the delivery tool and/or implant assembly in various embodiments during implantation of the implant assembly within the extra-articular space of the sacroiliac joint using various embodiments of a method.
Figure 63:
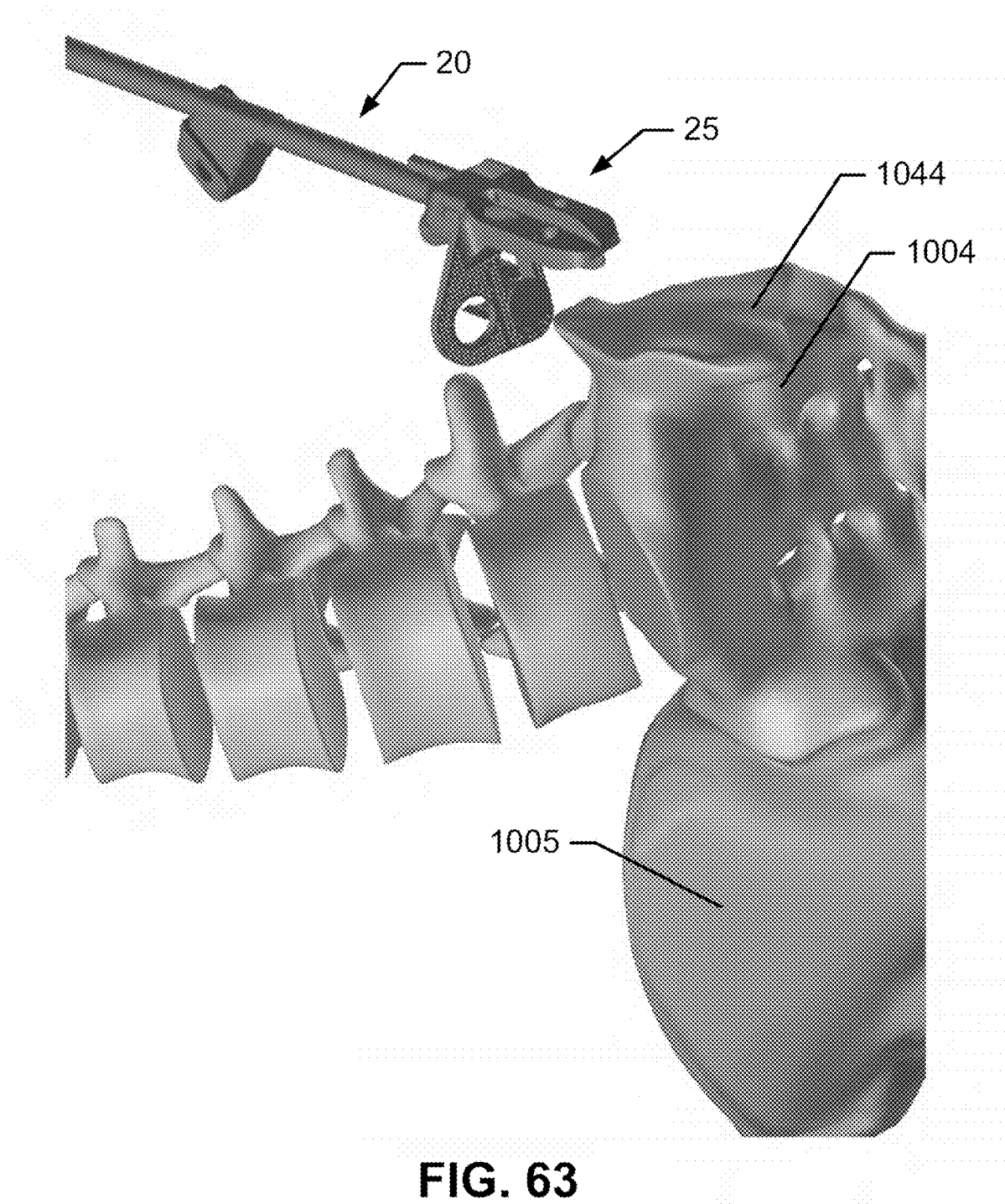
Figure 64:
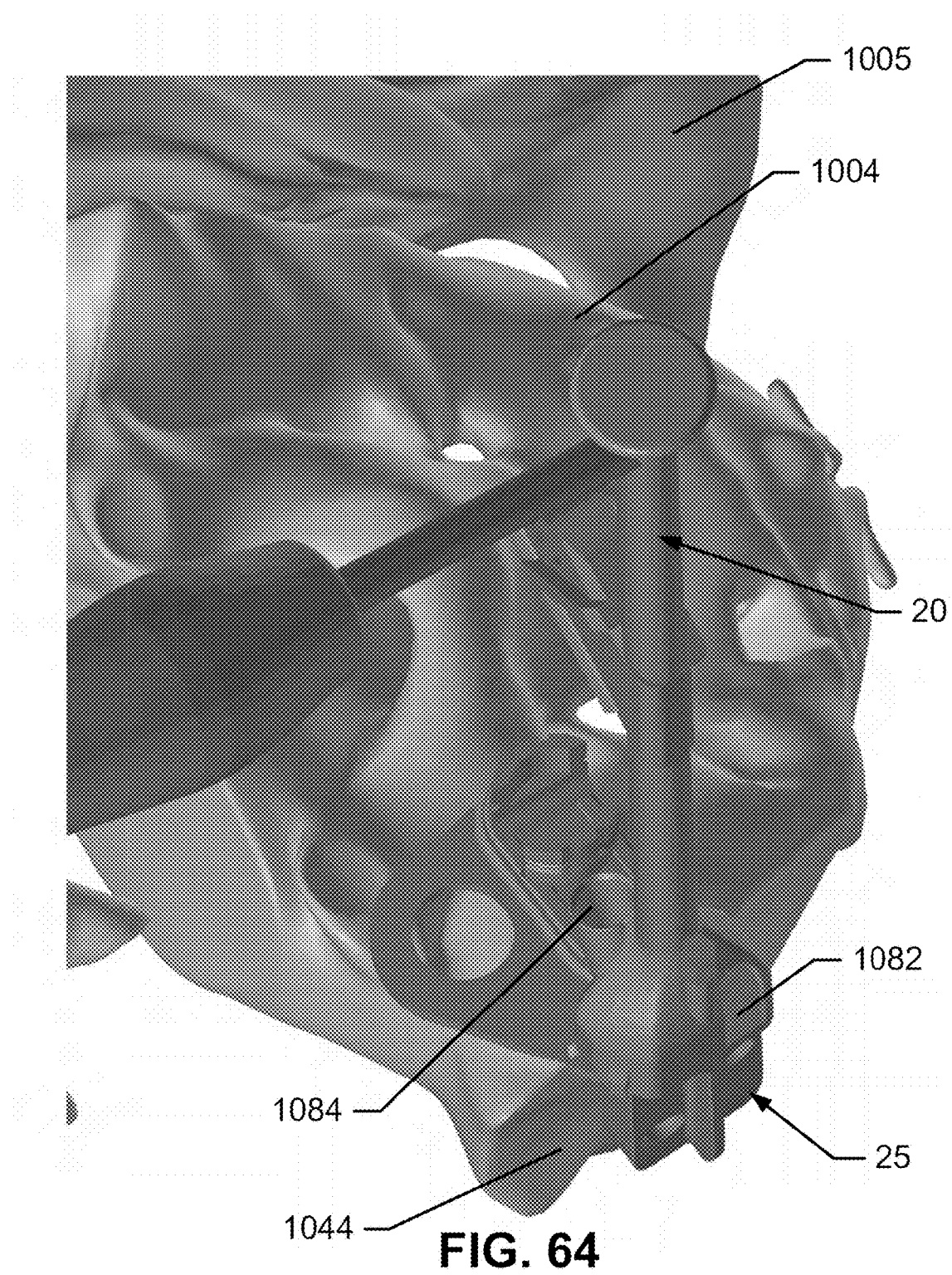
Figure 65:
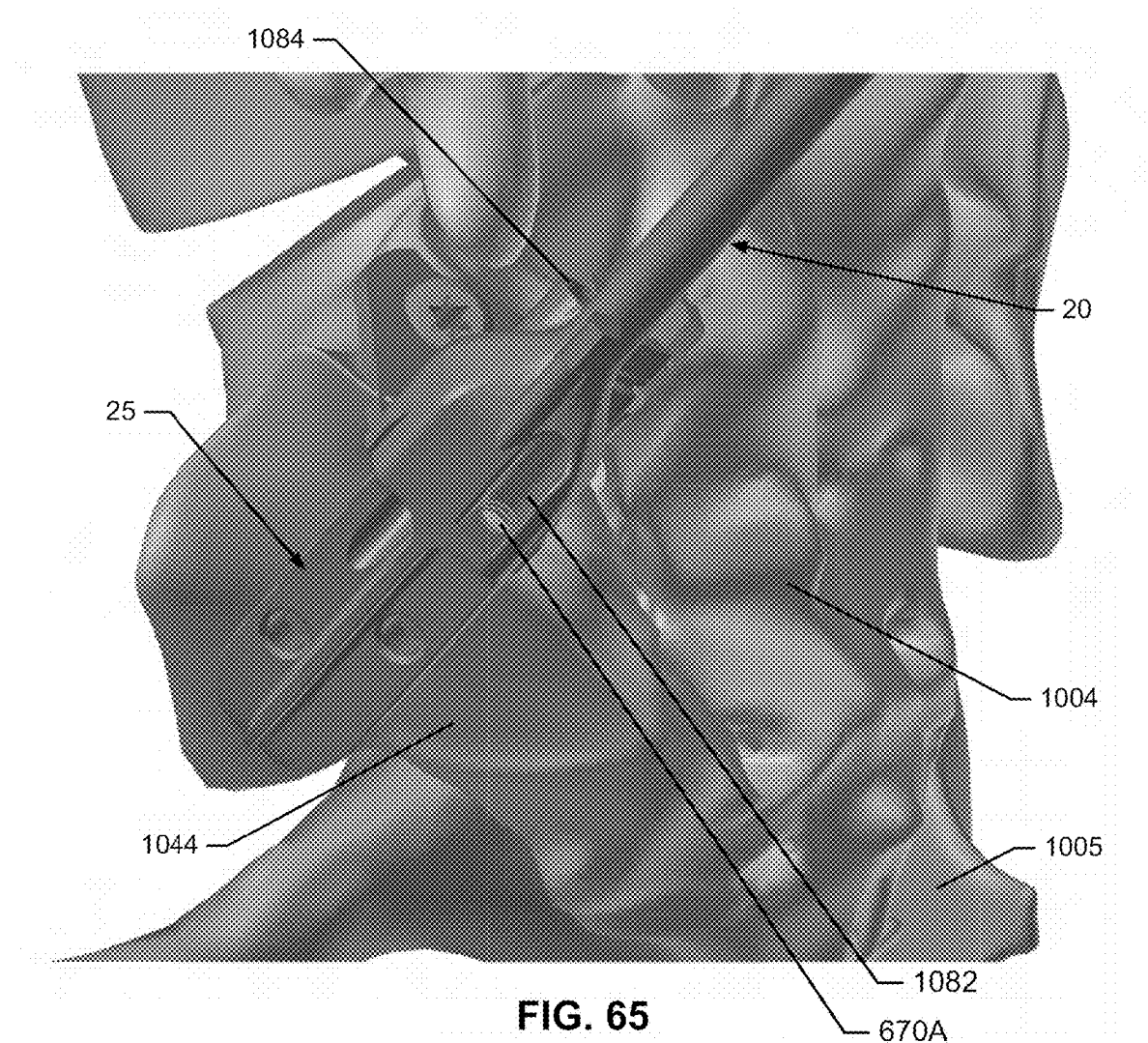
Figure 66:
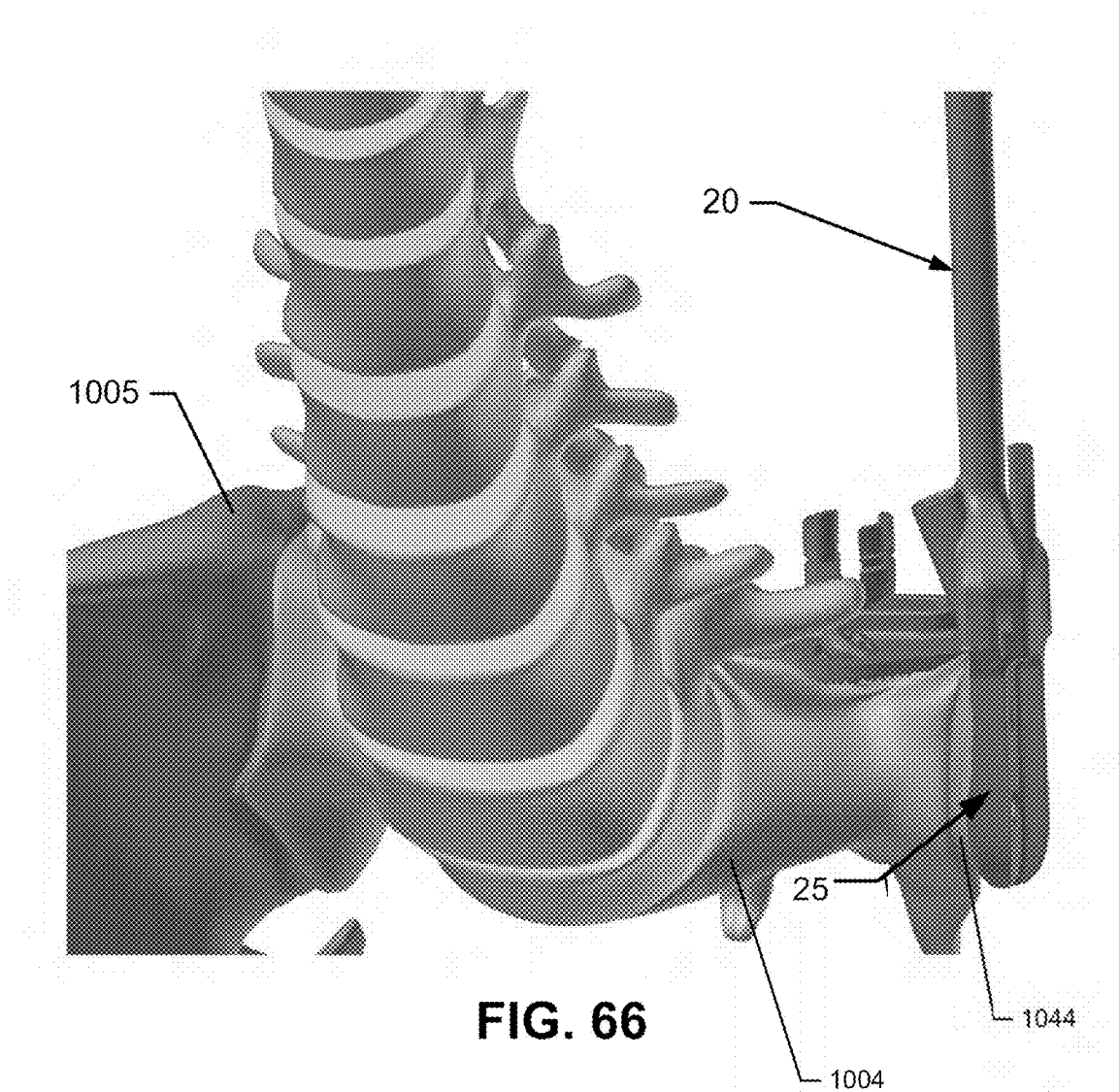
Figure 67:
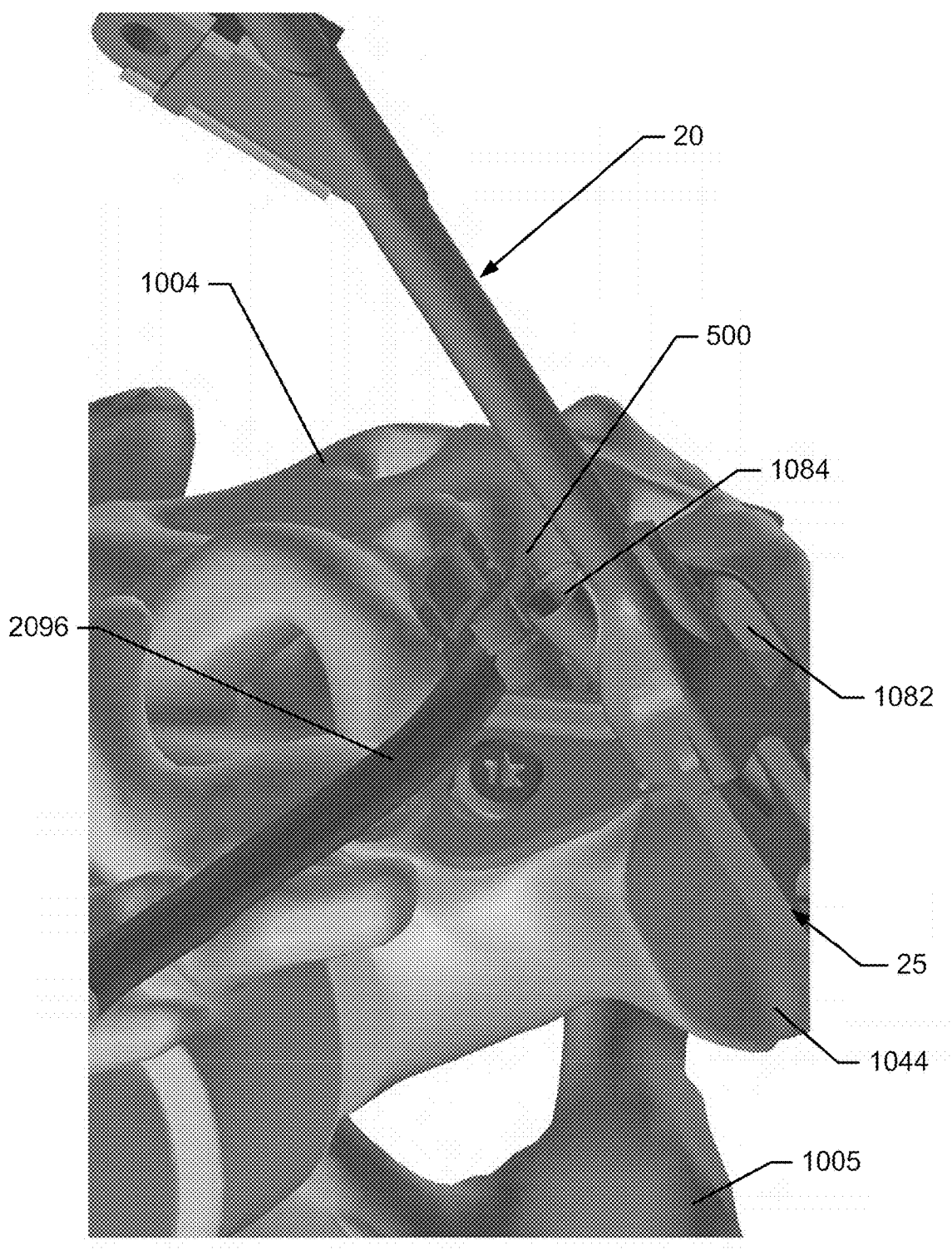
Figure 68:
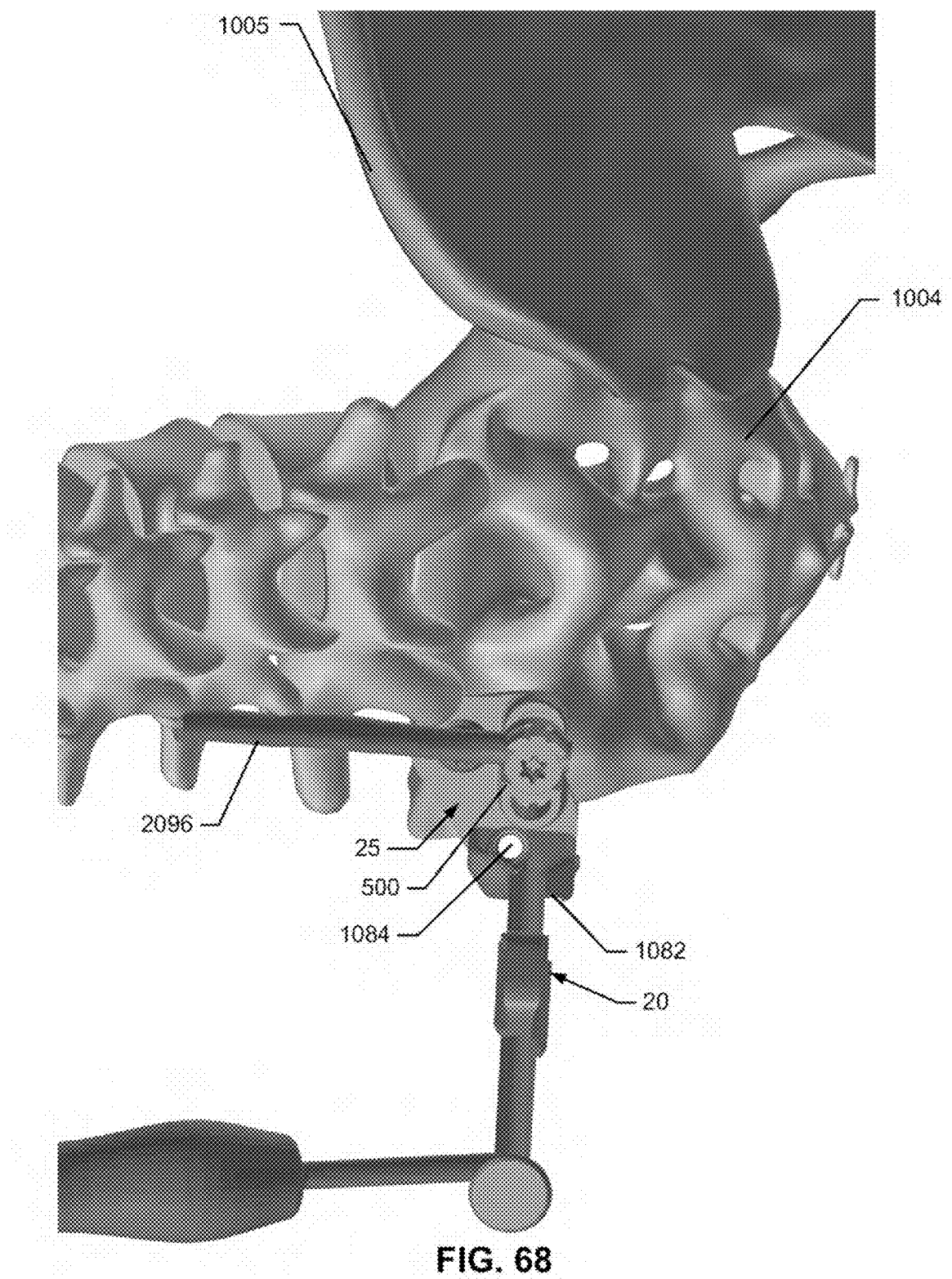
Figure 69:
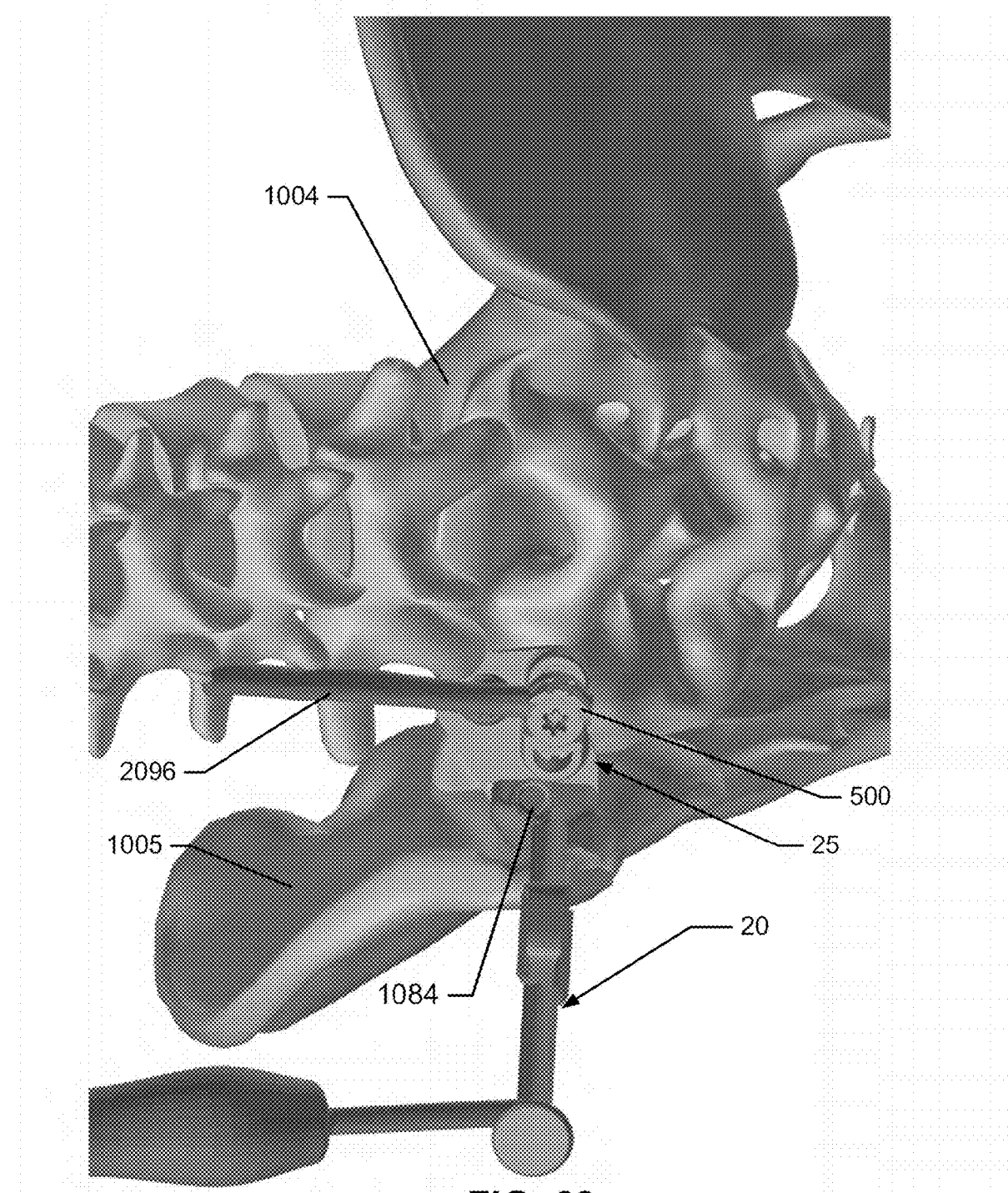
Figure 70:
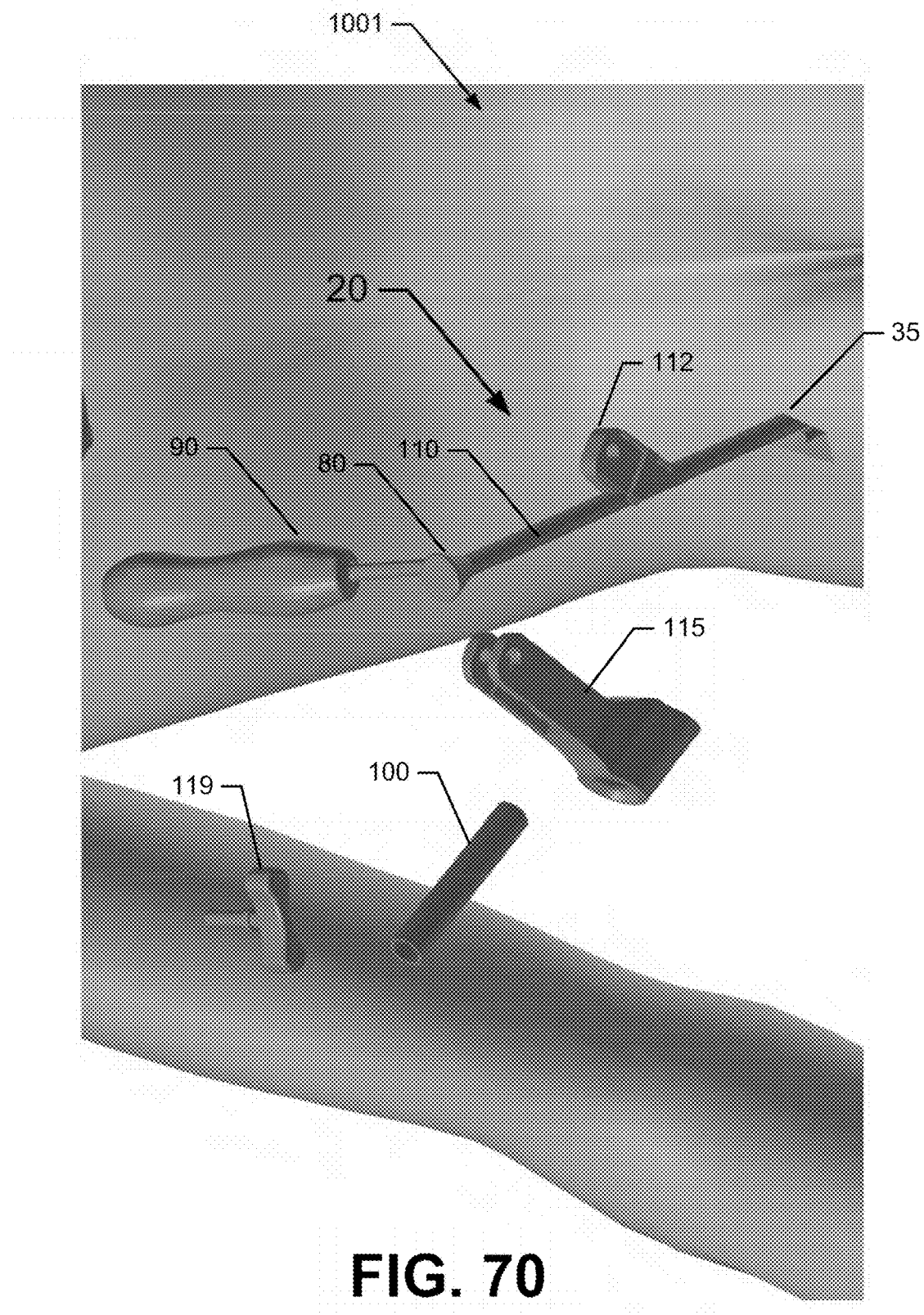
Figure 71:
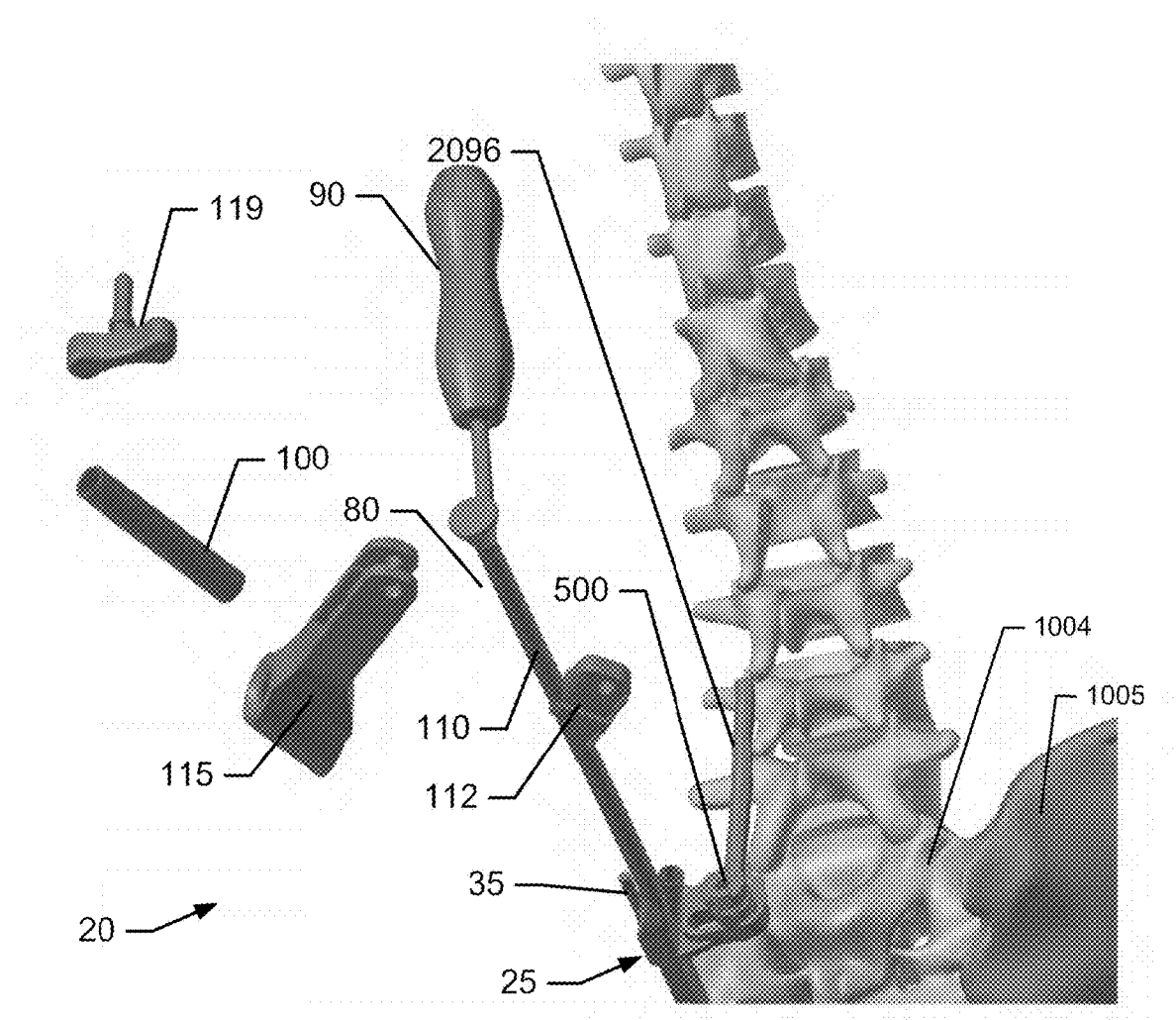
Figure 72:
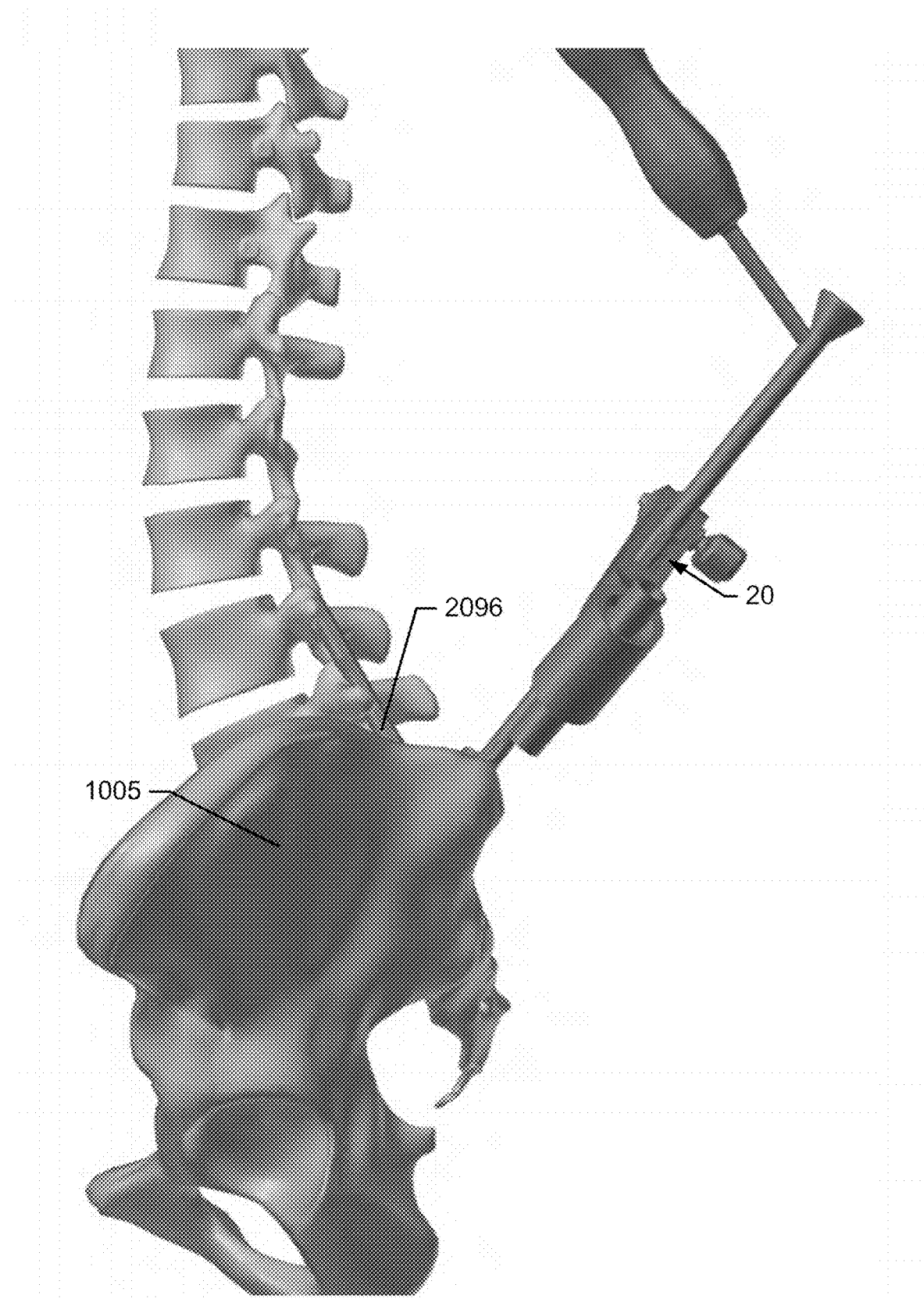
Figure 73:
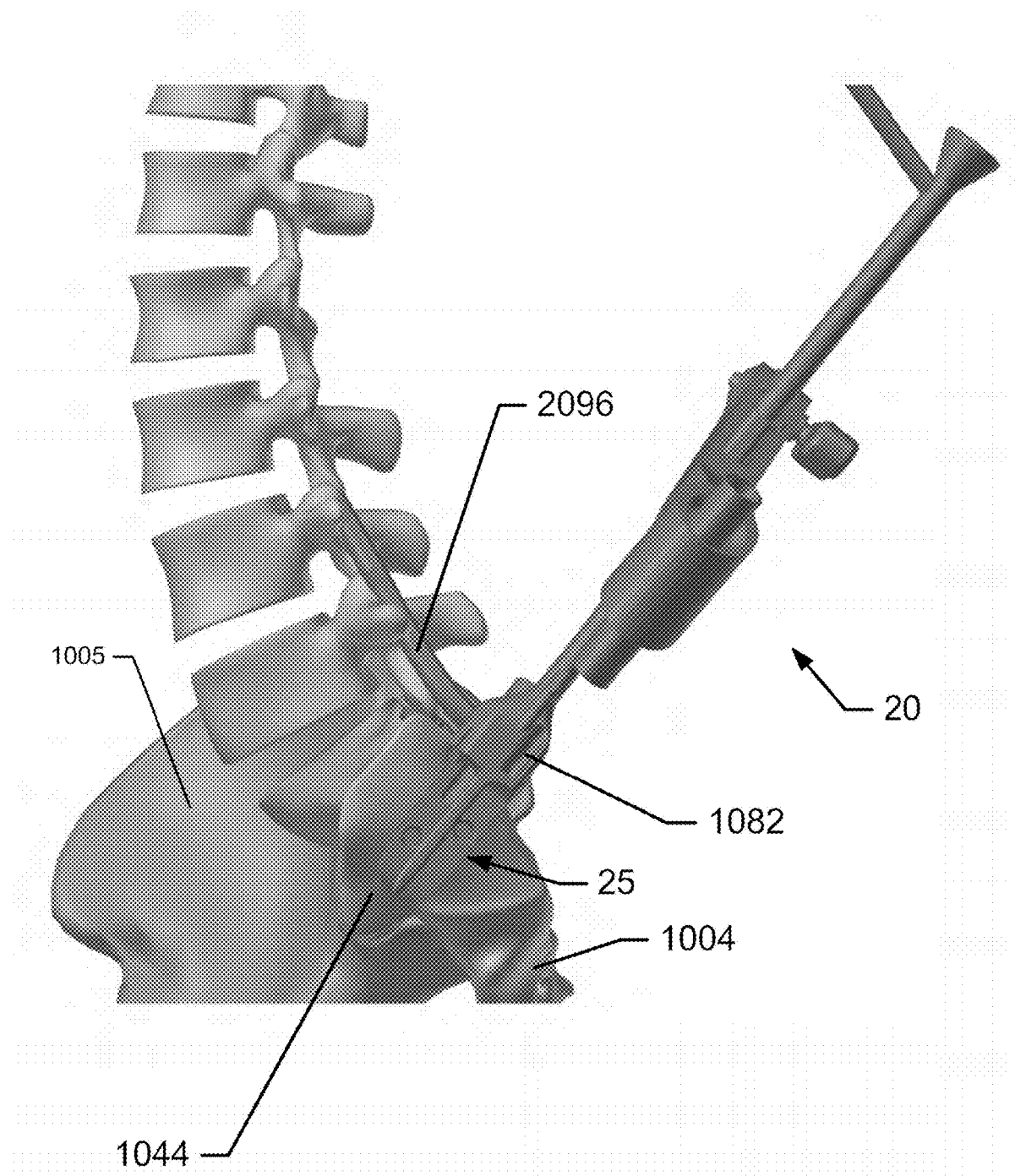
Figure 74:
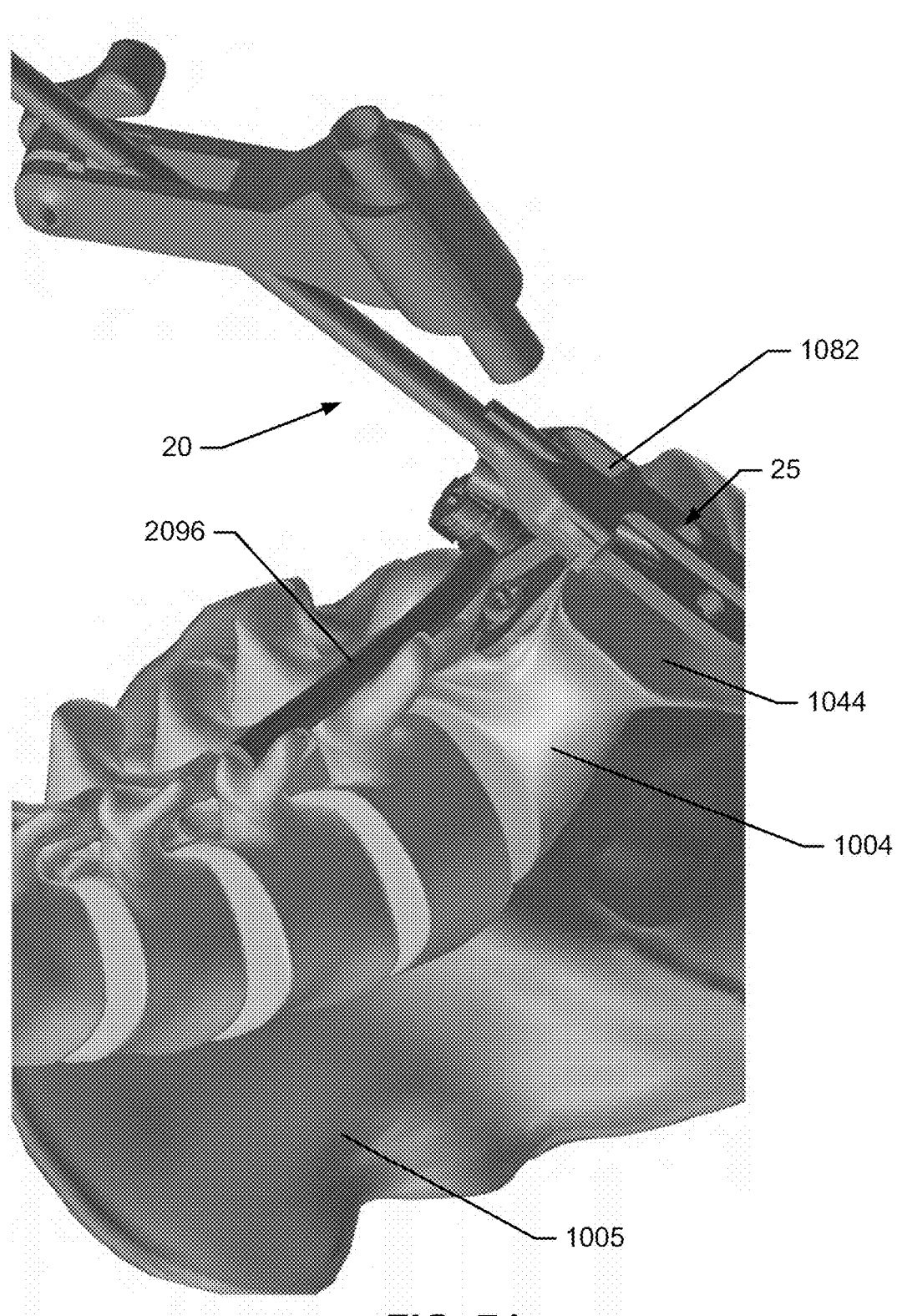
Figure 75:
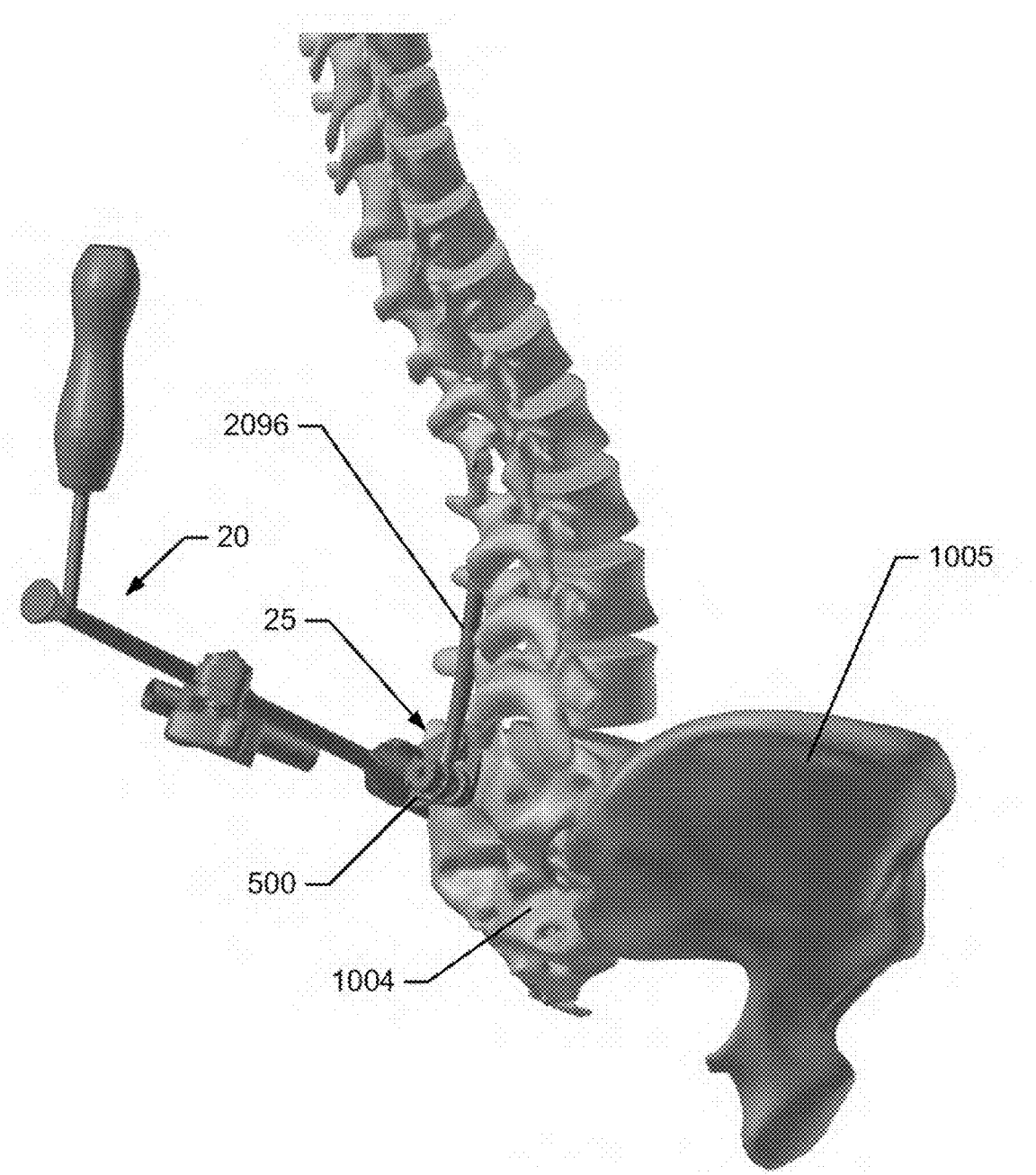
Figure 76:
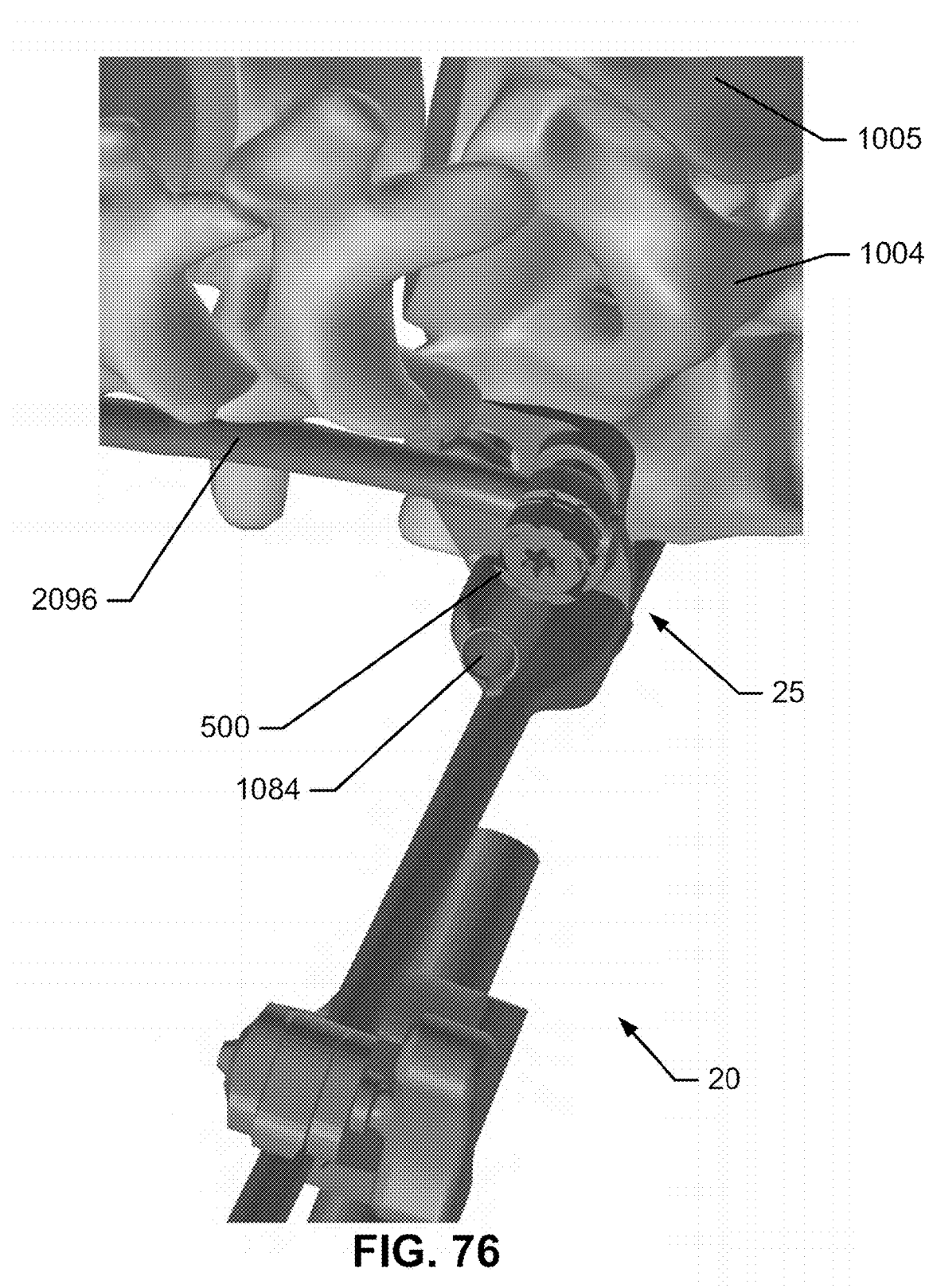
Figure 77:
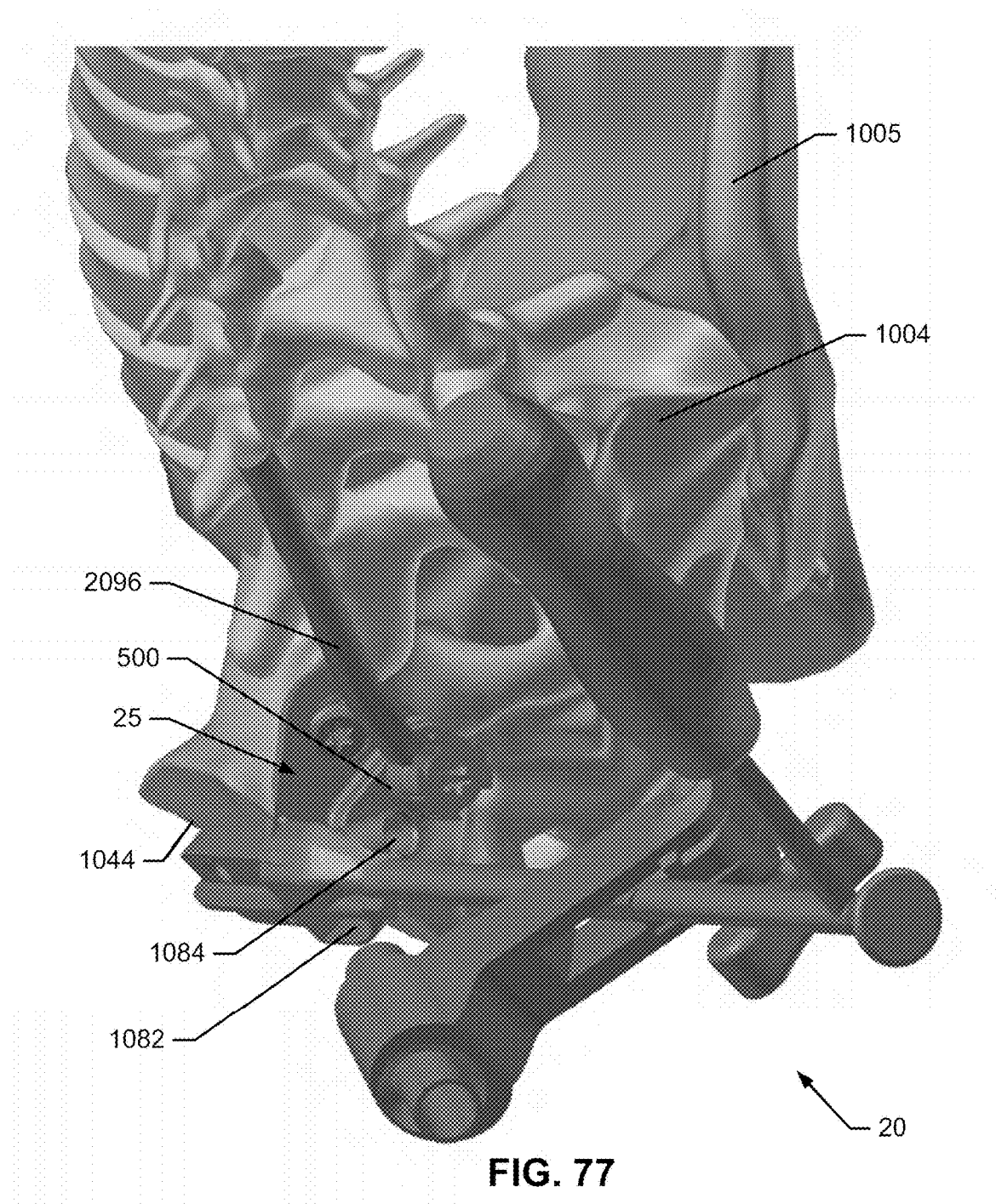
Figure 78:
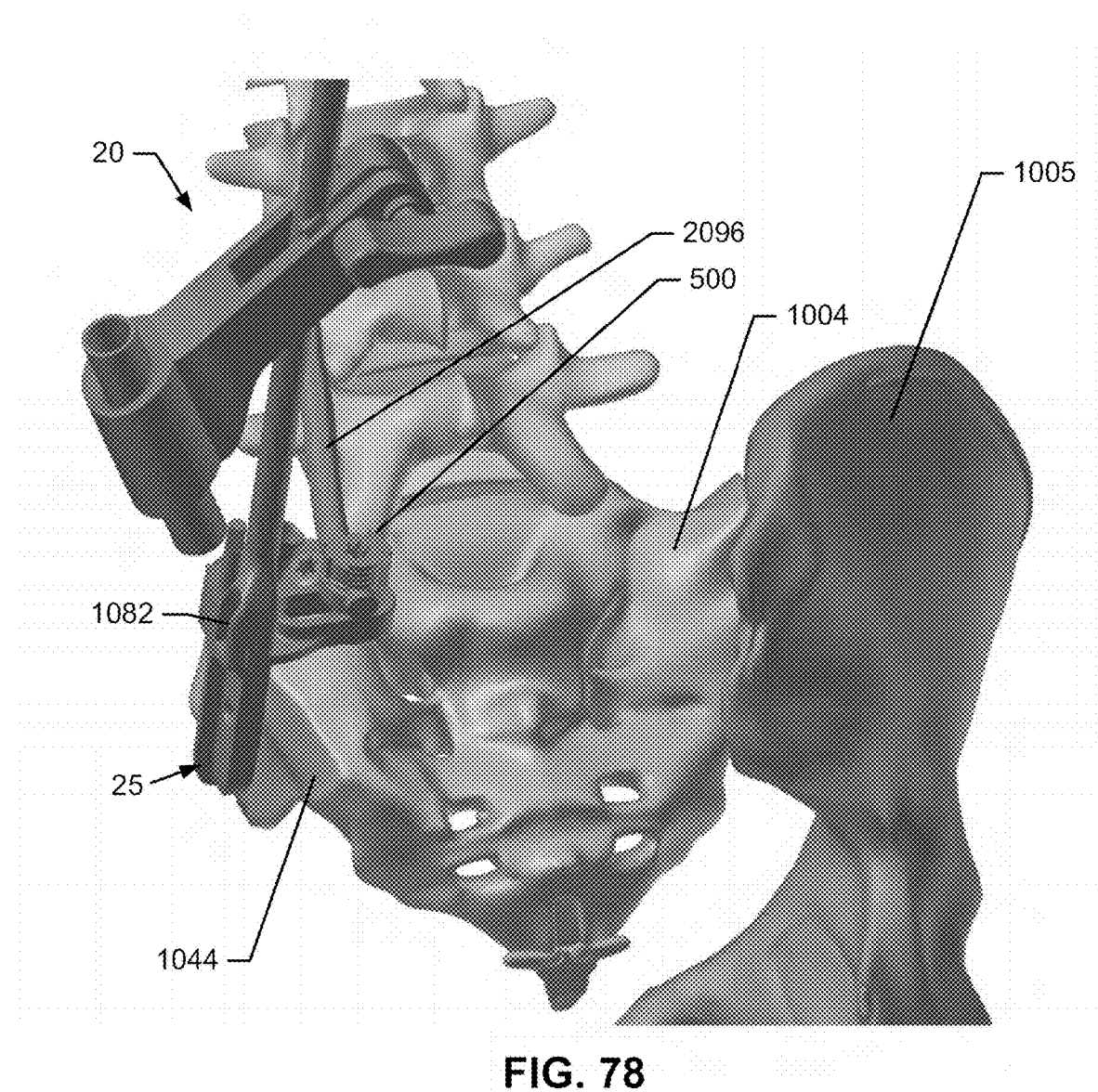
Figure 79:
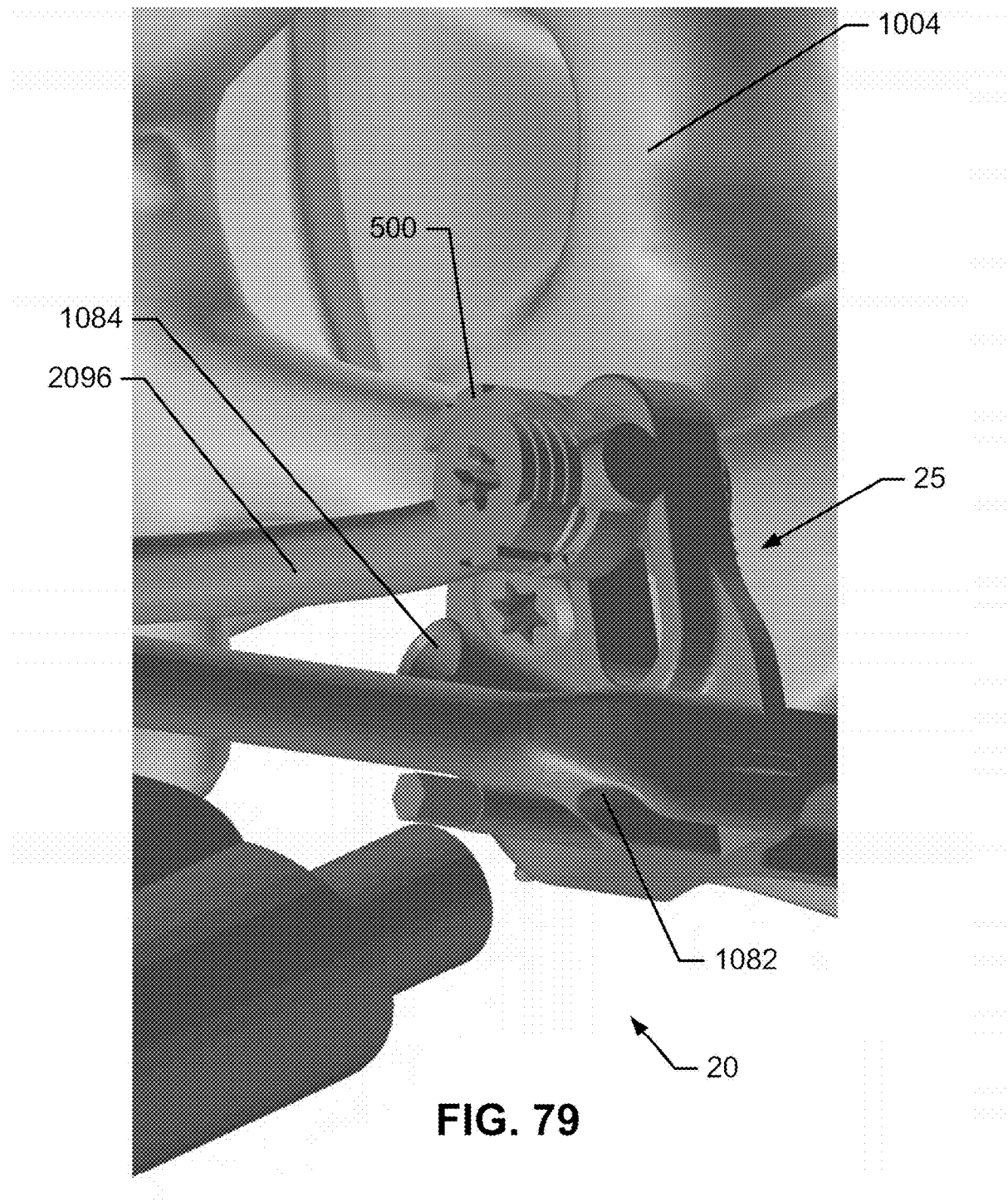
Figure 80:
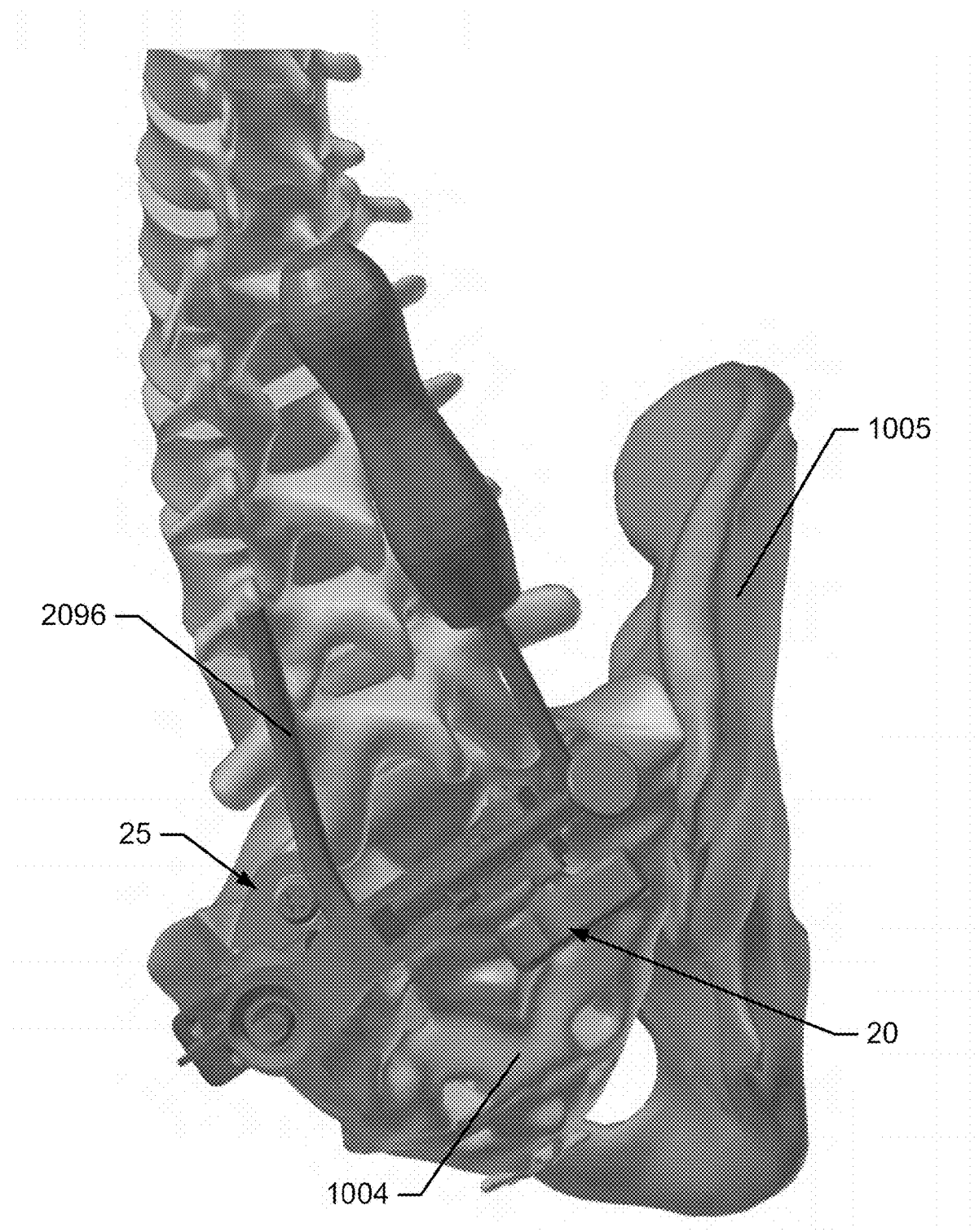
Figure 81:
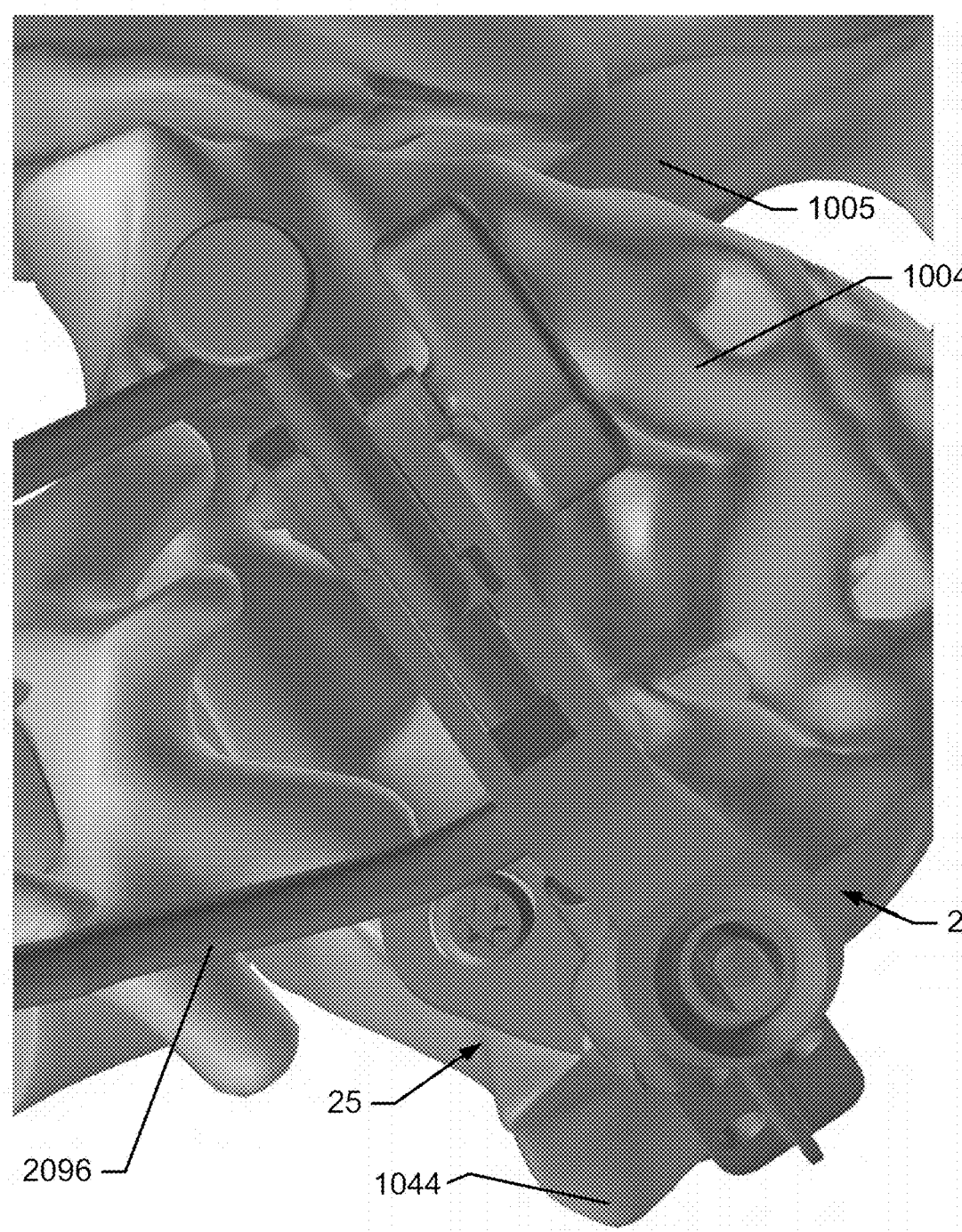
Figure 82:
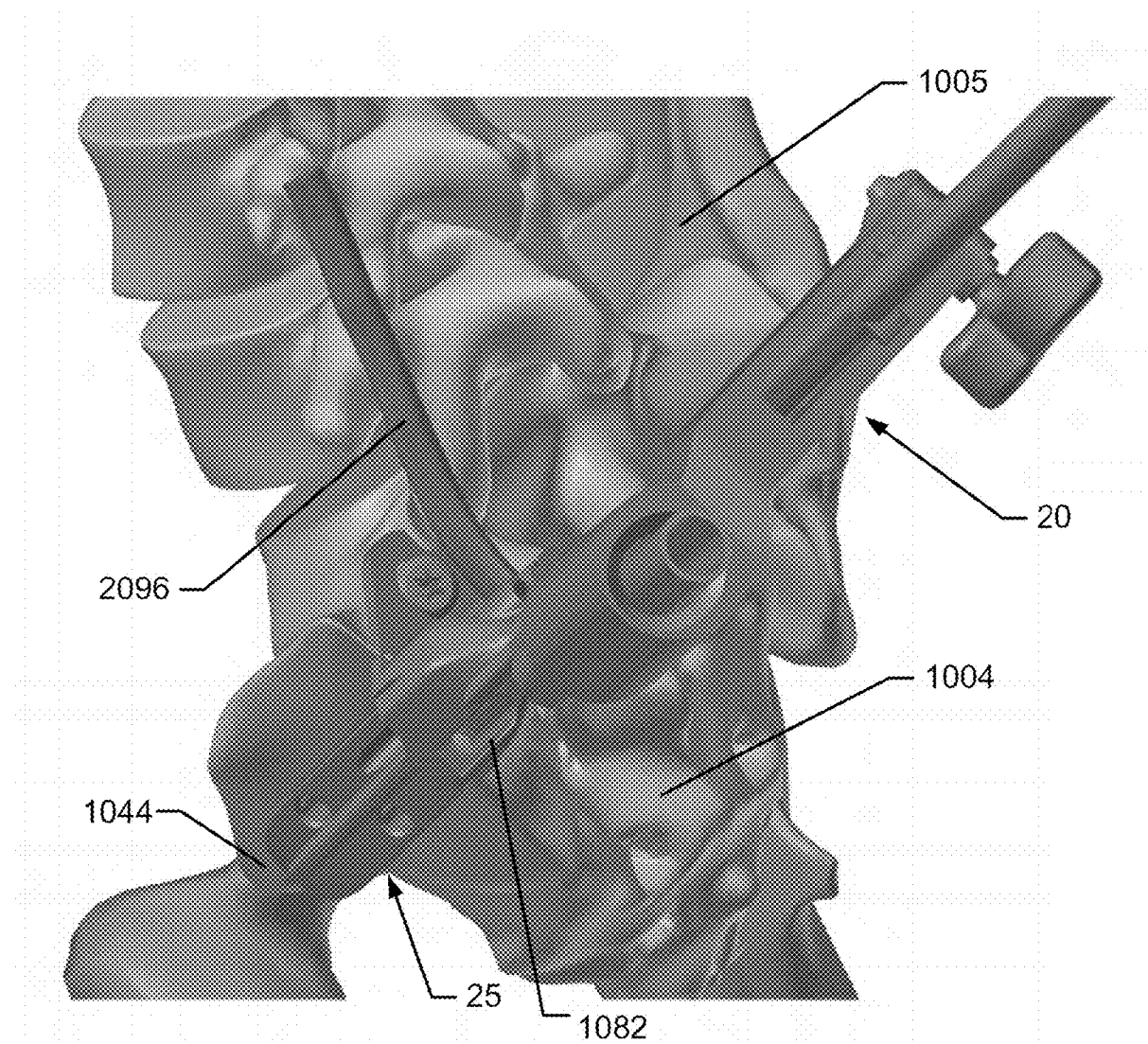
Figure 83:
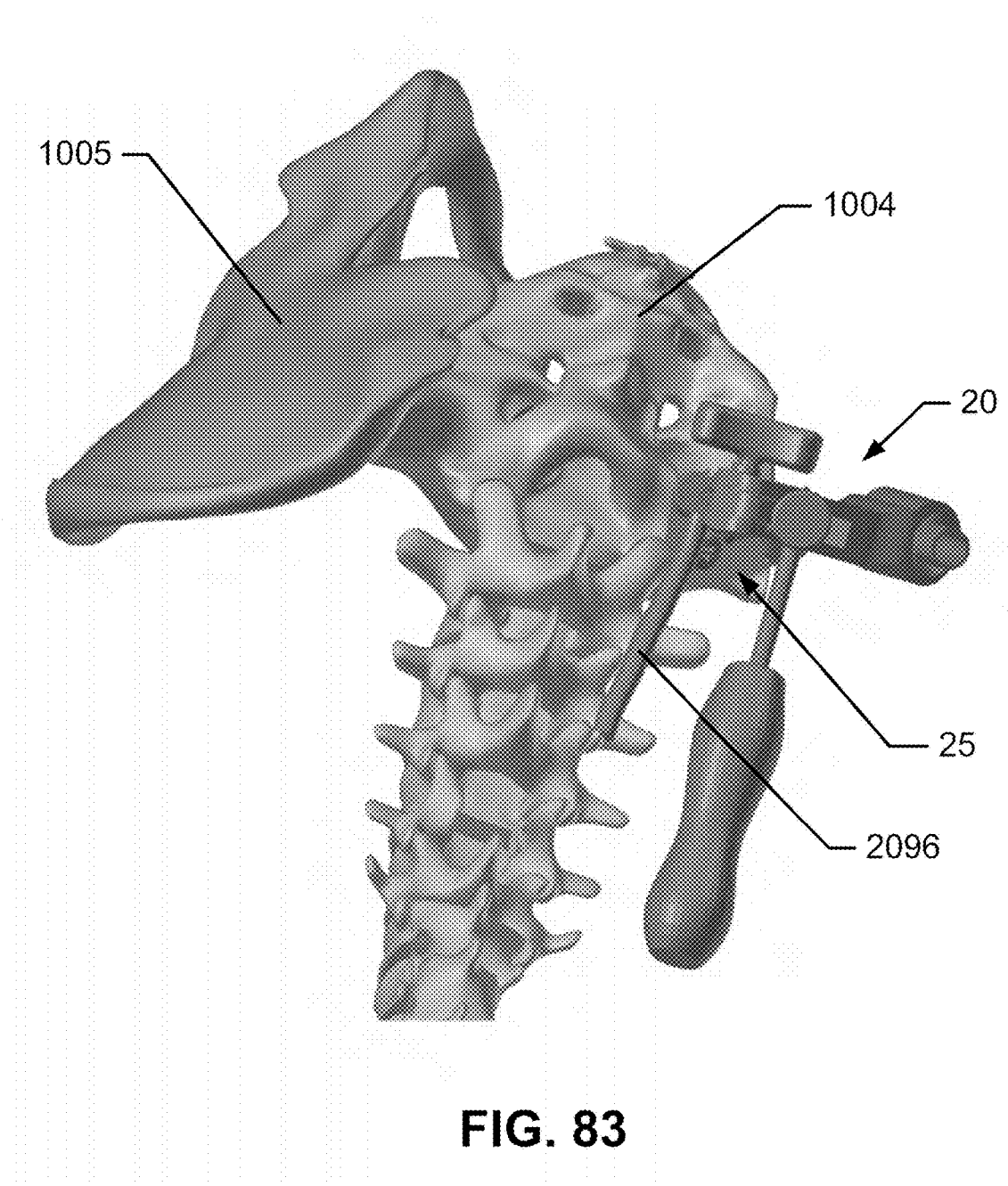
Figure 84:
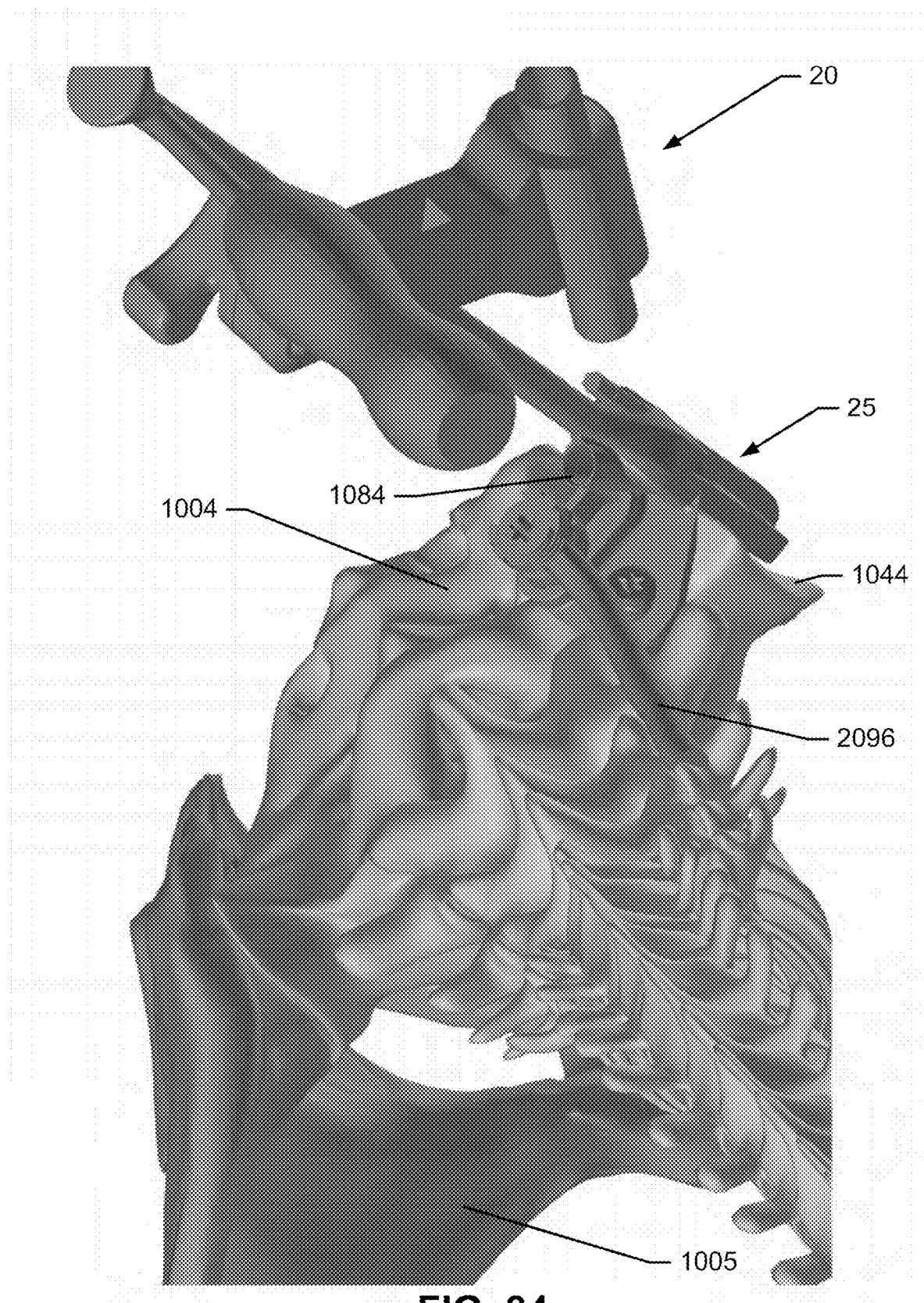
Figure 85:
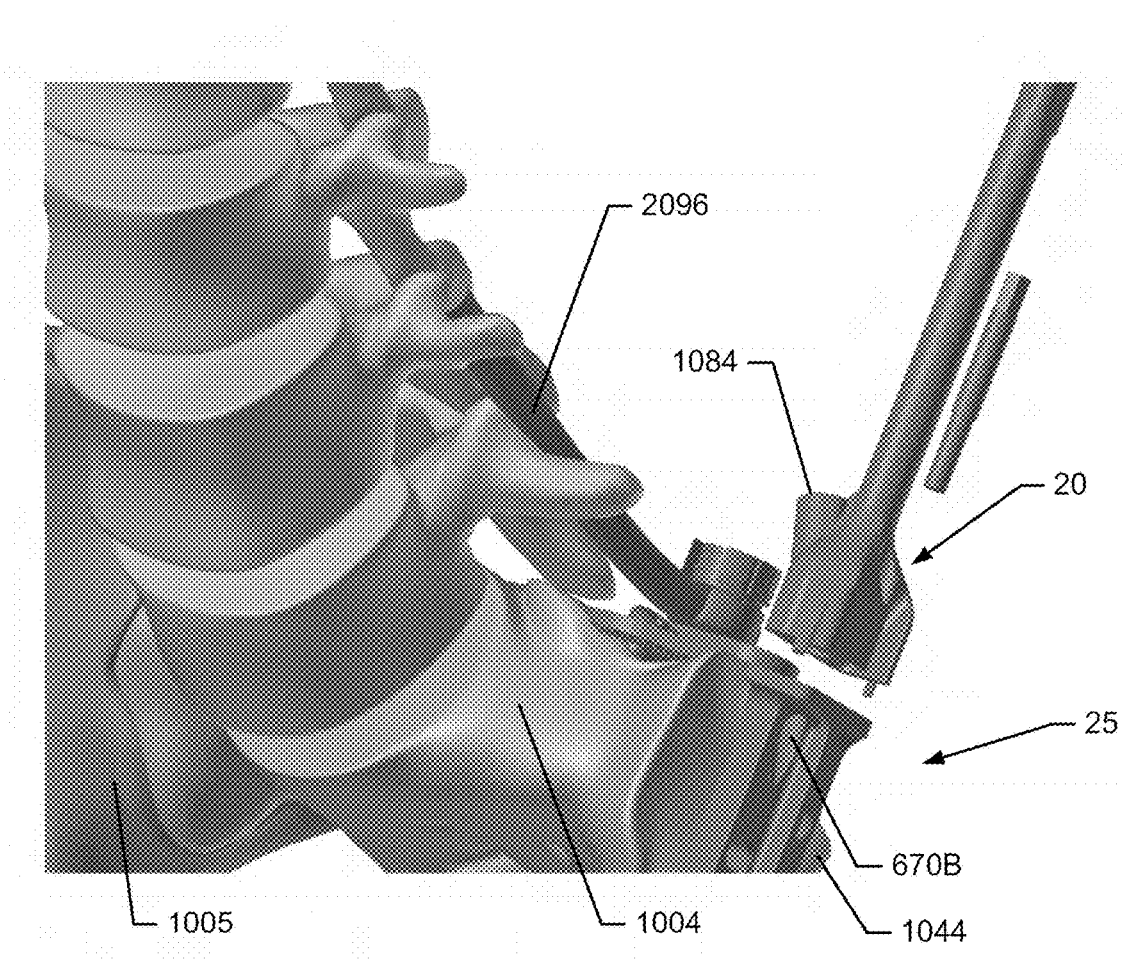
Figure 86:
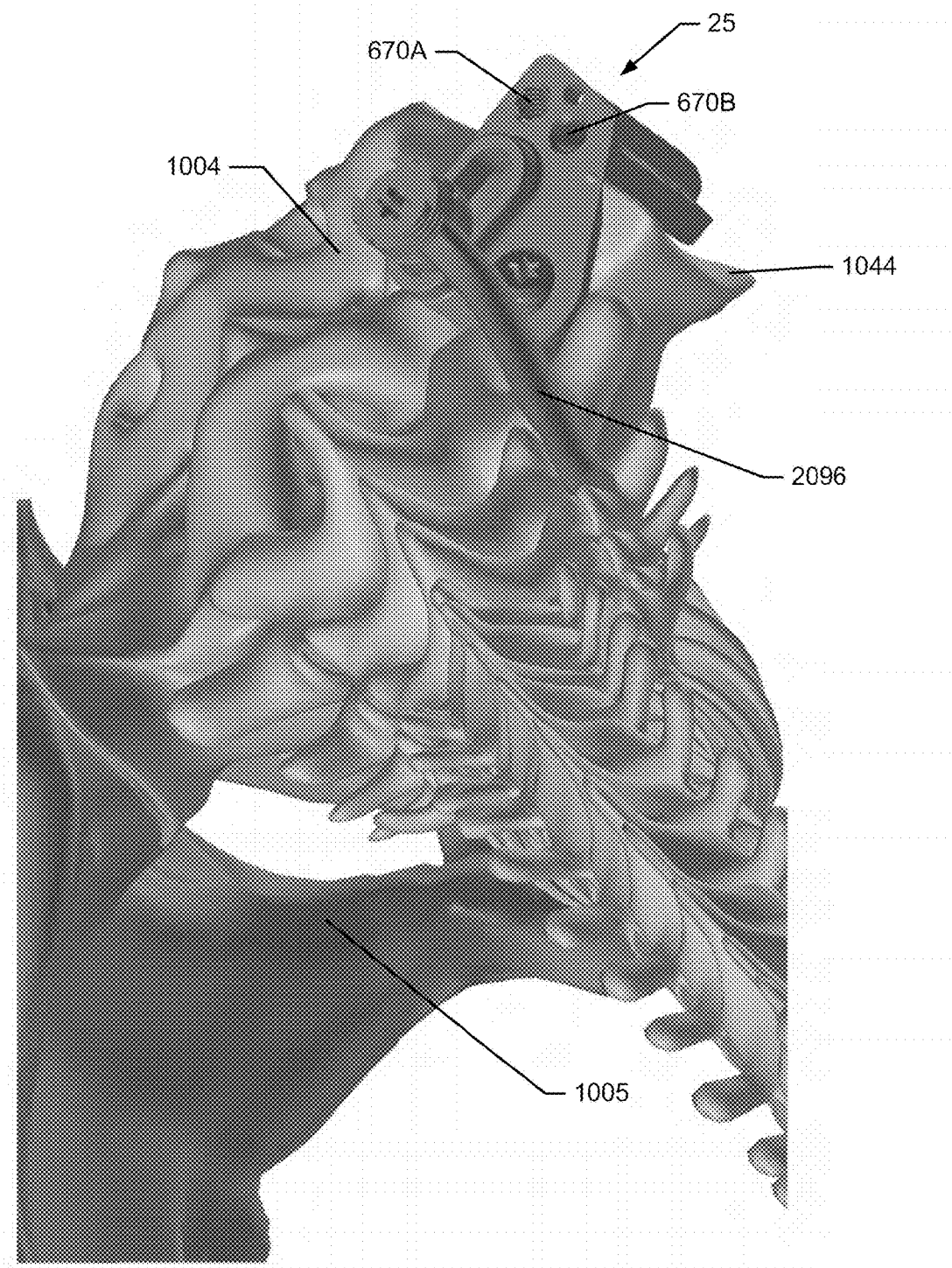
Figure 87:
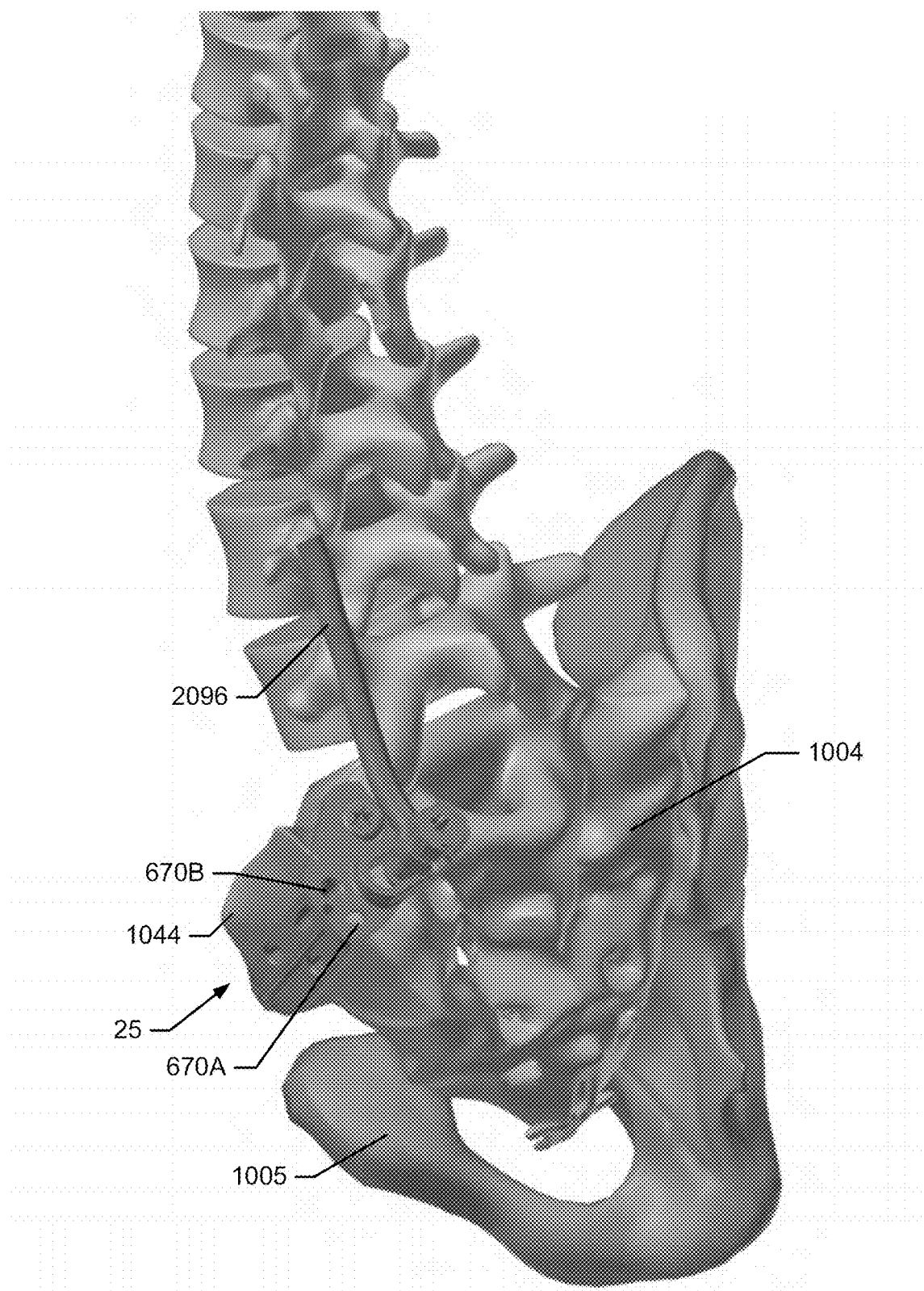
Figure 88:
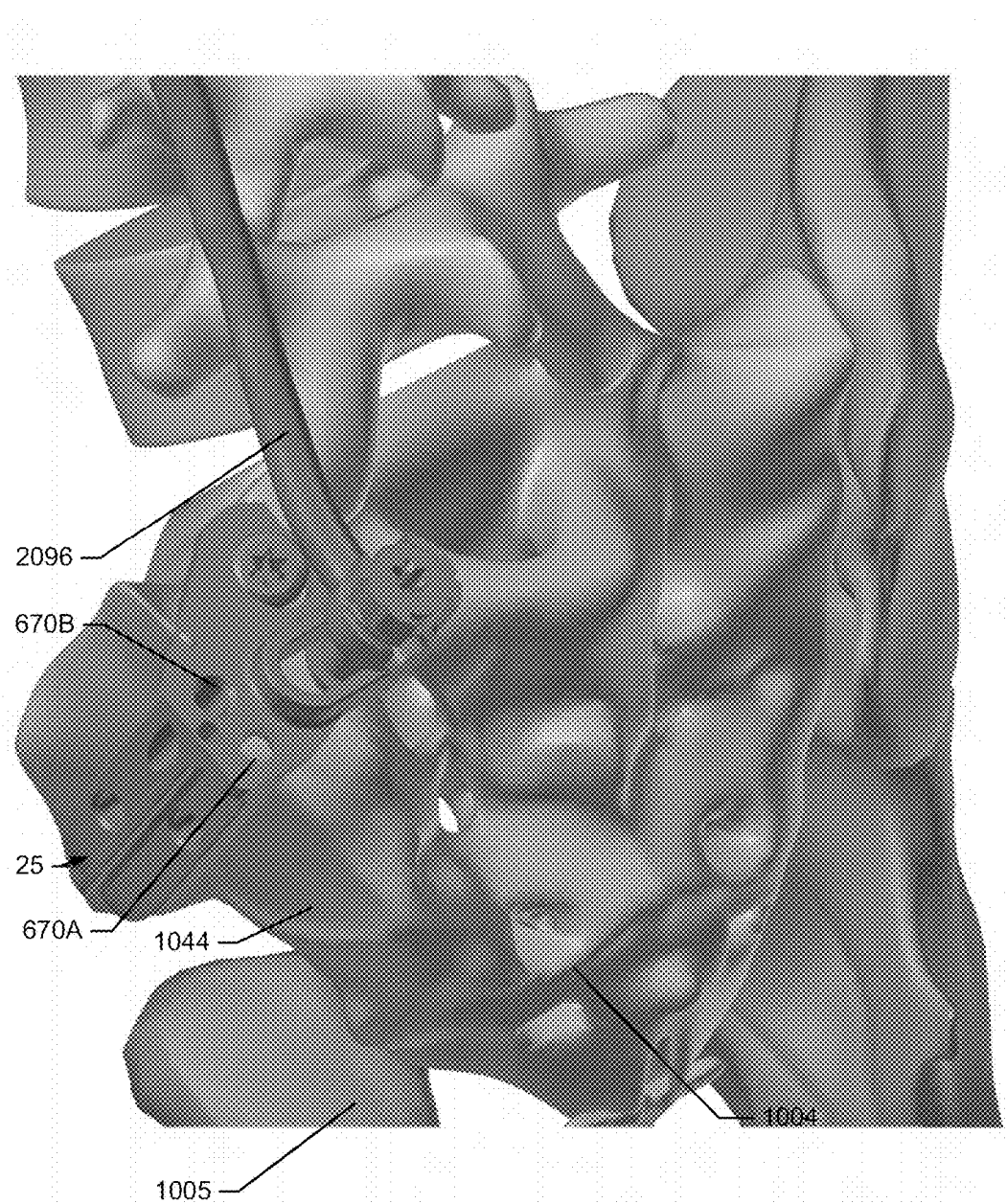
Figure 89:
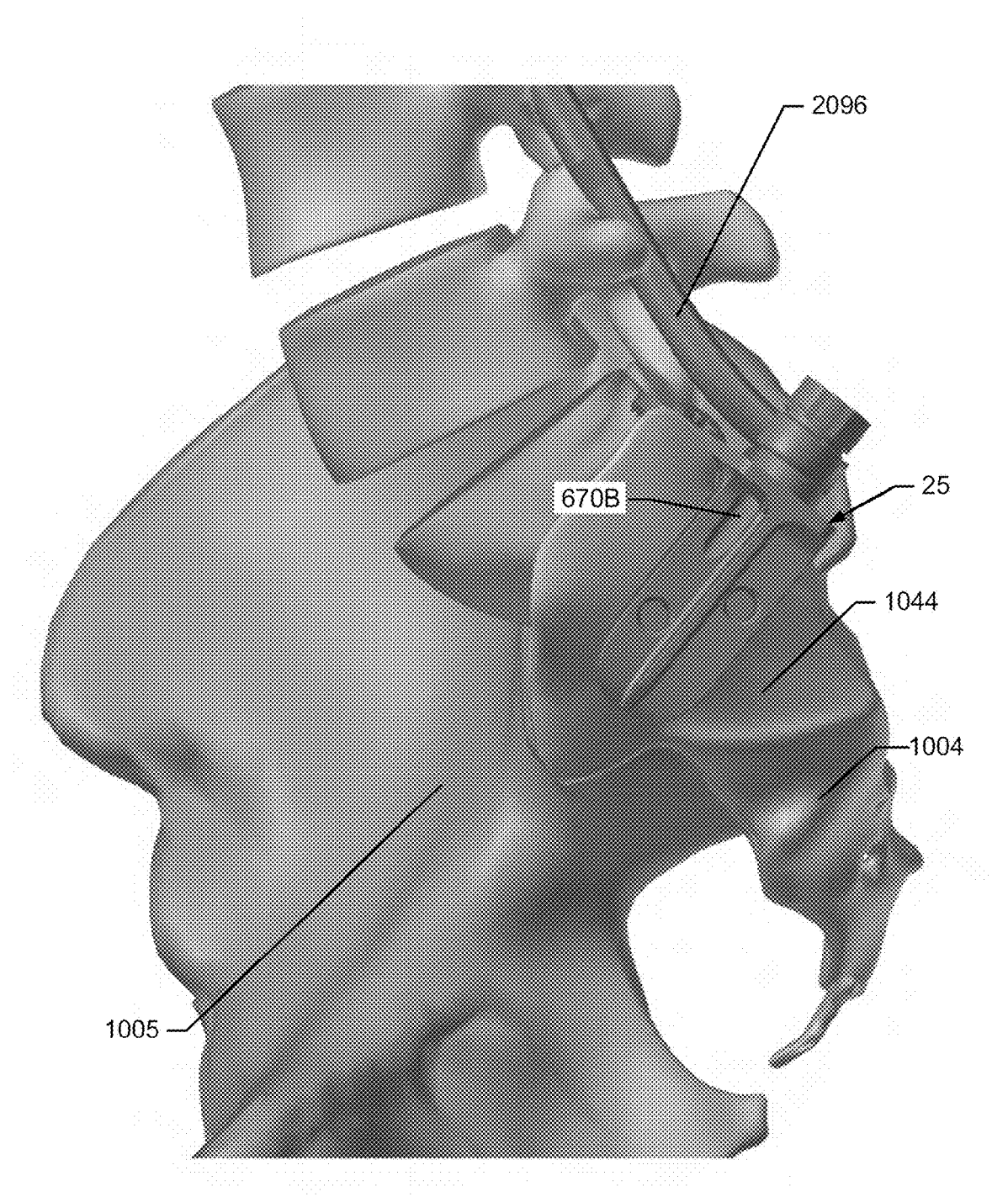
Figure 90:
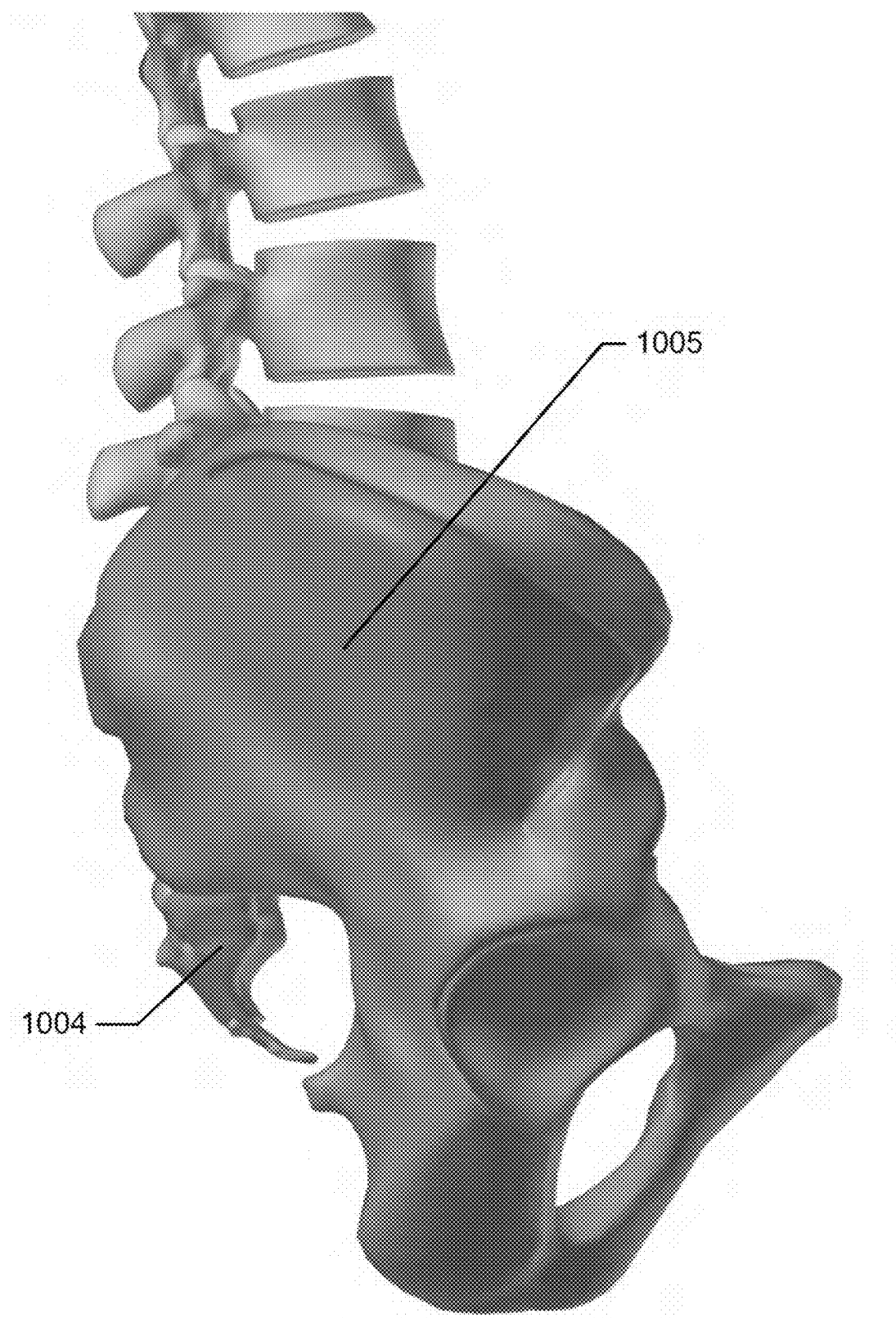
Figure 91:
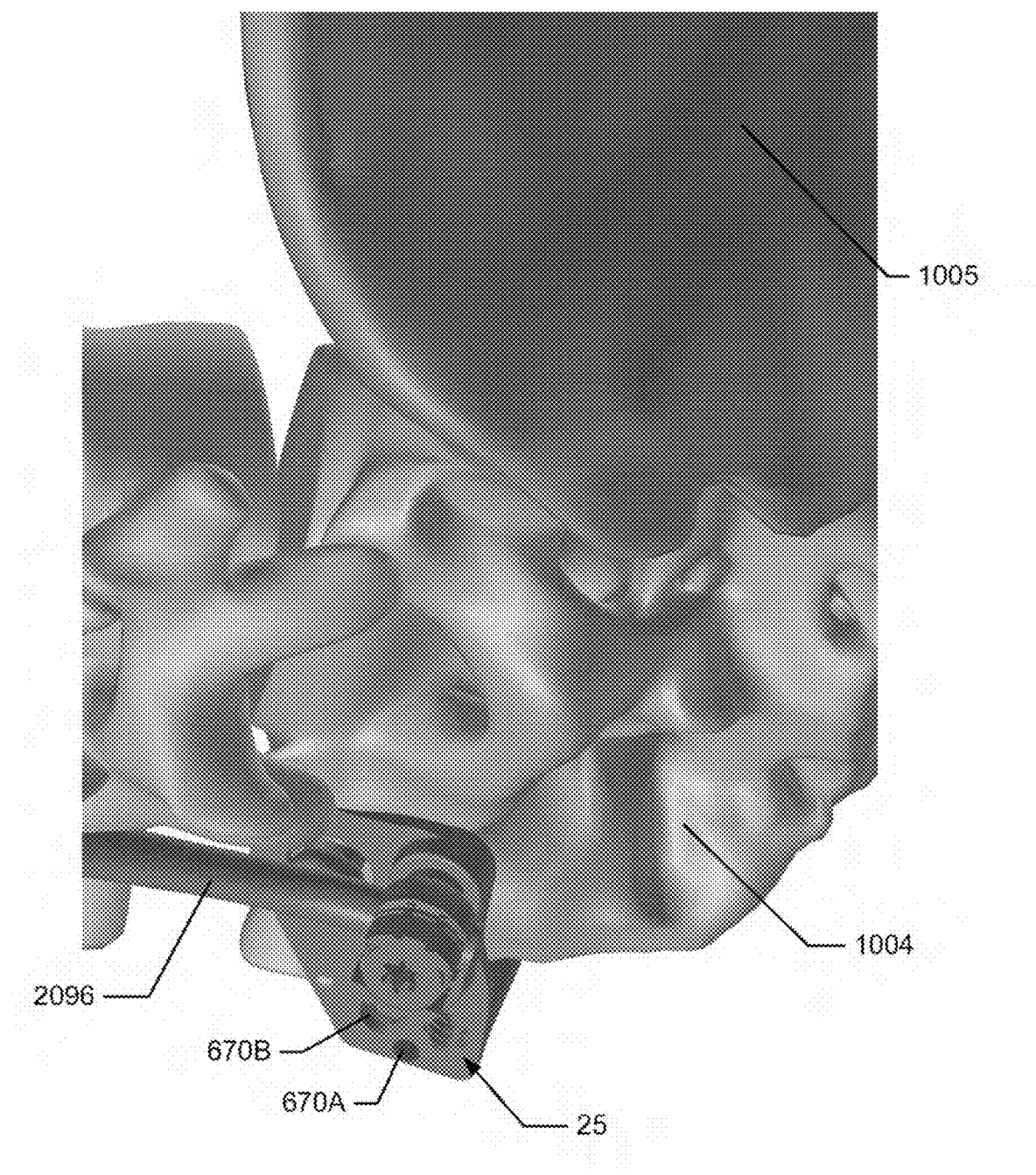

Now referring primarily to FIGS. 59 and 61, the implant receiving space 1029 and the sacroiliac joint implant body 25 can be configured having related dimensions such that placement of the insertion element 650 of the sacroiliac joint implant body 25 within the implant receiving space 1029 disposes the sacrum 1004 and the ilium 1005 in substantially immobilized relation and substantially avoids alteration of the positional relation of the sacrum 1004 and the ilium 1005 from the normal condition, or avoids driving together or driving apart the sacrum 1004 from the ilium 1005 outside of or substantially outside of the normal positional relation. In an embodiment, the insertion element 650 and the implant receiving space 1029 may be configured to immobilize the sacrum 1004 in relation to the ilium 1005 while maintaining the sacroiliac joint 1000 in substantially normal or substantially normal positional relation, or to return the sacroiliac joint 1000 to a substantially normal positional relation and thereby correct a degenerative condition of the sacroiliac joint 1000.

As a non-limiting example, configurations of an implant receiving space 1029 allow embodiments of the sacroiliac joint implant body 25 to be placed non-transversely between the articular surfaces 1016 of the extra-articular space 3007 of the sacroiliac joint 1000. While certain embodiments of the sacroiliac joint implant body 25 may only provide an insertion element 650 which locates within a correspondingly configured implant receiving space 1029 to engage at least a portion of the bone of the ilium 1005 or sacrum 1004, the invention is not so limited, and can further include one or more fins 50 engaging a portion of the bone 1073 of the sacrum 1004 and/or the ilium 1005.

As to those embodiments of the sacroiliac joint implant bodies 25 which further include one or more fins 50, the implant receiving space 1029 can further include one or more corresponding transverse receiving channels 1074, which correspondingly allow the one or more fins 50 to extend into the bone 1073 of the sacrum 1004 or the ilium 1005 (whether subchondral, cortical, cancellous, or the like). Alternatively, impact of the insertion plate 45 of the sacroiliac joint implant 25 into the implant receiving space 1029 without the transverse receiving channels 1074 can forcibly urge the one or more fins 50 into the bone 1073 of the sacrum 1004 and the ilium 1005. An anchor 30 members can be inserted through the bore 40 in the implant 25 and into the sacrum 1004 and ilium 1005 to fix the location of the fixation fusion implant 25 within the implant receiving space 1029.

Figure 57:
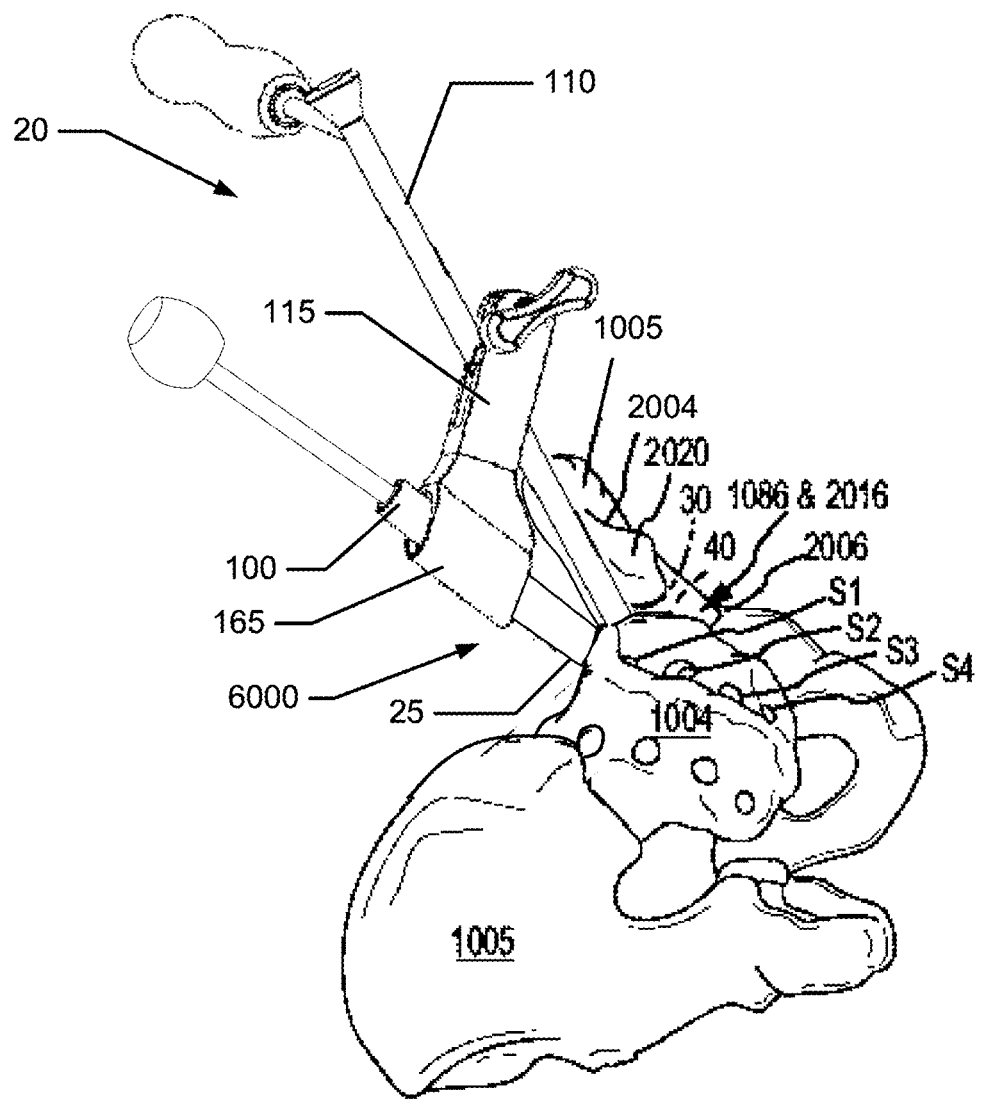
FIG. 57 is a lateral-inferior-posterior view of the implant assembly and delivery tool positioned within a patient's hip skeletal structure.
Figure 58:
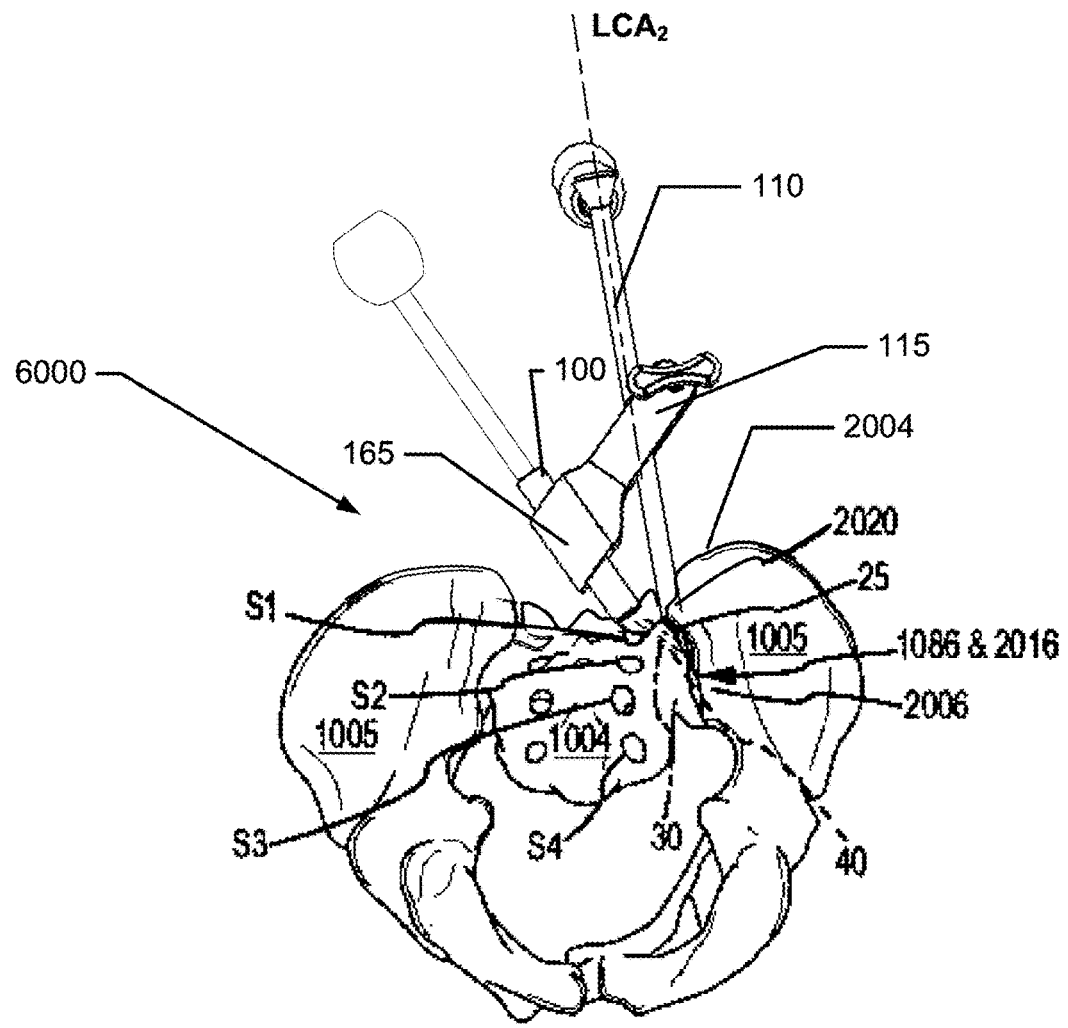
FIG. 58 is an inferior-posterior view of the implant assembly and delivery tool positioned within a patient's hip skeletal structure.

Reference is now made to FIGS. 57-59. FIG. 57 is a lateral-inferior-posterior view and FIG. 58 is an inferior-posterior view of the patient's hip skeletal structure 7, and accessing the extra-articular space 3007 via an extra-articular recess access region 6000. The S1 through S4 foramina can be seen at the respective indicators S1, S2, S3 and S4 in FIGS. 57 and 58.

Referring to FIG. 57, the delivery tool 20 has been configured such that the anchor arm 115 is oriented so as to deliver the anchor member 30 through anchor bore 40 of the implant body 25 into the sacrum 1004 and then optionally further into the ilium 1005. In other words, the anchor 30 is inserted through the bore 40 within the attachment element 652 and driven medial to lateral through the sacrum 1004 first and then into the implant followed by the ilium 1005 (optional). In the embodiment of FIG. 57, the anchor 30 may be a bone screw the same as or similar to an S2 alar iliac (S2AI) screw. Such a screw may penetrate the sacrum 1004 just lateral to the lateral edge of the S1 foramen and just superior of the superior edge of the S1 foramen. Thus, the anchor 30 can enter the bone of sacrum 1004 near the first sacral foramen (S2AI trajectory) then can further enter the bone of the ilium 1005. The implant body 25, as with any of the implantation locations and implant bodies 25 discussed herein can optionally be employed to be configured to serve as an attachment point for structural components of a spinal support system via an attachment fitting 500 mechanically attached in an adjustable locked engagement with the attachment element 652 of the implant body 25. In one non-limiting example, the attachment fitting 500 may be attached to an end of a spanning element of a spinal support system such as a rod 2096, as illustrated in FIG. 3.

Referring to FIG. 59, the insertion element 650 of the implant body 25 may be situated within the extra-articular region 3007 in one embodiment. Further, the implant body 25 is inserted into the extra-articular region 3007 via an extra-articular recess access region 6000. As illustrated in FIG. 58, this extra-articular recess access region 6000 is opposite to the posterior inferior overhang 2020 of the posterior superior iliac spine 2004 from the caudal portion 1086 of the sacroiliac joint articular region 1014 and posterior inferior access region 2016 leading to the sacroiliac joint articular region 1044 employed to implant the implant 25 in the caudal portion 1086 of the sacroiliac joint articular region 1044 in other embodiments, as discussed herein below.

As can be understood from FIG. 59, the insertion element 650 of the implant body 25 is oriented in the extra-articular region 3007. In the embodiment shown in FIG. 59, in which the insertion element 650 is an insertion plate 45, the orientation of the insertion plate 45 is generally coplanar with the plane of the extra-articular region 3007 and the narrow fins 50 extend into the sacrum 1004 and ilium 1005 bone defining each side of the extra-articular region 3007.

As illustrated in FIG. 59, in some embodiments, the insertion element 650 of the implant body 25 is oriented within the extra-articular region 3007 such that the longitudinal axis LAI of the insertion element 650 is generally perpendicular to the posterior boundary segment 3008 of the boundary 3000 of the sacroiliac joint articular region 1014. Also, the distal end 42 of the implant body 25, when implanted in the extra-articular region 3007, points towards the anterior-inferior corner 3010 of the boundary 3000 of the sacroiliac joint articular region 1014. The distal end 42 of the implant body 25 may extend across the posterior boundary segment 3008 of the extra-articular region 3007 and into the sacroiliac joint articular region 1044. Thus, when implanting the insertion element 650 of the implant body 25 via the extra-articular recess access region 6000, the general direction of travel for the implant distal end 42 is towards the anterior-inferior corner 3010, and the insertion element 650 can be positioned substantially within the extra-articular region 3007 or, alternatively, the insertion element 650 can be further advanced to also occupy a portion of the sacroiliac joint articular region 1044.

As discussed herein above, to implant the implant body 25 in the extra-articular region 3007, the delivery tool 20 is configured in one embodiment to drive the anchor 30 medial to lateral through the implant bore 40 into the sacrum 1004 and, optionally, further into the ilium 1005. However, in some embodiments, the delivery tool 20 and implant bore 40 may have as-manufactured configurations that allow the anchor 30 to be driven lateral to medial through the ilium 1005 into one or more additional bores 670 (see FIG. 11A).

Figure 50A:
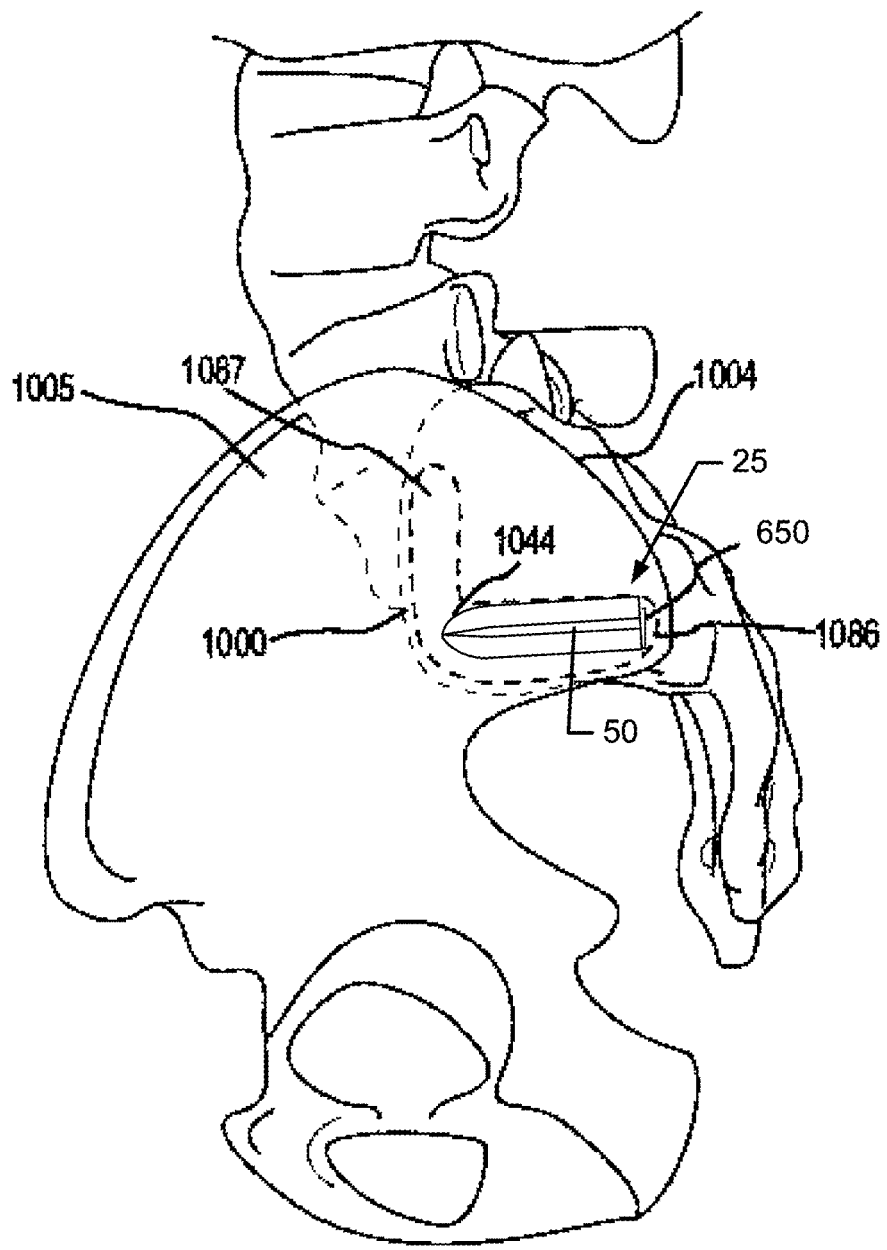
FIG. 50A is a lateral view of the hip region of the patient, illustrating the implant implanted in the caudal region of the sacroiliac join space.
Figure 50B:
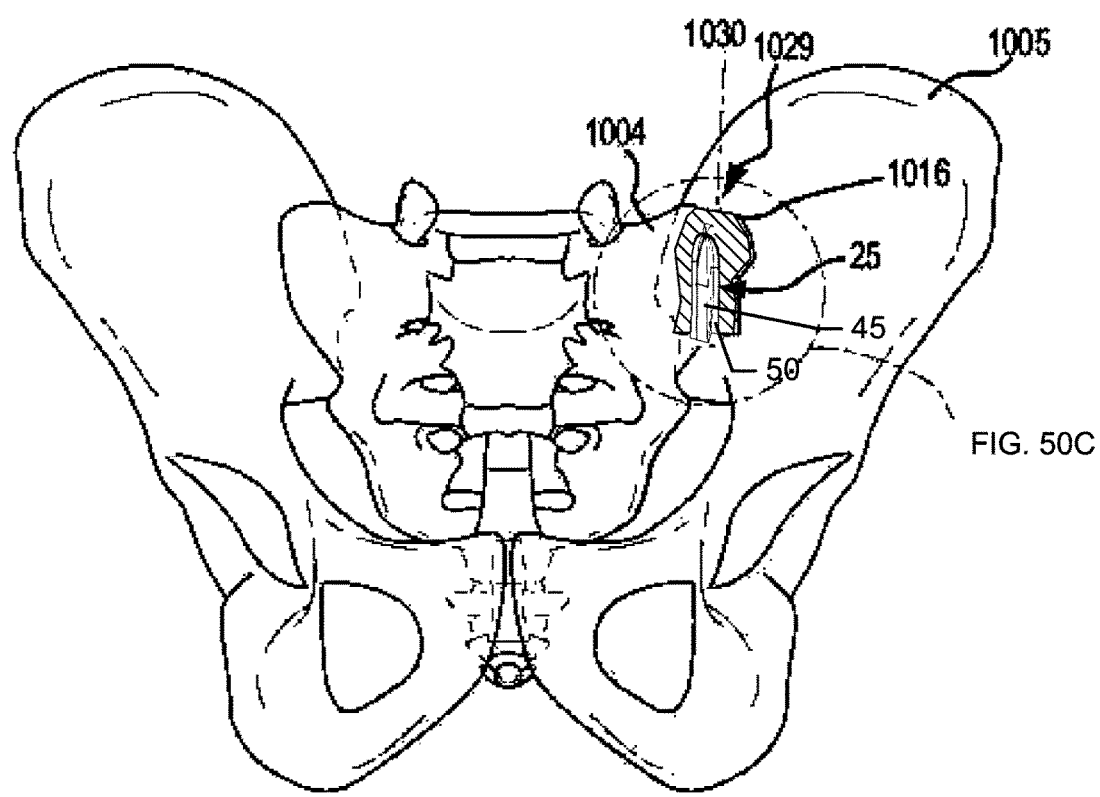
FIG. 50B is an anterior view of the hip region of the patient, illustrating the implant implanted in the caudal region of the sacroiliac join space.

While the preceding discussion is given in the context of the implant body 25 being implanted non-transversely in the extra-articular space 3007 of the sacroiliac joint 1000, in other embodiments, the implant body 25 may be implanted in other locations within the sacroiliac joint 1000. For example, as disclosed in U.S. patent application Ser. No. 12/998,712, which is incorporated herein by reference, in some embodiments, the implant body 25 may be implanted non-transversely in the caudal portion 1086 (see FIG. 50A) of the sacroiliac joint 1000 by the similar procedures or steps as above described with the incision and generation of the passage to the superior articular portion of the sacroiliac joint 1000. The implant body 25 may also be implanted in the sacroiliac joint 1000 in such a manner so as to extend between the cranial and caudal portions, as also disclosed in U.S. patent application Ser. No. 12/998,712.

ii. Insertion of Insertion Element of Implant Body into Implant Receiving Space

To begin a discussion of employing the delivery tool 20 to implant the implant body 25 in the sacroiliac joint 1000 once the implant receiving space 1029 has been created, reference is made to FIGS. 60I, 57, 58, and 59. As shown in FIGS. 60I, 57, 58, and 59, once the implant receiving space 1029 has been created as discussed above with respect to FIGS. 60A-60H, the implant body 25 can be supported off of the distal end 120 of the implant arm 110 of the delivery tool 20 and positioned such that the distal end 42 of the implant body 25 (specifically the insertion plate 45) begins to enter the sacroiliac joint articular region 1044 via the extra-articular recess access region 6000. In entering the sacroiliac joint space, insertion element 650 of the implant body 25 is oriented generally parallel to, and aligned with the contour of the articulating surfaces 1016 of the sacroiliac joint 1000.

Figure 60I:
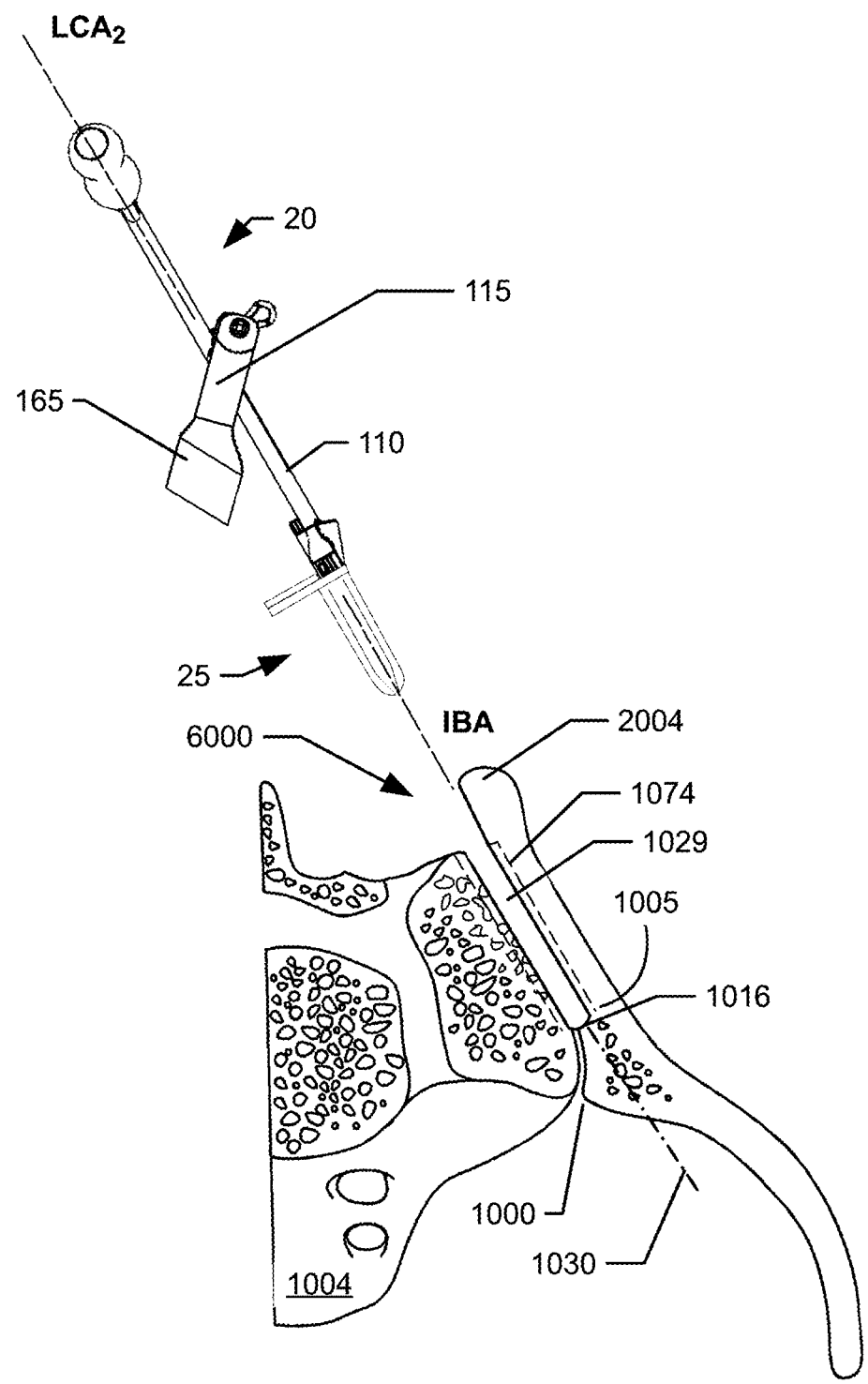

In various embodiments the contour of the insertion plate 45 may be aligned along the direction of the articulating surfaces 1016 defining the extra-articular recess of the sacroiliac joint 1000. In one embodiment, the implant receiving space 1029 may be prepared to receive a planar insertion plate 45, as illustrated in FIG. 60I. In another embodiment, the insertion element 650 may be custom contoured to conform with the existing contour of the articulating surfaces 1016 based on medical images of the sacroiliac joint 1000 obtained prior to producing the implant body 20. In an additional embodiment, the insertion element 650 may be produced so as to be deformable by the surgeon to adjust the contour of the insertion element 650 to approximately match the contour of the articulating surfaces 1016. In another additional embodiment, the insertion element 650 may be a threaded cylindrical element as described previously herein. In this other additional embodiment, the threaded cylindrical element may be twisted into a cylindrical bore formed in the joint space.

Referring back to FIG. 60I, the longitudinal axis LCA2 of the implant arm 110 of the delivery tool 20 has a generally anterior trajectory that is located within the joint plane 1030. Alternatively, according to particular embodiments, as a non-limiting example, the longitudinal axis LCA2 of the implant arm 110 of the delivery tool 20 can have a trajectory which can be defined as being generally lateral or, in particular embodiments, generally posterior. In some embodiments, when the implant body 25 is being delivered into the joint space, the implant arm 110 can be said to be at least one of generally superior or cephalad to the sciatic notch.

Figure 50C:
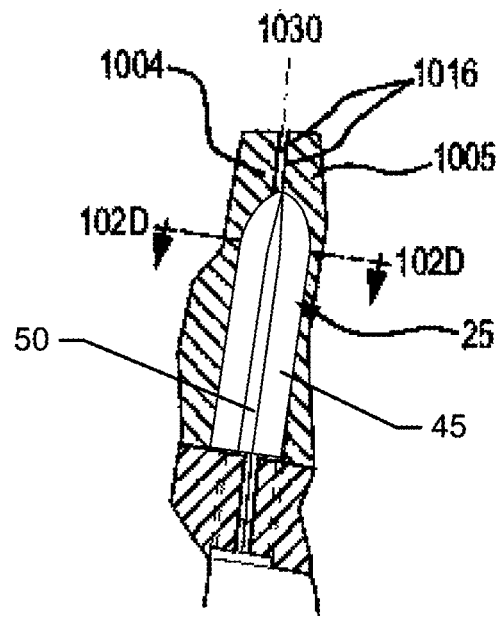
FIG. 50C is an enlarged view of the implant taken along the plane of the sacroiliac joint.
Figure 50D:
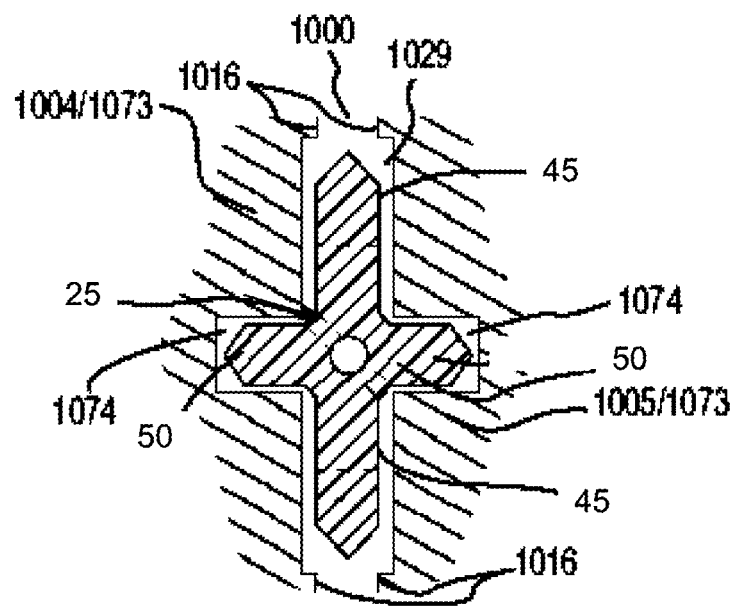
FIG. 50D is a transverse cross section of the implant and joint plane taken along section line 102D-102D of FIG. 50C.
Figure 53:
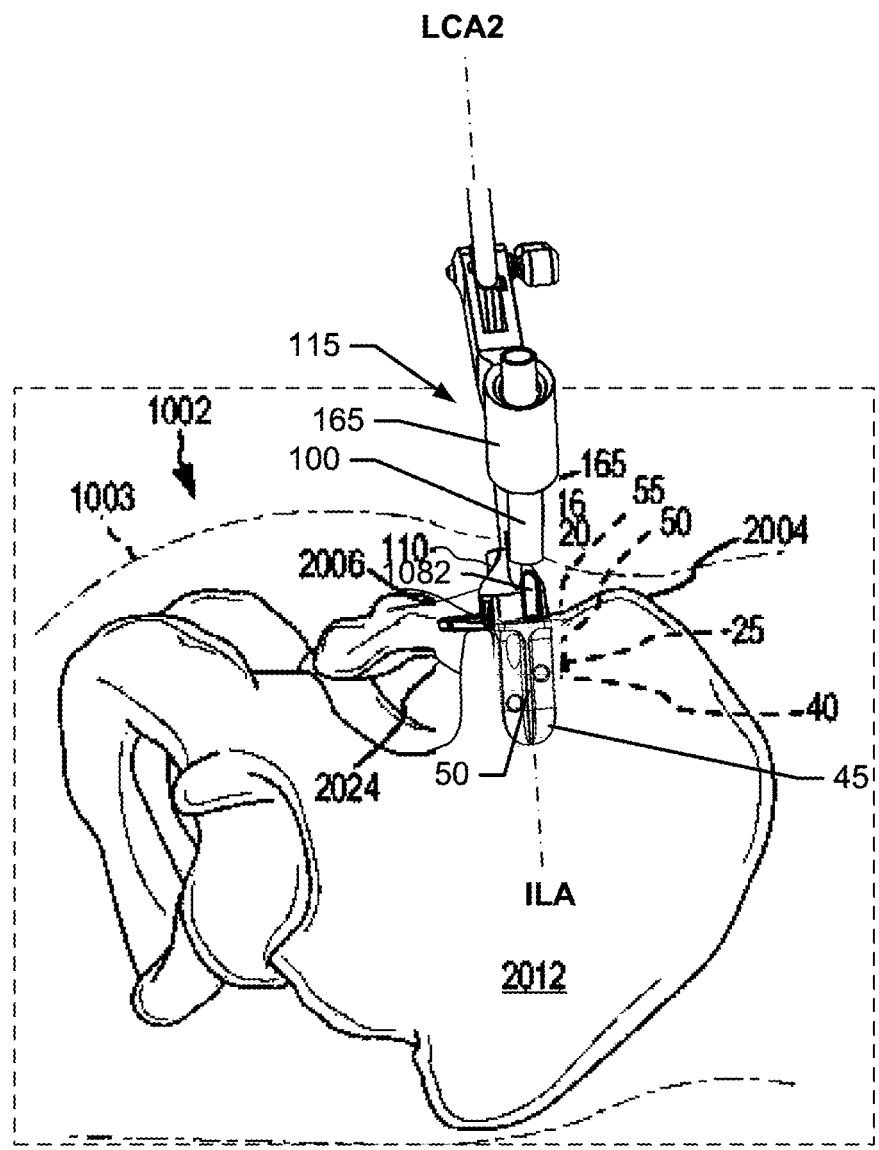
FIG. 53 is the lateral view of FIG. 52, with the implant assembly fully inserted into the prepared space in the sacroiliac joint.
Figure 60J:
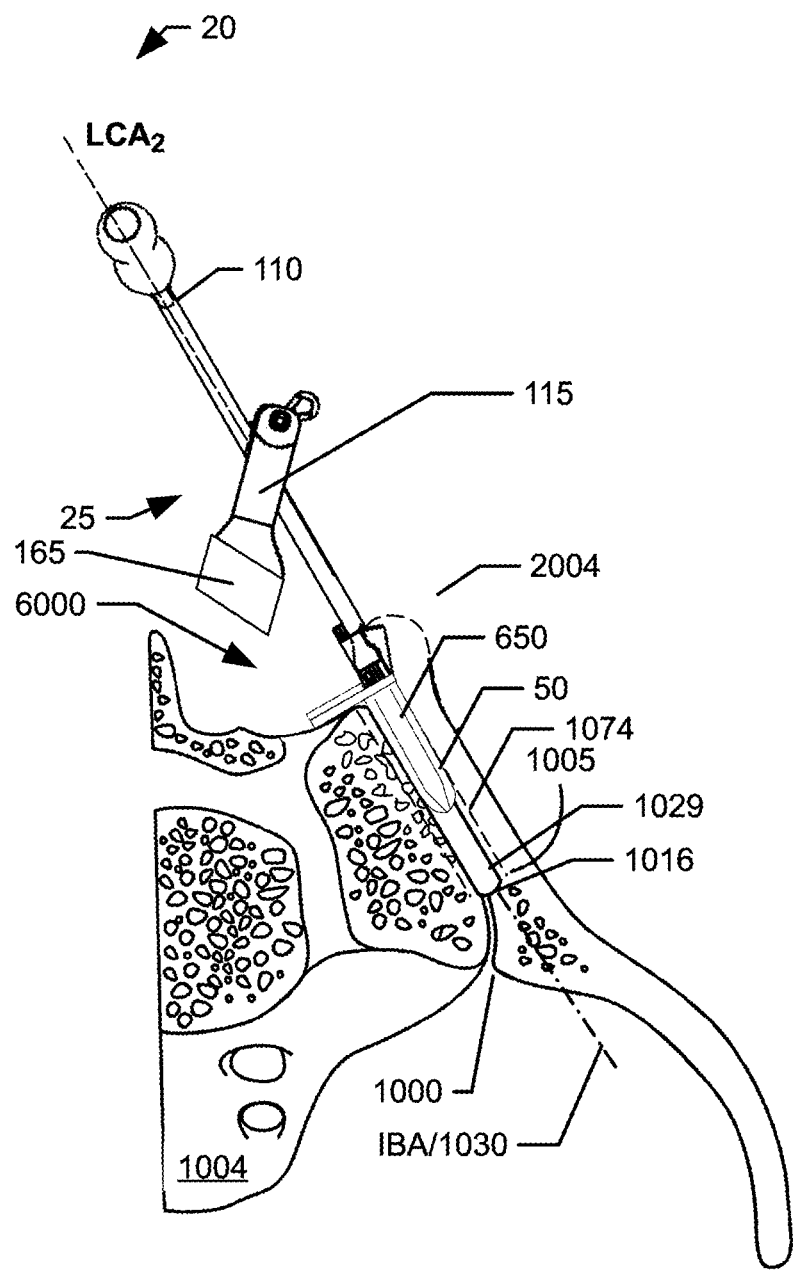
Figure 60K:
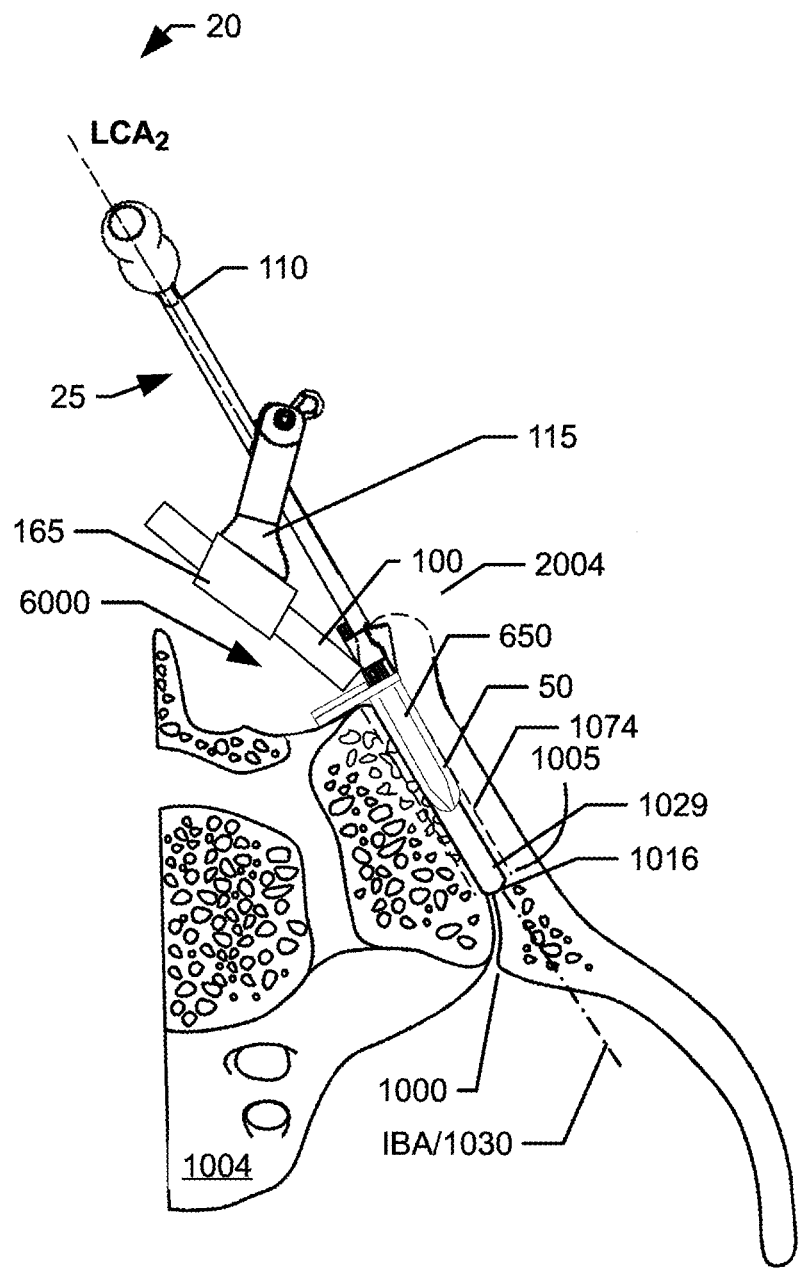
Figure 60L:
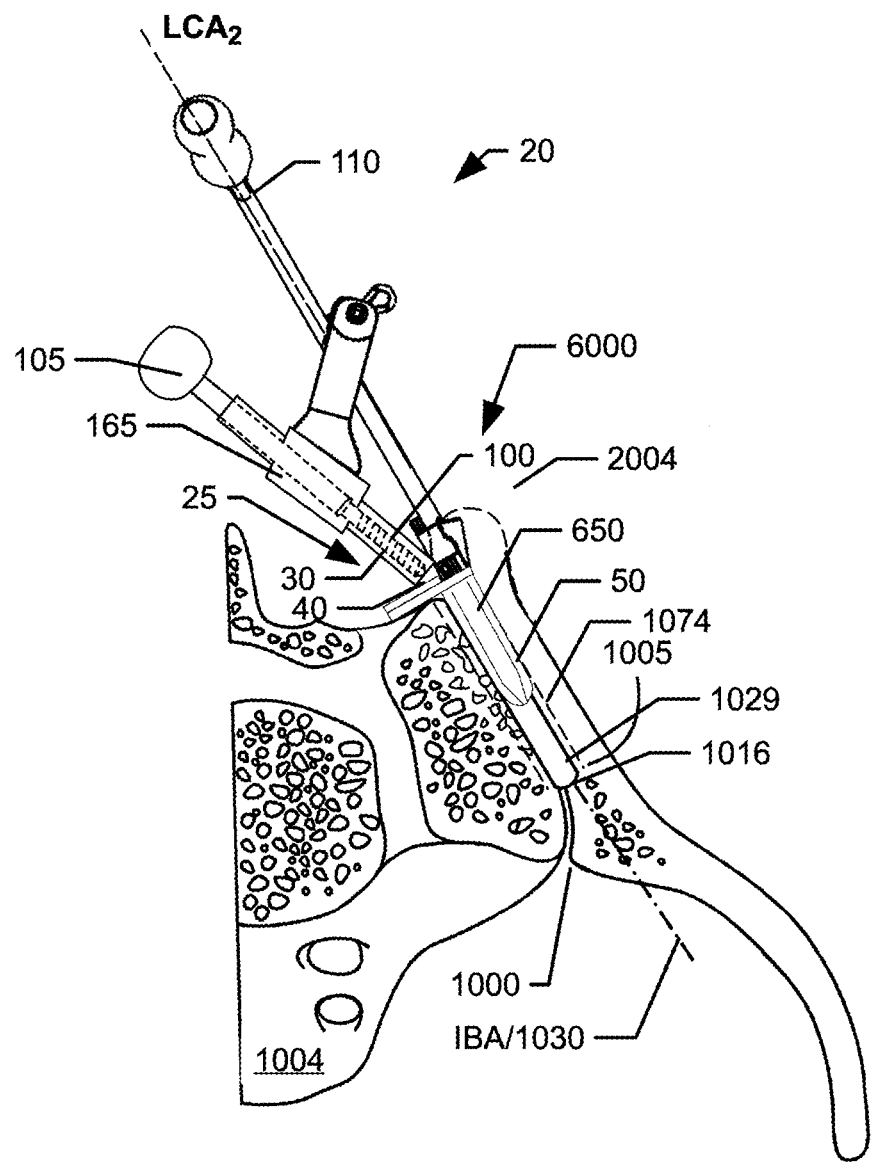

As illustrated in FIGS. 60J and 53, the insertion element 650 is fully received in the prepared sacroiliac space 1029 such that the plane of the insertion element 650 is oriented generally parallel to, and aligned with, the sacroiliac joint line 2019 (i.e., the plane of the insertion element 650 is generally located within the joint plane 1030), and the implant body's fins 50 are generally transverse to the joint plane 1030 and, in some embodiments, have even entered the bone material forming the sacrum and ilium articular surfaces of the sacroiliac joint (see, e.g., FIGS. 50C and 50D). As can be understood from FIG. 50J, the longitudinal axis IBA of the implant body 25 and the longitudinal axis LCA2 of the implant arm 110 may be coaxially aligned with each other and generally located in the sacroiliac joint plane 1030.

In addition, FIGS. 57 and 58 illustrate the sleeve 100 now received in the collar 165 of the anchor arm 115. As can be understood from FIGS. 60K, 57, and 58, the distal end of the sleeve 100 may extend through an incision in the patient's soft tissue such that the distal end of the sleeve 100 is positioned generally against the lateral surface of the ilium 1005. The longitudinal axis of the sleeve 100 and collar 165 of the anchor arm 115 can be understood to be generally coaxially aligned with the longitudinal axis of the bore 40 of the implant body 25.

Referring now to FIG. 59, the sacroiliac joint space boundary 3000 is defined along the sacrum 1004 and outlines the sacroiliac joint articular region 1044. The implant 25 positioned for implantation within the extra-articular space 3007 of the sacroiliac joint 1000. As shown in FIG. 59, the sacroiliac joint space boundary includes an inferior boundary segment 3002, an anterior boundary segment 3004, a superior boundary segment 3006, and a posterior boundary segment 3008. The inferior boundary segment 3002 is immediately adjacent, and extends along, the sciatic notch 2024.

The inferior boundary segment 3002 and anterior boundary segment 3004 intersect to form an anterior-inferior corner 3010. The anterior boundary segment 3004 and superior boundary segment 3006 intersect to form an anterior-superior corner 3012. The superior boundary segment 3006 and posterior boundary segment 3008 intersect to form a superior-posterior corner 3014. The posterior boundary segment 3008 and posterior inferior access region 2016 intersect to form a superior-posterior corner 3016 of the posterior inferior access region 2016. The inferior boundary segment 3002 and posterior inferior access region 2016 intersect to form an inferior-posterior corner 3018 of the posterior inferior access region 2016.

The inferior boundary segment 3002 extends between corners 3010 and 3018. The anterior boundary segment 3004 extends between corners 3010 and 3012. The superior boundary segment 3006 extends between corners 3012 and 3014 and provides an access into the cranial portion 1087 of the sacroiliac joint. The posterior boundary segment 3008 extends between corners 3014 and 3016. The posterior inferior access region 2016 extends between corners 3016 and 3018 and provides an access into the caudal region 1086 of the sacroiliac joint. The posterior boundary segment 3008 separates articular region 1044 and extra-articular region 3007, which includes the sacral fossa on the sacrum 1004 and the corresponding iliac tuberosity on the ilium 1005 and defined by the extra-articular region boundary 3009.

As shown in FIG. 59, the insertion element 650 of the implant body 25 is inserted via the implant arm 110 of the delivery tool 20 into the extra-articular space 3007 of the sacroiliac joint 1000. The implant 25 enters the extra-articular recess access region 6000, and is further advanced into the extra-articular space 3007 of the sacroiliac joint 1000 in an orientation such that the implant arm 110 and implant plate 45 are in the joint plane 1030 (see, for example, FIGS. 601-60J). Thus, the distal end 42 of the implant body 25 is heading generally perpendicular to, and towards, the anterior boundary segment 3004. Thus, when implanting the insertion element 650 of the implant body 25 via the extra-articular recess access region 6000, the general direction of travel for the implant distal end 42 is towards the anterior-inferior corner 3010, and the insertion element 650 can be positioned substantially within the extra-articular region 3007 or, alternatively, the insertion element 650 can be further advanced to also occupy a portion of the sacroiliac joint articular region 1044.

iii. Insertion of Anchor

Figure 60M:
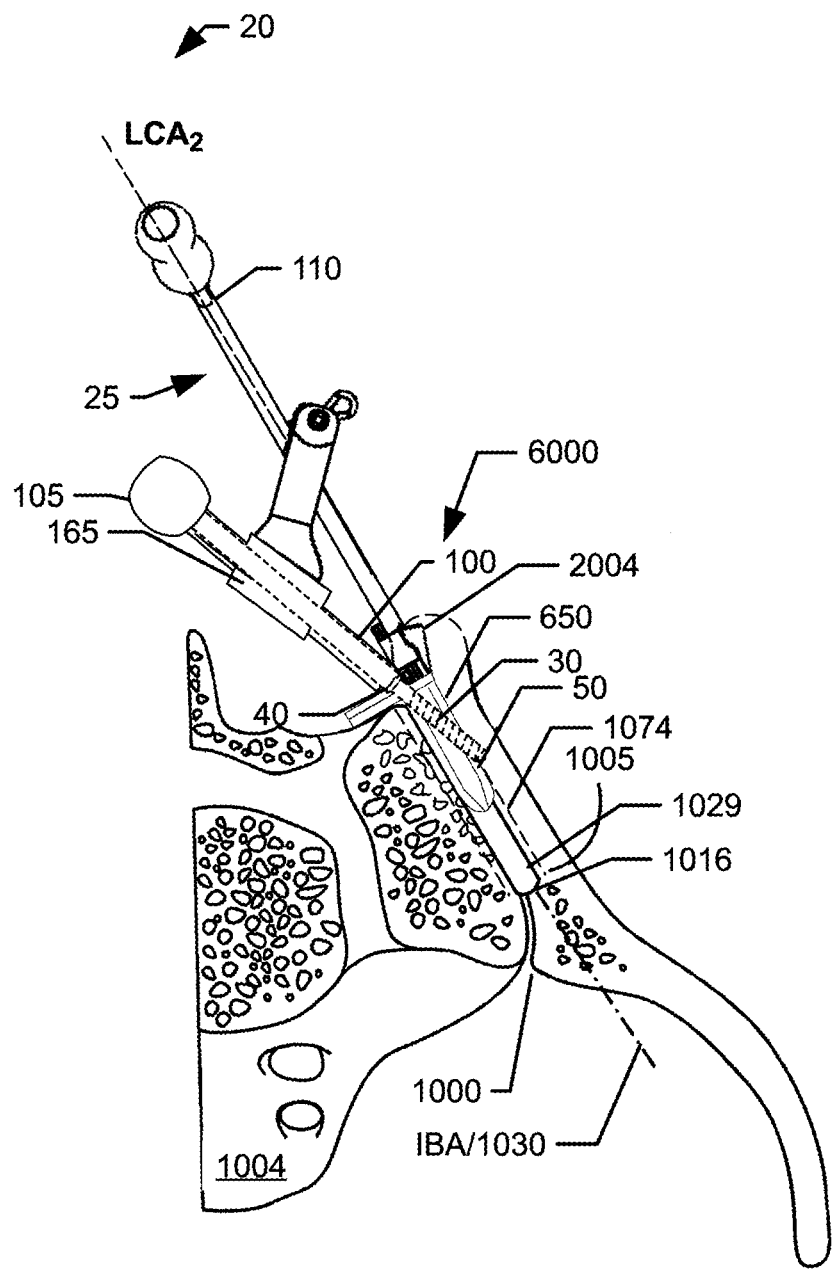
Figure 60N:
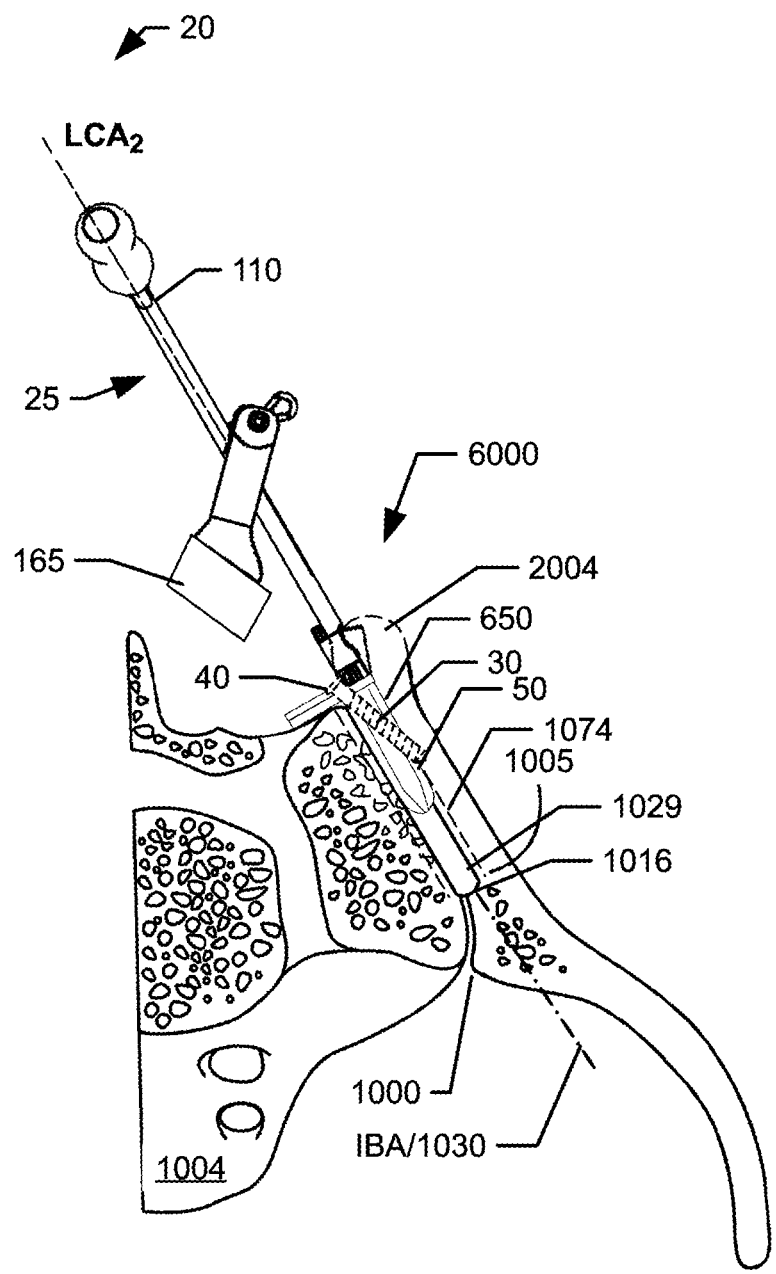
Figure 60O:
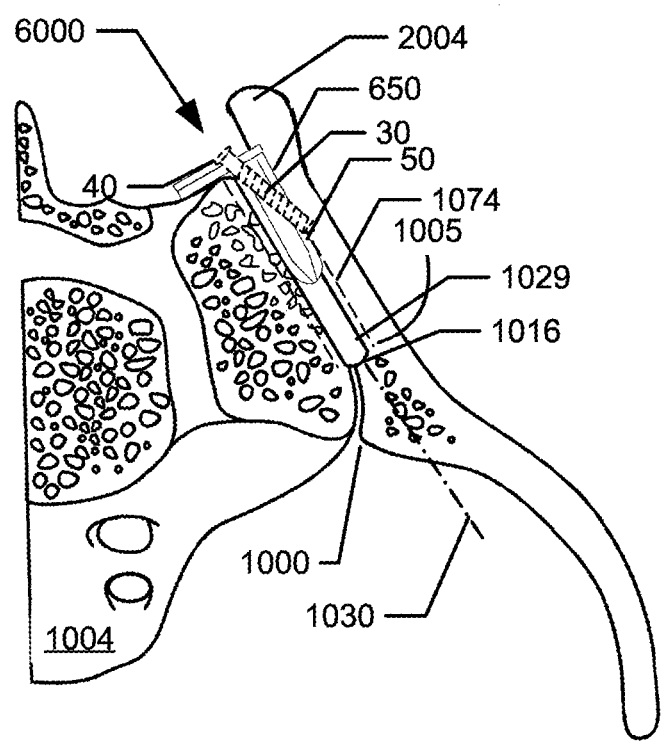
Figure 60P:
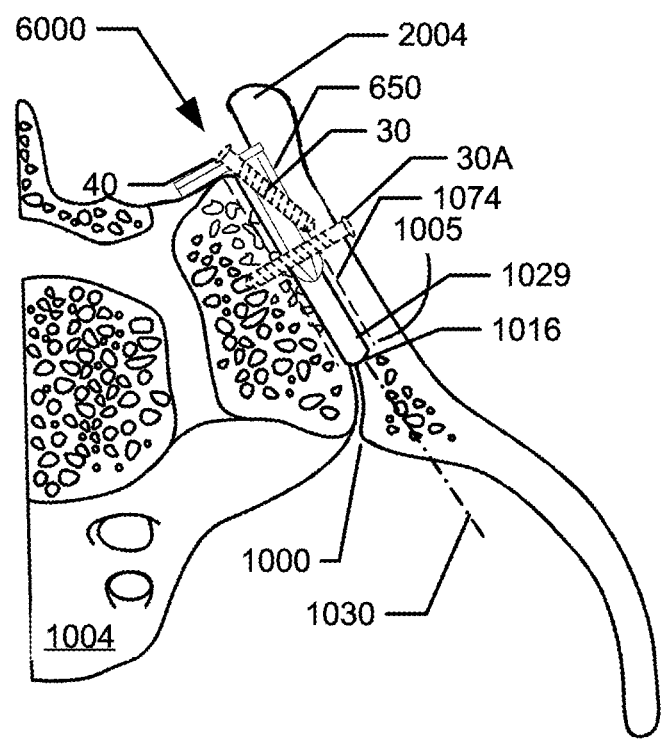

FIG. 58 is a posterior-inferior view of the hip region 1002 of the patient 1001. As can be understood from FIGS. 60L and 58, the anchor 30 is positioned in the lumen of the sleeve 100. A driving tool 105 (e.g., screw driver) is extended through the lumen of the sleeve 100 so the distal end of the tool 105 is engaged with a proximal end of the anchor member 30 (e.g., screw). As shown in FIG. 60M, the tool 105 is used to drive the anchor 30 distally through into the bore 40 of the implant 25 generally transverse to the joint line plane 1030 and into the bone of the sacrum 1004, in this embodiment. As a result, as indicated in FIG. 60N, the implant assembly 15 formed of the implant body 25 and anchor 30 is secured at the implantation site such that the implant body 25 is located in the prepared space 1029 of the sacroiliac joint space, and the anchor 30 extends through into the bore 40 of the implant 25 into the bone of the sacrum 1005 and into generally transverse to the joint space plane 1030 and optionally into the bone of the ilium 2004, as illustrated in FIG. 60N. The tool 105 and sleeve 100 can be removed from the anchor arm collar 165, and the incision associated with the sleeve 100 can be closed. Additionally, tool 105 can be a cutting tool 105 (e.g., drill bit, hole punch, or etc.) which can used in similar steps as above describe to remove bone or other tissues in the path where anchor 30 is to be placed. As indicated in FIG. 60O, the distal end of the implant arm 110 is decoupled from the proximal end of the implant 25 and removed. The incision associated with the implant arm can be closed.

As illustrated in FIG. 60P, in certain embodiments, the implant body 25 can be configured to have more than one implant bore 40 to receive additional anchors 30A. The anchors 30 and 30A prevent migration of the implant body 25 within the joint space. The anchors 30 and 30A also can draw the ilium and sacrum together about the implant body 25, increasing the sturdiness of the fixation of the implant 25 in the joint space, as demonstrated by the anchor 30A in FIG. 60P. Where the anchor 30 extends through the implant bore 40 and into the bone of both the sacrum 1004 and ilium 1005, the anchor 30 can be used to drawn the articular surfaces 1016 of the sacroiliac joint 1000 against the external surfaces of the insertion element 350 of the implant body 25. With the insertion element 350 implanted in the sacroiliac joint, the healing processes will cause the surfaces 1016 to fuse together about the insertion element 350.

FIG. 61 is a posterior view of the implantation area 1029 and the implant body 25 implanted within the implantation area 1029. In this view, the insertion element 650 situated in the joint space is obscured by the attachment element 652. As can be understood from FIG. 61, the extra-articular recess access region 6000 and implanted in the extra-articular space 3007 of the sacroiliac joint 1000. The anchor 30 can be understood to have been driven into the implant bore 40 transversely to the joint plane 1030 via a route in the sacrum 1004 that avoids contact with vascular and neurological structures, thereby avoiding potentially life threatening injury to such structures. The ability to blindly, yet safely, drive the anchor member 30 into the implant bore 40 while the implant 25 is hidden in the joint space is made possible by the cooperating configurations of the implant body 25 and the delivery tool 20. Specifically, the longitudinal axis LCA1 of the anchor arm 165 is coaxially aligned with the longitudinal axis BA of the implant bore 40 when the implant body 25 is supported off of the implant arm 110 of the delivery tool 20, thereby making it possible to safely drive the anchor 30 through the implant bore 40 and into the ilium 1005 bone and/or sacrum bone 1004 when the implant body 25 is hidden in the joint space on account of being delivered to the joint space via the delivery tool 20.

Figure 47A:
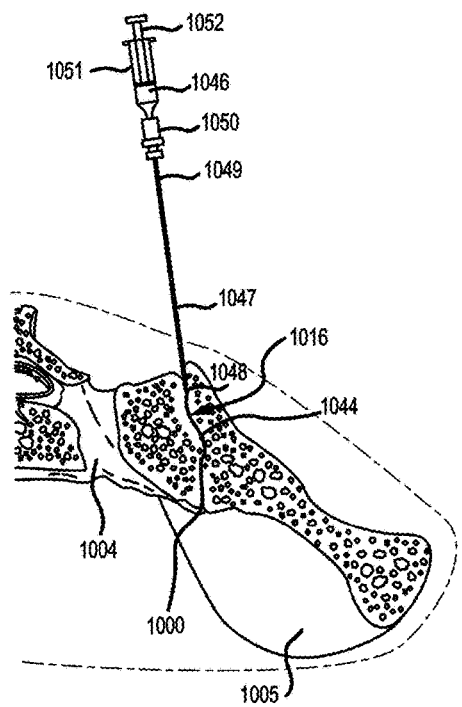
FIGS. 47A-47Q are each illustrations of a step in the methodology in one embodiment and are each illustrated as a transverse cross section taken along a plane extending medial-lateral and anterior posterior along section 99-99 in FIG. 46B.
Figure 47B:
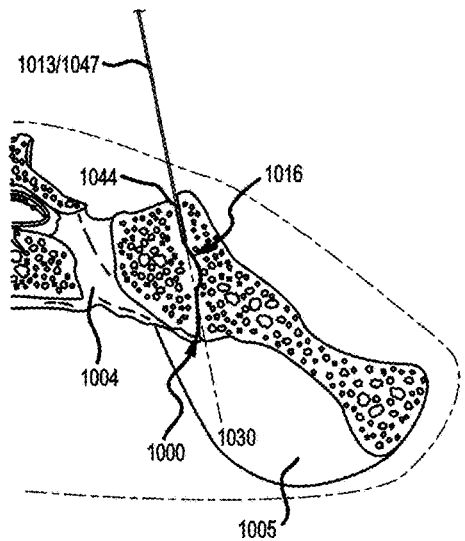

Anchor trajectory and placement may be guided and confirmed with imaging studies before the end of the surgical procedure or afterwards. For example, a surgeon may use fluoroscopy (and/or arteriography) to obtain an antero-posterior view, lateral view, an inlet view, an outlet-oblique view, Judet views of the pelvis, an internal (obturator) oblique view, a Ferguson view, an external (iliac) oblique view or other relevant views and further use radiographic boney landmarks such as the superimposed greater sciatic notches, superimposed iliac cortical densities or alar slope, sacral promontory, first sacral endplate, sacral foramina, arcuate sacral lines, iliopectineal line, ilioishial line, acetabular teardrop lines bony corridors of S1 or S2, superimposed acetabula, ventral and dorsal surfaces of the sacrum, etc.; or using an angiogram to identify vascular structures such as the superior gluteal artery, internal iliac artery and vein, iliolumbar vein, etc.

b. Implantation Via Intra-Articular Approach i. Preparation of Implant Receiving Space Now that the relevant anatomical landmarks have been identified with respect to FIGS. 44A-46B, the methodology associated with employing any of the above-described delivery tools 20 in implanting any of the above-described implant bodies 25 in the sacroiliac joint 1000 of a patient 1001 can be discussed. In doing so, reference will be made to FIGS. 47A-47P, which are each a step in the methodology and illustrated as the same transverse cross section taken in along a plane extending medial-lateral and anterior posterior along section line 99-99 in FIG. 46B. In this cross section, articular surfaces 1016 are covered by a thick layer of articular cartilage with a joint space existing between them, the FIGS. 47A-47P are simplified for illustrative purposes and do not show these features to scale. Now referring primarily to FIG. 47A, an embodiment of the method can include the step of placing a patient under sedation prone on a translucent operating table (or other suitable surface). The sacroiliac joint 1000 can be locally anesthetized to allow for injecting a radiographic contrast 1046 (as a non-limiting example, ISOVIEW 300 radiographic contrast) under fluoroscopic guidance into the inferior aspect of the sacroiliac joint 1000 to outline the articular surfaces 1016 of the sacroiliac joint 1000) defined between the sacrum 1004 and ilium 1005, the sacroiliac joint 1000 having an interarticular region 1044. Injection of the radiographic contrast 1046 within the sacroiliac joint 1000 can be accomplished utilizing a tubular member 1047 (such as a syringe needle) having first tubular member end 1048 which can be advanced between the articulating surfaces 1016 of the sacroiliac joint 1000 and having a second tubular member end 1049 which removably couples to a hub 1050. The hub 1050 can be configured to removably couple to a syringe barrel 1051 (or other device to contain and deliver an amount of radiographic contrast 1046). In the example of a syringe barrel 1051, the syringe barrel 1051 can have an internal volume capable of receiving an amount of the radiographic contrast 1046 sufficient for outlining the articular surfaces 1016 of the sacroiliac joint 1000, for example, under lateral fluoroscopy. A plunger 1052 can be slidingly received within the barrel 1051 to deliver the radiographic contrast 1046 through the tubular member 1047 into the sacroiliac joint 1000. The tubular member 1047 can have a gauge ranging between about 16 gauge and about 20 gauge and can further be incrementally marked on the external surface to allow determination of the depth at which the first needle end 1048 has advanced within the sacroiliac joint 1000. As the first needle end 1048 advances into the sacroiliac joint 1000 the radiographic dye 1046 can be delivered from within the syringe barrel 1051 into the sacroiliac joint 1000 to allow visualization of the sacroiliac joint 1000 and location of the tubular needle 1047 within the sacroiliac joint 1000.

Now referring primarily to FIG. 47B, once the first tubular member end 1048 has been sufficiently advanced into the sacroiliac joint 1000 and the articular surfaces 1016 of the sacroiliac joint 1000 have been sufficiently visualized, the hub 1050 can be removed from the tubular member 1047 leaving the tubular member 1047 fixed within the sacroiliac joint 1000 as an initial guide for tools subsequently used to locate or place the implant body 25 non-transversely between the articulating surfaces 1016 of the sacroiliac joint 1000 (e.g., locate the implant body 25 non-transversely to the joint plane 1030 generally defined by the articulating surfaces 1016 of the interarticular region 1044 of the sacroiliac joint 1000) or in removal of a portion of the sacroiliac joint 1000 within the region defined by the articular surfaces 1016 to generate an implant receiving space 1029 (see FIG. 47H). Alternately, one or more guide pins 1013 can be inserted along substantially the same path of the tubular member 1047 for fixed engagement within the sacroiliac joint 1000 and used in subsequent steps as a guide(s).

Figure 47C:
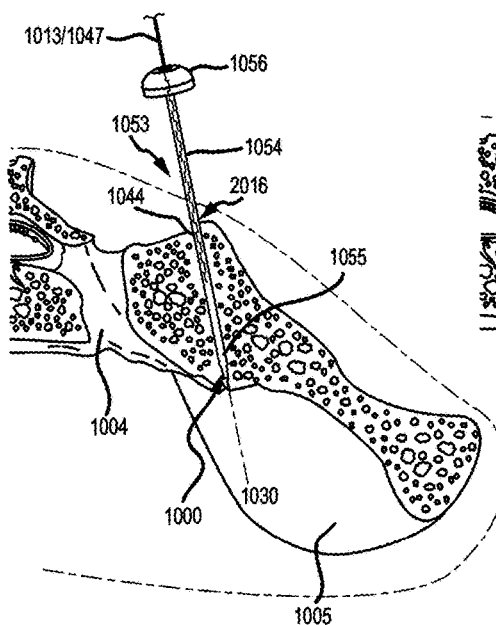

Now referring primarily to FIG. 47C, a small incision 1053 can be made in the skin at the posterior superior (or as to certain embodiments inferior) aspect of the sacroiliac joint 1000, extending proximal and distal to the tubular member 1047 along the line of the sacroiliac joint 1000 to provide a passage to access the interarticular space between the articulating surfaces 1016 (see FIG. 47B) of the sacroiliac joint 1000. More specifically, as can be understood from FIGS. 45A-45B, in one embodiment, the small incision 1053 can be made along the joint line 2019 of the sacroiliac joint 1000 in the tissue covering the posterior inferior access region 2016 of the sacroiliac joint articular region 1044. A cannulated probe 1054 can be slidingly engaged with the tubular member 1047 (or guide pin 1013) extending outwardly from the sacroiliac joint 1000 (while the sacroiliac joint may be shown in the figures as being substantially linear for illustrative purposes, it is to be understood that the normal irregular features of the sacroiliac joint have not been removed). The cannulated probe 1054 can have a probe body 1054 of generally cylindrical shape terminating in a spatulate tip 1055 at the end advanced into the sacroiliac joint 1000. A removable cannulated probe handle 1056 couples to the opposed end of the probe body 1054. The spatulate tip 1055 can be guided along the tubular needle 1047 or guide wire 1013 into the posterior portion of the sacroiliac joint 1000 and advanced to the anterior portion of the sacroiliac joint 1000 under lateral fluoroscopic visualization. The cannulated probe handle 1056 can then be removed providing the generally cylindrical probe body 1054 extending outwardly from the sacroiliac joint 1000 through the incision 1053 made in the skin. Alternatively, probe 1054 can be used to guide, advance or place a needle, guide wire or other instrument up to, near, or into the sacroiliac joint 1000.

Additionally, in particular embodiments, probe handle 1056 or the opposed end of the probe body 1054, or both, can be configured to have an interference fit or a Luer lock hub to communicate with a syringe barrel 1051 in order to advance contrast, in situ curable biocompatible materials, stem cells, or any other suitable materials through the cannulated probe 1054 or cannulated probe handle 1056.

Figure 47D:
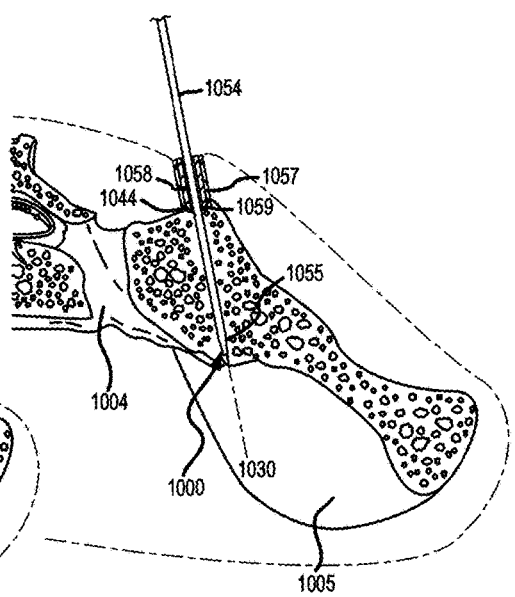

Now referring primarily to FIG. 47D, a passage from the incision 1053 (see FIG. 47C) to the sacroiliac joint 1000 can be generated by inserting a cannula 1057 into the incision. A soft tissue dilator 1058 having a blunt end 1059 can be advanced over the probe body 1054, or a plurality of soft tissue dilators of increasing size, until the blunt end 1059 of the soft tissue dilator 1058 and the corresponding cannula end contact the posterior aspect of the sacroiliac joint 1000. More specifically, as can be understood from FIGS. 44A-46B, in one embodiment, the ends of the dilator 1058 and cannula 1057 contact the joint line 2019 of the sacroiliac joint 1000 at the posterior inferior access region 2016 of the sacroiliac joint articular region 1044. The soft tissue dilator 1058 can be removed from within the cannula 1057. The external surface of the cannula 1057 can be sufficiently engaged with the surrounding tissue to avoid having the tissue resituate within the hollow inside of the cannula 1057. A non-limiting embodiment of the cannula 1057 provides a tubular body having substantially parallel opposed side walls which terminate in a radius at both ends (lozenge shape) into which a plurality of different jigs can be inserted. Alternatively, as a non-limiting example, according to particular embodiments, cannula 1057 and corresponding dilators 1058 and alignment jigs 1060 can be configured to have tubular bodies with an elliptical or circular cross section.

In some embodiments, the cannula 1057 may be additionally configured to have within or near its walls a light source such as, for example, a fiber optic or a LED light source to assist in visualization of the working area. Also, in some embodiments, irrigation and suction tubing may communicate with the inside passage of cannula 1057.

Now referring primarily to FIGS. 48A-48C, a cannula alignment jig 1060 can be advanced over the probe body 1054 (or guide pins 1013) and received within the cannula 1057. Substantially, identical cross hairs 1063, 1064 can be disposed on the upper jig surface 1065 and the lower jig surface 1066. Alignment of the cross hairs 1063, 1064 under x-ray with the sacroiliac joint 1000 can confirm that the cannula 1057 has proper orientation in relation to the paired articular surfaces 1016 of the sacroiliac joint 1000. The cannula 1057 properly oriented with the paired articular surfaces 1016 can then be disposed in fixed relation to the sacroiliac joint by placement of fasteners through the cannula 1057 into the sacrum 1004 or the ilium 1005.

Figure 49A:
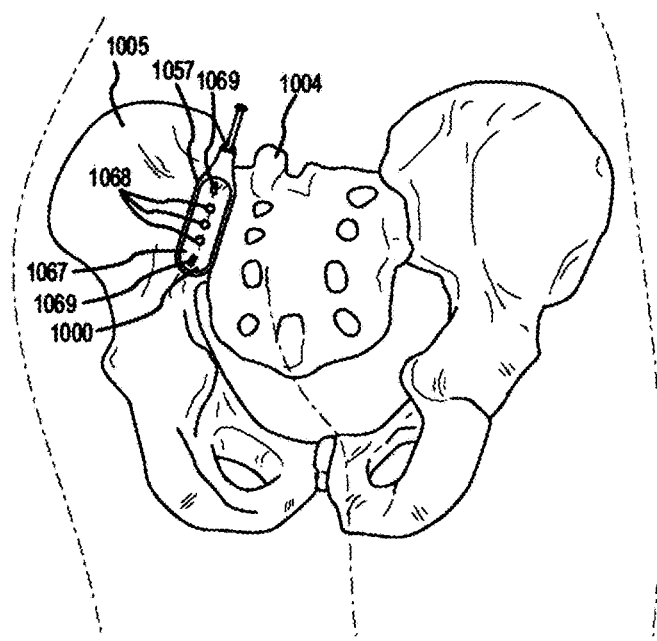
FIG. 49A is a posterior-lateral view of the hip region of the patient, illustrating the placement of a drill jig.
Figure 49B:
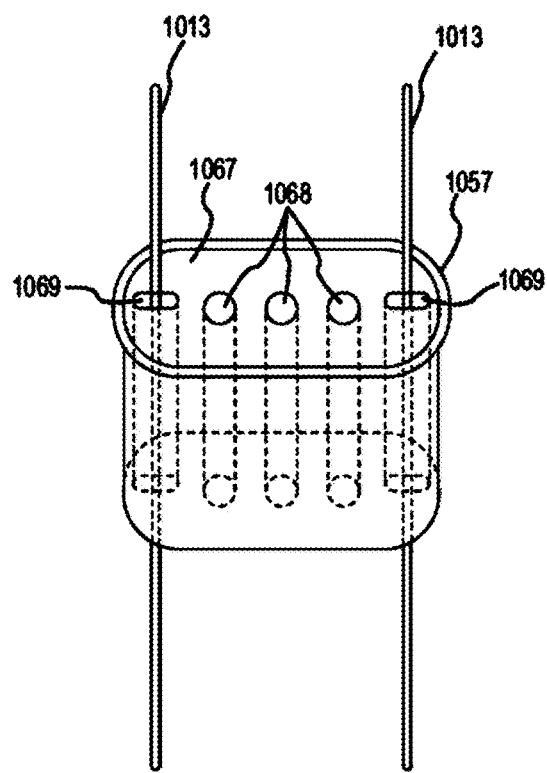
FIG. 49B is an isometric view of the drill jig illustrated in FIG. 49A.

Now referring to FIGS. 49A and 49B, a first drill jig 1067 can be advanced over the probe body 1054 (or guide pins 1013) and received within the cannula 1057. The probe body 1054 (or guide pins 1013) extending outwardly from the sacroiliac joint 1000 passes through a drill guide hole 1068 of the first drill jig 1067 (or a plurality of guide pins 1013 can extend through a corresponding plurality of guide pin holes 1069). The drill guide hole 1068 can take the form of a circular hole as shown in the Figures, a slot, or other configuration to restrict the movement of the drill bit 1062 (see FIG. 47E) within the drill jig 1060 and provide a guide for a drill bit 1062 in relation to the sacroiliac joint 1000. Guide pin holes 1069 can receive guide pins which can be positioned between the articular surfaces 1016 of the sacroiliac joint 1000 to demarcate the zone of desired treatment or safe working zones while using, for example, lateral fluoroscopy. As a non-limiting example, a first guide pin 1013 can be advanced through a first guide pin hole 1069, or alternatively a guide pin 1013 is first inserted into the sacroiliac joint 1000 and subsequently a guide jig 1067 is advanced over the guide pin 1013, the first guide pin 1013 can enter near inferior end 2022 of the posterior inferior access region 2016 of the sacroiliac joint articular region 1044 via the sacroiliac joint line 2019 to border a portion of the greater sciatic notch 2008 thereby allowing a medical person, computer guided surgical system, or other observer to more easily highlight under x-ray a border which should not be crossed during the procedure due to the presence of nerve and other structures. Additionally, as a non-limiting example, first guide pin 1013 can configured as an electrode, insulated from the operator and the patient's soft tissues, and may be connected to a monitor to signal to an operator or surgeon when implant body 25, configured with a stimulating electrode (NM), as discussed below, comes into contact with first guide pin. Similarly, a second guide pin 1013 can be placed in another guide pin hole 1069 to demarcate a second limit to a desired zone of treatment, or safe working zone. For example, a second guide pin 1013 can enter near the superior end 2018 of the posterior inferior access region 2016 of the sacroiliac joint articular region 1044 via the sacroiliac joint line 2019 to be positioned to border an area of the sacroiliac joint 1000 such as a transition zone between the extra-articular 3007 and the interarticular region 1044 which, for example, has been highlighted by contrast material as above described.

Referring to FIGS. 49C-49K, a cannula 1057 may be used to facilitate access to the surgical region during a procedure to implant the implant assembly 25 (not shown). In one embodiment, the cannula 1057 may be used in conjunction with a sacroiliac joint repair procedure via a known surgical access region including, but not limited to, the posterior inferior access region 2016 as illustrated in FIGS. 49C-49K. The cannula 1057 may include a cannula body 1057H forming a wall enclosing an internal volume 1057J, which opens to a proximal opening 1057A and a distal opening 1057B. Upon insertion of the cannula 1057 within the surgical access region, the internal volume 1057J may be maintained, thereby functioning as an opening through which surgical instruments, appliances, fasteners, and any other associated surgical equipment or supplies may be inserted or removed and through which the surgical procedure may be visually monitored.

The outer surface of the cannula body 1057H may include one or more contoured regions or projections to enhance the close fit of the cannula 1057 between the skeletal structures surrounding the surgical access region 2016. The outer surface of the body 1057H may form a cannula sacral contour 1057C on one side and may additionally form a cannula iliac contour 1057D on a side opposite to the cannula sacral contour 1057C. The cannula 1057 may also include a distal projection 1057E which extends distally beyond the cannula sacral contour 1057C and may be shaped to fit within a portion of the greater sciatic notch 2008 (see FIG. 49I). In addition, the outer distal surface of the cannula body 1057H may form a PSIS contact area 1057F to enhance the fit of the portion of the cannula 1057 contacting the posterior superior iliac spine (PSIS) 2004 (see FIG. 49G).

Figure 49C:
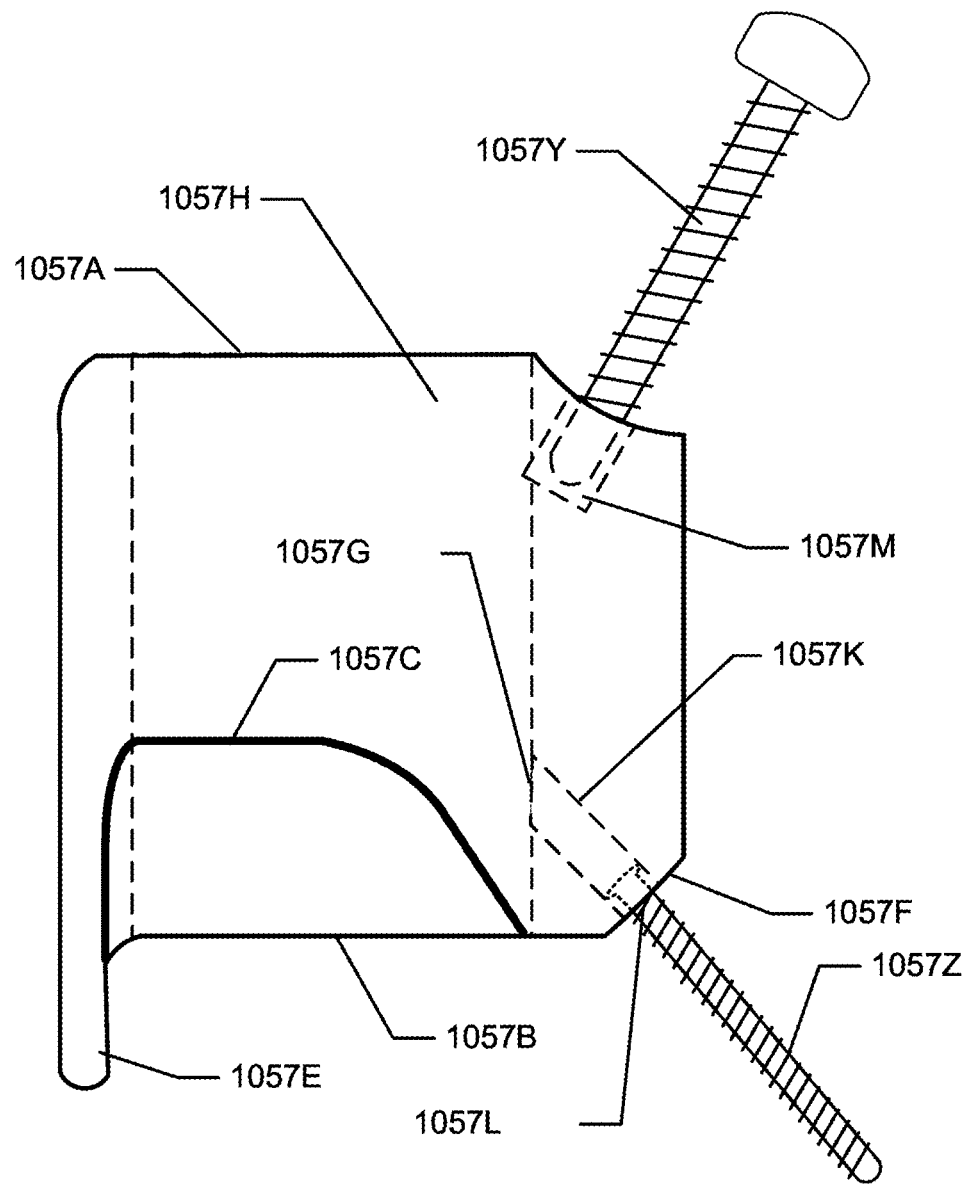
FIG. 49C-49E are side, top, and front views, respectively, of a cannula in an embodiment.
Figure 49D:
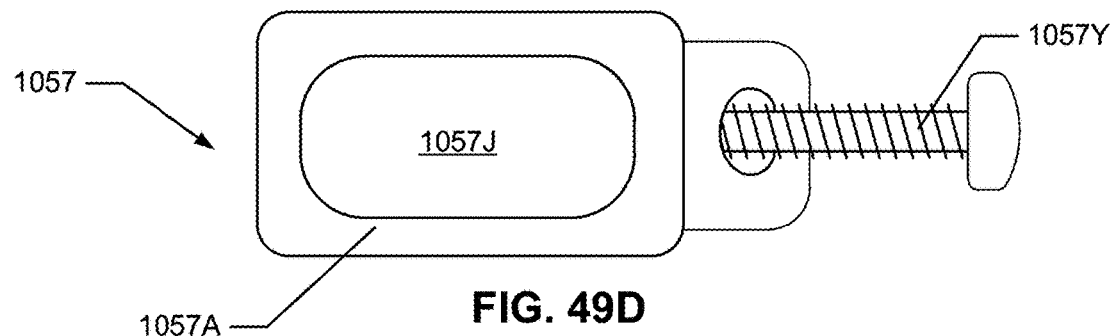
Figure 49E:
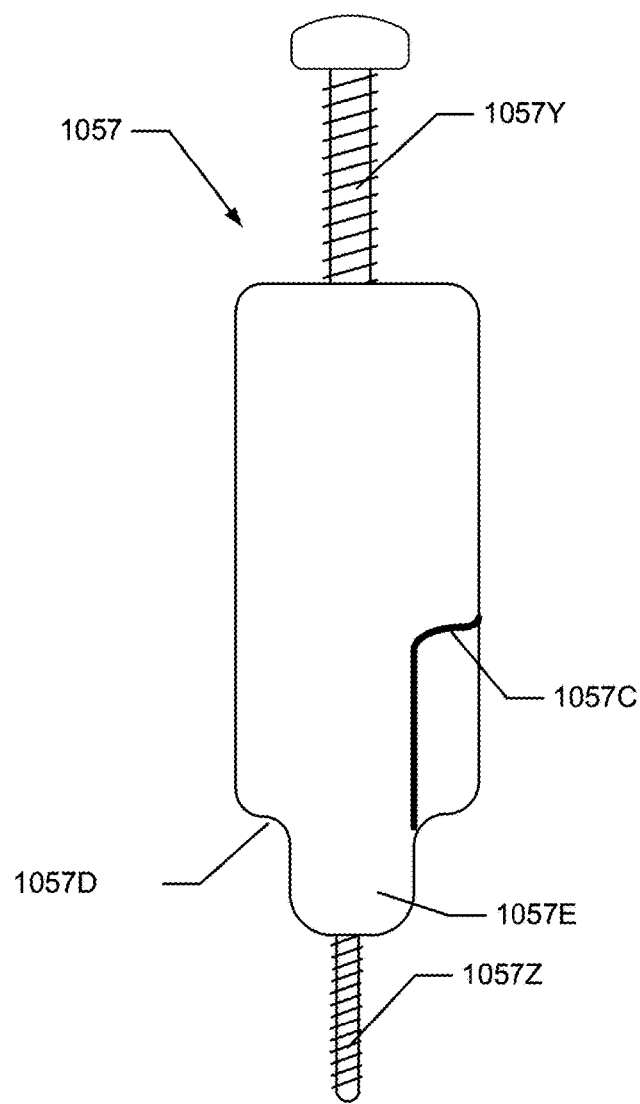
Figure 49F:
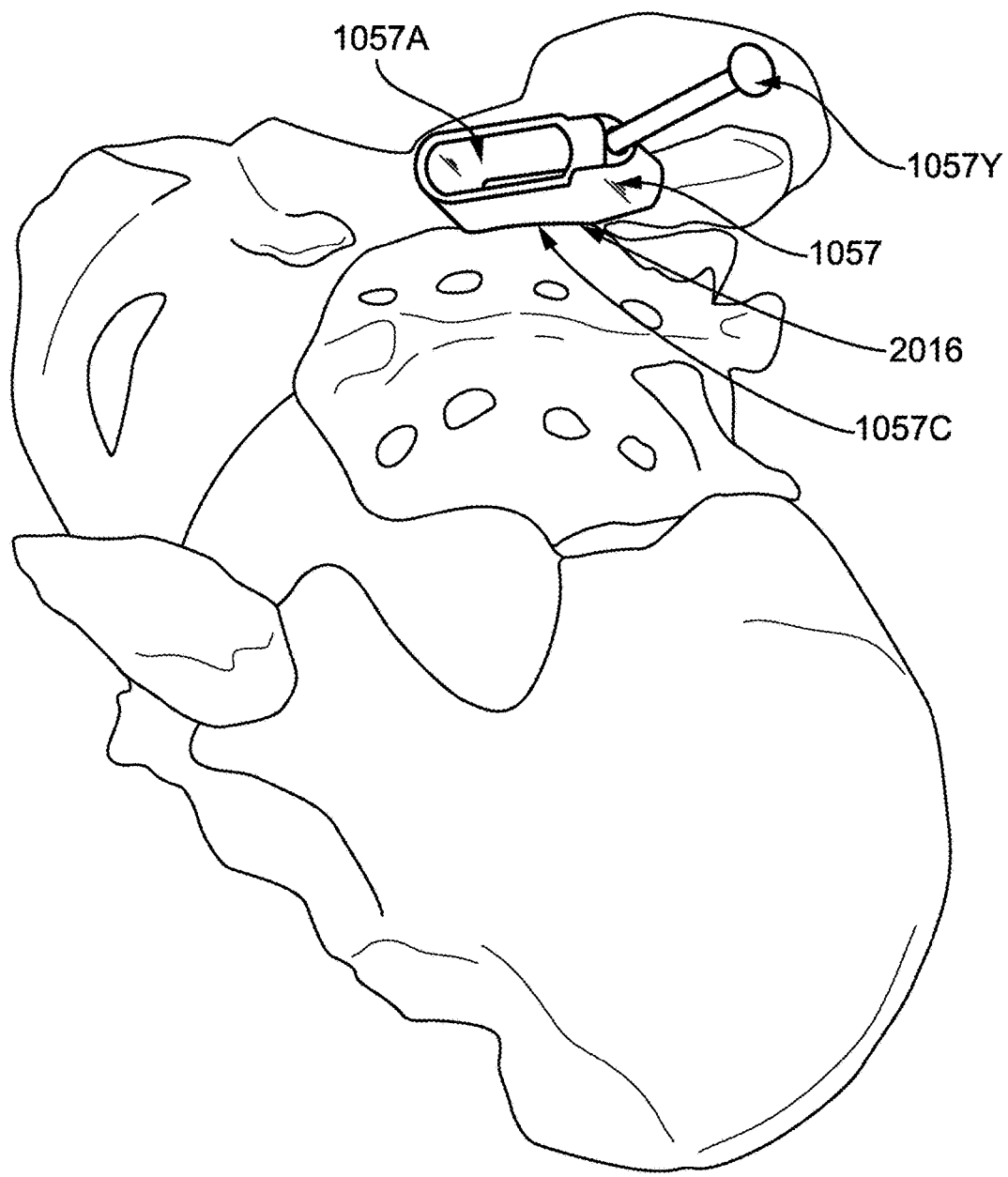
FIG. 49F is a posterior-lateral view of the hip region of the patient, illustrating the placement of the cannula illustrated in FIGS. 49C-49E for use during a sacroiliac joint procedure via a posterior inferior access region.

The cannula body 1057H may further define one or more additional bores configured to reversibly receive handles and/or fasteners used to situate the cannula within the surgical region and/or to reversibly receive fasteners used to fix the cannula in place within the surgical region during the surgical procedure. The cannula body 1057H may define a fastener bore 1057K passing through the cannula body 1057H from the outer surface into the internal volume 1057J of the cannula 1057. The cannula bore may open at one end to a cannula fastener bore proximal opening 1057G, which may be in communication with the internal volume 1057J of the cannula 1057. The cannula bore may also open at an opposite end to a cannula fastener bore distal opening 1057L which may be further configured to permit a fastener 1057Z to i) extend generally perpendicular to the cannula PSIS contact area 1057F; and/or, ii) be in a divergent relation relative to distal projection 1057E. Furthermore, the cannula 1057 may have a handle 1057Y extending from the cannula body 1057H for inserting, removing, and/or otherwise manipulating the cannula 1057 during a surgical procedure. As illustrated in FIG. 49C, the handle 1057Y may be reversibly attached to the cannula body 1057 via a handle bore 1057M formed with the cannula body 1057H. The handle bore 1057M may be provided with fastener features including, but not limited to, threads, that may cooperatively engage corresponding fastener features at a distal end 1057N of the handle 1057Y in order to implement the reversible attachment of the handle 1057Y to the cannula 1057.

Figure 49G:
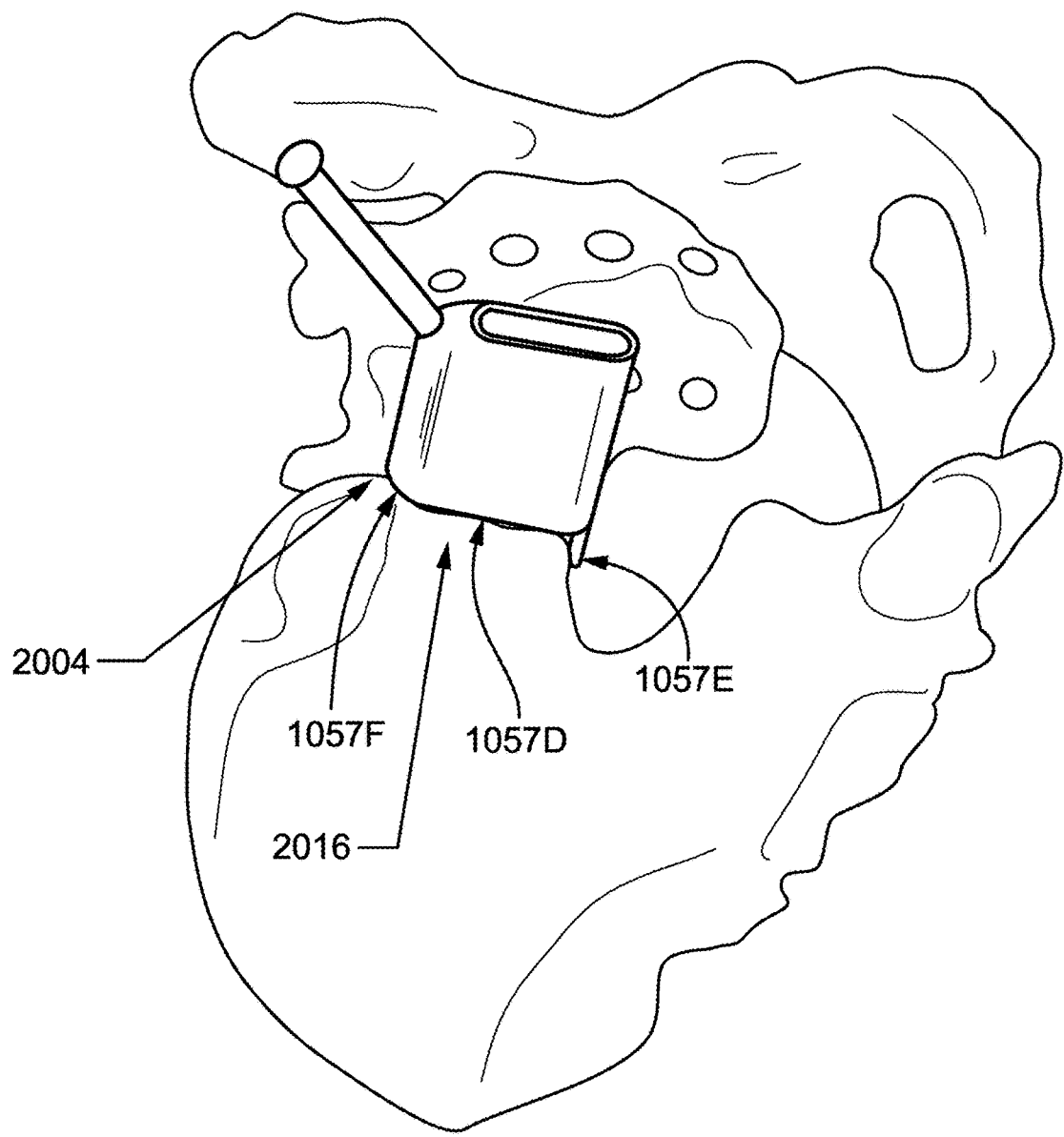
FIG. 49G is a posterior-lateral view of the hip region of the patient illustrating the placement of the cannula of FIGS. 49C-49E.
Figure 49H:
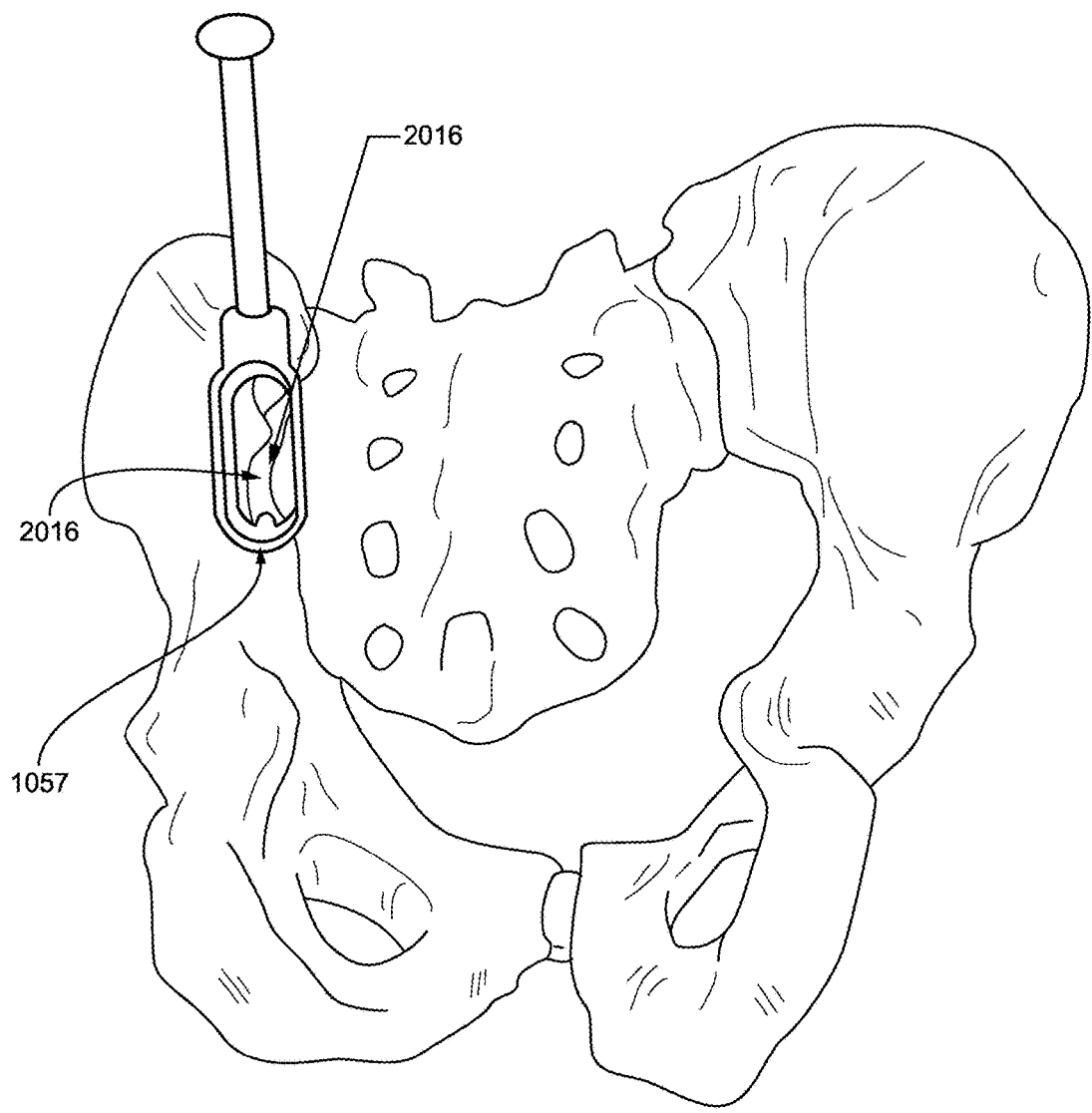
FIG. 49H is a posterior-lateral view of the hip region of the patient, illustrating the placement of the cannula of FIGS. 49C-49E, in which a posterior inferior access region of a sacroiliac joint articular region on a sacroiliac joint line is visible.
Figure 49I:
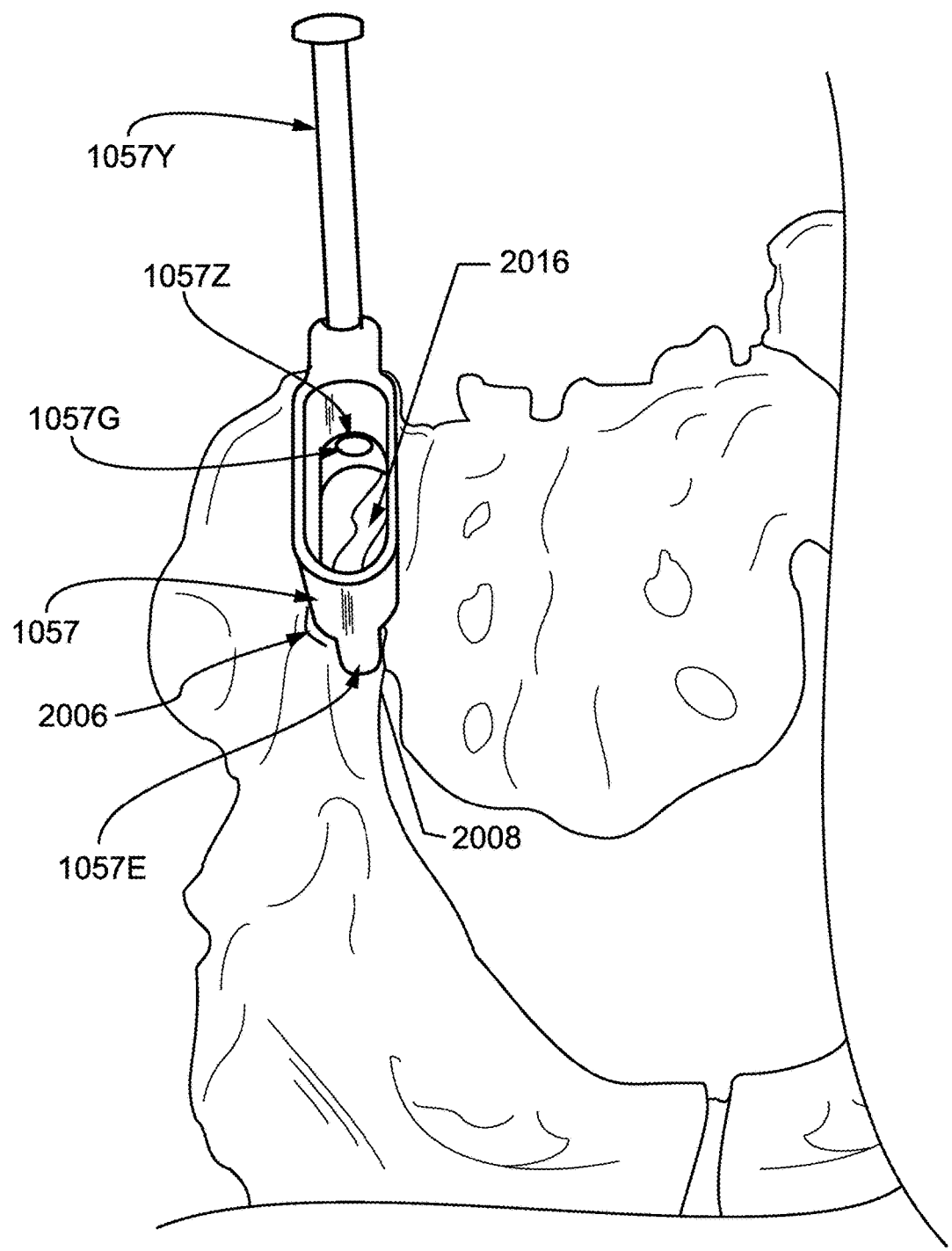
FIG. 49I is a generally posterior-inferior view of the hip region of the patient, illustrating the placement of the cannula of FIGS. 49C-49E.
Figure 49J:
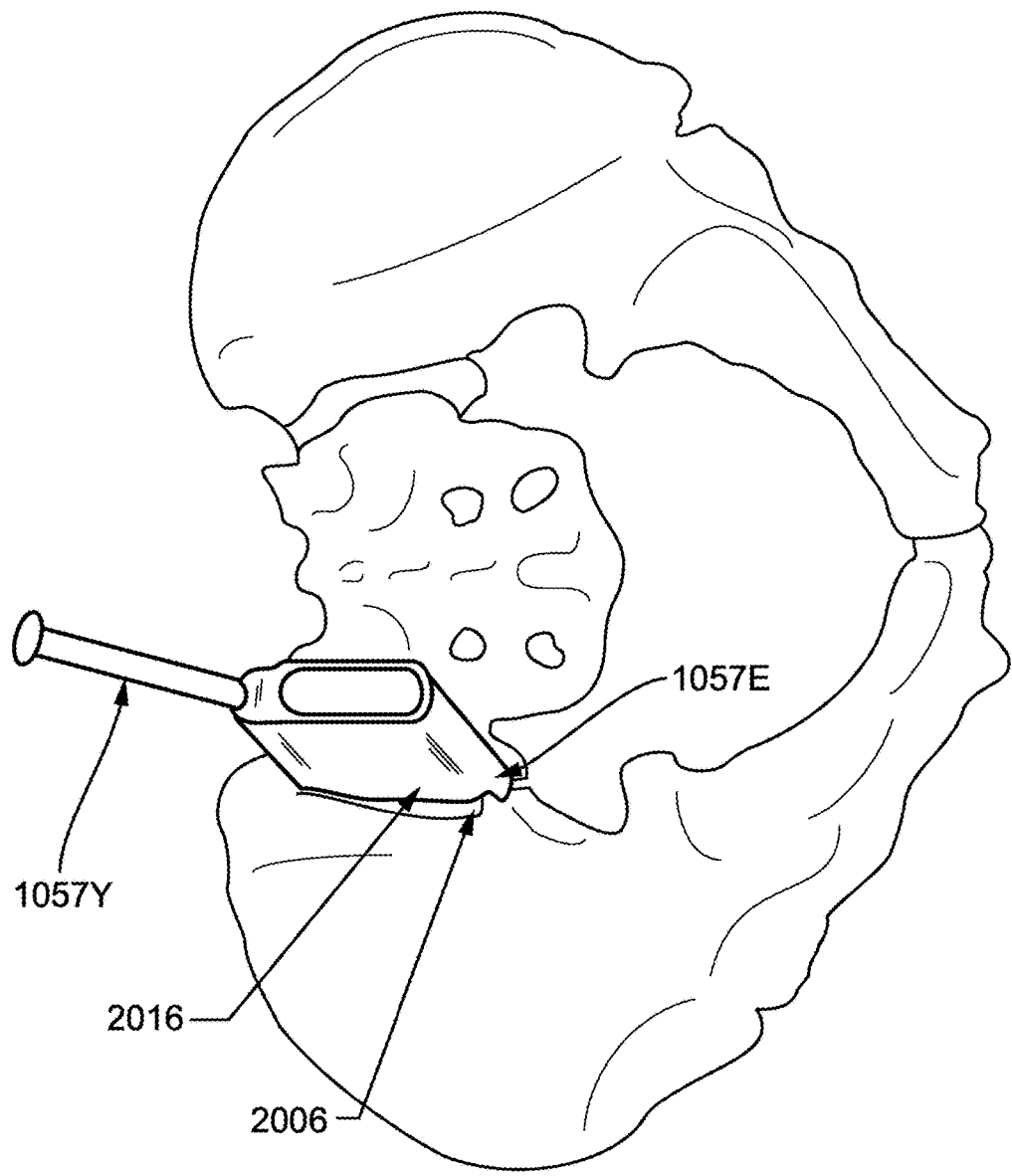
FIG. 49J is a generally posterior-inferior view of the hip region of the patient, illustrating the placement of the cannula of FIGS. 49C-49E.
Figure 49K:
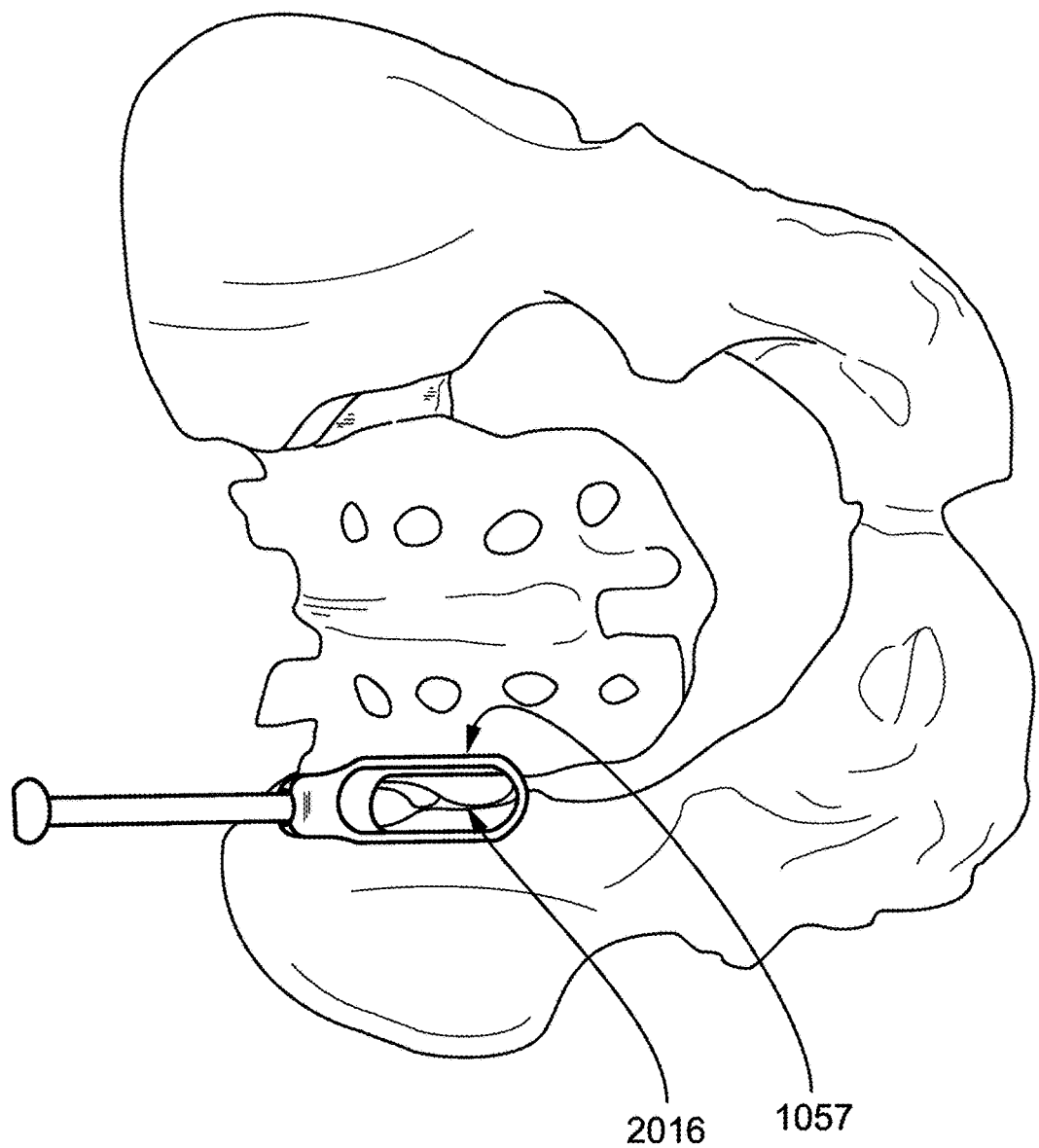
FIG. 49K is a posterior-lateral view of the hip region of the patient, illustrating the placement of the cannula of FIGS. 49C-49E, wherein a posterior inferior access region of a sacroiliac joint articular region on a sacroiliac joint line is visible.

Referring again to FIGS. 49C to 49K, a surgical procedure employing the cannula 1057 may be conducted using a method described herein below. A cannula 1057 may be positioned near a sacroiliac joint line 2019 and in an area including the posterior inferior access region 2016 such that the sacroiliac joint line 2019 may be visible and/or accessible via a cannula proximal opening 1057A, as illustrated in FIG. 49H. The cannula 1057 may be further positioned to align the distal extension 1057E with a portion of the greater sciatic notch 2008, as illustrated in FIG. 49I. The cannula 1057 may be further positioned to align the cannula PSIS contact area 1057F with a portion of a posterior superior iliac spine 2004 as illustrated in FIG. 49G. The cannula 1057 may then be disposed in fixed relation to the sacroiliac joint by placement of fasteners 1057Z through the cannula 1057 into the sacrum 1004 or the ilium 1005, as illustrated in FIG. 49I.

Figure 47E:
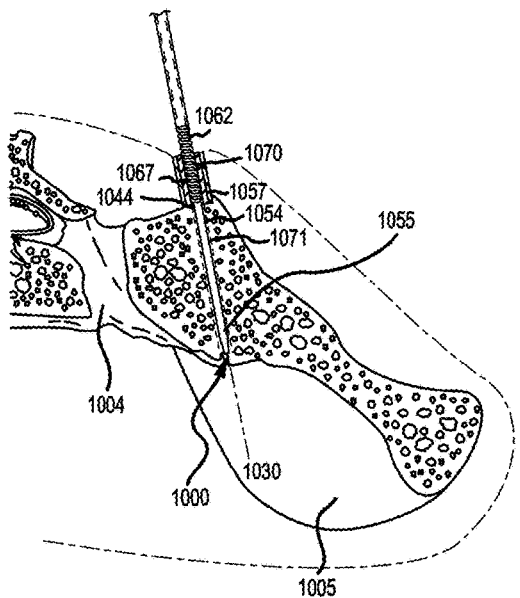

Now referring to FIG. 47E, a cannulated drill bit 1070 can be advanced over the probe body 1054 and within a drill guide hole 1068 (see FIGS. 49A and 49B) of the first drill jig 1067. The cannulated drill bit 1070 under fluoroscopic guidance can be advanced into the interarticular region 1044 between the articulating surfaces 1016 of the sacroiliac joint 1000 to produce a first bore 1071 (shown in broken line) to a determined depth. As to certain embodiments of the method, an amount of articular cartilage or other tissues from between the articular surfaces 1016 of the sacroiliac joint 1000 can be removed sufficient to allow embodiments of the implant body 25 to be implanted in replacement of the removed articular cartilage or tissue. Because the method removes the degenerative articular cartilage or tissue between the articular surfaces 1016 of the sacroiliac joint 1000, the articular surfaces 1016 of the sacroiliac joint 1000 can remain intact or substantially intact allowing implant body 25 to be non-transversely located between the articular surfaces 1016 of the sacroiliac joint 1000. Other instruments can be utilized separately or in combination with a cannulated drill bit 1062 for the removal of articular cartilage or tissue between articular surfaces 1016 such as: endoscopy tools, box chisels, side cutting router bits, burs, flexible burs and bits, hole saws, curettes, lasers (such as $CO_2$, Nd:YAG (neodymium-doped yttrium-aluminum-garnet), argon, and ruby), and electrosurgical equipment employing electromagnetic energy.

In an embodiment, the cutting electrode of the electrosurgical equipment may be a fine micro-needle, a lancet, a knife, a wire or band loop, a snare, an energized scalpel, or the like. The electrosurgical waveforms delivered by the cutting electrode may be set to promote two types of tissue effects, namely coagulation (temperature rises within cells, which then dehydrate and shrink) or cut (heating of cellular water occurs so rapidly that cells burst). The proportion of cells coagulated to those cut can be varied, resulting in a "blended" or "mixed" effect. Additionally, a fully rectified current, or a partially rectified current, or a fulguration current where a greater amount or lateral heat is produced can be employed to find the articular surfaces of the joint and aid in advancing a probe or guide wire into a position in between the articulating surfaces. These currents can effectively degrade the cartilage and allow advance into the joint without grossly penetrating much beyond the cartilage.

In one embodiment, the electrical energy delivered via the cutting electrode can be either monopolar or bipolar and operate with high frequency currents, for example, in the range of about 300 kHz and about 1000 kHz. The waveform of the delivered electrical energy may be a pure sinusoidal current waveform where the "crest factor" can be constant at about 1.4 for every sinus waveform, and a voltage peak of approximately 300 V to enable a "pure" cutting effect with the smallest possible coagulation effect. Alternatively, the electrical energy may be delivered as amplitude modulated current waveforms where the crest factor varies between 1.5 and 8, with decreasing crest factors providing less of a coagulation effect.

Figure 47F:
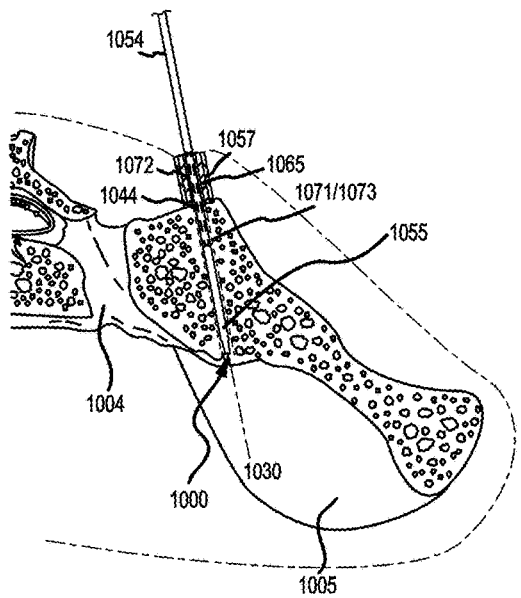

Now referring to FIG. 47F, as to certain embodiments of the invention, the first drill jig 1067 can be removed from within the cannula 1057 and a second drill jig 1072 can be advanced over the probe body 1054 and received within the cannula 1057; however, the invention is not limited to any particular number of drill jigs and as to certain embodiments of the method the first drill jig 1067 can include all the required drill guide hole(s) 1068 (or slots or other configurations of the drill guide) and as to other embodiments of the method a plurality of drill jigs can be utilized in serial order to provide all the drill guide holes 1068. As to the particular embodiment of the invention shown by the Figures, the first drill jig 1067 can provide one or more additional drill guide holes 1068 which guide in relation to the first bore 1071 a second or more cannulated drills 1062 of the same or different configuration to be inserted within and advanced into the sacroiliac joint 1000 to produce a second bore 1073 (generally shown in broken line as 1071/1073) or a plurality of bores within the sacroiliac joint 1000 spaced apart in predetermined pattern to allow removal of sufficient articular cartilage 1016 or other tissue from the interarticular space of sacroiliac joint 1000 for placement of embodiments of the sacroiliac joint implant 25 within the region defined by and between the paired articular surfaces 1016 of the sacroiliac joint 1000. As to certain methods of the invention, the first drill jig 1067 or the second drill jig 1072 or a plurality of drill jigs can be utilized in serial order to remove a portion of the sacroiliac joint 1000 for generation of an implant receiving space 1029 (see, for example, FIG. 47H). As these embodiments of the method, articular cartilage or other tissues and sufficient subchondral bone can be removed from between the articular surfaces 1016 of the sacroiliac joint 1000 sufficient to allow placement of certain embodiments of the sacroiliac joint implant body 25. In other embodiments, one or more transverse receiving channels 1074 aligned with the direction of the receiving space and extending in a direction perpendicular to the joint plane 1030 can be cut into at least one of the articular surfaces 1016 of said sacroiliac joint 1000 sufficient to receive certain elements of the implant body 25 including, but not limited to one or more fins 50, as illustrated in FIG. 5 in one embodiment of the implant body 25. The one or more transverse receiving channels 1074 can be cut a depth into the subchondral, cortical bone or cancellous bone of the sacrum 1004 and/or ilium 1005. A transverse receiving channel 1074 in one embodiment is illustrated in FIG. 47H as dashed lines.

Figure 47G:
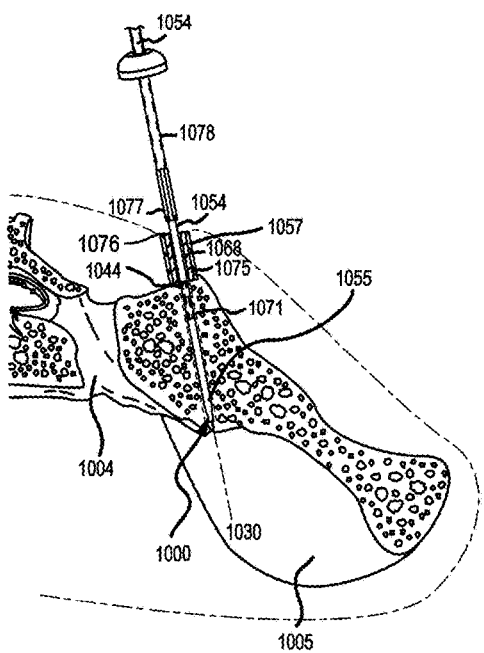
Figure 47H:
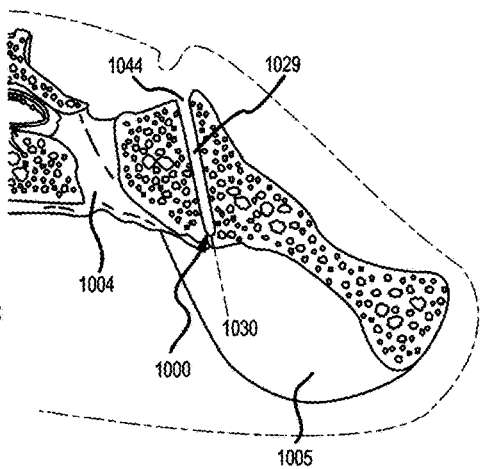
Figure 47I:
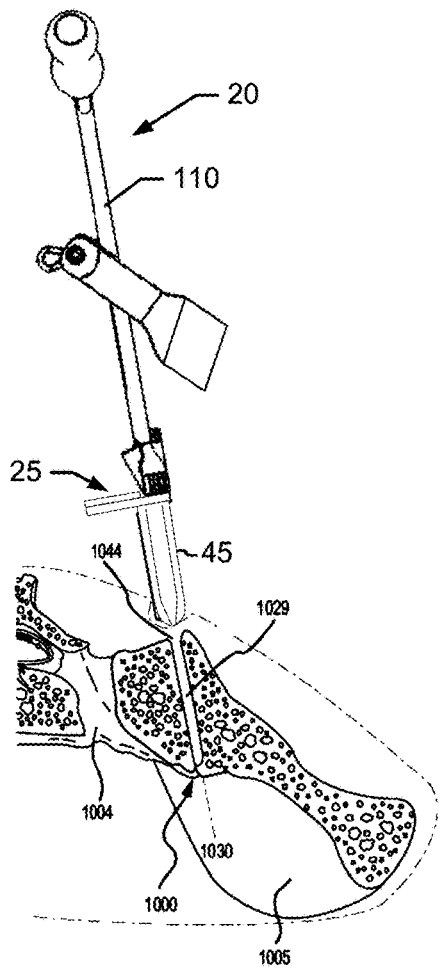

Now referring primarily to FIG. 47G, in a subsequent step, the last drill jig 1072 in the series can be removed from within the cannula 1057 and a broach jig 1075 can be advanced over the probe body 1054 and situated within the cannula 1057. The broach jig 1075 can include a broach guide hole 1076 which receives a first broach end 1077 of a cannulated broach 1078 advanced over the probe body 1054. The first broach end 1077 can have a configuration which can be advanced into the sacroiliac joint 1000. As to certain embodiments of the method, the first broach end 1077 can be adapted to remove an amount of articular cartilage and other tissue from between the articular surfaces 1016 within the articular region 1044 of the sacroiliac joint 1000 for non-transverse placement of the sacroiliac joint implant body 25. As to other embodiments of the method, the cannulated broach 1078 can further remove a sufficient portion of the sacroiliac joint 1000 to generate an implant receiving space 1029 to receive various embodiments of the sacroiliac joint implant 25 having a flattened elongate insertion plate 45, as illustrated in FIGS. 5, 9, and 12 in various embodiments by way of non-limiting examples. In yet other embodiments, the cannulated broach 1078 can further remove a sufficient portion of the sacroiliac joint 1000 to generate one or more transverse receiving channels 1074 to receive one or more fins 50 adapted to extend into the bone of the sacrum 1004 or the ilium 1005 in various embodiments of the sacroiliac joint implant 25 (see FIGS. 5, 9, and 12).

Now referring primarily to FIGS. 50A-50D, the implant receiving space 1029 and the sacroiliac joint implant body 25 can be configured having related dimension relations such that placement of the insertion plate 45 of the sacroiliac joint implant body 25 within the implant receiving space 1029 disposes the sacrum 1004 and the ilium 1005 in substantially immobilized relation and substantially avoids alteration of the positional relation of the sacrum 1004 and the ilium 1005 from the normal condition, or avoids driving together or driving apart the sacrum 1004 from the ilium 1005 outside of or substantially outside of the normal positional relation. In an embodiment, the insertion plate 45 and the implant receiving space 1029 may be configured to immobilize the sacrum 1004 in relation to the ilium 1005 while maintaining the sacroiliac joint 1000 in substantially normal or substantially normal positional relation, or to return the sacroiliac joint 1000 to a substantially normal positional relation and thereby correct a degenerative condition of the sacroiliac joint 1000.

As a non-limiting example, configurations of an implant receiving space 1029 allow embodiments of the sacroiliac joint implant body 25 to be placed non-transversely between the caudal portions 1086 of the articular surfaces 1016 of the sacroiliac joint 1000. While certain embodiments of the sacroiliac joint implant body 25 may only provide an insertion plate 45 which locates within a correspondingly configured implant receiving space 1029 to engage at least a portion of the bone of the ilium 1005 or sacrum 1004, the invention is not so limited, and can further include one or more fins 50 engaging a portion of the bone 1073 of the sacrum 1004 and/or the ilium 1005.

As to those embodiments of the sacroiliac joint implant bodies 25 which further include one or more fins 50, the implant receiving space 1029 can further include one or more corresponding transverse receiving channels 1074, which correspondingly allow the one or more fins 50 to extend into the bone 1073 of the sacrum 1004 or the ilium 1005 (whether subchondral, cortical, cancellous, or the like). Alternatively, impact of the insertion plate 45 of the sacroiliac joint implant 25 into the implant receiving space 1029 without the transverse receiving channels 1074 can forcibly urge the one or more fins 50 into the bone 1073 of the sacrum 1004 and the ilium 1005. An anchor 30 members can be inserted through the bore 40 in the implant 25 and into the sacrum 1004 and ilium 1005 to fix the location of the fixation fusion implant 25 within the implant receiving space 1029.

While the preceding discussion is given in the context of the implant body 25 being implanted non-transversely in the caudal portion 1086 of the sacroiliac joint 1000, in other embodiments, the implant body 25 may be implanted in other locations within the sacroiliac joint 1000. For example, as disclosed in U.S. patent application Ser. No. 12/998,712, which is incorporated herein by reference, in some embodiments, the implant body 25 may be implanted non-transversely in the cranial portion 1087 (see FIG. 50A) of the sacroiliac joint 1000 by the similar procedures or steps as above described with the incision and generation of the passage to the superior articular portion of the sacroiliac joint 1000. The implant body 25 may also be implanted in the sacroiliac joint 1000 in such a manner so as to extend between the cranial and caudal portions, as also disclosed in U.S. patent application Ser. No. 12/998,712.

ii. Insertion of Insertion Element of Implant Body into Implant Receiving Space

Figure 51A:
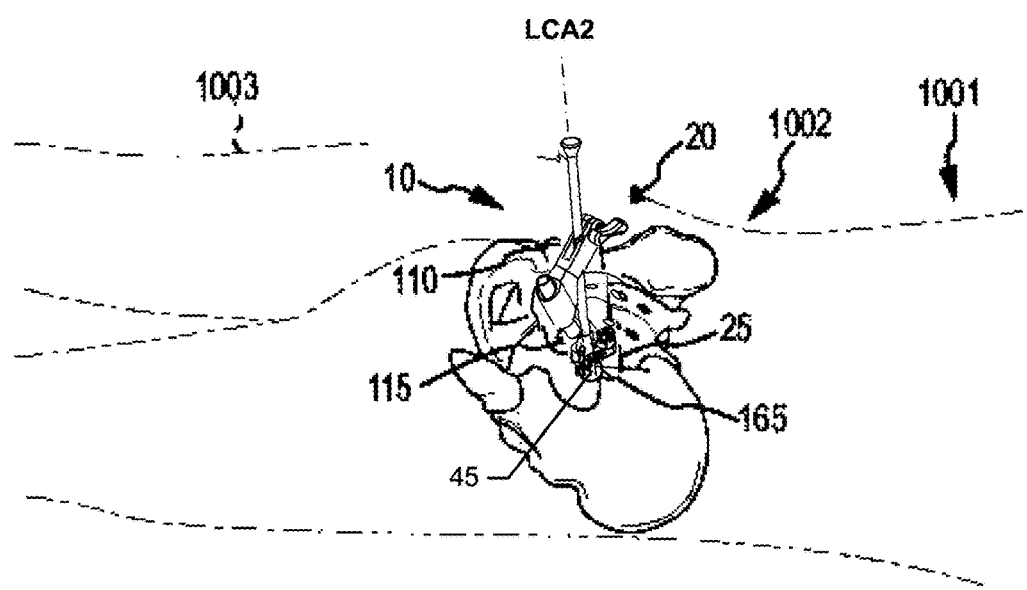
FIG. 51A is a lateral-posterior view of the hip region of the patient illustrating the position and alignment of a delivery tool being used to deliver the implant to the sacroiliac joint space.
Figure 51B:
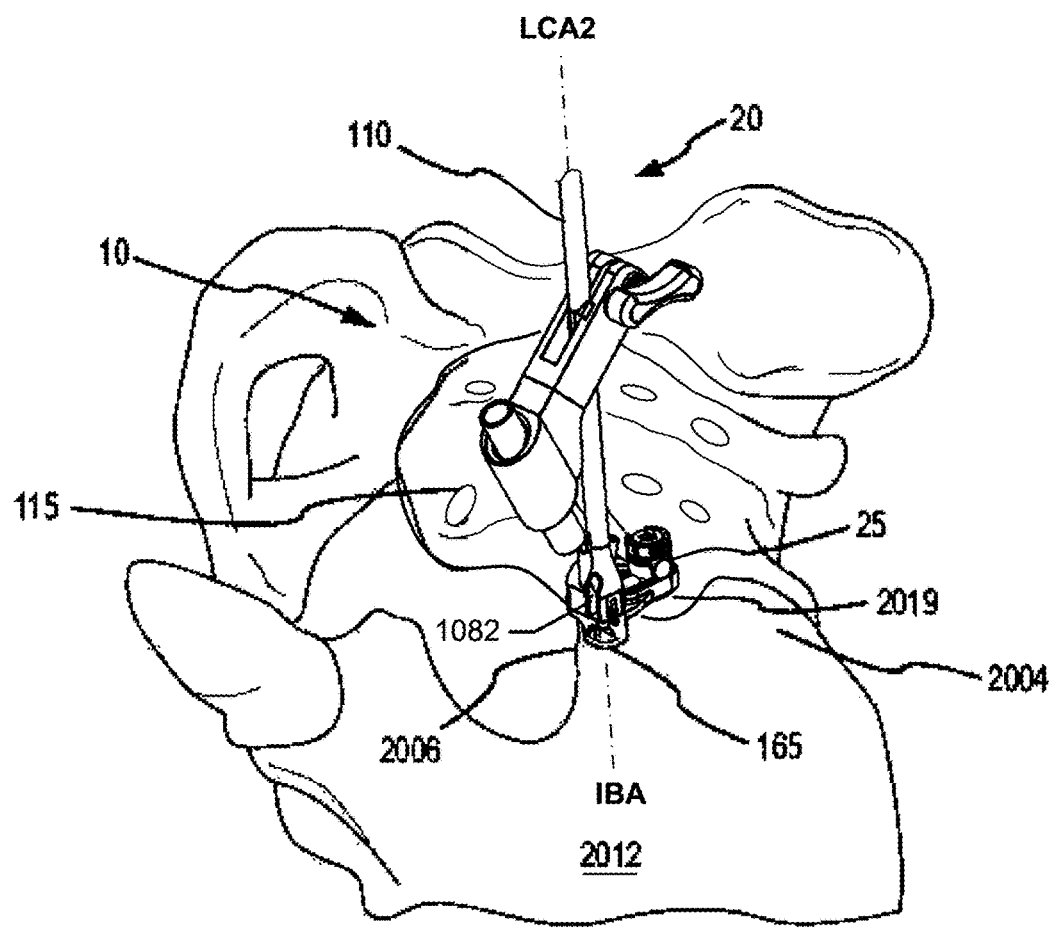
FIG. 51B is an enlarged view of the delivery tool and implant assembly within the hip region illustrated in FIG. 51A.
Figure 52:
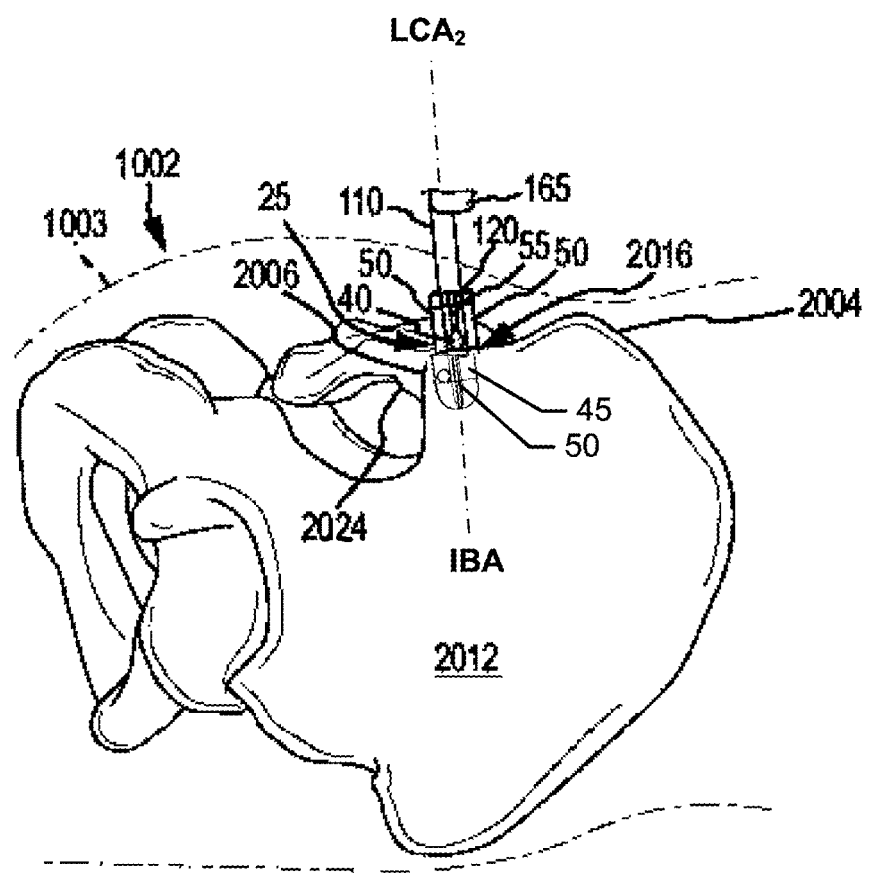
FIG. 52 is a lateral view of the hip region of the patient illustrating the position and alignment of a delivery tool being used to deliver the implant assembly to the sacroiliac joint space.

To begin a discussion of employing the delivery tool 20 to implant the implant body 25 in the sacroiliac joint 1000 once the implant receiving space 1029 has been created, reference is made to FIGS. 47I, 51A, 51B and 52. FIG. 51A is generally the same view as FIG. 45A, and FIG. 51B is an enlarged view of the hip region of FIG. 51A. FIG. 52 is generally the same enlarged view as FIG. 44B. As shown in FIGS. 47I, 51A, 51B and 52, once the implant receiving space 1029 has been created as discussed above with respect to FIGS. 47A-47H, the implant body 25 can be supported off of the distal end 120 of the implant arm 110 of the delivery tool 20 and positioned such that the distal end 42 of the implant body 25 (specifically the insertion plate 45) begins to enter the sacroiliac joint articular region 1044 via the posterior inferior access region 2016, which is described in detail above with respect to FIGS. 44A-46B. As can be understood from FIGS. 51A-52, in entering the sacroiliac joint space, the implant body 25 is oriented such that the plane of the insertion plate 45 is oriented generally parallel to, and aligned with, the sacroiliac joint line 2019. The longitudinal axis LCA2 of the implant arm 110 of the delivery tool 20 has a generally anterior trajectory that is located within the joint plane 1030. Alternatively, according to particular embodiments, as a non-limiting example, the longitudinal axis LCA2 of the implant arm 110 of the delivery tool 20 can have a trajectory which can be defined as being generally lateral or, in particular embodiments, generally posterior. In some embodiments, when the implant body 25 is being delivered into the joint space, the implant arm 110 can be said to be at least one of generally superior or cephalad to the sciatic notch.

Figure 47J:
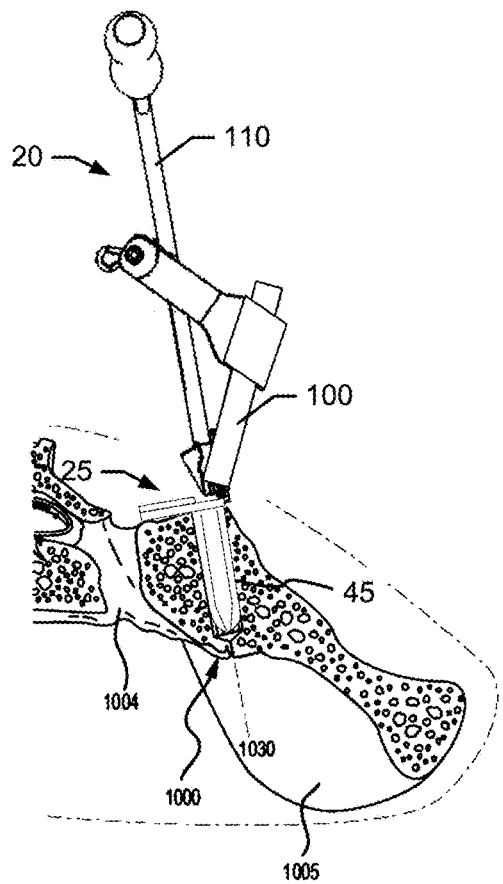

FIG. 53 is the same view as FIG. 52, except the insertion plate 45 of the implant body 25 has now been fully inserted into the prepared space 1029 in the sacroiliac joint 1000. As illustrated in FIGS. 47J and 53, the insertion plate 45 is fully received in the prepared sacroiliac space 1029 such that the plane of the insertion plate 45 is oriented generally parallel to, and aligned with, the sacroiliac joint line 2019 (i.e., the plane of the insertion plate 45 are generally located within the joint plane 1030), and the implant body's fins 50 are generally transverse to the joint plane 1030 and, in some embodiments, have even entered the bone material forming the sacrum and ilium articular surfaces of the sacroiliac joint (see, e.g., FIGS. 50C and 50D). As can be understood from FIG. 47J, the longitudinal axis IBA of the implant body 25 and the longitudinal axis LCA2 of the implant arm 110 may be coaxially aligned with each other and generally located in the sacroiliac joint plane 1030.

Figure 47K:
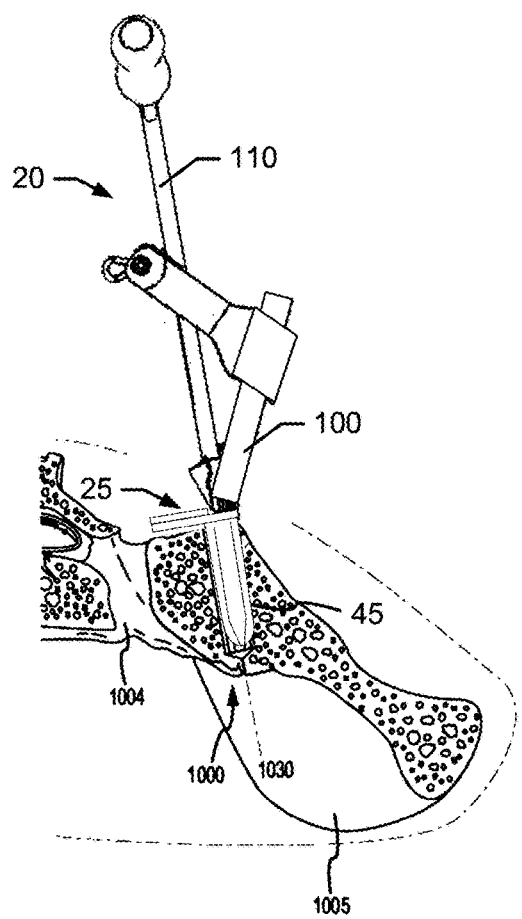

In addition, FIG. 53 illustrates the sleeve 100 is now received in the collar 165 of the anchor arm 115. As can be understood from FIGS. 47K and 53, the distal end of the sleeve 100 may extend through an incision in the patient's soft tissue such that the distal end of the sleeve 100 is positioned generally against the lateral surface of the ilium 1005. The longitudinal axis of the sleeve and collar of the anchor arm can be understood to be generally coaxially aligned with the longitudinal axis of the bore 40 of the implant body 25.

Figure 54:
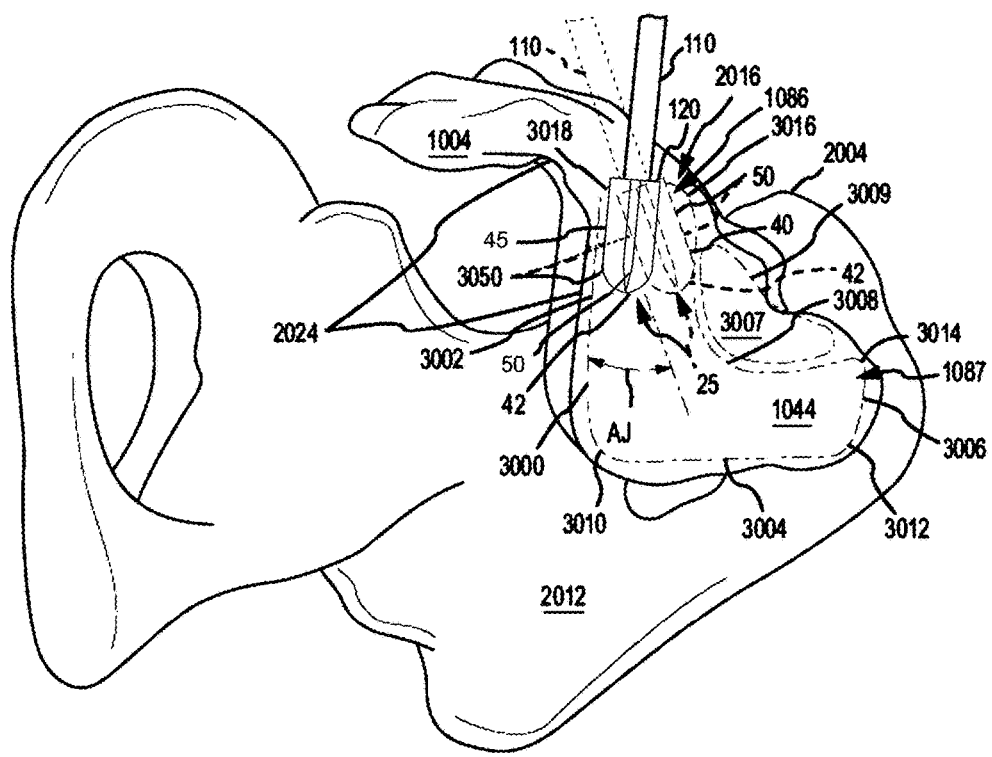
FIG. 54 is the lateral view of FIG. 53 with the ilium removed to expose the sacroiliac joint space boundary defined along the sacrum and the implant positioned for implantation within the joint space.

FIG. 54 is generally the same view as FIG. 53, except the ilium 1005 is removed to show the sacroiliac joint space boundary 3000 defined along the sacrum 1004 and outlining the sacroiliac joint articular region 1044, the implant 25 positioned for implantation within the sacroiliac joint articular region 1044. As shown in FIG. 54, the sacroiliac joint space boundary includes an inferior boundary segment 3002, an anterior boundary segment 3004, a superior boundary segment 3006, and a posterior boundary segment 3008. The inferior boundary segment 3002 is immediately adjacent, and extends along, the sciatic notch 2024.

The inferior boundary segment 3002 and anterior boundary segment 3004 intersect to form an anterior-inferior corner 3010. The anterior boundary segment 3004 and superior boundary segment 3006 intersect to form an anterior-superior corner 3012. The superior boundary segment 3006 and posterior boundary segment 3008 intersect to form a superior-posterior corner 3014. The posterior boundary segment 3008 and posterior inferior access region 2016 intersect to form a superior-posterior corner 3016 of the posterior inferior access region 2016. The inferior boundary segment 3002 and posterior inferior access region 2016 intersect to form an inferior-posterior corner 3018 of the posterior inferior access region 2016.

The inferior boundary segment 3002 extends between corners 3010 and 3018. The anterior boundary segment 3004 extends between corners 3010 and 3012. The superior boundary segment 3006 extends between corners 3012 and 3014 and provides an access into the cranial portion 1087 of the sacroiliac joint. The posterior boundary segment 3008 extends between corners 3014 and 3016. The posterior inferior access region 2016 extends between corners 3016 and 3018 and provides an access into the caudal region 1086 of the sacroiliac joint. The posterior boundary segment 3008 separates articular region 1044 and extra-articular region 3007, which includes the sacral fossa on the sacrum 1004 and the corresponding iliac tuberosity on the ilium 1005 and defined by the extra-articular region boundary 3009.

As shown in FIG. 54, the insertion plate 45 of the implant body 25 is inserted via the implant arm 110 of the delivery tool 20 into the caudal region 1086 of the sacroiliac joint articular region 1044. As shown via the insertion plate 45 and implant arm 110 shown in solid lines, in one embodiment, the implant 25 enters the posterior inferior access region 2016, and is further advanced into the caudal region 1086 of the sacroiliac joint articular region 1044, in an orientation such that the implant arm 110 and implant plate 45 are in the joint plane 1030 (see, for example, FIGS. 47I-47J) and the longitudinally extending edge 3050 of the implant plate 45 next to the inferior boundary segment 3002 is generally parallel to, and immediately adjacent to, the inferior boundary segment 3002. Thus, the distal end 42 of the implant is heading generally perpendicular to, and towards, the anterior boundary segment 3004.

As shown in FIG. 54 via the insertion plate 45 and implant arm 110 shown in dashed lines, in one embodiment, the insertion plate 45 enters the posterior inferior access region 2016, and is further advanced into the caudal region 1086 of the sacroiliac joint articular region 1044, in an orientation such that the implant arm 110 and plane of the insertion plate 45 are in the joint plane 1030 (see, for example, FIGS. 47I-47J) and the longitudinally extending edge 3050 of the insertion plate 45 next to the inferior boundary segment 3002 is somewhere between being generally parallel to the inferior boundary segment 3002 (as illustrated by the solid-lined implant 25 in FIG. 54) or forming an angle AJ with the inferior boundary segment 3002 of up to approximately 50 degrees. Thus, the distal end 42 of the implant shown in dashed lines can be said to head anywhere from generally perpendicular to, and towards, the anterior boundary segment 3004 to heading generally towards the superior-anterior corner 3012, or points in between.

In one embodiment, the insertion plate 45 may be first directed into the joint space as illustrated by the solid-lined implant body 25 in FIG. 54 after which the implant body 25 is rotated within the joint space to be positioned somewhere between, and including, the angled position depicted by the dashed-lined implant body 25. In other embodiments, the insertion plate 45 may be first directed into the joint space as illustrated by the dashed-lined implant body 25 in FIG. 54 after which the implant body 25 is rotated within the joint space to be positioned somewhere between, and including, the parallel position depicted by the solid-lined implant body 25.

iii. Insertion of Anchor

Figure 47L:
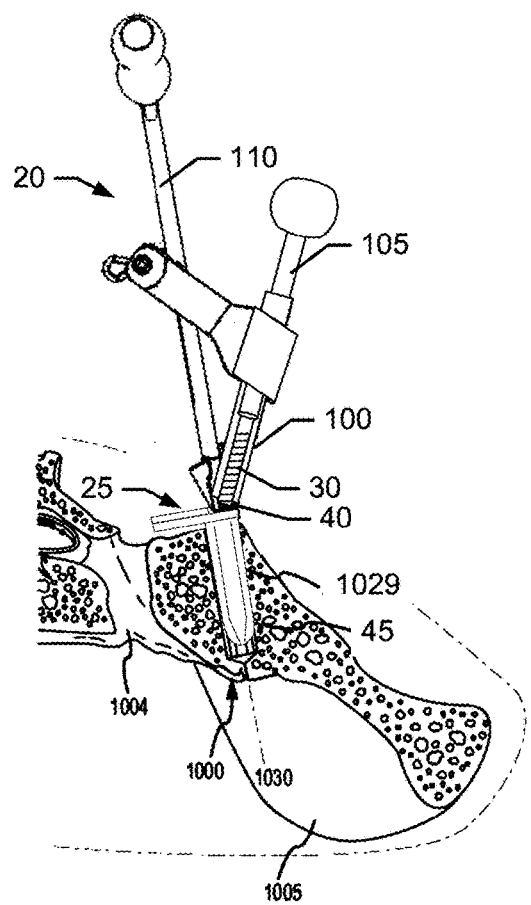
Figure 47M:
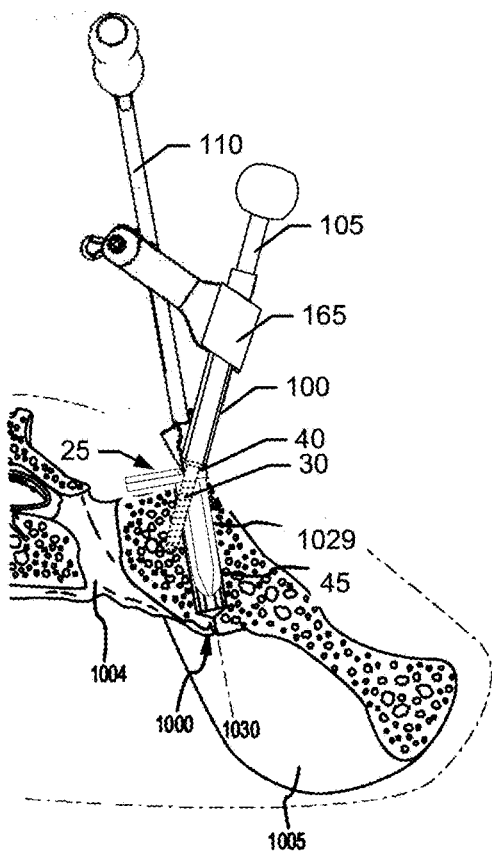
Figure 47N:
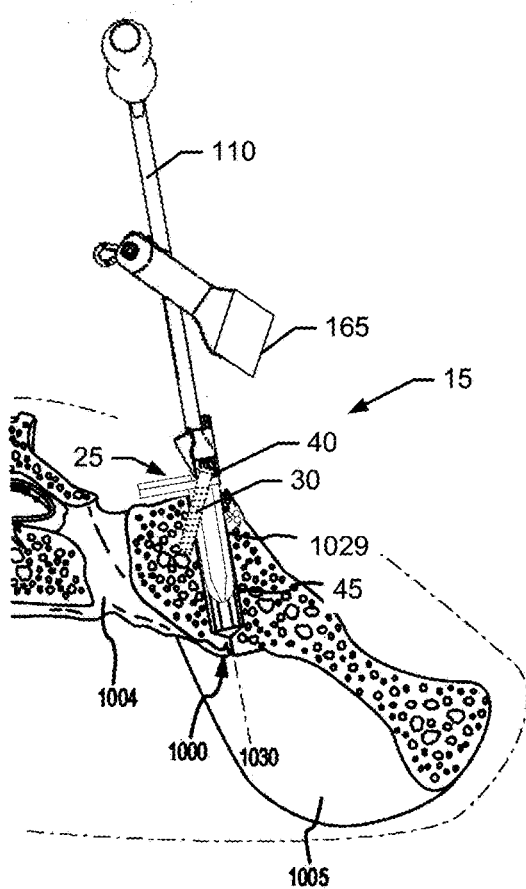
Figure 47O:
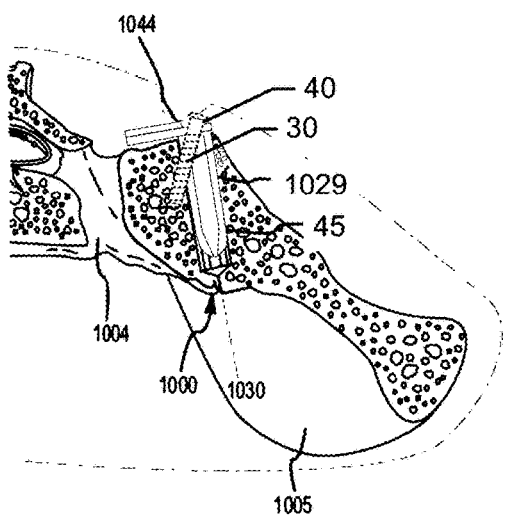
Figure 47P:
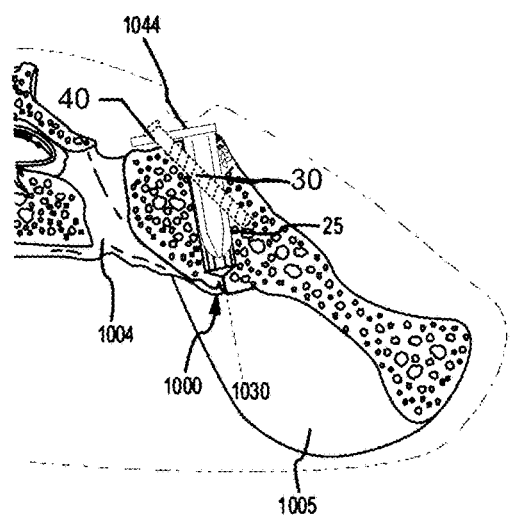
Figure 55:
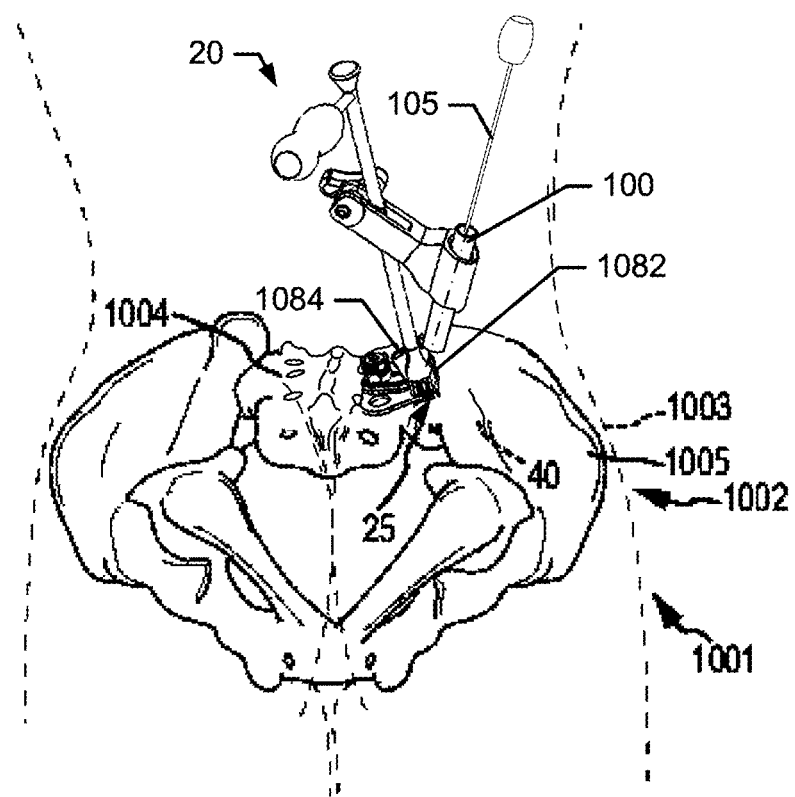
FIG. 55 is a posterior-inferior view of the hip region of the patient illustrating the position and alignment of a delivery tool being used to deliver the implant to the sacroiliac joint space; the soft tissues surrounding the skeletal hip bones are represented as dashed lines.

FIG. 55 is a posterior-inferior view of the hip region 1002 of the patient 1001, wherein the soft tissue 1003 surrounding the skeletal hip bones is shown in dashed lines. As can be understood from FIGS. 47L and 55, the anchor 30 is positioned in the lumen of the sleeve 100. A driving tool 105 (e.g., screw driver) is extended through the lumen of the sleeve 100 so the distal end of the tool 105 is engaged with a proximal end of the anchor member 30 (e.g., screw). As shown in FIG. 47M, the tool 105 is used to drive the anchor 30 distally through into the bore 40 of the implant 25 generally transverse to the joint line plane 1030 and into the bone of the sacrum 1004, in this embodiment. As a result, as indicated in FIG. 47N, the implant assembly 15 formed of the implant 25 and anchor 30 is secured at the implantation site such that the implant 25 is located in the prepared space 1029 of the sacroiliac joint space, and the anchor 30 extends through into the bore 40 of the implant 25 into the bone of the sacrum 1005 and into the implant bore 40 generally transverse to the joint space plane 1030. The tool 105 and sleeve 100 can be removed from the anchor arm collar 165, and the incision associated with the sleeve 100 can be closed. Additionally, tool 105 can be a cutting tool 105 (e.g., drill bit, hole punch, or etc.) which can used in similar steps as above describe to remove bone or other tissues in the path where anchor 30 is to be placed. As indicated in FIG. 47O, the distal end of the implant arm 110 is decoupled from the proximal end of the implant 25 and removed. The incision associated with the implant arm can be closed.

In other embodiments, illustrated in FIG. 47P, the anchor 30 may enter a bore 40 situated in a more medial position relative to the insertion plate 45; the implant body 25 of this embodiment is illustrated in FIG. 9. In this embodiment, the anchor 30 may enter the bore 40, penetrate the bone of the sacrum 1004, pass through a second bore formed within the insertion plate 45 and aligned with the first bore 40, and further penetrate the bone of the ilium 1005.

Figure 47Q:
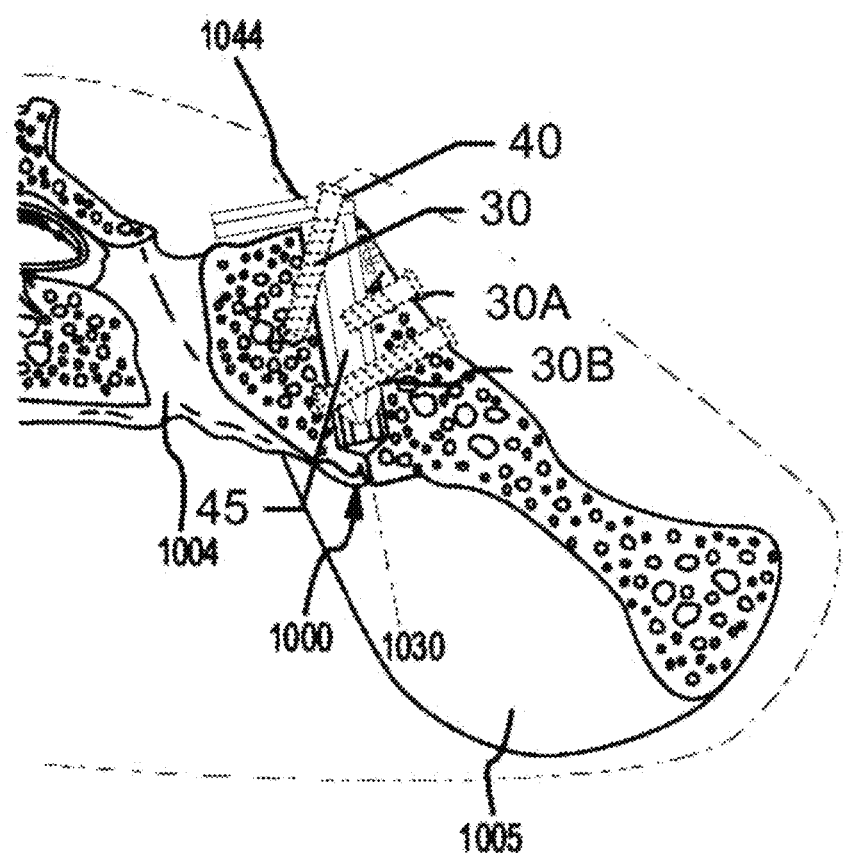

As illustrated in FIG. 47Q, in certain embodiments, the implant body 25 can be configured to have more than one implant bore 40 to receive additional anchors 30A and 30B. The anchors 30, 30A, and 30B prevent migration of the implant body 25 within the joint space. The anchors 30, 30A, and 30B also can draw the ilium and sacrum together about the implant body 25, increasing the sturdiness of the fixation of the implant in the joint space, as demonstrated by the anchor 30 in FIG. 47P and by anchor 30B in FIG. 47Q. Where the anchor 30 extends through the implant bore 40 and into the bone of both the sacrum 1004 and ilium 1005, the anchor 30 can be used to drawn the articular surfaces 1016 of the sacroiliac joint 1000 against the external surfaces of the insertion plate 45 of the implant body 25. With the insertion plate 45 implanted in the sacroiliac joint, the healing processes will cause the surfaces 1016 to fuse together about the insertion plate 45.

Figure 56:
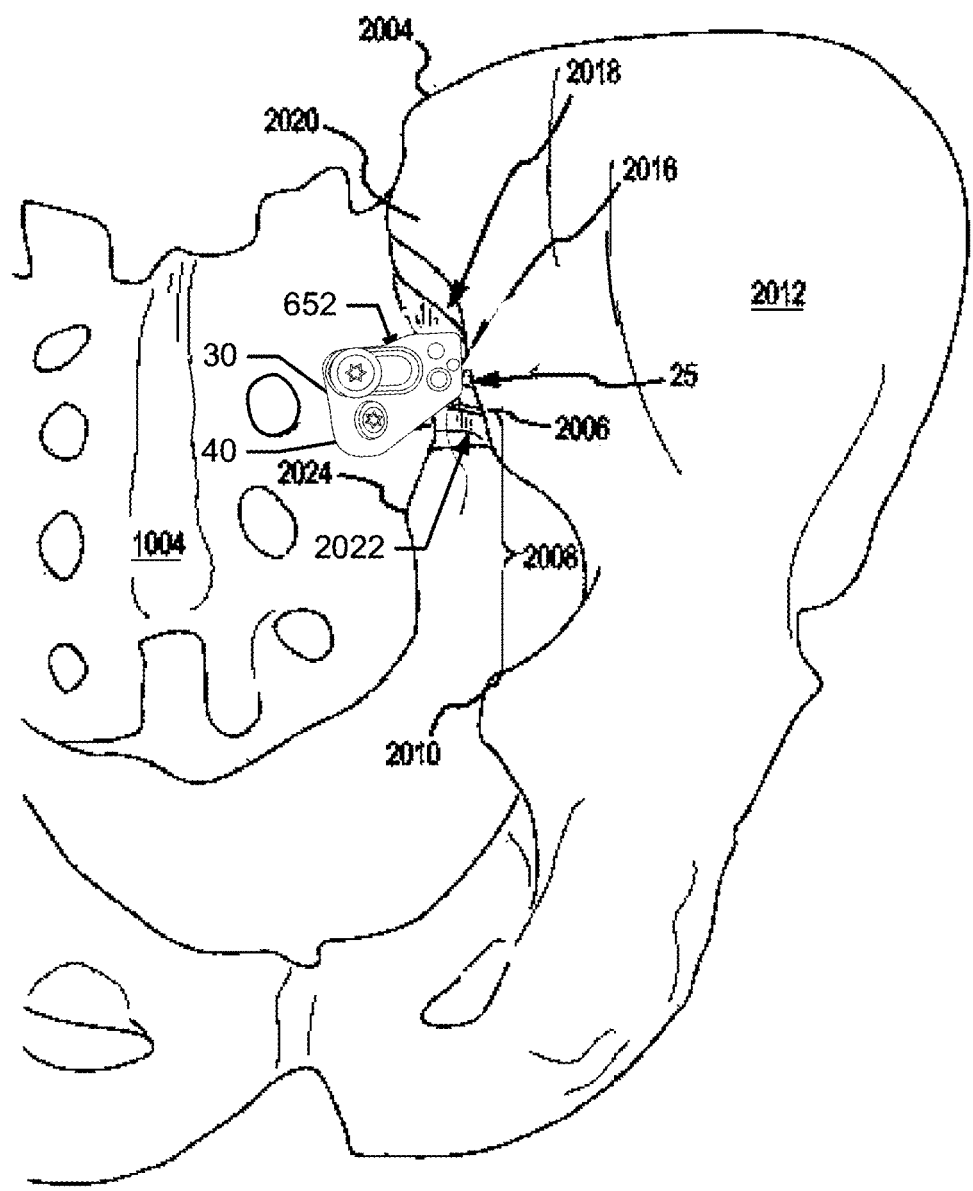
FIG. 56 is a posterior view of the implantation area and fully-inserted implant assembly.

FIG. 56 is a posterior view of the implantation area and the implant body 25 implanted within the implantation area. In this view, the insertion plate 45 situated in the joint space is obscured by the attachment element 652. As can be understood from FIG. 56, the implant body 25 can be seen positioned in the posterior inferior access region 2016 and implanted in the caudal area of the sacroiliac joint space. The anchor 30 can be understood to have been driven into the implant bore 40 transversely to the joint plane 1030 via a route in the ilium 1005 that avoids contact with vascular and neurological structures, thereby avoiding potentially life threatening injury to such structures. The ability to blindly, yet safely, drive the anchor member 30 into the implant bore 40 while the implant 25 is hidden in the joint space is made possible by the cooperating configurations of the implant body 25 and the delivery tool 20. Specifically, the longitudinal axis LCA1 of the anchor arm 165 is coaxially aligned with the longitudinal axis BA of the implant bore 40 when the implant body 25 is supported off of the implant arm 110 of the delivery tool 20, thereby making it possible to safely drive the anchor 30 through the implant bore 40 and into the ilium 1005 bone and/or sacrum bone 1004 when the implant body 25 is hidden in the joint space on account of being delivered to the joint space via the delivery tool 20.

The foregoing merely illustrates the principles of the invention. Various modifications and alterations to the described embodiments will be apparent to those skilled in the art in view of the teachings herein. It will thus be appreciated that those skilled in the art will be able to devise numerous systems, arrangements and methods which, although not explicitly shown or described herein, embody the principles of the invention and are thus within the spirit and scope of the present invention. From the above description and drawings, it will be understood by those of ordinary skill in the art that the particular embodiments shown and described are for purposes of illustrations only and are not intended to limit the scope of the present invention. References to details of particular embodiments are not intended to limit the scope of the invention.

What is claimed is:

1. A sacroiliac joint fusion and anchoring system, comprising:
   a) an implant assembly comprising:
      i) an implant body comprising;
         an insertion element comprising an elongate body with a proximal insertion element end and a distal insertion element end, and an attachment bore formed within the proximal insertion element end;
         an attachment element mechanically attached to and cantilevered off of the proximal insertion element end;
         wherein the attachment element comprises an anchor fitting formed within the attachment element or mechanically attached to the attachment element and an attachment fitting formed within the attachment element or mechanically attached to the attachment element, the attachment fitting configured to attach to an element of a spinal stabilization system; and
      ii) an anchor; and
   b) a delivery tool comprising:
      i) an implant arm comprising a distal implant arm end configured to releasably couple to the implant body; and
      ii) an anchor arm comprising a proximal anchor arm end coupled to the implant arm and a distal anchor arm end opposite to the proximal anchor arm end, wherein the distal anchor arm end distally ends in a sleeve configured to guide the anchor within a predetermined range of anchor insertion trajectories;
   wherein the sleeve is configured to guide the anchor through the anchor fitting within the predetermined range of anchor insertion trajectories when the distal implant arm end is releasably coupled to the implant body;
   wherein the attachment bore is configured to receive a corresponding attachment fastener situated within the distal implant arm end of the delivery tool, wherein corresponding engagement between the attachment bore and the attachment fastener is configured to maintain an orientation of the implant body and the delivery tool prior to and during implantation of the insertion element into a joint;
   wherein the attachment bore is a threaded bore and the attachment fastener is a screw; and
   wherein the attachment bore further comprises one or more alignment features chosen from: one or more additional threaded bores formed within the proximal insertion element end and separated by a lateral distance from the attachment bore; and one or more alignment peg receptacles configured to receive one or more corresponding alignment pegs projecting distally from an extreme distal face of the distal implant arm end of the implant arm of the delivery tool.

2. The system of claim 1, wherein the alignment peg receptacles are situated within a proximal surface of the attachment element within the lateral edge of the attachment element.

3. The system of claim 1, wherein the alignment peg receptacles are inset within the lateral edge of the attachment element.

4. The system of claim 1, wherein the alignment pegs are arranged in a pattern corresponding to an edge contour of the lateral edge of the attachment element.

5. The system of claim 1, wherein the sleeve of the anchor arm comprises a tubular guide with a proximal opening and a distal opening, wherein the proximal opening is configured to receive a distal tip of the anchor or other orthopedic fastener and the distal opening is configured to guide the distal tip of the anchor or other orthopedic fastener within a predetermined range of insertion trajectories.

6. The system of claim 1, wherein the sleeve of the anchor arm is narrow relative to a diameter of a head and shaft of an anchor or other orthopedic fastener, and wherein the sleeve is configured to guide the distal tip of the anchor or other orthopedic fastener within a narrow predetermined range of insertion trajectories.

7. The system of claim 1, wherein the sleeve of the anchor arm is wide relative to a diameter of a head and shaft of an anchor or other orthopedic fastener, and wherein the sleeve is configured to guide the distal tip of the anchor or other orthopedic fastener within a wide predetermined range of insertion trajectories.

8. The system of claim 1, wherein the sleeve is a conical sleeve comprising a proximal opening that is large relative to the distal opening, and wherein the conical sleeve is configured to guide the distal tip of the anchor or other orthopedic fastener within a wide predetermined range of insertion trajectories.

9. The system of claim 1, wherein the attachment element and the insertion element are oriented generally perpendicular to each other.

10. The system of claim 1, wherein the insertion element comprises a sacral side and an iliac side opposite the sacral side, the sacral and iliac sides extending between the proximal insertion element end and the distal insertion element end, wherein the attachment element extends in a cantilevered fashion beyond only one of the sacral side or the iliac side of the insertion element.

11. The system of claim 1, wherein the anchor fitting comprises a first anchor bore and a second anchor bore both extending through the attachment element.

12. The system of claim 11, wherein the attachment fitting is positioned between the first and second anchor bores.

13. The system of claim 1, wherein the attachment fitting is positioned between first and second fins of the insertion element, the first and second fins spaced apart from each other and extending a length between the proximal insertion element end and the distal insertion element end.

14. The system of claim 1, wherein the attachment fitting comprises a head configured to receive a rod and a threaded compression element to secure the rod in position.

15. The system of claim 14, wherein the head comprises an upward-opening groove to receive the rod therein.

16. The system of claim 1, wherein the attachment fitting is positioned medial to and not longitudinally in line with the insertion element.

17. The system of claim 1, wherein the element of a spinal stabilization system comprises a rod.

* * * * *